(12) United States Patent
Rion et al.

(10) Patent No.: US 8,961,393 B2
(45) Date of Patent: Feb. 24, 2015

(54) GASTRIC BAND DEVICES AND DRIVE SYSTEMS

(75) Inventors: Julien Rion, Morges (CH); Laurent Mosimann, Commugny (CH); Pierre Fridez, Froideville (CH); Tiago Bertolote, Geneva (CH); Denis Crottet, Delley (CH); Marcel Aeschlimann, Reconvilier (CH); Vincent Vaucher, Reconvilier (CH)

(73) Assignee: Apollo Endosurgery, Inc., Austin, TX (US)

( * ) Notice: Subject to any disclaimer, the term of this patent is extended or adjusted under 35 U.S.C. 154(b) by 839 days.

(21) Appl. No.: 12/946,757

(22) Filed: Nov. 15, 2010

(65) Prior Publication Data

US 2012/0123196 A1 May 17, 2012

(51) Int. Cl.
*A61F 2/04* (2013.01)
*A61F 5/00* (2006.01)
*A61F 2/00* (2006.01)

(52) U.S. Cl.
CPC ............. *A61F 5/0053* (2013.01); *A61F 2/0036* (2013.01)
USPC .......................................................... 600/37

(58) Field of Classification Search
CPC .......... A61F 2/0036; A61F 5/005; A61F 2/04
USPC .................... 600/29–32, 37; 128/897–899
See application file for complete search history.

(56) References Cited

U.S. PATENT DOCUMENTS

| | | | |
|---|---|---|---|
| 1,174,814 A | 3/1916 | Brennan et al. | |
| 1,830,947 A | 11/1931 | Klingel | |
| 1,999,683 A | 4/1935 | Borresen | |
| 2,163,048 A | 6/1939 | McKee | |
| 2,339,138 A | 1/1944 | Black | |
| 2,405,667 A | 8/1946 | Ottesen | |
| 2,438,231 A | 3/1948 | Schultz et al. | |
| 2,635,907 A | 4/1953 | Heimbuch | |
| 2,714,469 A | 8/1955 | Carlson | |
| 2,936,980 A | 5/1960 | Rapata | |
| 3,059,645 A | 10/1962 | Hasbrouck et al. | |

(Continued)

FOREIGN PATENT DOCUMENTS

| | | |
|---|---|---|
| CA | 949965 | 6/1974 |
| CN | 1250382 | 4/2000 |

(Continued)

OTHER PUBLICATIONS

Brown et al; "Symmetrical Pouch Dilation After Laparoscopic Adjustable Gastric Banding: Incidence and Management"; Obesity Surgery; V. 18, pp. 1104-1108; 2008.

(Continued)

*Primary Examiner* — Christine Matthews
*Assistant Examiner* — Joshua D Lannu
(74) *Attorney, Agent, or Firm* — Gordon & Jacobson, PC

(57) ABSTRACT

Gastric banding devices, and drive systems designed to operate gastric banding devices, are disclosed. The gastric banding devices and drive systems intend to increase performance, durability, and simplicity over known gastric banding systems. Embodiments include transmission systems configured to output a variable force. Embodiments also include banding structures biased to apply a constrictive force to a patient's stomach. Supporting, or skeletal, structures are also disclosed. Various drive systems designed to improve power efficiency are also disclosed.

39 Claims, 50 Drawing Sheets

(56) References Cited

U.S. PATENT DOCUMENTS

| | | |
|---|---|---|
| 3,189,961 A | 6/1965 | Heller |
| 3,667,081 A | 6/1972 | Burger |
| 3,840,018 A | 10/1974 | Heifetz |
| 3,955,834 A | 5/1976 | Ahlrot |
| 4,053,176 A | 10/1977 | Hilbush |
| 4,118,805 A | 10/1978 | Reimels |
| 4,133,315 A | 1/1979 | Berman et al. |
| 4,157,713 A | 6/1979 | Clarey |
| 4,176,412 A | 12/1979 | Peterson |
| 4,236,521 A | 12/1980 | Lauterjung |
| 4,271,827 A | 6/1981 | Angelchik |
| 4,299,012 A | 11/1981 | Oetiker |
| 4,399,809 A | 8/1983 | Baro et al. |
| 4,408,597 A | 10/1983 | Tenney, Jr. et al. |
| 4,417,567 A | 11/1983 | Trick |
| 4,424,208 A | 1/1984 | Wallace et al. |
| 4,442,153 A | 4/1984 | Meltsch |
| 4,485,805 A | 12/1984 | Foster, Jr. |
| 4,492,004 A | 1/1985 | Oetiker |
| 4,551,862 A | 11/1985 | Haber |
| 4,558,699 A | 12/1985 | Bashour |
| 4,559,699 A | 12/1985 | Owen et al. |
| 4,582,640 A | 4/1986 | Smestad et al. |
| 4,582,865 A | 4/1986 | Balazs et al. |
| 4,592,339 A | 6/1986 | Kuzmak et al. |
| 4,592,355 A | 6/1986 | Antebi |
| 4,601,713 A | 7/1986 | Fuqua |
| 4,671,351 A | 6/1987 | Rappe |
| 4,693,695 A | 9/1987 | Cheng |
| 4,694,827 A | 9/1987 | Weiner et al. |
| 4,696,288 A | 9/1987 | Kuzmak et al. |
| 4,708,140 A | 11/1987 | Baron |
| 4,716,154 A | 12/1987 | Malson et al. |
| 4,753,086 A | 6/1988 | Schmidt |
| 4,760,837 A | 8/1988 | Petit |
| 4,803,075 A | 2/1989 | Wallace et al. |
| 4,881,939 A | 11/1989 | Newman |
| 4,883,467 A | 11/1989 | Franetzki et al. |
| 4,886,787 A | 12/1989 | De Belder et al. |
| 4,896,787 A | 1/1990 | Delamour et al. |
| 4,915,690 A | 4/1990 | Cone et al. |
| 4,925,446 A | 5/1990 | Garay et al. |
| 4,944,659 A | 7/1990 | Labbe et al. |
| 4,958,791 A | 9/1990 | Nakamura |
| 4,969,899 A | 11/1990 | Cox, Jr. |
| 4,994,019 A | 2/1991 | Fernandez et al. |
| 5,045,060 A | 9/1991 | Melsky et al. |
| 5,074,868 A | 12/1991 | Kuzmak |
| 5,084,061 A | 1/1992 | Gau et al. |
| 5,089,019 A | 2/1992 | Grandjean |
| 5,091,171 A | 2/1992 | Yu et al. |
| 5,120,313 A | 6/1992 | Elftman |
| 5,143,724 A | 9/1992 | Leshchiner et al. |
| 5,152,770 A | 10/1992 | Bengmark et al. |
| 5,160,338 A | 11/1992 | Vincent |
| 5,188,609 A | 2/1993 | Bayless et al. |
| 5,224,494 A | 7/1993 | Enhorning |
| 5,226,429 A | 7/1993 | Kuzmak |
| 5,246,456 A | 9/1993 | Wilkinson |
| 5,246,698 A | 9/1993 | Leshchiner et al. |
| 5,259,399 A | 11/1993 | Brown |
| 5,326,349 A | 7/1994 | Baraff |
| 5,356,883 A | 10/1994 | Kuo et al. |
| 5,360,445 A | 11/1994 | Goldowsky |
| 5,391,156 A | 2/1995 | Hildwein et al. |
| 5,399,351 A | 3/1995 | Leshchiner et al. |
| 5,449,363 A | 9/1995 | Brust et al. |
| 5,449,368 A | 9/1995 | Kuzmak |
| 5,458,568 A | 10/1995 | Racchini et al. |
| 5,496,312 A | 3/1996 | Klicek |
| 5,509,888 A | 4/1996 | Miller |
| 5,531,716 A | 7/1996 | Luzio et al. |
| 5,535,752 A | 7/1996 | Halperin et al. |
| 5,554,113 A | 9/1996 | Novak et al. |
| 5,562,714 A | 10/1996 | Grevious |
| 5,601,604 A | 2/1997 | Vincent |
| 5,607,418 A | 3/1997 | Arzbaecher |
| 5,633,001 A | 5/1997 | Agerup |
| 5,653,718 A | 8/1997 | Yoon |
| 5,658,298 A | 8/1997 | Vincent et al. |
| 5,676,162 A | 10/1997 | Larson, Jr. et al. |
| 5,695,504 A | 12/1997 | Gifford, III et al. |
| 5,704,893 A | 1/1998 | Timm |
| 5,713,911 A | 2/1998 | Racenet et al. |
| 5,733,257 A | 3/1998 | Sternby |
| 5,748,200 A | 5/1998 | Funahashi |
| 5,759,015 A | 6/1998 | Van Lintel et al. |
| 5,766,232 A | 6/1998 | Grevious et al. |
| 5,769,877 A | 6/1998 | Barreras, Sr. |
| 5,785,295 A | 7/1998 | Tsai |
| 5,817,113 A | 10/1998 | Gifford, III et al. |
| 5,827,529 A | 10/1998 | Ono et al. |
| 5,833,698 A | 11/1998 | Hinchliffe et al. |
| 5,861,014 A | 1/1999 | Familoni |
| RE36,176 E | 3/1999 | Kuzmak |
| 5,886,042 A | 3/1999 | Yu et al. |
| 5,904,697 A | 5/1999 | Gifford, III et al. |
| 5,910,149 A | 6/1999 | Kuzmak |
| 5,928,195 A | 7/1999 | Malamud et al. |
| 5,938,669 A | 8/1999 | Klaiber et al. |
| 5,944,696 A | 8/1999 | Bayless et al. |
| 5,944,751 A | 8/1999 | Laub |
| 5,993,473 A | 11/1999 | Chan et al. |
| 6,013,679 A | 1/2000 | Kuo et al. |
| 6,024,340 A | 2/2000 | Lazarus et al. |
| 6,024,704 A | 2/2000 | Meador et al. |
| 6,042,345 A | 3/2000 | Bishop et al. |
| 6,048,309 A | 4/2000 | Flom et al. |
| 6,067,991 A | 5/2000 | Forsell |
| 6,074,341 A | 6/2000 | Anderson et al. |
| 6,074,378 A | 6/2000 | Mouri et al. |
| 6,083,249 A | 7/2000 | Familoni |
| 6,090,131 A | 7/2000 | Daley |
| 6,102,678 A | 8/2000 | Peclat |
| 6,102,922 A | 8/2000 | Jakobsson et al. |
| 6,164,933 A | 12/2000 | Tani et al. |
| 6,171,321 B1 | 1/2001 | Gifford, III et al. |
| 6,193,734 B1 | 2/2001 | Bolduc et al. |
| 6,203,523 B1 | 3/2001 | Haller et al. |
| 6,210,345 B1 | 4/2001 | Van Brunt |
| 6,210,347 B1 | 4/2001 | Forsell |
| 6,221,024 B1 | 4/2001 | Miesel |
| 6,224,857 B1 | 5/2001 | Romeo et al. |
| 6,306,088 B1 | 10/2001 | Krausman et al. |
| 6,327,503 B1 | 12/2001 | Familoni |
| 6,371,965 B2 | 4/2002 | Gifford, III et al. |
| 6,387,105 B1 | 5/2002 | Gifford, III et al. |
| 6,417,750 B1 | 7/2002 | Sohn |
| 6,419,696 B1 | 7/2002 | Ortiz et al. |
| 6,432,040 B1 | 8/2002 | Meah |
| 6,439,539 B1 | 8/2002 | Powell |
| 6,443,957 B1 | 9/2002 | Addis |
| 6,443,965 B1 | 9/2002 | Gifford, III et al. |
| 6,450,173 B1 | 9/2002 | Forsell |
| 6,450,946 B1 | 9/2002 | Forsell |
| 6,451,034 B1 | 9/2002 | Gifford, III et al. |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyas Garza |
| 6,457,801 B1 | 10/2002 | Fish et al. |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,474,584 B2 | 11/2002 | Ekich |
| 6,475,136 B1 | 11/2002 | Forsell |
| 6,485,496 B1 | 11/2002 | Suyker et al. |
| 6,491,704 B2 | 12/2002 | Gifford, III et al. |
| 6,491,705 B2 | 12/2002 | Gifford, III et al. |
| 6,511,490 B2 | 1/2003 | Robert |
| 6,517,556 B1 | 2/2003 | Monassevitch |

(56) References Cited

U.S. PATENT DOCUMENTS

| | | |
|---|---|---|
| 6,527,701 B1 | 3/2003 | Sayet et al. |
| 6,547,801 B1 | 4/2003 | Dargent et al. |
| 6,565,582 B2 | 5/2003 | Gifford, III et al. |
| 6,579,301 B1 | 6/2003 | Bales et al. |
| 6,594,971 B1 * | 7/2003 | Addy et al. ............ 53/413 |
| 6,601,604 B1 | 8/2003 | Cooper |
| 6,615,084 B1 | 9/2003 | Cigaina |
| 6,632,239 B2 | 10/2003 | Snyder et al. |
| 6,646,628 B2 | 11/2003 | Shirochi et al. |
| 6,676,674 B1 | 1/2004 | Dudai |
| 6,681,135 B1 | 1/2004 | Davis et al. |
| 6,685,668 B1 | 2/2004 | Cho et al. |
| 6,691,047 B1 | 2/2004 | Fredricks |
| 6,715,731 B1 | 4/2004 | Post et al. |
| 6,729,600 B2 | 5/2004 | Mattes et al. |
| 6,754,527 B2 | 6/2004 | Stroebel et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 6,871,090 B1 | 3/2005 | He et al. |
| 6,889,086 B2 | 5/2005 | Mass et al. |
| 6,916,326 B2 | 7/2005 | Benchetrit |
| 6,940,467 B2 | 9/2005 | Fischer et al. |
| 6,966,875 B1 | 11/2005 | Longobardi |
| 7,017,583 B2 | 3/2006 | Forsell |
| 7,017,883 B2 | 3/2006 | Bayer et al. |
| 7,021,147 B1 | 4/2006 | Subramanian et al. |
| 7,037,344 B2 | 5/2006 | Kagan et al. |
| 7,040,349 B2 | 5/2006 | Moler et al. |
| 7,048,519 B2 | 5/2006 | Fong et al. |
| 7,054,690 B2 | 5/2006 | Imran |
| 7,058,434 B2 | 6/2006 | Wang et al. |
| 7,060,080 B2 | 6/2006 | Bachmann |
| 7,066,486 B2 | 6/2006 | Lee |
| 7,118,526 B2 | 10/2006 | Egle |
| 7,119,062 B1 | 10/2006 | Alvis et al. |
| 7,128,750 B1 | 10/2006 | Stergiopulos |
| 7,144,400 B2 | 12/2006 | Byrum et al. |
| 7,172,607 B2 | 2/2007 | Hofle et al. |
| 7,177,693 B2 | 2/2007 | Starkebsum |
| 7,191,007 B2 | 3/2007 | Desai et al. |
| 7,198,250 B2 | 4/2007 | East |
| 7,204,821 B1 | 4/2007 | Clare et al. |
| 7,206,637 B2 | 4/2007 | Salo |
| 7,223,239 B2 | 5/2007 | Schulze et al. |
| 7,238,191 B2 | 7/2007 | Bachmann |
| 7,240,607 B2 | 7/2007 | Fish |
| 7,255,675 B2 | 8/2007 | Gertner et al. |
| 7,263,405 B2 | 8/2007 | Boveja et al. |
| 7,282,023 B2 | 10/2007 | Frering |
| 7,284,966 B2 | 10/2007 | Xu et al. |
| 7,288,064 B2 | 10/2007 | Boustani et al. |
| 7,297,103 B2 | 11/2007 | Jarsaillon et al. |
| 7,299,082 B2 | 11/2007 | Feldman et al. |
| 7,310,557 B2 | 12/2007 | Maschino et al. |
| 7,311,503 B2 | 12/2007 | Van Lintel et al. |
| 7,311,716 B2 | 12/2007 | Byrum |
| 7,311,717 B2 | 12/2007 | Egle |
| 7,314,443 B2 | 1/2008 | Jordan et al. |
| 7,314,636 B2 | 1/2008 | Caseres et al. |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,353,747 B2 | 4/2008 | Swayze et al. |
| 7,364,542 B2 | 4/2008 | Jambor et al. |
| 7,366,571 B2 | 4/2008 | Armstrong |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,457,668 B2 | 11/2008 | Cancel et al. |
| 7,481,763 B2 | 1/2009 | Hassler et al. |
| 7,500,944 B2 | 3/2009 | Byrum et al. |
| 7,502,649 B2 | 3/2009 | Ben-Haim et al. |
| 7,530,943 B2 | 5/2009 | Lechner |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,670,279 B2 | 3/2010 | Gertner |
| 7,699,770 B2 | 4/2010 | Hassler, Jr. et al. |
| 7,712,470 B2 | 5/2010 | Gertner |
| 7,727,141 B2 | 6/2010 | Hassler, Jr. et al. |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,775,967 B2 | 8/2010 | Gertner |
| 7,794,386 B2 | 9/2010 | Brooks |
| 7,811,298 B2 | 10/2010 | Birk |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos et al. |
| 7,862,502 B2 | 1/2011 | Pool et al. |
| 7,879,068 B2 | 2/2011 | Dlugos et al. |
| 7,951,067 B2 | 5/2011 | Byrum et al. |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0139208 A1 | 10/2002 | Yatskov |
| 2002/0183765 A1 | 12/2002 | Adams |
| 2002/0198548 A1 | 12/2002 | Robert |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0055311 A1 | 3/2003 | Neukermans et al. |
| 2003/0060873 A1 | 3/2003 | Gertner et al. |
| 2003/0066536 A1 | 4/2003 | Forsell |
| 2003/0073880 A1 | 4/2003 | Polsky et al. |
| 2003/0093157 A1 | 5/2003 | Casares et al. |
| 2003/0100910 A1 | 5/2003 | Gifford, III et al. |
| 2003/0120288 A1 | 6/2003 | Benchetrit |
| 2003/0148995 A1 | 8/2003 | Piron et al. |
| 2003/0158564 A1 | 8/2003 | Benchetrit |
| 2003/0158569 A1 | 8/2003 | Wazne |
| 2003/0181890 A1 | 9/2003 | Schulze et al. |
| 2003/0181917 A1 | 9/2003 | Gertner |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0049209 A1 | 3/2004 | Benchetrit |
| 2004/0059393 A1 | 3/2004 | Policker et al. |
| 2004/0068847 A1 | 4/2004 | Belisle et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0002984 A1 | 1/2005 | Byrum et al. |
| 2005/0038484 A1 | 2/2005 | Knudson et al. |

(56) References Cited

U.S. PATENT DOCUMENTS

| | | |
|---|---|---|
| 2005/0038498 A1 | 2/2005 | Dubrow et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0100779 A1 | 5/2005 | Gertner |
| 2005/0104457 A1 | 5/2005 | Jordan et al. |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Knudson et al. |
| 2005/0136122 A1 | 6/2005 | Sadozai et al. |
| 2005/0142152 A1 | 6/2005 | Leshchiner et al. |
| 2005/0143765 A1 | 6/2005 | Bachmann et al. |
| 2005/0143766 A1 | 6/2005 | Bachmann et al. |
| 2005/0154274 A1 | 7/2005 | Jarsaillon et al. |
| 2005/0171568 A1 | 8/2005 | Duffy |
| 2005/0183730 A1 | 8/2005 | Byrum |
| 2005/0192531 A1 | 9/2005 | Birk |
| 2005/0192601 A1 | 9/2005 | Demarais |
| 2005/0192629 A1 | 9/2005 | Saadat et al. |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0277899 A1 | 12/2005 | Conlon et al. |
| 2005/0283041 A1 | 12/2005 | Egle |
| 2005/0288739 A1 | 12/2005 | Hassler, Jr. et al. |
| 2005/0288740 A1 | 12/2005 | Hassler, Jr. et al. |
| 2006/0015138 A1 | 1/2006 | Gertner |
| 2006/0020298 A1 | 1/2006 | Camilleri et al. |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0161186 A1 | 7/2006 | Hassler, Jr. et al. |
| 2006/0167531 A1 | 7/2006 | Gertner et al. |
| 2006/0173238 A1 | 8/2006 | Starkebaum |
| 2006/0173424 A1 | 8/2006 | Conlon |
| 2006/0178555 A1 | 8/2006 | Bortolotti |
| 2006/0183967 A1 | 8/2006 | Lechner |
| 2006/0189887 A1 | 8/2006 | Hassler, Jr. et al. |
| 2006/0189888 A1 | 8/2006 | Hassler, Jr. et al. |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212051 A1 | 9/2006 | Snyder et al. |
| 2006/0212053 A1 | 9/2006 | Gertner |
| 2006/0235448 A1 | 10/2006 | Roslin et al. |
| 2006/0246137 A1 | 11/2006 | Hermitte et al. |
| 2006/0247721 A1 | 11/2006 | Maschino et al. |
| 2006/0247722 A1 | 11/2006 | Maschino et al. |
| 2006/0252982 A1 | 11/2006 | Hassler, Jr. et al. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0276812 A1 | 12/2006 | Hill et al. |
| 2006/0293627 A1 | 12/2006 | Byrum et al. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1 | 1/2007 | Gross et al. |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1 | 4/2007 | Hull, Sr. et al. |
| 2007/0125826 A1 | 6/2007 | Shelton |
| 2007/0156013 A1 | 7/2007 | Birk |
| 2007/0167672 A1 | 7/2007 | Dlugos et al. |
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann et al. |
| 2007/0250086 A1 | 10/2007 | Wiley et al. |
| 2007/0255335 A1 | 11/2007 | Herbert et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2007/0265646 A1 | 11/2007 | McCoy et al. |
| 2007/0298005 A1 | 12/2007 | Thibault |
| 2008/0009680 A1 | 1/2008 | Hassler, Jr. |
| 2008/0015406 A1 | 1/2008 | Dlugos et al. |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097496 A1 | 4/2008 | Chang et al. |
| 2008/0108862 A1 | 5/2008 | Jordan et al. |
| 2008/0147002 A1 | 6/2008 | Gertner |
| 2008/0161717 A1 | 7/2008 | Gertner |
| 2008/0161875 A1 | 7/2008 | Stone |
| 2008/0166028 A1 | 7/2008 | Turek et al. |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0195092 A1 | 8/2008 | Kim et al. |
| 2008/0208240 A1 | 8/2008 | Paz |
| 2008/0221598 A1 | 9/2008 | Dlugos et al. |
| 2008/0243071 A1 | 10/2008 | Quijano et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton et al. |
| 2008/0287974 A1 | 11/2008 | Widenhouse et al. |
| 2008/0287976 A1 | 11/2008 | Weaner et al. |
| 2008/0300618 A1 | 12/2008 | Gertner |
| 2008/0319435 A1 | 12/2008 | Rioux et al. |
| 2009/0054914 A1 | 2/2009 | Lechner |
| 2009/0062825 A1 | 3/2009 | Pool et al. |
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz et al. |
| 2009/0157106 A1 | 6/2009 | Marcotte et al. |

(56) References Cited

U.S. PATENT DOCUMENTS

| | | |
|---|---|---|
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0187202 A1 | 7/2009 | Ortiz et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0204141 A1 | 8/2009 | Dlugos, Jr. et al. |
| 2009/0204179 A1 | 8/2009 | Dlugos, Jr. et al. |
| 2009/0209995 A1 | 8/2009 | Byrum et al. |
| 2009/0216255 A1 | 8/2009 | Coe et al. |
| 2009/0220176 A1 | 9/2009 | Fusco |
| 2009/0222031 A1 | 9/2009 | Axelsson |
| 2009/0222065 A1 | 9/2009 | Dlugos, Jr. et al. |
| 2009/0228063 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2009/0312785 A1 | 12/2009 | Stone et al. |
| 2010/0010291 A1 | 1/2010 | Birk et al. |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0145378 A1 | 6/2010 | Gertner |
| 2010/0152532 A1 | 6/2010 | Marcotte |
| 2010/0168508 A1 | 7/2010 | Gertner |
| 2010/0185049 A1 | 7/2010 | Birk et al. |
| 2010/0191265 A1 | 7/2010 | Lau et al. |
| 2010/0191271 A1 | 7/2010 | Lau et al. |
| 2010/0204647 A1 | 8/2010 | Gertner |
| 2010/0204723 A1 | 8/2010 | Gertner |
| 2010/0226988 A1 | 9/2010 | Lebreton |
| 2010/0228080 A1 | 9/2010 | Tavori et al. |
| 2010/0234682 A1 | 9/2010 | Gertner |
| 2010/0249803 A1 | 9/2010 | Griffiths |
| 2010/0280310 A1 | 11/2010 | Raven |
| 2010/0305397 A1 | 12/2010 | Birk et al. |
| 2010/0312147 A1 | 12/2010 | Gertner |
| 2010/0324358 A1 | 12/2010 | Birk et al. |
| 2010/0324359 A1 | 12/2010 | Birk |
| 2011/0201874 A1 | 8/2011 | Birk et al. |
| 2011/0270018 A1* | 11/2011 | Honaryar et al. ............ 600/37 |

FOREIGN PATENT DOCUMENTS

| | | |
|---|---|---|
| CN | 1367670 | 9/2002 |
| DE | 4225524 | 2/1994 |
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 | 9/2000 |
| EP | 1072282 | 1/2001 |
| EP | 1105073 | 6/2001 |
| EP | 1396242 | 3/2004 |
| EP | 1396243 | 3/2004 |
| EP | 1491167 | 12/2004 |
| EP | 1491168 | 12/2004 |
| EP | 1529502 | 5/2005 |
| EP | 1547549 | 6/2005 |
| EP | 1574189 | 9/2005 |
| EP | 1600183 | 11/2005 |
| EP | 1602346 | 12/2005 |
| EP | 1704833 | 9/2006 |
| EP | 1719480 | 11/2006 |
| EP | 1754890 | 11/2006 |
| EP | 1736123 | 12/2006 |
| EP | 1736195 | 12/2006 |
| EP | 1736202 | 12/2006 |
| EP | 1743605 | 1/2007 |
| EP | 1829504 | 9/2007 |
| EP | 1829505 | 9/2007 |
| EP | 1829506 | 9/2007 |
| EP | 1967168 | 9/2008 |
| EP | 1992315 | 11/2008 |
| EP | 2074970 | 7/2009 |
| EP | 2074971 | 7/2009 |
| EP | 2087862 | 8/2009 |
| EP | 2095796 | 9/2009 |
| EP | 2095798 | 9/2009 |
| FR | 1566202 | 5/1969 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2855744 | 12/2004 |
| FR | 2921822 | 4/2009 |
| GB | 1174814 | 12/1969 |
| GB | 2090747 | 7/1982 |
| JP | 57-171676 | 10/1982 |
| JP | 1-67309 | 4/1989 |
| JP | 2-019147 | 1/1990 |
| JP | 2-132104 | 11/1990 |
| JP | 3-105702 | 11/1991 |
| JP | 11-244395 | 9/1999 |
| JP | 2003-526410 | 9/2003 |
| JP | 2005-131380 | 5/2005 |
| JP | 2005-334658 | 12/2005 |
| SE | 8503144 | 12/1986 |
| WO | WO 86/00079 | 1/1986 |
| WO | WO 86/00912 | 2/1986 |
| WO | WO 89/11701 | 11/1989 |
| WO | WO 90/00369 | 1/1990 |
| WO | WO 92/20349 | 11/1992 |
| WO | WO 94/02517 | 2/1994 |
| WO | WO 96/33751 | 1/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO 00/09047 | 2/2000 |
| WO | WO 00/09048 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO 01/68007 | 9/2001 |
| WO | WO 01/70131 | 9/2001 |
| WO | WO 01/85071 | 11/2001 |
| WO | WO 02/05753 | 1/2002 |
| WO | WO 02/09792 | 2/2002 |
| WO | WO 02/19953 | 3/2002 |
| WO | WO 02/26317 | 4/2002 |
| WO | WO 02/053093 | 7/2002 |
| WO | WO 02/065948 | 8/2002 |
| WO | WO 02/096326 | 12/2002 |
| WO | WO 03/007782 | 1/2003 |
| WO | WO 03/055420 | 7/2003 |
| WO | WO 03/057092 | 7/2003 |
| WO | WO 03/059215 | 7/2003 |
| WO | WO 03/077191 | 9/2003 |
| WO | WO 03/101352 | 12/2003 |
| WO | WO 03/105732 | 12/2003 |
| WO | WO 2004/014245 | 2/2004 |
| WO | WO 2004/019671 | 3/2004 |

(56) References Cited

FOREIGN PATENT DOCUMENTS

| WO | WO 2004/108025 | 12/2004 |
|---|---|---|
| WO | WO 2004/112563 | 12/2004 |
| WO | WO 2005/007232 | 1/2005 |
| WO | WO 2005/009305 | 2/2005 |
| WO | WO 2005/067994 | 5/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/109300 | 9/2008 |
| WO | WO 2008/134755 | 11/2008 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.
Dixon et al.; "Pregnancy After Lap-Band Surgery: Management of the Band to Achieve Healthy Weight Outcomes"; Obesity Surgery; V. 11, pp. 59-65; 2001.
Neary et al.; "Peptide YY(3-36) and Glucagon-Like Peptide-1 $_{(7-36)}$ Inhibit Food Intake Additively"; Endocrinology; V.146; pp. 5120-5127; 2005.
Padidela et al.; "Elevated basal and post-feed glucagon-like petide 1 (GLP-1) concentrations in the neonatel period"; European Journal of Endocrinology; v. 160; pp. 53-58; 2009.
Shi et al.; "Sexually Dimorphic Responses to Fat Loss After Caloric Restriction or Surgical Lipectomy"; Am. J. Physiol. Endocrinol. Metab.; V. 293; E316-E326; 2007.
Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.
Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.
Adrian et al.; "Mechanism of Pancreatic Polypeptide Release in Man." The Lancet; pp. 161-163; Jan. 22, 1977.
Anson; "Shape Memory Alloys—Medical Applications," Source: Materials World, vol. 7, No. 12, pp. 745-747, Dec. 1999.
Asakawa et al; "Antagonism of Ghrelin Receptor Reduces Food Intake and Body Weight Gain in Mice"; Gut.; V.52; pp. 947-952; 2003.
Baggio et al. "Biology of Incretins: GLP-1 and GIP"; Gastroenrology; V. 132; pp. 2131-2157; 2007.
Ballantyne; "Peptide YY(1-36) and Peptide YY(3-36): Part I. Distribution, Release, and Actions"; Obesity Surgery; V.16; pp. 651-658; 2006.
Ballantyne; "Peptide YY(1-36) and Peptide YY(3-36): Part II. Changes after Gastrointestinal Surgery and Bariatric Surgery"; Obesity Surgery; V.16; pp. 795-803; 2006.
Berne et al; "Physiology"; V. 5; pp. 55-57, 210, 428, 540, 554, 579, 584, 591; 2004.
BioEnterics Corporation, an Inamed Company, BioEnterics Intragastric Balloon; Directions for Use Published Document, P/N. 94200 Rev: B, pp. 1-56.
BioEnterics Lap-Band Adjustable Gastric Banding System, Inamed Health, pub., pp. 1-115; Aug. 28, 2003.
Boulant et al.; "Cholecystokinin in Transient Lower Oesophageal Sphincter Relaxation Due to Gastric Distension in Humans"; Gut.; V. 40; pp. 575-581; 1997.
Bradjewin et al.; "Dose Ranging Study of the Effects of Cholecystokinin in Healthy Volunteers"; J. Psychiatr. Neurosci.; V. 16 (2); pp. 91-95; 1991.
Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.
Chaptini et al.; "Neuroendocrine Regulation of Food Intake"; Current Opinion in Gastroenterology; V. 24; pp. 223-229; 2008.
Chaudhri; "Can Gut Hormones Control Appetite and Prevent Obesity?" Diabetes Care; V. 31; Supp 2; pp. S284-S289; Feb. 2008.
Cohen et al.; "Oxyntomodulin Suppresses Appetite and Reduces Food Intake in Humans"; J. Clin. Endocrinol. Metab.; V. 88; No. 10; pp. 4696-4701; 2003.
Corno et al.; "A new implantable device for telemetric control of pulmonary blood flow"; New ideas; received Apr. 24, 2004; received in revised form Jul. 12, 2002; 10 pages.
Corno et al.; "FlowWatch™ in clipped and in clipped position"; Interact Cardio Vase Thorac Surg 2002; 1:46-49; Copyright @ 2002 The European Association for Cardio-thoracic Surgery; 1 page.
Cummings et al.; "Plasma Ghrelin Levels After Diet-Induced Weight Loss or Gastric Bypass Surgery"; N. Engl J. Med; V. 346, No. 21; pp. 1623-1630; May 23, 2002.
Cummings; "Gastrointestinal Regulation of Foot Intake"; The Food Journal of Clinical Investigation; V. 117, N. 1; pp. 13-23; Jan. 2007.
Dakin et al.; "Oxyntomodulin Inhibits Food Intake in the Rat"; Endocrinology; V. 142; No. 10; pp. 4244-4250; 2001.
Dakin et al.; "Peripheral Oxyntomodulin Reduces Food Intake and Body Weight gain in Rats"; Endocrinology; V. 145; No. 6; pp. 2687-2695; Jun. 2004.
Davison; "Activation of Vagal-Gastric Mechanoreceptors by Cholecystokinin"; Proc. West. Pharmocol. Soc.; V. 29; pp. 363-366; 1986.
De Waele et al.; "Endoscopic Volume Adjustment of Intragastric Balloons for Intolerance"; Obesity Surgery; V. 11; pp. 223-224; 2001.
De Waele et al.; "Intragastric Balloons for Preoperative Weight Reduction"; Obesity Surgery; V. 58; pp. 58-60; 2001.
Desai et al.; "Molecular Weight of Heparin Using 13C Nuclear Magnetic Resonance Spectroscopy" Journal of Pharmaceutical Science, V. 84, I 2; 1995, Abstract only.
Doldi et al.; "Intragastric Balloon: Another Option for Treatment of Obesity and Morbid Obesity"; Hepato-Gastroenterology; V. 51, N. 55; pp. 294-307; Jan.-Feb. 2004.
Doldi et al.; "Treatment of Morbid Obesity with Intragastric Balloon in Association with Diet"; Obesity Surgery; V. 10, pp. 583-587; 2000.
Doldi et al; "Intragastric Balloon in Obese Patients"; Obesity Surgery; V. 10, 578-581; 2000.
Ekblad et al.; "Distribution of Pancreatic Peptide and Peptide-YY"; Peptides; V. 23; pp. 251-261; 2002.
El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.
Galloro et al; "Preliminary Endoscopic Technical Report of an New Silicone Intragastric Balloon in the Treatment of Morbid Obesity"; Obesity Surgery; V. 9, pp. 68-71; 1999.
GinShiCel MH Hydroxy Propyl Methyl Cellulose, Web Page http://www.ginshicel.cn/MHPC.html, Nov. 12, 2008.
Girard; "The incretins: From the concept to their use in the treatment of type 2 diabetes. Part A: Incretins: Concept and physiological functions"; Diabetes and Metabolism; V. 34; pp. 550-559; 2008.
Greenough et al.; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.
Grise et al.; "Peptide YY Inhibits Growth of Human Breast Cancer in Vitro and in Vivo"; Journal of Surgical Research; V. 82; pp. 151-155; 1999.

(56) References Cited

OTHER PUBLICATIONS

Grundy; "Signaling the State of the Digestive Tract"; Autonomic Neuroscience: Basic and Clinical; V. 125; pp. 76-80; 2006.
Grundy; "Vagal Control of Gastrointestinal Function"; Bailliere's Clinical Gastroenterology; V. 2; No. 1; pp. 23-43; 1988.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Hameed et al.; "Gut hormones and appetite control." Oral Diseases; V. 15; pp. 18-26; 2009.
Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.
Hodson et al.; "Management of Obesity with the New Intragastric Balloon"; Obesity Surgery; V. 11, pp. 327-329, 2001.
Holzer; "Gastrointestinal Afferents as Targets of Novel Drugs for the Treatment of Functional Bowel Disorders and Visceral Pain"; European Journal of Pharmacology; V. 429; pp. 177-193; 2001.
Houpt; "Gastrointestinal Factors in Hunger and Satiety." Neuroscience and Behavioral Reviews; V. 6; pp. 145-164; 1982.
Iverson et al.; "Recent Advances in Microscale Pumping Technologies: A Review and Evaluation"; Microfluid Nanofluid; vol. 5; pp. 145-174; Feb. 19, 2008.
Jones; "Molecular, pharmacological, and clinical aspects of liraglutide, a oncedaily human GLP-1 analogue"; Molecular and Cellular Endocrinology; V. 297; pp. 137-140; 2009.
Kerem et al.; "Exogenous Ghrelin Enhances Endocrine and Exocrine Regeneration in Pancreatectomized Rats"; J Gastrointest Surg.; V. 13; pp. 775-783, 2009.
Kesty et al.; "Hormone-based therapies in the regulation of fuel metabolism and body weight"; Expert Opin. Biol. Ther.; V. 8; No. 11; pp. 1733-1747; 2008.
Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.
Kojima et al.; "A role for pancreatic polypeptide in feeding and body weight regulation." Peptides; V. 28; pp. 459-463; 2007.
Kulicke et al. "Visco-Elastic Propeerties of Sodium Hyaluronate Solutions," American Institute of Physics; pp. 585-587; 2008.
Lap-Band AP System Adjustable Gastric Banding System With Omniform™ Design: Directions for Use (DFU); Allergan, 16 pages; 2009.
Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.
Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.
Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.
Mathus-Vliegen et al. "Treating Morbid and Supermorbid Obesity" International Journal of Gastroenterology; V. 5, No. 1, pp. 9-12; 2000.
Medeiros et al.; "Processing and metabolism of Peptide-YY: Pivotal roles of Dipeptidase-IV, Aminopeptidase-P, and Endopeptidase-24.11"; Endocrinology; V. 134, No. 5; pp. 2088-2094; 1994.
Naslund et al. "Pranidal subcutaneous injections of glucagon-like peptide-1 cause weight loss in obese human subjects"; British Journal of Nutrition; V. 91; pp. 439-446; 2004.
Potier et al.; "Protein, amino acids, and the control of food intake"; Current Opinion in Clinical Nutrition and Metabolic Care; V. 12; pp. 54-58; 2009.
Qian et al.; "Pulmonary delivery of a GLP-1 receptor agonist, BMS-686117"; International Journal of Pharmaceutics; V. 366; pp. 218-220; 2008.
Rang et al.; "Pharmacology"; V. 5; pp. 203, 397, 402, 524; 2004.
Raybould et al.; "Integration of Postprandial Gastrointestinal Tract: Role of CCK and Sensory Pathways"; Annals of New York Academy of Science; pp. 143-156; 1994.
Renshaw et al. "Peptide YY: A Potential Therapy for Obesity"; Current Drug Targets; V. 6; pp. 171-179; 2005.
Sannino et al.; "Crosslinking of Cellulose Derivatives and Hyaluronic Acid with Water-Soluble Carbodiimide" Polymer 46; pp. 11206-11212; 2005.
Shechter et al.; "Reversible PEGylation of peptide YY3-36 prolongs its inhibition of food intake in mice"; FEBS Letters; V. 579; pp. 2439-2444; 2005.
Silver et al.; "Physical Properties of Hyaluronic Acid and Hydroxypropylmethylcellulose in Solution: Evaluation of Coating Abillity" Journal of Applied Biomaterials, V. 5; pp. 89-98, 1994.
Small et al.; "Gut hormones and the control of appetite"; Trends in Endocrinology and Metabolism; V. 15. No. 6; pp. 259-263; Aug. 2004.
Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.
Tezel; "The Science of Hyaluronic Acid Dermal Fillers," Journal of Cosmetic and Laser Therapy (2008) 10: pp. 35-42.
Tolhurst et al.; "Nutritional regulation of glucagon-like peptide1 secretion"; J. Physiol.; V. 587, No. 1; pp. 27-32; 2009.
Totte et al.; "Weight Reduction by Means of Intragastric Device: Experience with the Bioenterics Intragastric Balloon"; Obesity Surgery; V. 11, pp. 519-523; 2001.
Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.
Tseng et al; "Peptide YY and cancer: Current findings and potential clinical applications"; Peptides; V. 23; pp. 389-395; 2002.
Valassi et al.; "Neuroendocrine control of food intake"; Nut. Metab. & Cariovasc. Disease; V. 18; pp. 158-168; 2008.
Van Der Lely et al.; "Biological, Physiological, Pathophysiological Aspects of Ghrelin"; Endocrine Reviews; V. 25, No. 3; pp. 426-457; 2004.
Verdich et al. "A Meta-Analysis of the Effect of Glucagon-Like-Peptide-1 (7-36) Amide on ad Libitum Energy Intake in Humans"; J. Clin. Endocrinal. Metab. V. 86; pp. 4382-4389; Sep. 2001.
Wahlen et al.; "The BioEnterics Intragastric Balloon (BIB): How to Use It"; Obesity Surgery; V. 11; pp. 524-527; 2001.
Wang et al.; "Plasma Ghrelin Modulation in Gastric Band Operation and Sleeve Gastrectomy"; Obes. Surg.; pp. 357-362; 2008.
Weiner et al.; "Preparation of Extremely Obese Patients for Laparoscopic Gastric Banding by Gastric Balloon Therapy"; Obesity Surgery; V. 9, pp. 261-264, 1999.
Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.
Yuzuriha et al.; "Gastrointestinal Hormones (anorexigenic peptide YY and orexigenic ghrelin) influence neural tube development"; FASEB J.; V. 21; pp. 2108-2112; 2007.

* cited by examiner

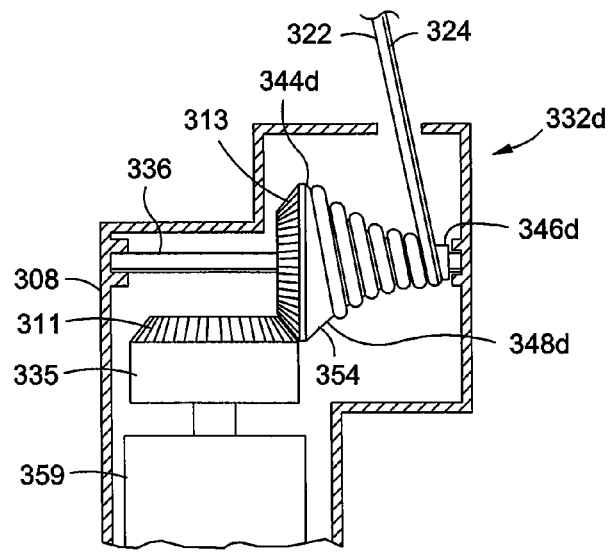
FIG. 3D
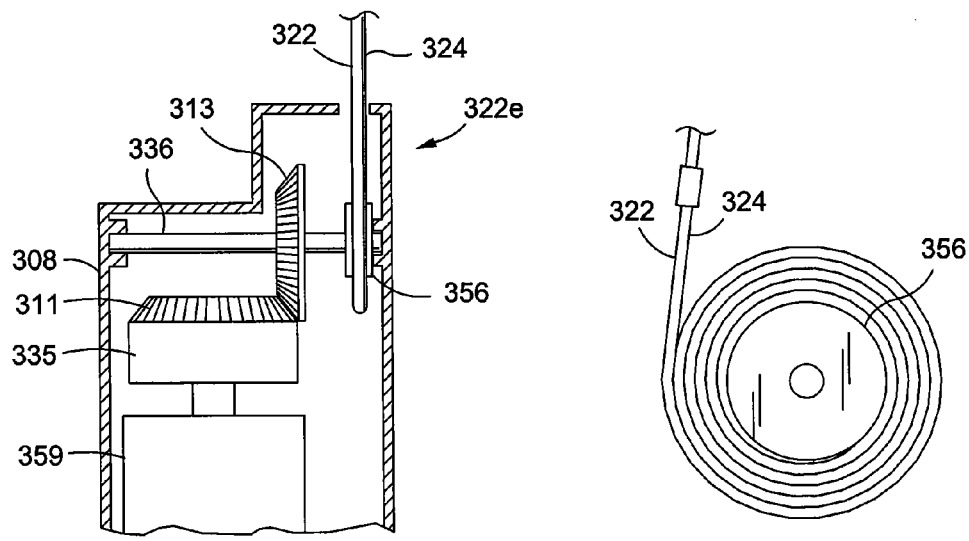
FIG. 3E　　　　FIG. 3F

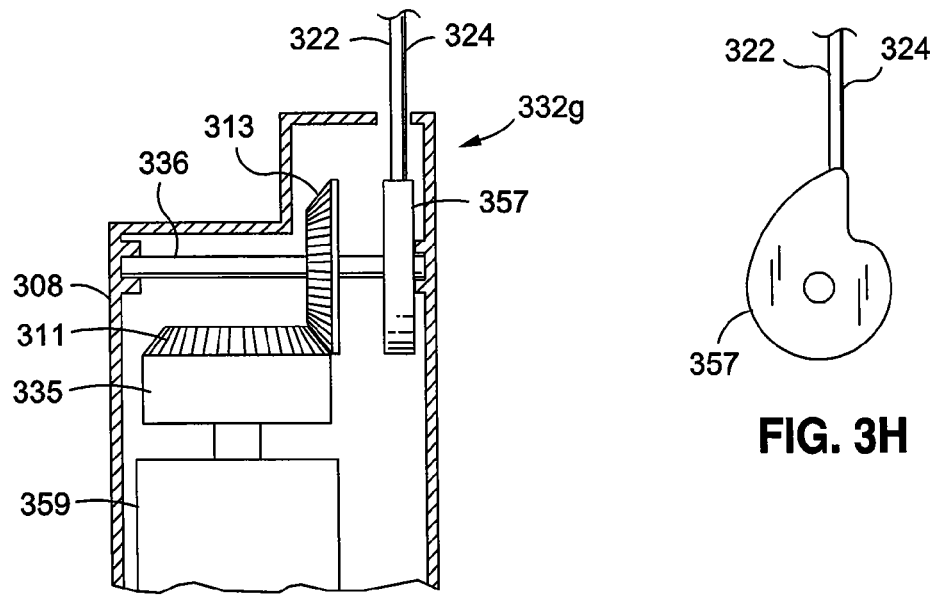
FIG. 3G
FIG. 3H
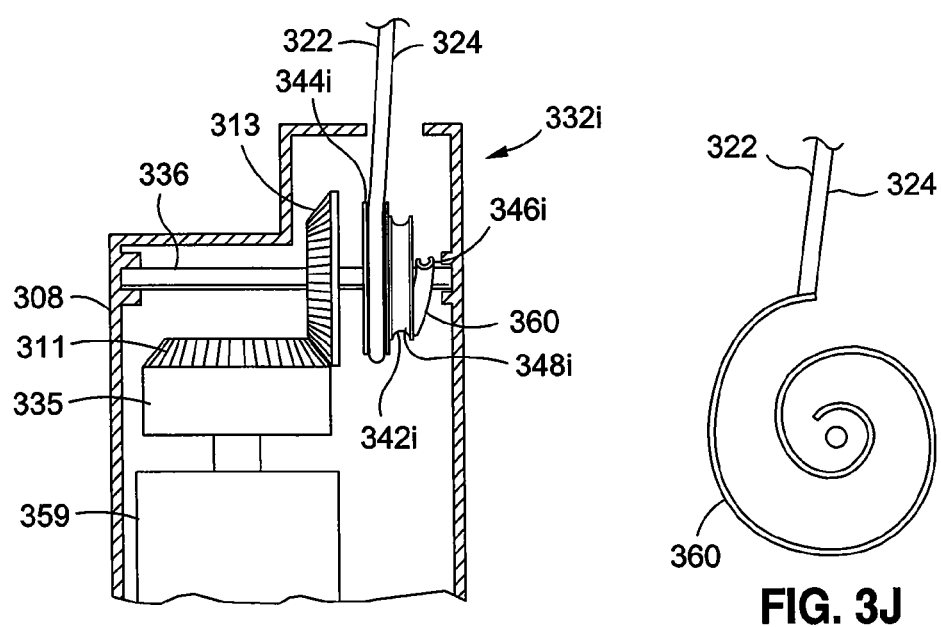
FIG. 3I
FIG. 3J

GASTRIC BAND DEVICES AND DRIVE SYSTEMS

FIELD

The present invention generally relates to medical systems and apparatus and uses thereof for treating obesity and/or obesity-related diseases, and more specifically, relates to gastric band devices and drive systems for operating gastric band devices.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the food's passage into a lower portion of the stomach. When the stoma is of an appropriate size that is restricted by a gastric band, food held in the upper portion of the stomach provides a feeling of satiety or fullness that discourages overeating. Unlike gastric bypass procedures, gastric band apparatus are reversible and require no permanent modification to the gastrointestinal tract.

Existing gastric bands periodically require adjustment to maintain an effective constriction about the portion of the patient's stomach to be constricted. Such adjustments are desired to account for changes in the stomach tissue, reduction of fat, or other factors causing movement and/or size change of the portion of the patient's stomach to be constricted. Some attempts have been made to allow for such adjustment of gastric bands. For example, hydraulic gastric bands utilize a fluid such as saline to fill an inflatable portion of the gastric band using a subcutaneous injection port of the gastric band. Adjustments to the amount of inflation may be made by injecting or extracting the fluid through the patient's skin into or out of the injection port, which then directs the fluid into or out of the inflatable portion of the gastric band. These types of adjustments may be undesirable because of the discomfort caused by the injections.

Further, other types of gastric bands include motorized systems designed to alleviate the pain and discomfort associated with the fluid controlled bands. Examples of motorized gastric bands are illustrated and discussed in Forsell, U.S. Pat. No. 6,470,892, and Dargent, et al., U.S. Pat. No. 6,547,801. Such gastric bands may be controlled telemetrically, through control and/or power signals transmitted from outside the patient's body to inside the patient's body. A physician, or the patient, may control the adjustments made to the band. The physician or patient may easily and remotely adjust the band, without having to insert a needle into the patient's body.

However, motorized gastric bands have drawbacks, mostly deriving from the requirement that a small motor be placed within the patient's body for an extended period of time, and be required to operate effectively for an extended period of time. It is preferable the motor be small, to allow the gastric band to easily fit within the patient's body. A small motor also reduces the total displacement of the gastric band within the patient's body. Yet, a small motor may not be durable, and may not be able to exert a great force against the patient's stomach. It is also preferred the motor be powerful, to exert a large constrictive force to the patient's stomach over a series of repeated constrictions. Exotic and expensive motors may be used to provide such a desired effect. However, the gastric band itself may also be structured to assist a motor during operation, to increase the power efficiency and durability of the motor. A well-designed gastric band may not only promote efficiency and durability, but may also generally improve performance and simplicity of the device, while reducing production costs.

Accordingly, it is desirable to develop a gastric band device that increases performance of the gastric band during operation, and allows the gastric band to operate over an extended period of time without failure. It is additionally desirable to develop drive systems and transmission systems that more efficiently deliver a constrictive force to the patient's stomach.

SUMMARY

Generally described herein are gastric band devices and drive systems for operating gastric band devices, that seek to improve on gastric band devices and drive systems as known in the art. The gastric band devices and drive systems discussed in this disclosure seek to give effect to a series of desired characteristics that improve upon existing gastric band technology.

Such desired characteristics may include a small size. It is generally desired that the gastric band devices and drive systems be capable of passing through a 15 mm standard trocar device.

Other desired characteristics may include a speed requirement. It is generally desired that the gastric band device be capable of fully constricting a patient's stomach in no more than six minutes, and preferably between two to three minutes or less.

Other desired characteristics may include a reliability requirement. The gastric band device should be able to achieve over 1,000 constrictions, or preferably over 50,000 constrictions without failure.

Other desired characteristics may include a large-scale manufacturing requirement. A large number, on the order of thousands of gastric band devices, should be easily and reliably produced over a year long period.

Other desired characteristics may include a structural rigidity requirement. The gastric band device should be structured to withstand forces caused by the natural movements of the patient's body and digestive tract.

Other desired characteristics may include a biocompatibility and MRI (Magnetic Resonance Imaging) compatibility requirement. The gastric band device should be corrosion resistant, and should be able to resist a sterilization cycle of 132 degrees Celsius during 20 hours. In addition, the gastric band device should be able to be cut with standard surgical cutting instruments. The gastric band device should also preferably be MRI compatible up to 3 Tesla.

Other desired characteristics may include a power requirement. The gastric band device should be able to operate initially at no more than approximately 100 milliwatts to form a diameter change in from approximately 29 millimeters to 15 millimeters. In addition, the motor system should be able to detect blocking of the constriction process, and should be able to retain a degree of constriction when unpowered. Furthermore, the adjustment cycle should be divided into a minimum of 10-20 steps.

These desired characteristics are representative, and do not limit the scope and breadth of the gastric band devices and drive systems discussed throughout this application. However, the gastric band system may be configured to achieve these desired characteristics using certain design principles.

For example, the total friction of the gastric band device should be reduced, to increase total power efficiency and longevity of the device.

In addition, a periodic or pulsing action may constrict the patient's stomach more effectively.

Corrugated materials may enable a large deformation of the material in response to a relatively low applied force.

A variable transmission may promote power efficiency, as a low force should be present during initial constriction, and a high force should be present during the latter parts of constriction. The patient's stomach generally increases resistance to constriction as is it compressed further. A variable transmission may also promote a faster initial constriction and a slower latter constriction.

A gastric band device may be biased to naturally exert a force towards the stomach, or to a middle point of the constrictive cycle, to assist the motor in constriction.

A multi-step, or ratcheting-type process may decrease the total power needed to constrict the stomach. In addition, a periodic or pulsating action may reduce the total power needed to constrict the stomach.

A substantially central, evenly distributed constrictive force reduces the power needed to constrict the patient's stomach. In response to an even force, the stomach is not drawn in one direction, but rather is compressed simultaneously from all radial directions, towards the center of the constricted region.

The gastric band may be designed to have asymmetric activation, where the closing of the gastric band may require a high force and a low speed, and the opening may require a low force and a high speed.

The gastric band may be designed to have a substantially constant outer diameter, preventing disturbance of nearby tissue. Long term implantation of a gastric band device can cause tissue to grow around the device. A constant diameter, and/or a constant cross section may prevent deformation of these surrounding tissues.

The gastric band should be structured to be stabilized against axial forces, such as the force exerted when the patient vomits. A stabilized gastric band prevents damage to the gastric band and movement of the gastric band, in response to such axial forces.

The gastric band should be cushioned, or have a wide structure, to distribute the force from the gastric band evenly to the patient's stomach. A wider and softer gastric band may more evenly compress the patient's stomach, preventing damage to the stomach.

The gastric band should be covered with a membrane, to promote biocompatibility and aesthetic functions.

In light of these design principles, the following gastric band devices and drive systems are disclosed in this application to implement these principles and others and to improve on prior gastric band systems.

In one embodiment, the gastric band device comprises a plurality of force transmission devices, or lever devices, positioned to extend towards a central region of the gastric band, when the gastric band is positioned in a loop around a portion of the patient's stomach. Each lever device has an end extending towards the central region of the gastric band, substantially perpendicular to the inner surface of the gastric band. The lever devices apply a constrictive force to the patient's stomach.

In one embodiment, a drive system is configured to drive a gastric band device. The drive system comprises a motor system and a drive element being driven by the motor system. In various embodiments of the drive system, the motor system may comprise a motor and a series of engaging mechanisms, configured to drive the drive element. In addition, the motor system may be configured to drive a single drive element or multiple drive elements. The drive elements may be driven in opposite directions. Also, the motor system may be configured to rotate or twist a drive element. Further, the drive element may comprise a strap-like band, or a cord. In addition, the drive element may comprise a ring, a screw, or a string-of-pearl device. The motor may be an AC or DC motor, or may have piezoelectric properties. In addition, the motor may be shaped to have a narrow diameter. The motor may be shaped to have a hollow axis. The motor may be positioned external to the body. The drive system may include a position measurement system.

In one embodiment, the gastric band device comprises a cord coupled to a cylindrical transmission device. The cord extends around a portion of the patient's stomach and applies a degree of constriction to the patient's stomach. The cord wraps around the cylindrical transmission device. Rotation of the cylindrical transmission device tensions the cord and constricts the stomach. The cylindrical transmission device may be configured to vary a force output by the cord in response to a constant input force applied to the cylindrical transmission device.

In one embodiment, the gastric band device comprises a plurality of force transmission devices, or slide supports, positioned to extend towards a central region of the band, when the band is positioned in a loop around a portion of the patient's stomach. Each slide support has an end extending towards the central region of the band, substantially perpendicular to the inner surface of the band. The slide supports apply a constrictive force to the patient's stomach.

In one embodiment, the gastric band device comprises a plurality of force transmission devices, or springs, positioned to extend towards a central region of the gastric band, when the gastric band is positioned in a loop around a portion of the patient's stomach. Each spring has an end extending towards the central region of the gastric band, substantially perpendicular to the inner surface of the gastric band. The springs apply a constrictive force to the patient's stomach.

In one embodiment, the gastric band device comprises a plurality of force transmission devices, or mechanical actuators, positioned to extend towards a central region of the gastric band, when the gastric band is positioned in a loop around a portion of the patient's stomach. Each mechanical actuator has an end extending towards the central region of the gastric band substantially perpendicular to the inner surface of the gastric band. The mechanical actuators apply a constrictive force to the patient's stomach.

In one embodiment, the gastric band device comprises a plurality of force transmission devices, or hydraulic piston actuators, positioned to extend towards a central region of the gastric band, when the gastric band is positioned in a loop around a portion of the patient's stomach. Each hydraulic piston actuator has an end extending towards the central region of the gastric band, substantially perpendicular to the inner surface of the gastric band. The hydraulic piston actuators apply a constrictive force to the patient's stomach.

In one embodiment, the gastric band device comprises a spring extending in a loop around a portion of the patient's stomach. The spring may be biased to form a ring having a rest diameter (a diameter the ring would have in the absence of an applied force) that constricts the patient's stomach. The spring bias assists the motor to increase the degree of constriction applied the patient's stomach.

In one embodiment, the gastric band device comprises a gastric band configured to be positioned in a loop around a portion of the patient's stomach. An axis extends through the center of the loop. The gastric band has a pivotal portion and a rotatable portion positioned at a distance from the pivotal portion along the axis. The rotatable portion rotates to compress the patient's stomach, and vary a radial distance of the rotatable portion from the axis.

In one embodiment, the gastric band device comprises an incompressible body configured to apply a degree of constriction to the patient's stomach. The incompressible body deflects in response to a compression force applied to the incompressible body. The deflection compresses the stomach. The incompressible body may encircle a portion of the patient's stomach.

In one embodiment, the gastric band device comprises a rotatable constriction device configured to be positioned in a loop around a portion of the patient's stomach. The rotatable constriction device has a first end and a second end, the first end being rotatable relative to the second end. The rotation of the first end relative to the second end causes the rotatable constriction device to twist, causing a diameter of the rotatable constriction device to decrease. The decreased diameter increases a degree of constriction applied to the patient's stomach.

In one embodiment, the gastric band device comprises a stretchable constriction device configured to be positioned in a loop around a portion of the patient's stomach. The stretchable constriction device is capable of stretching along an axis, or in a direction radial to the axis. The stretchable constriction device is structured such that a change in the axial length of the stretchable constriction device varies the radial diameter of the stretchable constriction device. A stretching or compression force may be applied to the stretchable constriction device to vary the radial diameter.

In one embodiment, the gastric band device comprises a plurality of force transmission surfaces configured to encircle a portion of the patient's stomach. The force transmission surfaces form an inner region containing, or being complementary with, the portion of the patient's stomach to be constricted. A sliding, or translating motion of the force transmission surfaces relative to the inner region varies the size of the inner region and the degree of constriction applied to the stomach. The force transmission surfaces may be coupled to a gastric band, and configured to slide relative to the gastric band.

In one embodiment, the gastric band device comprises a cord configured to encircle a portion of the patient's stomach. The cord may form loops around the patient's stomach. A tension force may be applied to the cord to increase the degree of constriction applied by the cord to the patient's stomach.

In one embodiment, the gastric band device comprises a collar configured to encircle a portion of the patient's stomach. The collar may have two ends, the two ends being positioned at a distance from each other to define a degree of constriction applied by the collar to the patient's stomach. The two ends may be connected with a connector device, or a cord. The cord may be routed through routing devices to connect the ends of the collar together. The routing devices may comprise leverage devices or mechanical advantage devices.

In one embodiment, the gastric band device comprises an electroactive polymer device configured to apply a force to the patient's stomach. The degree of force varies in response to a voltage applied to the electroactive polymer device. The electroactive polymer device may change in size, dimensions, or shape, to vary the force applied to the patient's stomach. The electroactive polymer device may comprise a gastric band extending in a loop around a portion of the patient's stomach. The gastric band may deform to vary the degree of constriction applied by the gastric band to the patient's stomach.

BRIEF DESCRIPTION OF THE DRAWINGS

FIGS. 3B-3E illustrate perspective views of transmission systems according to embodiments of the present invention.

FIG. 3F illustrates a side view of a spool according to an embodiment of the present invention.

FIG. 3G illustrates a perspective view of a transmission system according to an embodiment of the present invention.

FIG. 3H illustrates a side view of a spool according to an embodiment of the present invention.

FIG. 3I illustrates a perspective view of a transmission system according to an embodiment of the present invention.

FIG. 3J illustrates a side view of a spool according to an embodiment of the present invention.

DETAILED DESCRIPTION

The present invention relates to gastric band devices configured to apply a degree of constriction to a patient's stomach, and drive systems configured to vary the degree of constriction applied by the gastric band devices to the stomach.

Figure 1A:
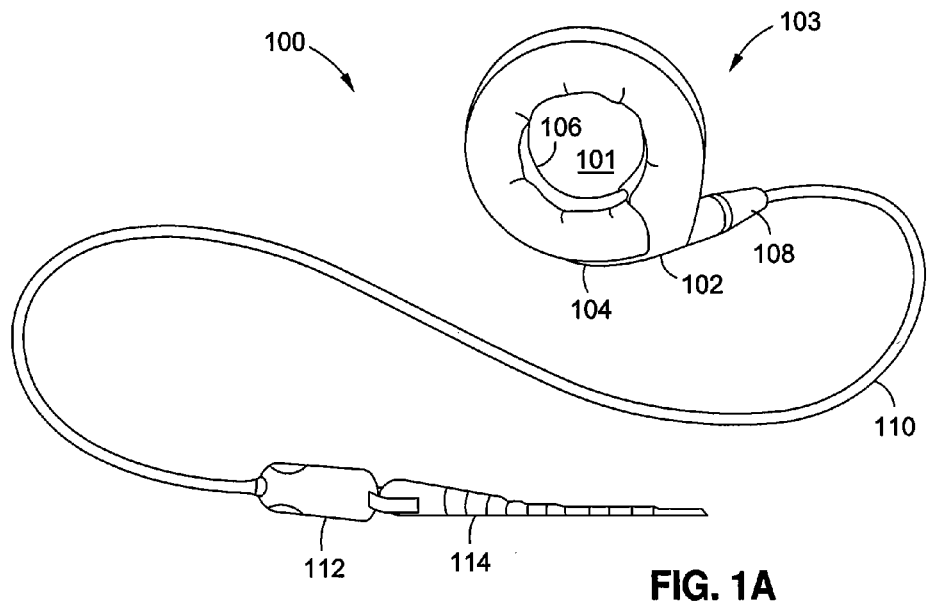
FIG. 1A illustrates a perspective view of the exterior of a gastric band device according to an embodiment of the present invention.

FIG. 1A illustrates an embodiment of the present invention comprising a gastric band device 100 for the treatment of obesity. FIG. 1A illustrates an exterior view of the gastric band device 100, displaying a ring-like structure 103 encircling an inner region 101. The ring-like structure 103 is formed from a band 116 (shown in FIG. 1B) having a first end 118 (shown in FIG. 1B) and a second end 120 (shown in FIG. 1B). The band 116 is formed into a loop around a portion of a patient's stomach, and a clip 102 couples the first end 118 of the band 116 to the second end 120 of the band 116. A grip flange 104 extends from the clip 102. A bio-compatible membrane 106 covers the band 116. A motor housing 108 is positioned near the coupling point between the first end 118 of the band 116 and the second end 120 of the band 116. A cable 110 extends out from the motor housing 108 and couples to an antenna pod 112. The antenna pod 112 is coupled to an attachment tab 114.

The band 116 (shown in FIG. 1B) is designed to encircle a portion of the patient's stomach. The band 116 is preferably positioned around the cardia of the stomach. This region may be referred to as the esophageal junction of the stomach, or the location where the esophagus connects to the stomach. The band 116 may also be positioned around the fundus of the stomach. The gastric band device 100 is configured to apply a degree of constriction to the portion of the patient's stomach to which it is applied. The constriction narrows the size, or diameter of the portion of the patient's stomach to which it is applied.

The purpose of constricting the patient's stomach is to assist the patient in losing weight. A constriction of the patient's stomach forms a stoma that serves to restrict the flow of food through the patient's digestive tract. A restricted flow of food will more quickly produce satiety signals sent to the patient's brain when the patient eats. The patient will feel full more quickly while eating and will eat less. The decreased food intake will cause the patient to lose weight.

It is preferable that the degree of constriction applied to the patient's stomach be variable, so that a high degree of constriction or a low degree of constriction is not always applied to the patient's stomach. A high degree of constriction may be desirable during the time the patient is eating, but may be undesirable during other times, for example, when the patient is sleeping. In addition, the degree of constriction may need to be adjusted according to various changing biological characteristics of the patient, including a varied size of the stomach. Furthermore, the degree of constriction may need to be changed in order to control the rate of the patient's weight loss. A physician may need to monitor the degree of constriction, and vary the degree of constriction frequently over an extended period of time.

The gastric band device 100 is designed to be inserted laparoscopically into a patient's body, meaning that the gastric band device 100 is inserted using laparoscopic tools. Prior to insertion, the gastric band device 100 is configured such that the first end 118 of the band 116 (shown in FIG. 1B) is not clipped to the second end 120 of the band 116 (shown in FIG. 1B), and the band 116 extends length-wise, with the clip 102 positioned at the second end 120 of the band 116 and the motor housing 108 positioned at the first end 118 of the band 116. The gastric band device 100 is then inserted into the patient's body cavity, and the band 116 is formed into a loop around a portion of the patient's stomach using laparoscopic tools. The attachment tab 114, the antenna pod 112, the control cable 110 and the motor housing 108 are passed through the clip 102 in sequence to form the loop. The clip 102 connects the first end 118 of the band 116 to the second end 120 of the band 116. The inner region 101 formed by the looping of the band 116 contains, and is complementary with, the portion of the patient's stomach to be constricted.

The grip flange 104 provides a grip point for the physician, to allow the physician to manipulate the gastric band device 100 with laparoscopic tools. The grip flange 104 extends outward from one end of the clip 102 and is made flexible to aid the physician during implantation of the gastric band device 100. The flexibility of the grip flange 104 also prevents the clip 102 from disengaging if the grip flange 104 is forced or deflected in a direction after the gastric band device 100 is implanted.

The physician may also position the antenna pod 112 within the patient's body after the band 116 (shown in FIG. 1B) has been positioned in a loop around a portion of the patient's stomach. The attachment tab 114 may be used as a connection device to secure the antenna pod 112 against the patient's body tissue. The attachment tab 114 may be looped over itself and tied off, or sutured against the patient's body tissue. The attachment tab 114 is also sized and structured to allow a physician to easily manipulate the attachment tab 114 with laparoscopic tools. A portion of the attachment tab 114 may be severed by the physician after implantation, to reduce the length of the tab 114.

The antenna pod 112 is preferably positioned within the patient's body, but near the outer surface of the patient's body, for example, near the patient's sternum. The antenna pod 112 is positioned near the outer surface of the patient's body so that it more easily receives control and/or power signals sent telemetrically from an external controller (not shown). The antenna pod 112 may also more easily send signals telemetrically to the external controller if it is positioned near the outer surface of the patient's body.

The control and/or power signals received by the antenna pod 112 are processed within the antenna pod 112 and are transmitted to a motor system 158 (shown in FIG. 1B) contained within the motor housing 108. The cable 110 transmits the processed control and/or power signals to the motor system 158. The power signals are used to provide power to the motor system 158, and the control signals are used to control operation of the motor system 158. The antenna pod 112 may also contain a battery system (e.g., a battery) used to power the gastric band device 100. The battery may have a suitable design to allow it to power the gastric band device 100 for a desired length of time (e.g., the planned duration of implantation).

Figure 1B:
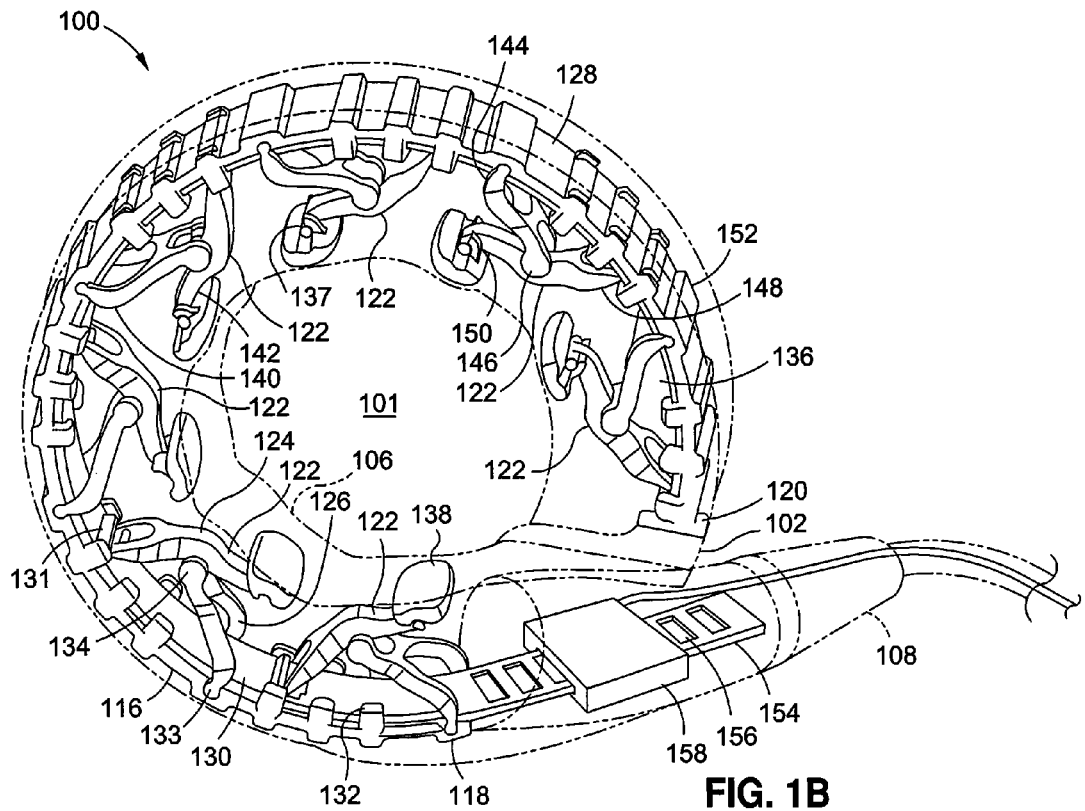
FIG. 1B illustrates a perspective view of the interior of a gastric band device according to an embodiment of the present invention.

The motor system 158 (shown in FIG. 1B) serves as an actuator that varies the size of the inner region 101 formed by the band 116 (shown in FIG. 1B). Because the inner region 101 is complementary with the portion of the patient's stomach being constricted, a reduction of the size of the inner region 101 correspondingly results in an increased degree of constriction applied by the gastric band device 100 to the patient's stomach. An increase in the size of the inner region 101 results in a decreased degree of constriction applied by the gastric band device 100 to the patient's stomach.

FIG. 1B illustrates the mechanism used to vary the size of the inner region 101, and correspondingly vary the degree of constriction applied by the gastric band device 100 to the patient's stomach. FIG. 1B illustrates a perspective view of one embodiment of the gastric band device 100 shown in FIG. 1A, as revealed through the membrane 106, the clip 102, and the motor housing 108.

The mechanism used to vary the degree of constriction includes a band 116 and a plurality of force transmission devices, or lever devices 122 coupled to an interior surface of the band 116.

The band 116 has a first end 118 and a second end 120, and is configured in the shape of a loop around a portion of the patient's stomach, as discussed in relation to FIG. 1A. In one embodiment, the first end 118 of the band 116 may be firmly fixed to the clip 102, and the second end 120 of the band 116 may be firmly fixed to the motor housing 108. The clip 102 then releasably secures the first end 118 of the band 116 to the second end 120 of the band 116 to form the loop. However, in one embodiment, the first end 118 of the band 116 may be directly coupled to the second end 120 of the band 116. When the band 116 is configured in the loop, it bounds the inner region 101, which is complementary with the portion of the stomach to be constricted.

The band 116 has a substantially strap-like, or lengthened rectangular shape. The band 116 is made from a material being strong, yet flexible to allow the band 116 to be formed into a loop using laparoscopic tools. For example, the band 116 may be made from a durable plastic, or the like.

The band 116 may be formed from two bands, an outer band 128 and an inner band 130, or equivalently referred to as a first band 128 and a second band 130. The inner band 130 may be slidably coupled to the outer band 128, and may be positioned against an interior surface of the outer band 128. The inner band 130 is concentric with the outer band 128 and both have a substantially strap-like shape. The inner band 130 is configured to slide along the interior surface of the outer band 128 and slide, or rotate, around a circumference formed by the outer band 128. The inner band 130 is configured to slide along the interior surface of the outer band 128 substantially free of friction.

A plurality of retainer devices 132 comprising clamps, latches, or hooks may be integral with the outer band 128 and extend over a portion of the inner band 130. The retainer devices 132 may slidably couple the inner band 130 to the outer band 128, preventing movement of the inner band 130 in a direction away from the outer band 128, yet allowing sliding movement of the inner band 130 in a direction along the outer band 128.

It is understood that embodiments of the present invention may include a band 116 having various shapes equivalent to the shape shown in FIG. 1B, including a curved rod-like shape, a curved triangular shape, or the equivalent. The loop formed by the band 116 may necessarily extend around the entirety of the area of the patient's stomach to be constricted, but rather may form a loop around only a portion of the patient's stomach to be constricted. In other words, the loop may form a "C" shape around the portion of the patient's stomach, or the loop may entirely encircle the area of the patient's stomach to be constricted, forming an "O" shape.

A plurality of force transmission devices, or lever devices 122 as shown in FIG. 1B, are coupled to the band 116. Each lever device 122 extends towards a central or inner region 101 of the band 116 that is formed when the band 116 is configured in the shape of a loop. A first end 140 of the lever device 122 couples to the band 116 and a second end 142 of the lever device 122 extends in a direction away from the band 116, and towards the inner region 101. Each lever device 122 extends towards the inner region 101 substantially perpendicular to the portion of the band 116 to which the lever device 122 is attached. The lever device 122 may then direct a force in a direction substantially radial, towards the center of the inner region 101. The radial force allows the patient's stomach to be evenly forced along the circumference of the patient's stomach, towards the center of the patient's stomach, or in a centripetal manner.

The second end 142 of the lever device 122 defines the boundaries of the inner region 101. Each lever device 122 is configured to exert a force against the inner region 101, or against the portion of the patient's stomach being complementary with the inner region 101. In other words, the second end 142 of each lever device 122 presses against the portion to the patient's stomach, to apply a degree of constriction against the patient's stomach. The degree of constriction is related to the size of the inner region 101 defined by the second ends 142 of the lever devices 122.

In the embodiment shown in FIG. 1B, each lever device 122 has a substantially triangular shape. The triangular shape is formed by the connection of two force transmission supports or lever arms 124, 126. For clarity, one lever arm 124 will be referred to as the first lever arm 124 and the other lever arm 126 will be referred to as the second lever arm 126.

In the embodiment shown in FIG. 1B, the first lever arm 124 has a first end 148 coupled to the band 116 and a second end 150 extending away from the band 116. The second end 150 of the first lever arm 124 defines the second end 142 of the lever device 122. The first lever arm 124 has a substantially columnar, or mast-like shape, with the first end 148 of the first lever arm 124 having a forked shape. The forked shape forms two attachment points connecting the first lever arm 124 to the band 116.

A pivot device 131 is positioned at the first end 148 of the first lever arm 124. The pivot device 131 may comprise a cylindrical-shaped device that rotates within a cylindrical-shaped housing. It is understood the pivot device 131 may be equivalently replaced with any device allowing the first lever arm 124 to pivot relative to the band 116.

In the embodiment shown in FIG. 1B, the second lever arm 126 has a first end 144 coupled to the band 116 and a second end 146 extending away from the band 116. The first end 144 of the second lever arm 126 is coupled to the band 116 with a pivot device 133, which may be structured equivalently as the pivot device 131 coupling the first lever arm 124 to the band 116. A boss 152 formed in the outer band 128 may provide support for the pivot device 133 coupling the second lever arm 126 to the band 116. The second end 146 of the second lever arm 126 couples to the first lever arm 124 with a pivot device 134, which may be structured equivalently as the aforementioned pivot devices 131, 133.

The second lever arm 126 has a substantially columnar or mast-like shape, with the first end 144 of the second lever arm 126 having a forked shape. The forked shape forms two attachment points connecting the second lever arm 126 to the band 116. In the embodiment shown in FIG. 1B, the second lever arm 126 has a length of approximately one-half the length of the first lever arm 124, and connects to the first lever arm 124 at approximately the midpoint of the first lever arm 124.

Both the first lever arm 124 and the second lever arm 126 are made of rigid material, such as a hard plastic or metal. The generally rigid material allows the arms 124, 126 to be sturdy and not deform when a force is transmitted to the patient's stomach.

The connection between the first lever arm 124 and the second lever arm 126 forms an interior region 136 having a generally triangular shape. This interior region 136 is bounded on three sides by the first lever arm 124, the second lever arm 126, and the band 116.

The connection between the first lever arm 124 and the second lever arm 126 also produces an extended portion 125 (shown in FIG. 1F) of the first lever arm 124 that extends in a direction away from the interior region 136.

Figure 1C:
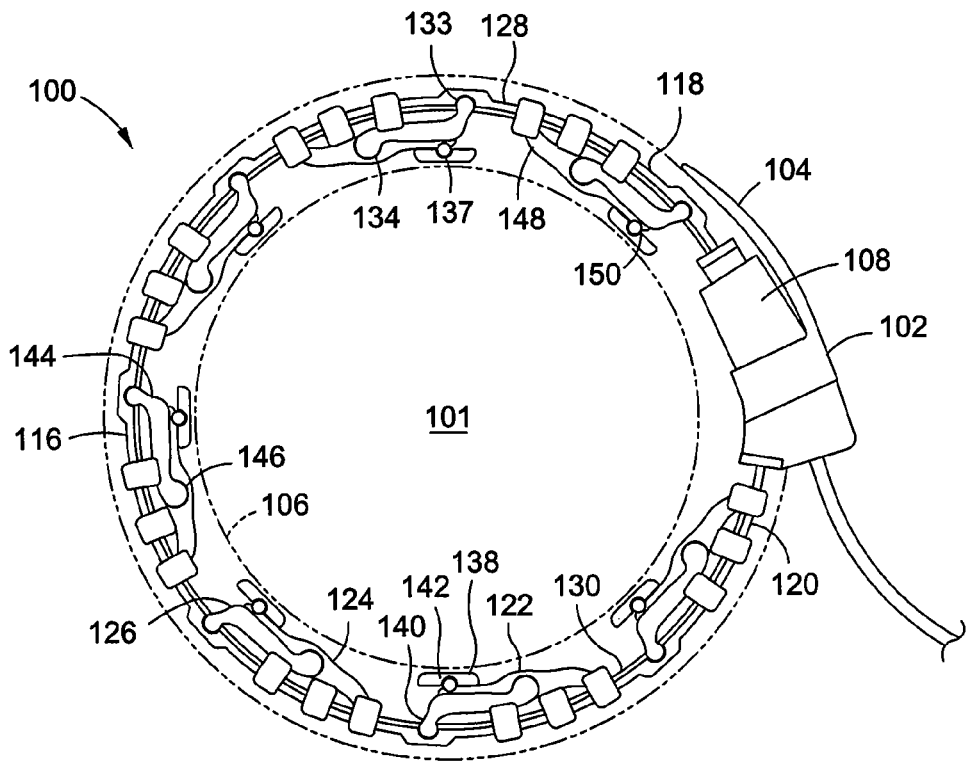
FIGS. 1C-1E illustrate side views of the interior of a gastric band device according to an embodiment of the present invention.
Figure 1D:
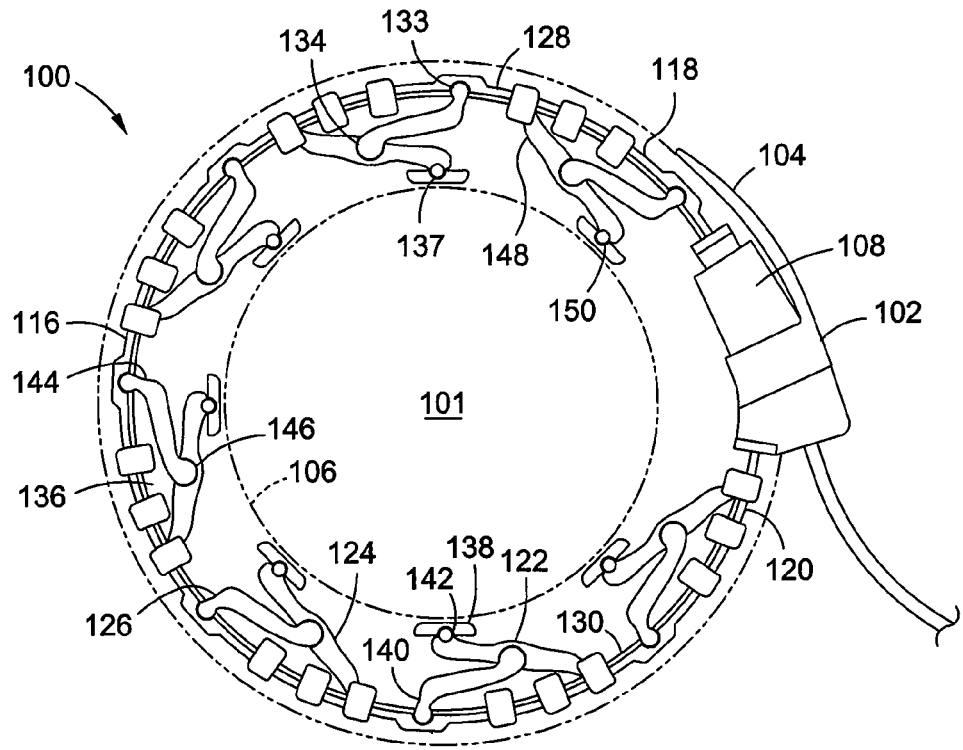
Figure 1E:
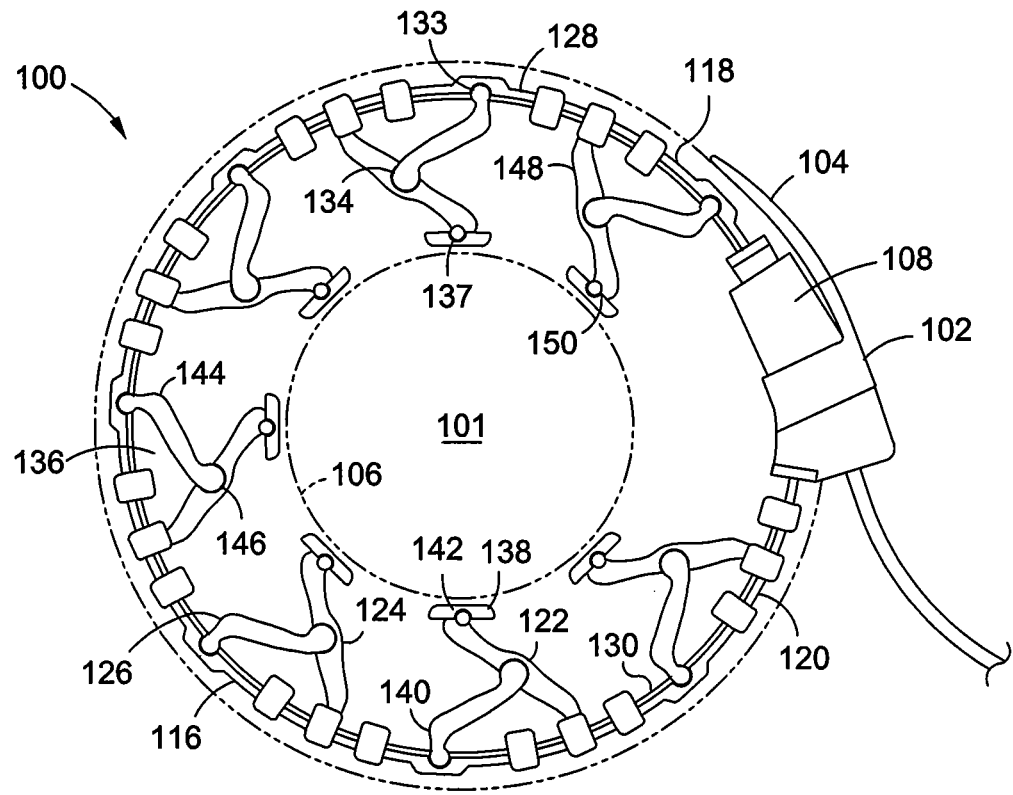
Figure 1F:
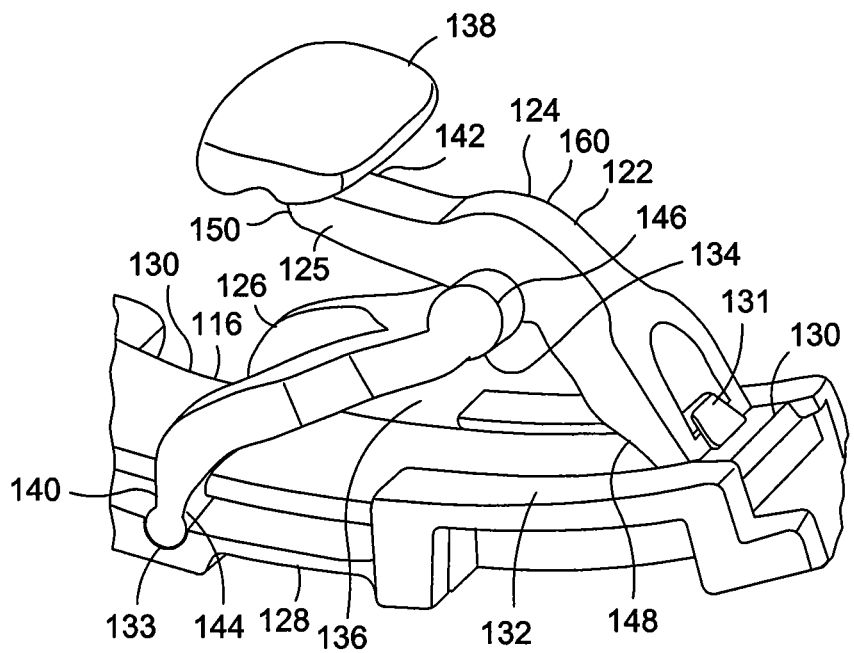
FIG. 1F illustrates a close-up perspective view of a force transmission device according to an embodiment of the present invention.
Figure 1G:
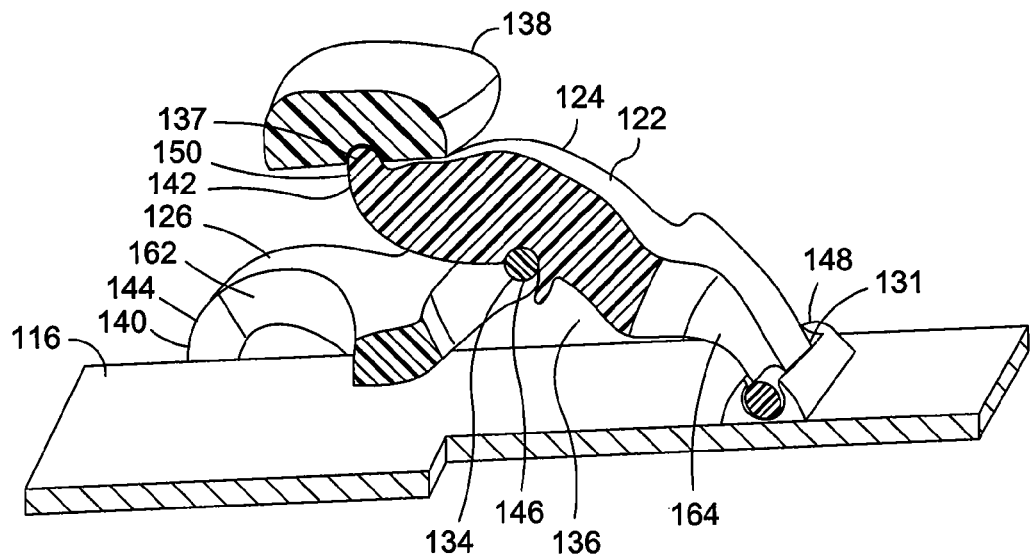
FIG. 1G illustrates a close-up cut-away perspective view of a force transmission device according to an embodiment of the present invention.
Figure 1H:
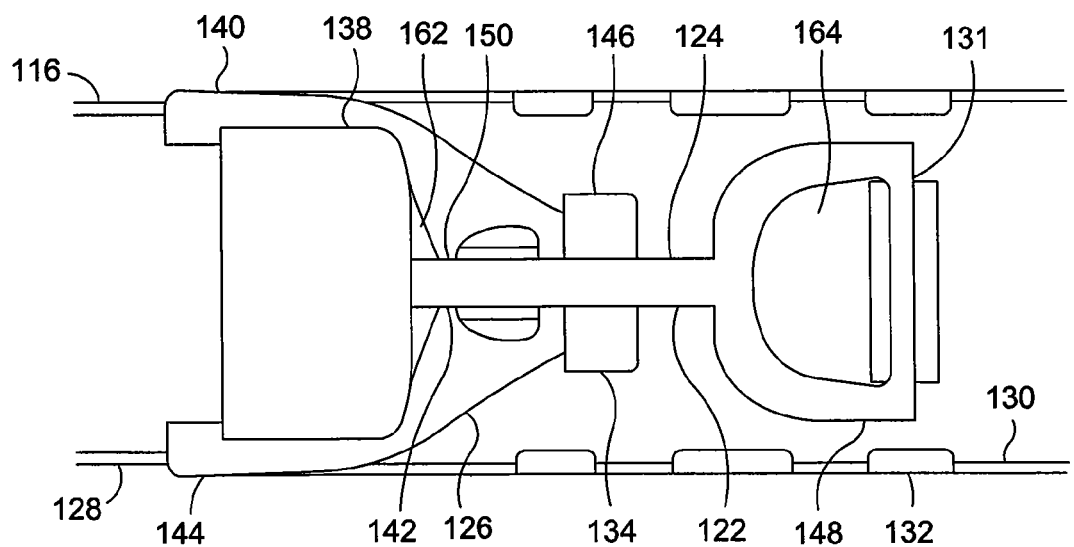
FIG. 1H illustrates a close-up top view of a force transmission device according to an embodiment of the present invention.
Figure 1I:
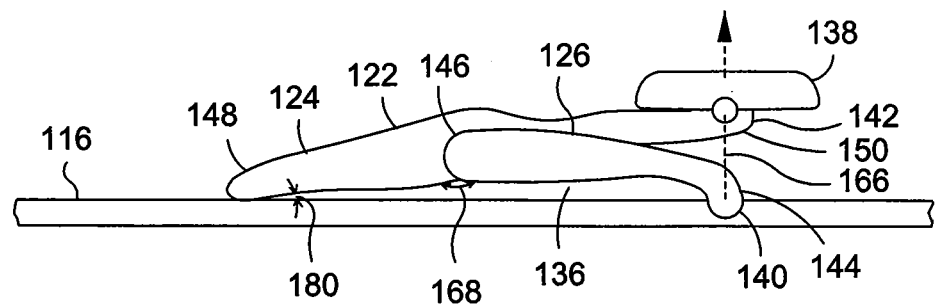
FIGS. 1I-1K illustrate side views of a force transmission device according to an embodiment of the present invention.
Figure 1J:
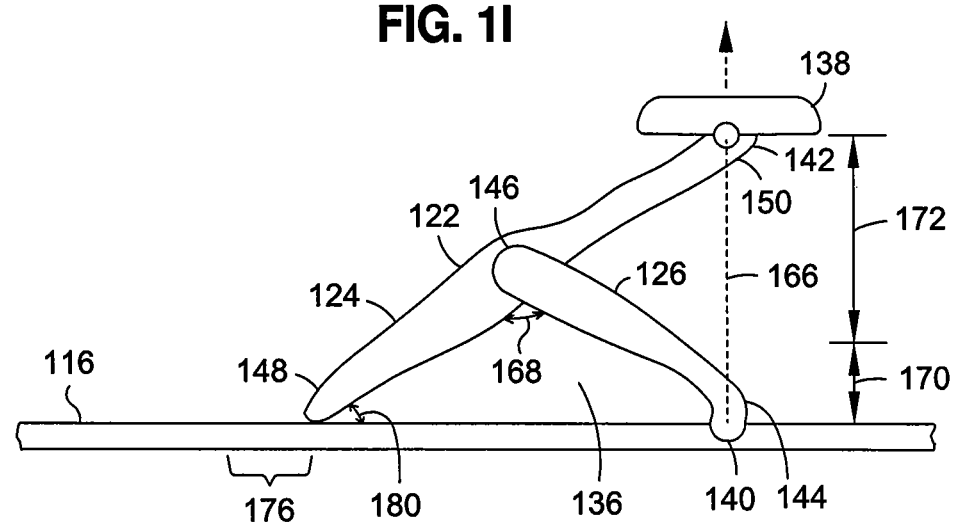
Figure 1K:
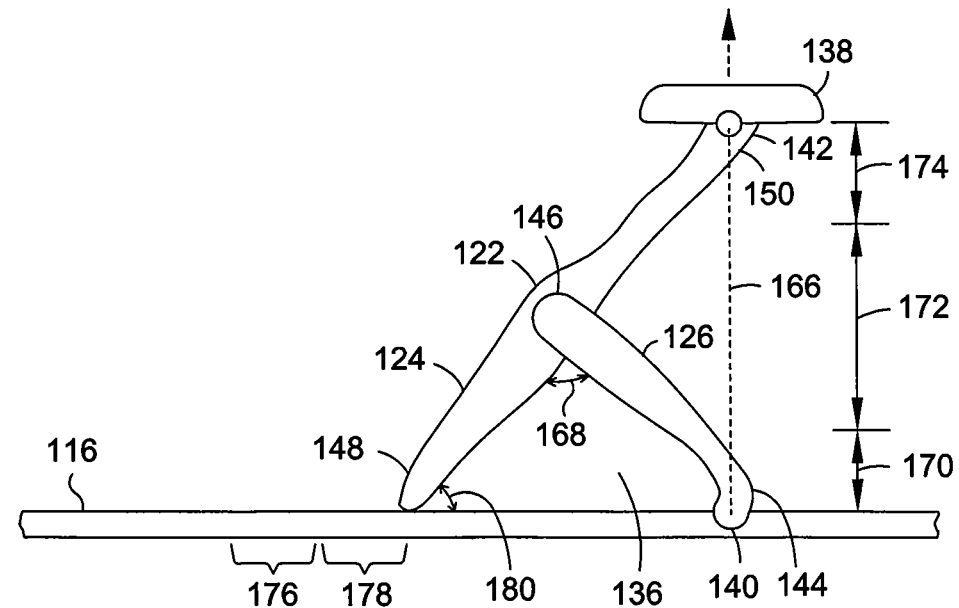

The connection between the first lever arm 124 and the second lever arm 126 also produces an angle 168, illustrated in FIGS. 1I-1K. The size of this angle 168 defines the distance between the first end 148 of the first lever arm 124, and the first end 144 of the second lever arm 126. The size of the angle 168 additionally defines a distance 166 (shown in FIGS. 1I-1K) of the second end 150 of the first lever arm 124 from the band 116, which defines a size of the inner region 101, and accordingly defines a degree of constriction applied by the gastric band device 100 to the patient's stomach. The size of the angle 168 additionally defines the size of the interior region 136 bounded by the arms 124, 126, and the band 116.

The first end 148 of the first lever arm 124 may pivotally be coupled to the inner band 130 via a pivot device 131. In addition, the first end 144 of the second lever arm 126 may pivotally be coupled to the outer band 128 via a pivot device 133. As the inner band 130 may be slidable relative to the outer band 128, the position of the first lever arm 124 may vary relative to the position of the second lever arm 126, based on the relative movement of the inner band 130 and the outer band 128.

In the embodiment shown in FIG. 1B, an end of the outer band 128, being the first end 118 of the band 116, may directly and firmly be coupled to the motor housing 108. In addition, the other end of the outer band 128, being the second end 120 of the band 116, may be coupled to the motor housing 108 through the clip 102. However, an end 154 of the inner band 130, being near the first end 118 of the band 116, may be slidable relative to the outer band 128 and to the motor housing 108. In addition, an opposite end (more clearly shown in FIG. 1C) of the inner band 130, being near the second end 120 of the band 116, may also be slidable relative to the motor housing 108. The opposite end of the inner band 130 is not directly coupled to the motor housing 108. The first end 154 of the inner band 130 may engage with the motor system 158, which is configured to drive the inner band 130 to slide relative to the outer band 128. Grip devices 156 positioned along the inner band 130 may allow the motor system 158 to engage the inner band 130.

The motor system 158 may comprise any standard mechanical motor system capable of driving a drive element (or element to be driven) in a particular direction. In the embodiment shown in FIG. 1B, the motor system 158 extends or retracts a length of the first end 154 of the inner band 130 to slide the inner band 130 relative to the outer band 128. The control and power signals for the motor system 158 may be provided from the antenna pod 112, which is coupled to the motor system 158 via the cable 110. As the motor system 158 drives the inner band 130 relative to the outer band 128, the size of the angle 168 (shown in FIGS. 1I-1K) varies, which varies the degree of constriction applied to the patient's stomach, as discussed above.

Additional elements shown in the embodiment of FIG. 1B include a pad 138, which may be positioned at the second end 150 of a corresponding first lever arm 124. The pad 138 may have a generally rectangular shape, and may be pivotally coupled to the second end 150 of the first lever arm 124 through a pivot device 137. The pivot device 137 may be structured as any of the other pivot devices discussed above. In addition, the pad 138 may also have any equivalent shape that provides a large surface area to transmit a force between the lever device 122 and the patient's stomach. The pad 138 has a large surface area that extends the force exerted by the lever device 122 over a larger surface area than possible without the pad 138. The pad 138 distributes the force exerted by the lever device 122, for example, to prevent the patient's stomach from being punctured by the force exerted by the lever device 122. The pad 138 may be made from a deformable material, such as a soft plastic, to help cushion the force of the lever device 122. In addition, the pad 138 may be made from a non-deformable material, such as a hard plastic, to rigidly transfer the force of the lever device 122 without deformation. The pad 138 may also be integrated within the membrane 106.

The gastric band device 100 may also include a membrane 106, which provides biocompatibility between the gastric band device 100 and the patient's stomach. The membrane 106 may be made from a flexible material, such as silicone, which allows the membrane 106 to stretch to conform to the motion of the lever device 122. In addition, the membrane 106 also serves to prevent body tissue from entering and interacting with the moving portions of the gastric band device 100, or cavities of the gastric band device 100 changing in size, for example, the interior region 136.

In one embodiment, the membrane 106 may have a corrugated surface comprising a series of alternating ridges and grooves. The corrugated surface may reduce the force required to deform the membrane 106, and may allow the membrane 106 to be expanded, or stretched, over a longer distance.

In the embodiment shown in FIG. 1B, the lever devices 122 are positioned equidistant from one another along the interior of the band 116. The equal spacing allows for an even, centralized distribution of force to the patient's stomach. The number of lever devices 122 shown in FIG. 1B includes an exemplary number of seven lever devices 122. However, the number of lever devices 122 may be varied from two lever devices 122 to a number comprising as many lever devices 122 as can feasibly fit along the interior of the band 116 and provide acceptable functionality. It is also possible, in one embodiment, that only one lever device 122 is located along the interior of the band 116, and compresses the patient's stomach in only one direction.

FIGS. 1C-1E illustrate the operation of the gastric banding device 100 to vary a degree of constriction applied to the patient's stomach. FIG. 1C illustrates the gastric banding device 100 in a retracted, or undeployed state. In this configuration, the degree of constriction applied by the gastric banding device 100 is at a relative minimum. The distance 166 (shown in FIGS. 1I-1K) of the second ends 142 of the lever devices 122 from the band is also at a relative minimum in this configuration. The lever devices 122 bound an inner region 101 having a diameter, the diameter being relatively large in this configuration.

FIG. 1D illustrates the gastric banding device 100 in a partially extended or partially deployed state. In this configuration, the inner band 130 has been slid relative to the outer band 128, the first end 148 of the first lever arm 124 has been drawn to the first end 144 of the second lever arm 126, and the distance 166 (shown in FIGS. 1I-1K) of the second ends 142 of the lever devices 122 from the band has been increased. The degree of constriction applied to the patient's stomach is greater than that shown in FIG. 1C. The inner region 101 has a size being smaller than shown in FIG. 1C.

FIG. 1E illustrates the gastric banding device 100 in a more fully extended state than shown in FIG. 1D. In this configuration, the inner band 130 has continued to slide relative to the outer band 128, and the first end 148 of the first lever arm 124 has been drawn more closely to the first end 144 of the second lever arm 126 than shown in FIG. 1D. The distance 166 (shown in FIGS. 1I-1K) of the second ends 142 of the lever devices 122 from the band has been increased from the configuration shown in FIG. 1D. The degree of constriction applied to the patient's stomach is greater than that shown in FIG. 1D. The inner region 101 has a size being smaller than shown in FIG. 1D. From the state shown in FIG. 1C to the state shown in FIG. 1E, the size of the inner region 101 has been reduced by a substantially even force applied centripetally to the inner region 101. In addition, an outer diameter of the band 116 has not varied during constriction.

FIG. 1F illustrates a close up perspective view of a lever device 122 according to one embodiment of the present invention. The shape and structure of the first lever arm 124 and the second lever arm 126 is illustrated herein. It is noted that a portion of the first lever arm 124 may include a bossed portion 160 to more easily accommodate the connection with the second lever arm 126.

FIG. 1G illustrates a close-up perspective cut-away view of a lever device 122 according to one embodiment of the invention. The cut-away view more clearly illustrates the operation of the pivot device 137 used to couple the pad 138 to the first lever arm 124, and the pivot device 131 used to couple the first lever arm 124 to the band 116. The cut-away view also illustrates an interior portion 162 of the second lever arm 126 formed by the forked portion of the second lever arm 126, and an interior portion 164 of the first lever arm 124 formed by the forked portion of the first level arm 124.

FIG. 1H illustrates a top view of a lever device 122. FIG. 1H more clearly illustrates a width of the lever device 122 relative to the band 116.

FIGS. 1I-1K illustrate a side schematic view of a lever device 122 during operation, according to one embodiment of the present invention. FIGS. 1I-1K are used, in part, to describe a form of variable output transmission formed by the lever device 122.

FIG. 1I illustrates the lever device 122 in a substantially retracted state, similar to the state shown in FIG. 1C. In this embodiment, a length of the second lever arm 126 is approximately one-half a length of the first lever arm 124. This configuration allows the second end 150 of the first lever arm 124 to be positioned substantially directly above the first end 144 of the second lever arm 126.

In addition, the second lever arm 126 couples to a midpoint of the first lever arm 124, between the first end 148 and the second end 150 of the first lever arm 124. The connection between the first lever arm 124 and the second lever arm 126 forms an angle 168 being a pivot region. In addition, an angle 180 is formed between the first lever arm 124 and the band 116. The second end 150 of the first lever arm 124, and equivalently, the second end 142 of the lever device 122, is positioned at a distance 166 from the band 116. The angle 180 may have a value of about 20 degrees as shown in FIG. 1I, although this value may be varied as desired without deviating from the scope of this invention.

FIG. 1J illustrates a side schematic view of the lever device 122 in a partially deployed state. The configuration shown in FIG. 1J is similar to the state shown in FIG. 1D. In FIG. 1J, the first end 148 of the first lever arm 124 has been slid closer to the first end 144 of the second lever arm 126 by a lateral change in distance 176. The lateral change in distance 176 has varied the size of the angle 168 between the first lever arm 124 and the second lever arm 126, and the angle 180 between the first lever arm 124 and the band 116. In addition, the lateral change in distance 176 has increased the total distance 166 of the second end 150 of the first lever arm 124 from the band 116. The total distance 166 above the band 116 is now a combination of the initial distance 170 (being shown as distance 166 in FIG. 1I) of the second end 150 and the increased distance 172 due to the lateral change in distance 176. It is also noted the second end 150 of the first lever arm 124 remains positioned substantially above the first end 144 of the second lever arm 126.

FIG. 1K illustrates a side schematic view of the lever device 122 in a more fully deployed state than shown in FIG. 1J. The configuration shown in FIG. 1K is similar to the state shown in FIG. 1E. In FIG. 1K, the first end 148 of the first lever arm 124 has been slid closer to the first end 144 of the second lever arm 126 by a second lateral change in distance 178. The second lateral change in distance 178 is equal in length to the initial lateral change in distance 176 shown in FIG. 1J. The second lateral change in distance 178 has varied the size of the angle 168 between the first lever arm 124 and the second lever arm 126, and the angle 180 between the first lever arm 124 and the band 116. In addition, the second lateral change in distance 178 has increased the total distance 166 of the second end 150 of the first lever arm 124 from the band 116. The total distance 166 above the band 116 is now a combination of the initial distance 170 of the second end 150 and the increased distance 172 due to the initial lateral change in distance 176 and the second increased distance 174 due to the second lateral change in distance 178. The second end 150 of the first lever arm 124 remains positioned substantially above the first end 144 of the second lever arm 126. The angle 180 may have a value of 60 degrees as shown in FIG. 1K, although this value may be varied as desired without deviating from the scope of this invention.

Of particular note in FIG. 1K is that the second increased distance 174 is substantially smaller than the initial increased distance 172, even though the length of the initial lateral change in distance 176 and the second lateral change in distance 178 remained the same. The total distance 166 of the second end 150 of the first lever arm 124 above the band 116 will vary relative to the tangent of the angle 180 that forms between the first lever arm 124 and the band 116. In addition, a constant force applied to produce a constant lateral change in distance 176, 178, and resulting in a decreasing total distance 166 change, will produce a force exerted by the second end 150 of the first lever arm 124 that increases from the configuration shown in FIG. 1J to FIG. 1K. Thus, the configuration shown in FIGS. 1I-1K has produced a form of transmission, producing a variable output force in response to a constant input force.

The variable output force mechanism illustrated in FIGS. 1I-1K provides many benefits for constricting the stomach of a patient. When constricting a patient's stomach, the force required during an initial constriction is relatively small, and increases as the degree of constriction is increased. As the stomach is constricted to a smaller size, it will increasingly resist constriction. Thus, a motor used to drive a constriction mechanism will need to output a variable constriction force throughout this range of constriction. However, in the embodiment shown in FIGS. 1I-1K, a motor may output a constant force, and the lever device 122 will automatically increase the force applied to the patient's stomach, based on the structure of the lever device 122.

Additional benefits of the variable output force mechanism illustrated in FIGS. 1I-1K include an increased force used to stretch a membrane 106 covering the gastric band device 100. The membrane 106 typically increases in resistance as the constriction of the patient's stomach increases. A variable output force mechanism automatically increases the force applied by the lever device 122 required to stretch the membrane 106. In addition, the variable output force mechanism also varies the rate, or speed, at which the second end 150 of the first lever arm 124 increases in distance 166 from the band 116. At an intermediate level of constriction, for example, as shown in FIG. 1J, the second end 150 of the first lever arm 124 moves relatively quickly away from the band 116. The decreasing speed aids the gastric band device 100 to quickly constrict the stomach at low degrees of constriction, and slowly constrict the stomach at high degrees of constriction. The variable speed prevents damage to the stomach at high degrees of constriction, and allows the gastric band device 100 to quickly vary in diameter during relatively low degrees of constriction.

Further benefits of the mechanism illustrated in FIGS. 1I-1K include a constant lateral position of the second end 150 of the first lever arm 124 relative to the band 116. Throughout the range of motion as shown in FIGS. 1I-1K, the second end 150 of the first lever arm 124 remains substantially above the first end 144 of the second lever arm 126. Thus, the patient's stomach will not experience any slipping, sliding, or lateral force exerted by the lever device 122. In addition, the half-lever length of the second lever arm 126 increases the total clearance of the lever device 122, allowing for a large diameter change in response to a small change in lateral distance between the arms 124, 126. In addition, the half-lever design potentially allows a greater number of lever devices 122 to be positioned along the band 116 than in, for example, the embodiment shown in FIG. 1L.

Figure 1L:
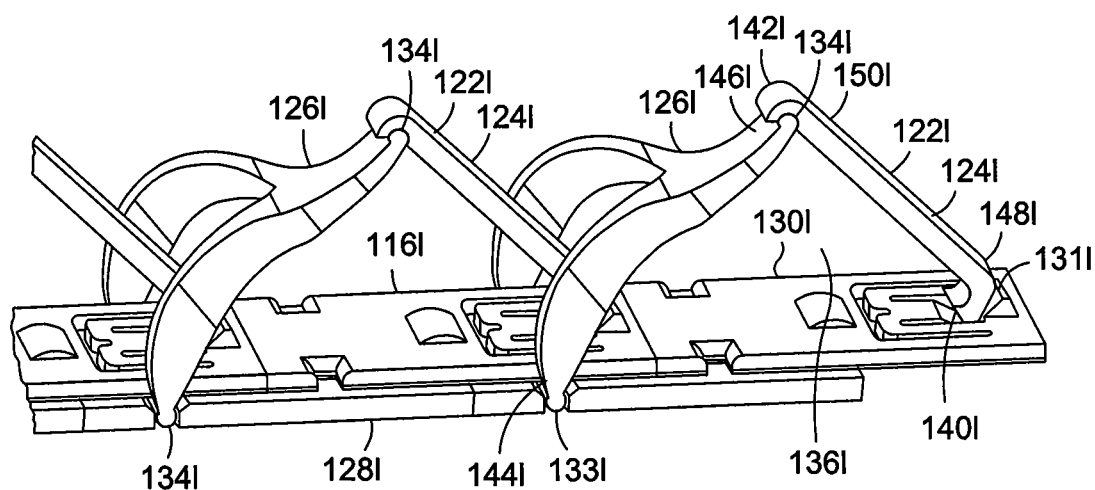
FIG. 1L illustrates a close-up perspective view of force transmission devices according to an embodiment of the present invention.

FIG. 1L illustrates a lever device 122*l* comprising a first lever arm 124*l* and a second lever arm 126*l* having substantially equal lengths. The first end 140*l* of the lever device 122*l* couples to the band 116*l* and the second end 142*l* of the lever device extends a distance away from the band 116*l*. The first lever arm 124*l* has a first end 148*l* which couples to the band 116*l*, specifically, the inner band 130*l*. A second end 150*l* of the first lever arm 124*l* extends a distance away from the band 116*l*. The second lever arm 126*l* has a first end 144*l* that couples to the outer band 128*l* with a pivot device 133*l* and a second end 146*l* that extends a distance away from the band 116*l*. The first lever arm 124*l* and the second lever arm 126*l* are coupled to each other at the second ends 146*l*, 150*l* of each of the arms 126*l*, 124*l*, through a pivot device 134*l*. An interior region 136*l* is formed. In this embodiment, the first lever arm 124*l* does not include a forked portion. Furthermore, the pivot device 131*l* pivotally coupling the first lever arm 124*l* to the band 116*l* comprises a notch element.

Figure 1M:
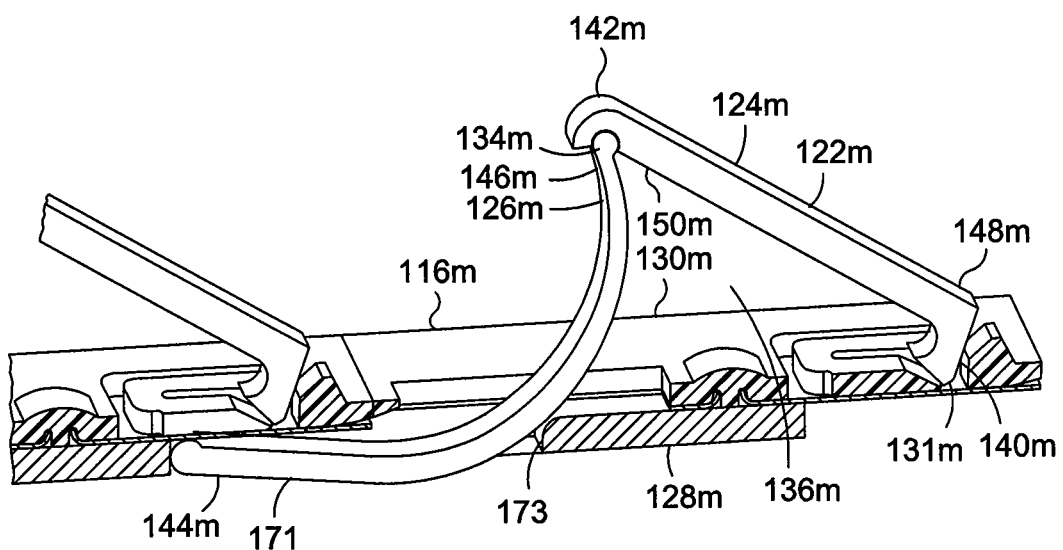
FIG. 1M illustrates a close-up partially cut-away perspective view of force transmission devices according to an embodiment of the present invention.

FIG. 1M illustrates a partial cut-away view of a lever device 122*m* having a first end 140*m* and a second end 142*m*. The lever device 122*m* comprises a first lever arm 124*m* and a second lever arm 126*m* having substantially equal length. The first lever arm 124*m* and the second lever arm 126*m* are coupled to each other with a pivot device 134*m*, at the second ends 150*m*, 146*m* of each of the arms 124*m*, 126*m*. An interior region 136*m* is formed. In addition, in this embodiment, the first lever arm 124*m* and the second lever arm 126*m* do not include a forked portion. The second lever arm 126*m* has a first end 144*m* coupled to the band 116. The second lever arm 126*m* comprises a curved bar, having a portion 171 extending underneath the inner band 130*m*. The outer band 128*m* includes a deflection structure 173 designed to deflect the second lever arm 126*m* away from the band 116*m* during the relative motion of the outer 128*m* and inner 130*m* bands. The pivot device 131*m* pivotally coupling the first lever arm 124*m* to the band 116*m* comprises a notch element, similar to the embodiment shown in FIG. 1L.

Figure 1N:
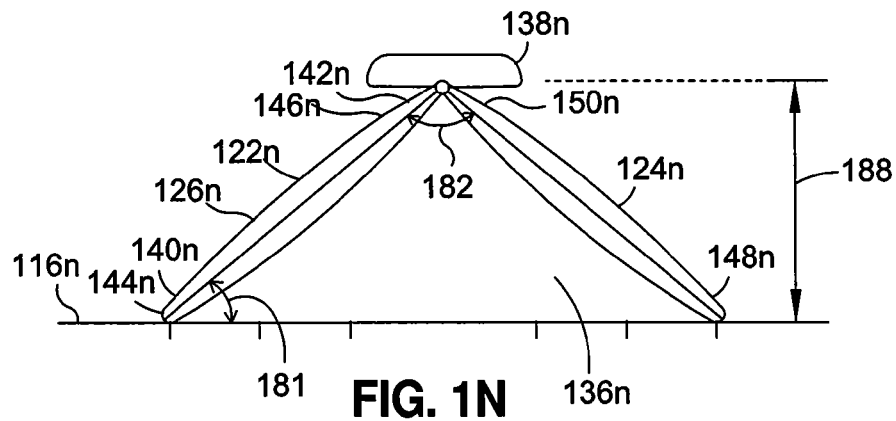
FIGS. 1N-1S illustrate side views of a force transmission device according to embodiments of the present invention.
Figure 1O:
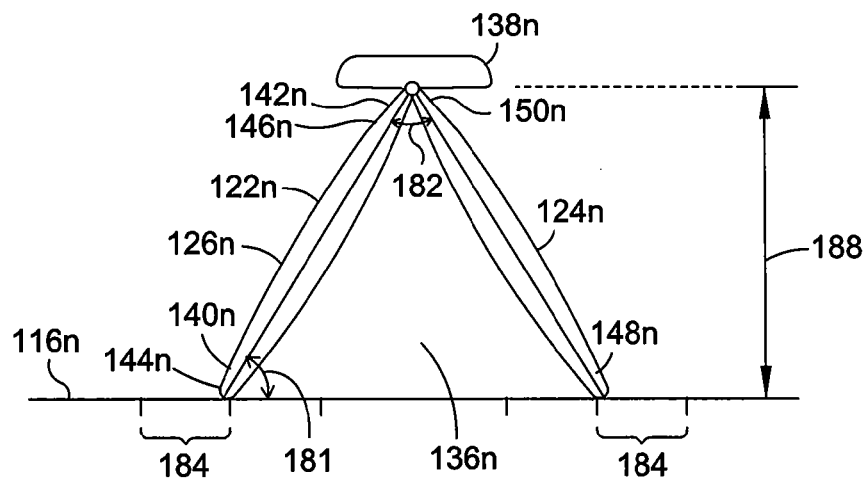
Figure 1P:
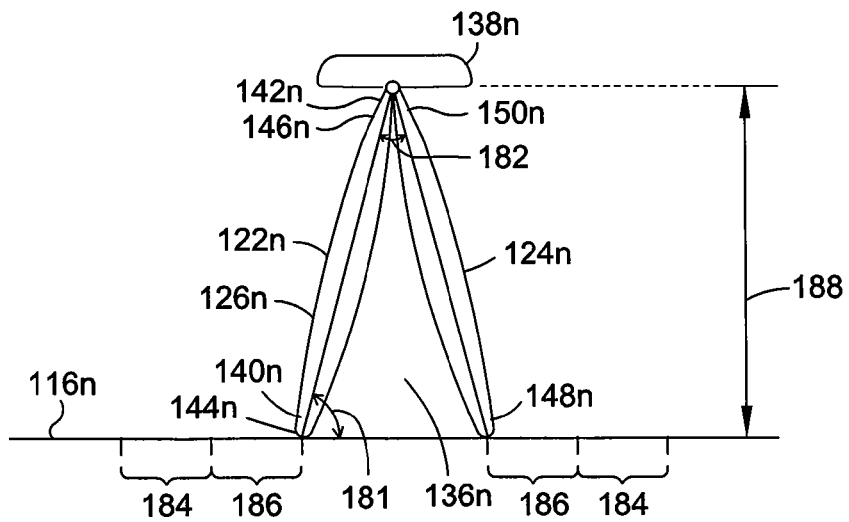

FIGS. 1N-1P illustrate a side schematic view of a lever device 122*n* during operation, according to an embodiment of the present invention. The lever device 122*n* has a first end 140*n* coupled to the band 116*n* and a second end 142*n* extending away from the band 116*n*. In the embodiment shown in FIGS. 1N-1P, the first lever arm 124*n* and the second lever arm 126*n* are coupled to each other at the second ends 150*n*, 146*n* of the respective arms 124*n*, 126*n*, similar to the embodiment shown in FIG. 1L. The first end 148*n* of the first lever arm 124*n* is coupled to the band 116*n*. The first end 144*n* of the second lever arm 126*n* is coupled to the band 116*n*. An interior region 136*n* is formed. A pad 138*n* is coupled to the second end 142*n* of the lever device 122*n*. In operation, each lever arm 124*n*, 126*n* is drawn towards each other at an equal rate. This effect may be produced with a motor system as shown, for example, in FIG. 2B. Referring to the band 116 embodiment shown in FIG. 1B, each arm 124*n*, 126*n* may be similarly connected to a different band 128, 130. Both bands 128, 130 may be rotated, causing both lever arms 124*n*, 126*n* to be drawn towards each other.

In FIG. 1N, the second end 142*n* of the lever device 122*n* is positioned at a distance 188 from the band 116*n*. The lever arms 124*n*, 126*n* couple together to form an angle 182. The second lever arm 126*n* couples to the band 116*n* to form an angle 181.

In FIG. 1O, each lever arm 124*n*, 126*n* has been drawn towards each other by a lateral distance 184, which has decreased the size of the angle 182, and has increased the size of the angle 181 formed between the second lever arm 126*n* and the band 116*n*. The distance 188 of the second end 142*n* of the lever device 122*n* from the band 116*n* has correspondingly increased.

In FIG. 1P, each lever arm 124*n*, 126*n* has been drawn towards each other by a second lateral distance 186, which has additionally decreased the size of the angle 182, and has additionally increased the size of the angle 181 formed between the second lever arm 126*n* and the band 116. The distance 188 of the second end 142*n* of the lever device 122*n* from the band 116 has correspondingly increased. However, similar to the embodiment shown in FIGS. 1I-1K, the distance 188 change in FIG. 1P is smaller than shown in FIG. 1O. Thus, similar to the embodiment shown in FIGS. 1I-1K, a variable output force mechanism is illustrated in FIGS. 1N-1P.

In the embodiment shown in FIGS. 1N-1P, force will need to be applied to each lever arm 124*n*, 126*n* to drawn the arms 124*n*, 126*n* closer to each other. This operation may increase the total friction produced by the force mechanism, however, the second ends 150, 146 of the respective lever arms 124*n*, 126*n* do not vary in lateral position. Thus, the portion of the patient's stomach being constricted will not experience a laterally shifting force in the embodiment shown in FIGS. 1N-1P. In addition, the total force required to draw the arms 124*n*, 126*n* together may be less than shown in the embodiment of FIGS. 1I-1K. In FIGS. 1N-1P, both lever arms 126*n*, 124*n* are drawn by respective lateral distances 184, 186 to raise the distance 188 of the second end 142*n* of the lever device 122*n* from the band 116*n*. The same work to be done, in FIGS. 1N-1P extended over a longer distance, reduces the force required to compress the patient's stomach.

Figure 1Q:
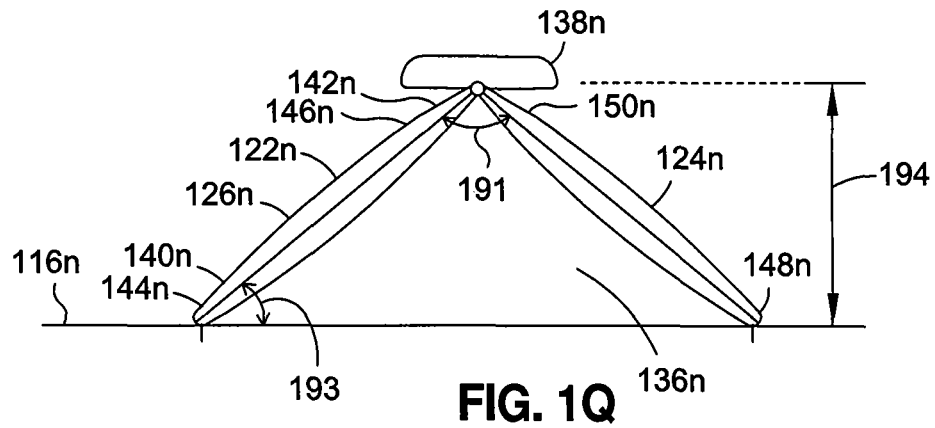
Figure 1R:
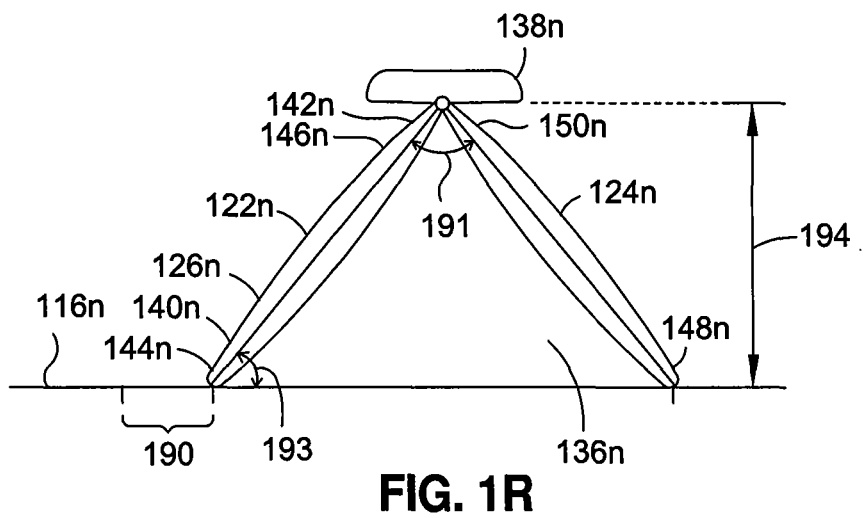
Figure 1S:
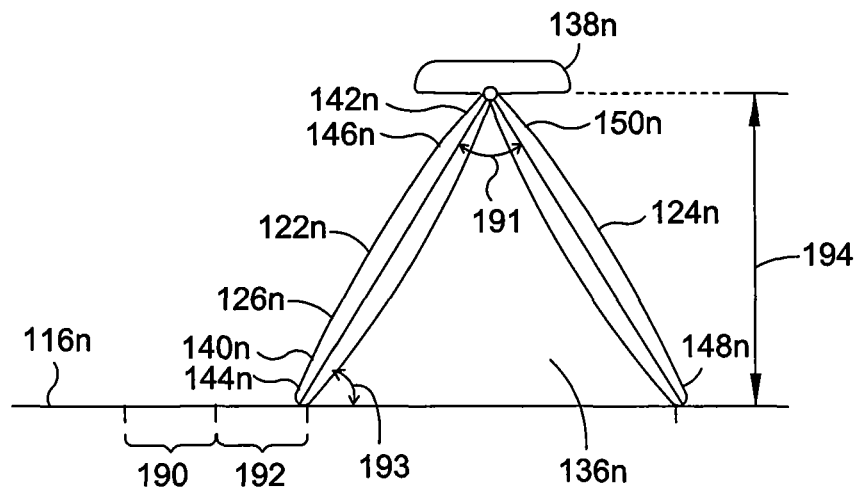

FIGS. 1Q-1S illustrate a side schematic view of the lever device 122*n* during operation, according to an embodiment of the present invention. In the embodiment shown in FIGS. 1Q-1S, the first lever arm 124*n* and the second lever arm 126*n* are coupled to each other at the second ends 150*n*, 146*n* of the respective arms 124*n*, 126*n*. In operation, the second lever arm 126*n* is drawn towards a fixed position first lever arm 124*n*, similar to the operation shown in FIGS. 1I-1K (drawing the first lever arm 124 to a fixed position second lever arm 126).

In FIG. 1Q, the second end 142*n* of the lever device 122*n* is positioned at a distance 194 from the band 116*n*. The arms 124*n*, 126*n* are coupled together to form an angle 191. The second lever arm 126*n* couples to the band 116*n* to form an angle 193.

In FIG. 1R, the second lever arm 126*n* has been drawn towards the first lever arm 124*n* by a lateral distance 190, which has decreased the size of the angle 191, and has increased the size of the angle 193 formed between the second lever arm 126*n* and the band 116*n*. The distance 194 of the second end 142*n* of the lever device 122*n* from the band 116*n* has correspondingly increased.

In FIG. 1S, the second lever arm 126*n* has been drawn towards the first lever arm 124*n* by a second lateral distance 192, which has additionally decreased the size of the angle 191, and has additionally increased the size of the angle 193 formed between the second lever arm 126*n* and the band 116*n*. The distance 194 of the second end 142 of the lever device 122*n* from the band 116*n* has correspondingly increased. However, similar to the embodiments shown in FIGS. 1I-1K, and FIGS. 1N-1P, the distance 194 change in FIG. 1S is smaller than shown in FIG. 1R. Thus, similar to the embodiments shown in FIGS. 1I-1K, and FIGS. 1N-1P, a variable output force mechanism is illustrated in FIGS. 1Q-1S.

In the embodiment shown in FIGS. 1Q-1S, force is applied to only one lever arm 126*n* to be drawn closer to the other lever arm 124*c*. This operation may require less force than the mechanism shown in FIGS. 1N-1P, as the total friction produced by the mechanism shown in FIGS. 1Q-1S may be less than the friction produced by the mechanism shown in FIGS. 1N-1P. However, the total friction produced by the mechanism shown in FIGS. 1N-1P is still greater than shown in FIGS. 1I-1K, as the majority of the stomach's reaction force is received by the fixed support, or the second lever arm 126 in FIGS. 1I-1K. In addition, the second ends 150*n*, 146*n* of the respective lever arms 124*n*, 126*n* have varied in lateral position, which will produce a shifting lateral force applied to the portion of the patient's stomach.

The gastric banding devices shown in FIGS. 1A-1S are considered to be exemplary in nature, or designed to serve as an example, and may be varied without deviating from the scope of this invention. For example, the shape and structure of any of the lever devices 122, 122*l*, 122*m*, 122*n* may be varied to produce an equivalent result. In addition, the structure of the band 116, 116*l*, 116*m*, 116*n* may be varied to produce an equivalent result. The band 116, 116*l*, 116*m*, 116*n* may form a loop over only a portion of the patient's stomach, meaning the two ends of the band may not connect to completely encircle the stomach.

The lever devices 122, 122*l*, 122*m*, 122*n* may not form an empty interior region 136, 136*l*, 136*m*, 136*n*, as the interior region 136, 136*l*, 136*m*, 136*n* may be filled with a compressible substance. The lever arms 124, 124*l*, 124*m*, 124*n*, 126, 126*l*, 126*m*, 126*n* may be connected as a single bent piece of material, for example, a single bar bent to form an angle.

The gastric banding device 100 illustrated in the various embodiments throughout FIGS. 1A-1S provides many benefits that allow the gastric banding device 100 to efficiently constrict a patient's stomach. During operation, an outer diameter of the band 116, 116*l*, 116*m*, 116*n* does not vary, which decreases movement relative to the remainder of the patient's body. This may prevent damage to the area surrounding the gastric banding device 100 during operation of the device 100.

In addition, each lever device 122, 122*l*, 122*m*, 122*n* extends from the band 116 towards the inner region 101 formed when the band 116 is positioned in the loop. The lever devices 122, 122*l*, 122*m*, 122*n* thus form a skeletal structure that strengthens the device 100 against longitudinal forces exerted by the patient's stomach (e.g., during convulsive movements of the stomach, or during eating activities). In addition, the skeletal structure reduces the strength of a membrane 106 necessary to maintain stability of the band. The skeletal structure, rather than the membrane 106, provides stability for the device 100. A weaker membrane, for example a weak rubber membrane, may be used, reducing the total force required to stretch the membrane, and increasing the efficiency of the device 100.

In addition, as discussed in relation to FIGS. 1I-1K and 1N-1S, the lever devices 122, 122*l*, 122*m*, 122*n* in these embodiments are configured to form a variable output force mechanism, varying an output force in response to a constant input force applied by a motor system. The variable output force mechanism promotes power efficiency by allowing the device 100 to exert a successively greater force against the patient's stomach as the degree of constriction applied to the stomach increases.

In addition, each lever device 122, 122*l*, 122*m*, 122*n* is preferably positioned equidistant along the band 116, which produces a substantially even radial force directed towards the center portion of the patient's stomach to be constricted.

Figure 2A:
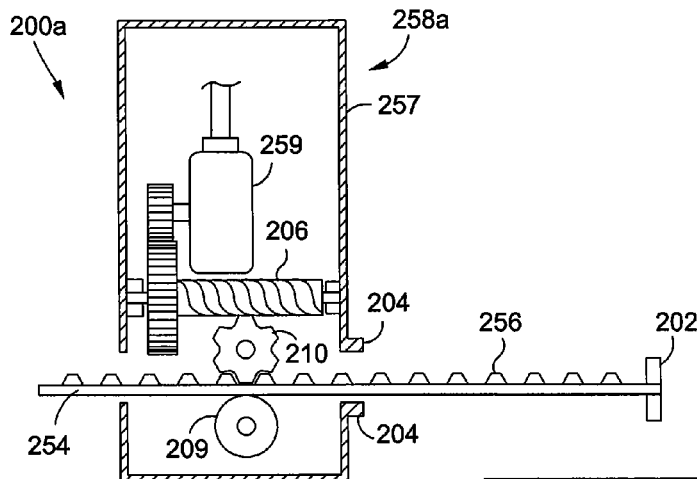
FIGS. 2A-2E illustrate side schematic views of drive systems according to embodiments of the present invention.

FIG. 2A illustrates a drive system 200*a* that may be used, for example, to operate the motion of the force transmission devices, or the lever devices 122 discussed above in relation to FIGS. 1A-1S. The drive system 200*a* may also be used to drive any of the other gastric band devices discussed throughout this disclosure. Any of the drive systems shown in FIGS. 2A-2O may be used with any of the gastric band devices discussed throughout this disclosure. As applied to the embodiment shown in FIGS. 1A-1S, the drive system 200*a* may be contained within the motor housing 108 illustrated in FIGS. 1A and 1B, and may include the motor system 158 discussed above in relation to FIGS. 1A-1S (shown as motor system 258*a* in FIG. 2A).

The drive system 200*a* shown in FIG. 2A includes a motor system 258*a* and a drive element that is driven by the motor system. The drive element comprises the device or material being driven by the motor system. In the embodiment shown in FIG. 2A the drive element may comprise a band 254, or the first end of a portion of a gastric band, or, for example, the first end 154 of the inner band 130 as illustrated in FIG. 1B. However, it is understood that the drive element may comprise any element capable of being driven by a motor system to convey a force to a portion of a gastric band.

In the embodiment shown in FIG. 2A, the motor system 258*a* includes a motor 259, a screw gear 206, an engagement gear 210, a control wheel 209, and a motor system housing 257. The motor 259 may comprise a lavet style motor, or a stepper motor, as is known in the art. The motor 259 couples to the screw gear 206, and drives the screw gear 206 to rotate the engagement gear 210. The engagement gear 210 engages the band 254, and drives the band 254 in a direction. A control wheel 209 may press the band 254 against the engagement gear 210, to maintain the mechanical engagement between the band 254 and the engagement gear 210.

The motor system housing 257 may include openings that allow the band 254 to extend therethrough. A stop bumper 204 may be positioned along the motor system housing 257 to prevent the band 254 from disengaging from the motor system housing 257.

The band 254 may include grip devices 256 that allow the engagement gear 210 to firmly engage the drive element 201. In the embodiment shown in FIG. 2A, the grip devices 256 may comprise a plurality of teeth, although it is understood the shape of the grip devices 256 may be varied without deviating from the scope of this invention (e.g., a notched shape or a bumped shape). A stop plug 202 may be positioned at an end of the band 254, to contact the stop bumper 204 and prevent the band 254 from disengaging from the motor 259.

In operation, the motor 259 shown in FIG. 2A causes the engagement gear 210 to rotate, causing the band 254 to slide relative to the engagement gear 210. The drive element 201 correspondingly applies a force to the portion of the gastric band device to which it is attached.

Figure 2B:
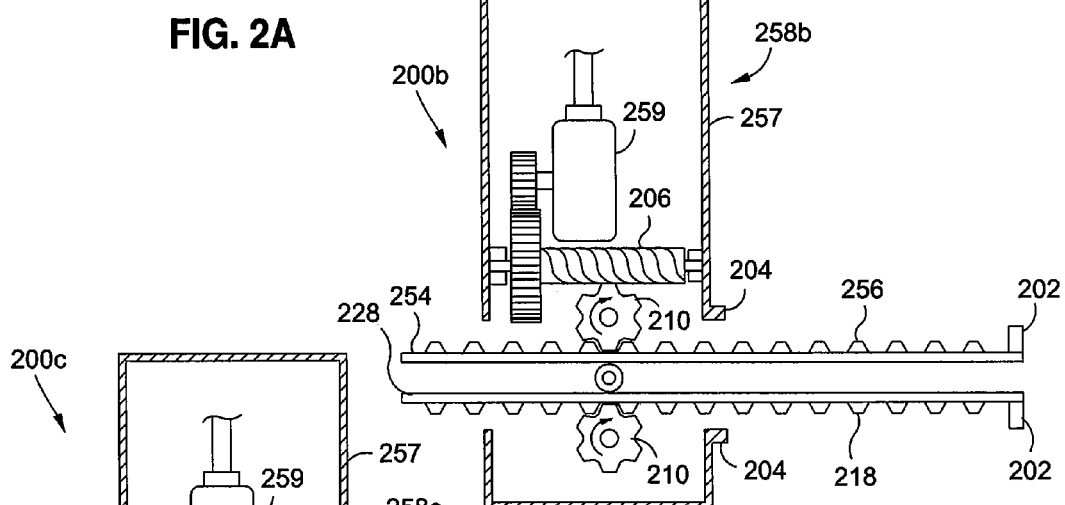

FIG. 2B illustrates a drive system 200*b* including two drive elements, shown as two bands 254, 228 engaged with the motor system. In this embodiment, the motor system 258*b* includes two engagement gears 210, each gear 210 driven to rotate in a different direction. Each gear 210 engages a different band 254, 228, and drives the respective band 254, 228 in opposite directions during operation.

In the embodiment shown in FIG. 2B, the band 254 may have a plurality of grip devices 256 configured to engage an engagement gear 210. The other band 228 may also have a plurality of grip devices 218 configured to engage an engagement gear 210. The bands 254, 228 may comprise the respective first ends of the respective first band 130 and the second band 128 as shown in FIG. 1B, and may be used to produce the mechanics illustrated in FIGS. 1N-1P. However, the bands 254, 228 shown in FIG. 2B may be equivalently replaced with any elements used to exert a force in a gastric band device.

Figure 2C:
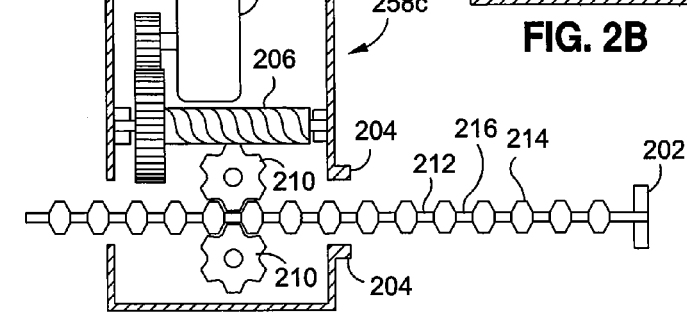

FIG. 2C illustrates a drive system 200c including a drive element comprising a string-of-pearl device 212. The string-of-pearl device 212 comprises a sequence of hard beads 214 positioned along a flexible core 216. The hard beads 214 are sized to have a greater diameter than the flexible core 216. The hard beads 214 are drawn through engagement gears 210, which cause the string-of-pearl device 212 to transmit a force to a portion of the gastric band device. The flexible core 216 is flexible, to allow the string-of-pearl device 212 to flex, but is also rigid enough to allow the string-of-pearl device 212 to exert an axial force in a direction towards or away from the motor system 258c.

The benefit of a string-of-pearl device 212, rather than a strap-like device, or band 254 represented in FIG. 2A, is that the string-of-pearl device 212 may be sized smaller than the band 254. The smaller size may allow the string-of-pearl device 212 to be more easily severed using surgical devices, which may allow for easier removal of the band from the patient's stomach, if necessary. The flexible core 216 may be structured to be severable using surgical devices (e.g., laparoscopically installed surgical scissors).

Figure 2D:
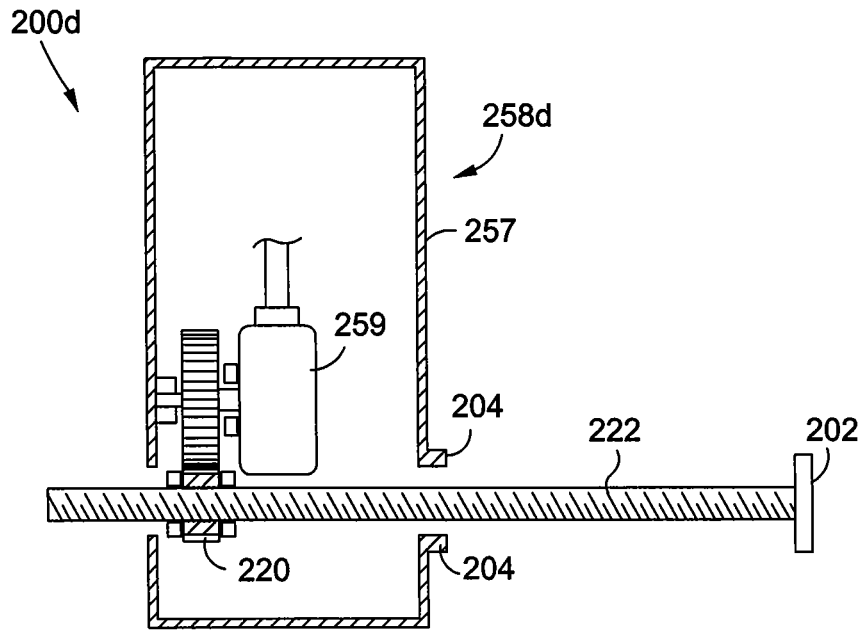

FIG. 2D illustrates a drive system 200d including a drive element comprising a threaded screw device 222. The threaded screw device 222 comprises a helical screw thread wrapped around a flexible core. The motor system 258d includes a motor 259 that engages the threaded screw device 222 with a nut actuator 220, which surrounds the threaded screw device 222 and rotates around the threaded screw device 222. The motor 259 is oriented in a plane perpendicular to the axis of the threaded screw device 222. The relative rotation of the nut actuator 220 around the threaded screw device 222 causes the threaded screw device 222 to slide relative to the nut actuator 220, and transmit a force to a portion of the gastric band device.

Figure 2E:
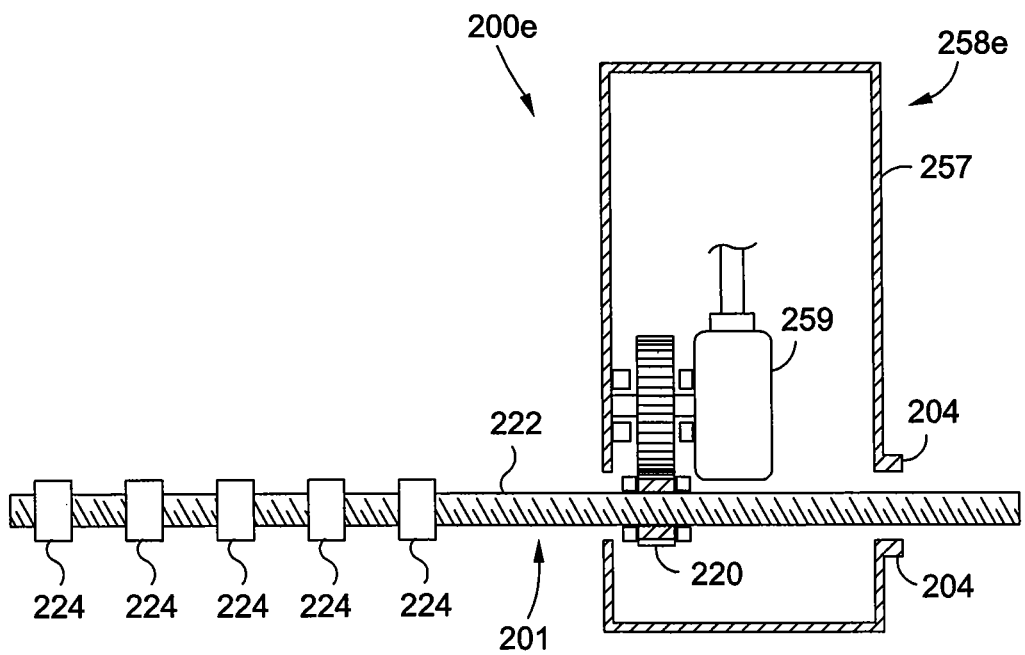

FIG. 2E illustrates a drive system 200e including a motor system 258e with a plurality of slide nuts 224 positioned around the length of the threaded screw device 222. In this embodiment, unlike the embodiment shown in FIG. 2D, the threaded screw device 222 is configured to rotate along with the nut actuator 220. Thus, the threaded screw device 222 rotates during operation of the motor 259. The slide nuts 224 are configured to slide along the length of the threaded screw device 222 in response to rotation of the threaded screw device 222. Each slide nut 224 may be threaded to correspond with the threading on the threaded screw device 222. The slide nut 224 may be fixed to any mechanism desired to receive the force produced by the motor 259 (e.g., a lever device 122 shown in FIG. 1B). The movement of the slide nut 224 along the threaded screw device 222 may transfer the force from the motor 259 to the mechanism desired to receive the force. For example, a slide nut 224 may be coupled to a first end 148, 144 of a respective lever arm 124, 126 shown in FIG. 1B. The movement of the slide nut 224 causes the respective lever arm 124, 126 to move, resulting in a varied degree of constriction applied by the respective lever device 122.

The pitch of the threading along the threaded screw device 222 may also be varied along the length of the threaded screw device 222, to allow for different movement rates of the slide nuts 224. The pitch of the threading of each slide nut 224 may also be varied to produce nuts 224 moving at various rates along the threaded screw device 222.

Figure 2F:
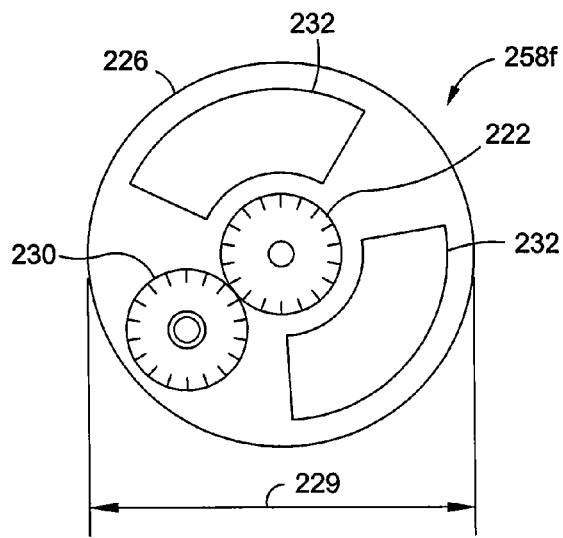
FIGS. 2F-2H illustrate schematic views of motor systems, viewed in line along an axis extending through the motor systems, according to embodiments of the present invention.

FIG. 2F illustrates a motor system 258f including a cylindrically shaped motor 226. The cylindrically shaped motor 226 is schematically represented by two motor coils 232 and a screw gear system 230. The cylindrically shaped motor 226 is capable of driving a drive element, which in FIG. 2F is represented by a threaded screw device 222, viewed in line along the axis of the threaded screw device 222. In this embodiment, the threaded screw device 222 extends substantially through the center of the cylindrically shaped motor 226.

The cylindrically shaped motor 226 may comprise a stepper motor that operates as known in the art. In this embodiment, the motor coils 232 produce an electromotive force, capable of rotating the screw gear system 230 and accordingly driving the threaded screw device 222. The size of the motor coils 232 defines the total force that may be output to the threaded screw device 222. Thus, it may be desirable to provide large sized motor coils 232, to output a large amount of force to the patient's stomach. However, a drawback to larger sized motor coils 232 is that the larger size increases the total diameter 229 of the cylindrically shaped motor 226. This result may be undesirable, as a larger size 229 of the cylindrically shaped motor 226 may increase the total size of a gastric band device placed within a patient's body, which may produce a greater disturbance within the patient's body. Also, a gastric band device having a large size may be more difficult to insert laparoscopically into a patient's body (e.g., through a trocar).

Figure 2G:
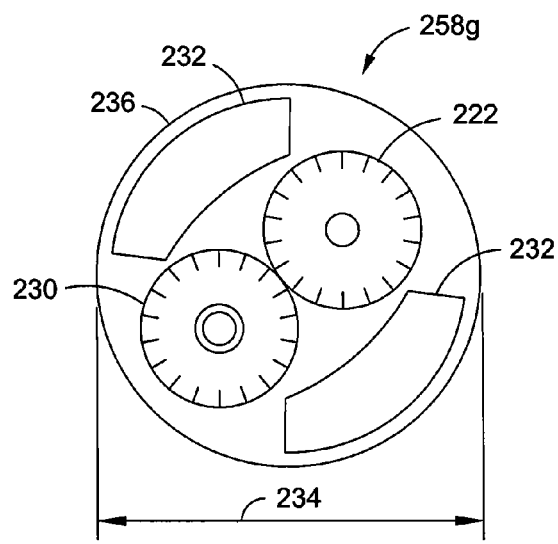

FIG. 2G illustrates a motor system 258g including a cylindrically shaped motor 236 having a smaller diameter 234 than the motor 226 illustrated in FIG. 2F. The motor 236 includes similar components as the motor 226 shown in FIG. 2F, including the screw gear system 230, and motor coils 232. The screw gear system 230 engages and drives a threaded screw device 222. However, unlike the configuration of the motor 226 shown in FIG. 2F, the threaded screw device 222 does not pass through substantially the center of the cylindrically, shaped motor 236. Rather, the threaded screw device 222 is configured to extend or be offset from the center of the motor 236, or biased towards one side. The screw gear system 230 is also positioned offset from the center of the motor 236, or biased towards one side of the interior of the motor 236. The motor coils 232 are positioned to substantially encircle the threaded screw device 222 and the screw gear system 230. The offset position of the screw gear system 230 and the threaded screw device 222 allows the diameter 234 of the motor 236 to be reduced without reducing the size of the motor coils 232. Thus, the total size of the gastric band device to which the motor 236 is affixed may be reduced, providing for easier laparoscopic introduction of the band (e.g., allowing for a smaller sized trocar), and reduced disturbance of the interior of the patient's body.

Figure 2H:
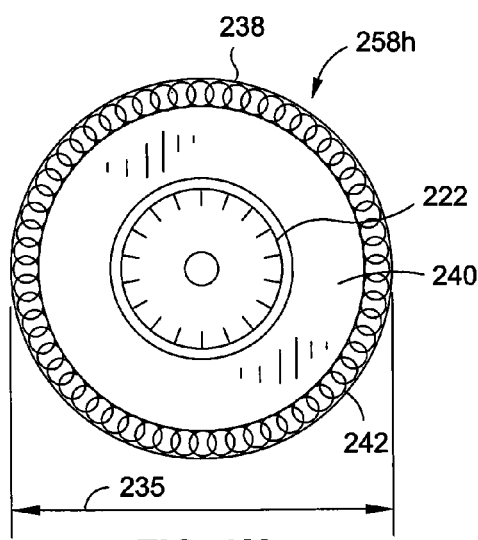
Figure 2I:
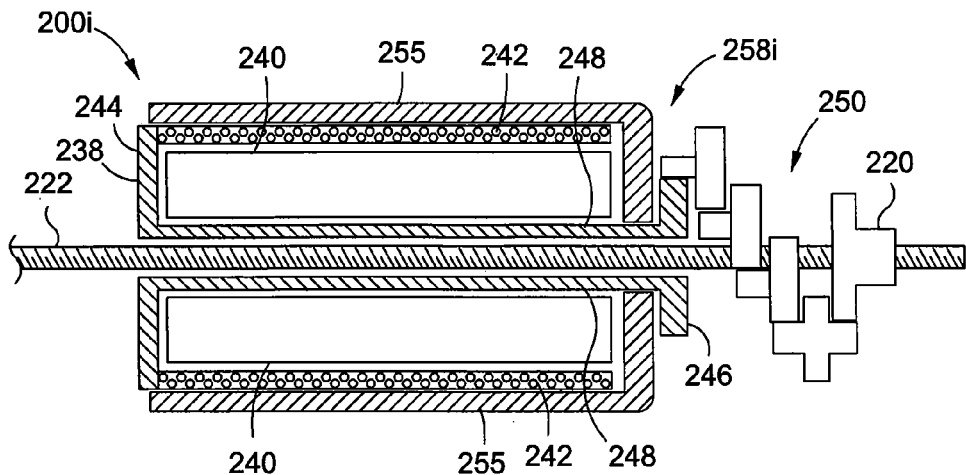
FIGS. 2I-2M illustrate side schematic views of drive systems according to embodiments of the present invention.

FIG. 2H illustrates a motor system 258h including a hollow center motor 238. The hollow center motor 238 includes a cylindrical coil 242 extending around a magnetic core 240. A drive element, which in FIG. 2H is represented by a threaded screw device 222, extends substantially through the center of the hollow center motor 238, and is surrounded by the magnetic core 240. The diameter 235 of the hollow center motor 238 is preferably smaller than the diameter 229 of the motor 226 shown in FIG. 2F, due to a longitudinal positioning of a gear system 250, as illustrated in FIG. 2I, and the orientation of the magnetic core 240 and the cylindrical coil 242. The diameter 235 of the hollow center motor 238 is preferably similarly sized, or has a similar size than the diameter 234 of the motor 236 shown in FIG. 2G. The motor 238 may be operated on a DC power system.

FIG. 2I illustrates a schematic side view of a motor system 258i including the hollow center motor 238 embodiment shown in FIG. 2H. The motor system 258i comprises a component of the drive system 200i configured to drive the drive element. FIG. 2I illustrates the hollow center motor 238 enclosed within a hollow center motor housing 255, which substantially encircles the hollow center motor 238. The magnetic core 240 and the cylindrical coil 242 of the hollow center motor 238 substantially encircle the drive element, represented as a threaded screw device 222 in FIG. 2I. The cylindrical coil 242 couples to a rotary element 244 (not shown in FIG. 2H). The rotary element 244 couples to a drive shaft 248 (not shown in FIG. 2H) that extends along the axial length of the motor 238, and is encircled by the magnetic core 240 and the cylindrical coil 242. At one end of the drive shaft 248, a rotary gear 246 is positioned that engages with a gear system 250. The gear system 250 may comprise a circular arrangement of gears. The gear system 250 couples to a nut actuator 220, which engages and drives the threaded screw device 222.

The cylindrical coil 242 is configured to rotate around the magnetic core 240. The rotary element 244 coupled to the cylindrical coil 242 rotates with the cylindrical coil 242 and rotates the drive shaft 248. The drive shaft 248 consequently rotates the nut actuator 220, which causes the threaded screw device 222 to be driven in a direction along the axis of the hollow center motor 238.

The configuration of motor system 258i as shown in FIG. 2I produces the benefit of a decreased radial size of the motor system 258i. The position of the gear system 250 at one end of the housing 255 reduces the total diameter of the motor system 258i. In addition, the size of the magnetic core 240 and the cylindrical coil 242 may be increased length-wise along the axis of the hollow center motor 238 to increase the force output of the motor system 258, without increasing a radial size of the motor system 258i. The length of the motor 238 thus becomes an important parameter for the generation of motor power. Thus, the motor system 258i as shown in FIG. 2I may more easily be laparoscopically implanted into the patient's body, and may provide a superior force output.

Figure 2J:
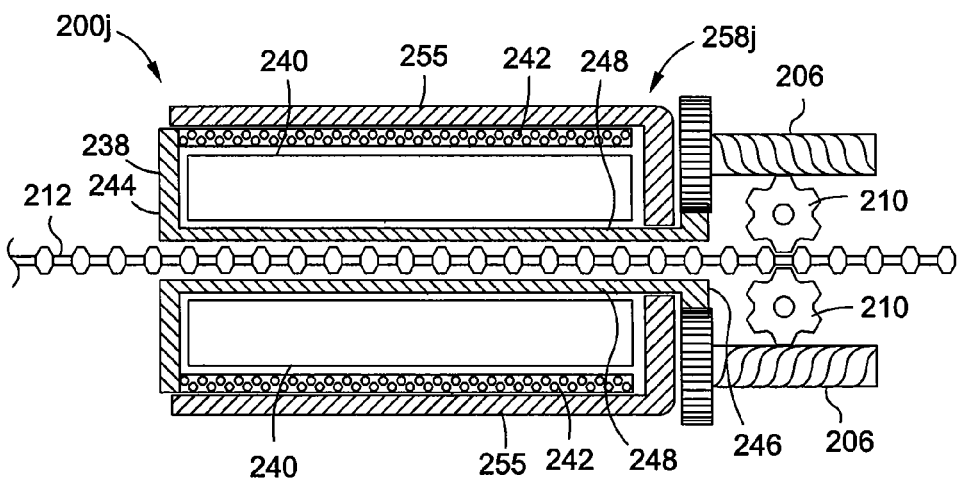

FIG. 2J illustrates a motor system 258j as shown in FIG. 2I, implemented with a string-of-pearl device 212 as the drive element. The motor system 258j comprises a component of the drive system 200j that is configured to drive the drive element. In this embodiment, the rotary gear 246 engages two screw gears 206, or Archimedes-type screws, which couples to the two respective engagement gears 210. The engagement gears 210 drive the string-of-pearl device 212, the string-of-pearl device 212 transmitting a force to the portion of the gastric band device to which it is coupled.

Figure 2K:
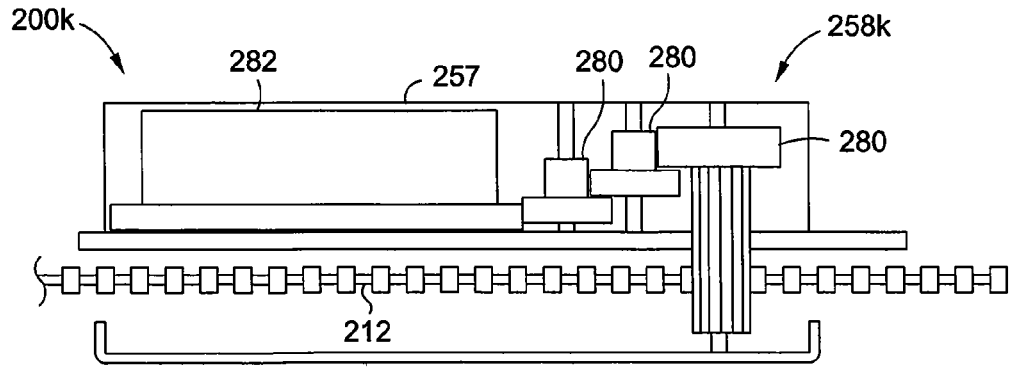

FIG. 2K illustrates a drive system 200k including a motor system 258k using a piezoelectric motor 282. The piezoelectric motor 282 couples to plurality of gears 280, which drive a drive element, represented as a string-of-pearl device 212 in FIG. 2K. The piezoelectric motor 282 is self-blocking, which prevents movement of the drive element when the device is unpowered. The piezoelectric motor 282 may comprise a variety of piezoelectric motor types. These types may include a rotative motor, a vibratory motor, a motor operating on coordinated elliptical movements, a motor actuated with two excitations in different directions, a motor operating on a drive rail riding along bending piezo elements, a motor wherein half of the motor is actuated at a time to generate an asymmetric deformation and force, a motor rotating a screw nut, a motor creating a traveling wave for a rotor to be driven along, a motor operating via a ratcheting system, a wobble motor, and a worm-like or successive activation drive system involving clamping and releasing of a drive element.

The piezoelectric motor 282 may provide benefits over motors requiring magnets and/or coils, as shown, for example in FIGS. 2F-2J. Motors that require magnets and/or coils, referred to as electromagnetic motors, generally have favorable power efficiency, operate at low voltages, and may operate in a closed loop. In addition, electromagnetic motors are relatively inexpensive and reliable. However, electromagnetic motors may corrode, and may produce a large amount of thermal energy. In addition, electromagnetic motors are artifacts in an MRI scan, may have a torque induced in response to the MRI field, and may have components that demagnetize in response to an MRI field. In addition, many electromagnetic motors are not self-blocking, and may require an added mechanism to assure that the degree of constriction does not vary when the motor is unpowered. Piezoelectric motors, however, are intrinsically self-blocking and may lack the corrosive properties of electromagnetic motors. In addition, piezoelectric motors may produce a lower perturbation in MRI systems, and may be easier to sterilize using traditional medical sterilization techniques. Furthermore, piezoelectric motors may produce a more controlled operation, at lower speeds than electromagnetic motors. However, piezoelectric motors may require a high voltage to operate and may wear easily. Piezoelectric motors may also be relatively expensive compared to traditional electromagnetic motors.

Figure 2L:
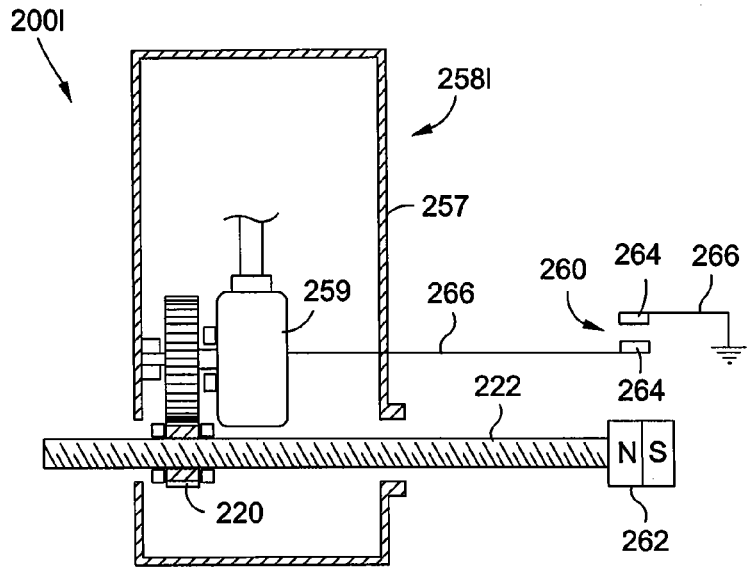

FIG. 2L illustrates a drive system 200l including a magnetic position sensor system 260 as a component of the motor system 258l. The magnetic position sensor system 260 may include a magnetic indicator device 262 and electrical contacts 264. The magnetic indicator device 262 may be positioned along a portion of the drive element, represented as a threaded screw device 222 in FIG. 2L. The electrical contacts 264 may be coupled to the motor 259 via electrical lead lines 266.

The electrical contacts 264 may be positioned to be responsive to a magnetic force produced by the magnetic indicator device 262. For example, the magnetic indicator device 262 may comprise a magnet having a magnetic field. Because the magnet is coupled to the threaded screw device 222, the magnet moves during operation of the motor 259. If the electrical contacts 264 are positioned along the path of the magnet 262, the strength of the magnetic field detected by the electrical contacts 264 increases as the magnet passes nearby. The electrical contacts 264 may be configured to be magnetically responsive, and contact when the magnet is close nearby. The connection between the electrical contacts 264 may provide an electrical signal to the motor 259. Thus, the electrical contacts 264 serve as a position detector to provide information to the motor 259 about the relative location of the threaded screw element 222 (e.g., a signal is produced when the magnet is nearby).

It is understood that the above example is exemplary in nature, and the operation of the magnetic position sensor system 260 may vary from the above-discussed model. For example, a plurality of electrical contacts 264, or a plurality of magnetic indicator devices 262 may be used to provide a variety of information about the position of the drive element 201. Each electrical contact 264 may be positioned in line along the path of the magnetic indicator device 262, and may provide an electrical signal to the motor 259 indicating the magnetic indicator device 262 is nearby. Similarly, the plurality of magnetic indicator devices 262 may be positioned in line along the drive element 201, each configured to exert a different magnetic force to the electrical contact 264. A combination of these methods may be used. In addition, the magnetic indicator device 262 may comprise a mechanism to actuate an electromagnet that indicates the position of the drive element 201. Furthermore, each electrical contact 264 may not be directly responsive to the magnetic indicator device 262, but rather may be actuated by another mechanism relying on an electromagnetic field to sense position. In addition, the magnetic position sensor system may include a variety of other configurations and mechanisms capable of detecting position via a magnetic field, or an electromagnetic field.

It is also understood that the magnetic position sensor system 260 may provide a signal directly to a control device separate from the motor 259, for example, an antenna pod 112 as shown in FIG. 1A. The antenna pod 112 may relay the signal to an external control device, which may be read by a physician to indicate the extent the patient's stomach has been constricted. This information may be used by the physician to transmit a signal back to the antenna pod 112, to vary a degree of constriction applied by the gastric band device.

Figure 2N:
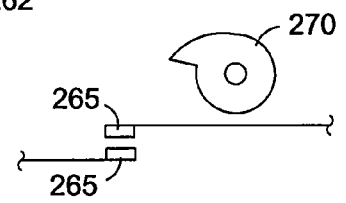
FIG. 2N illustrates a schematic view of the position sensor system shown in FIG. 2M.
Figure 2M:
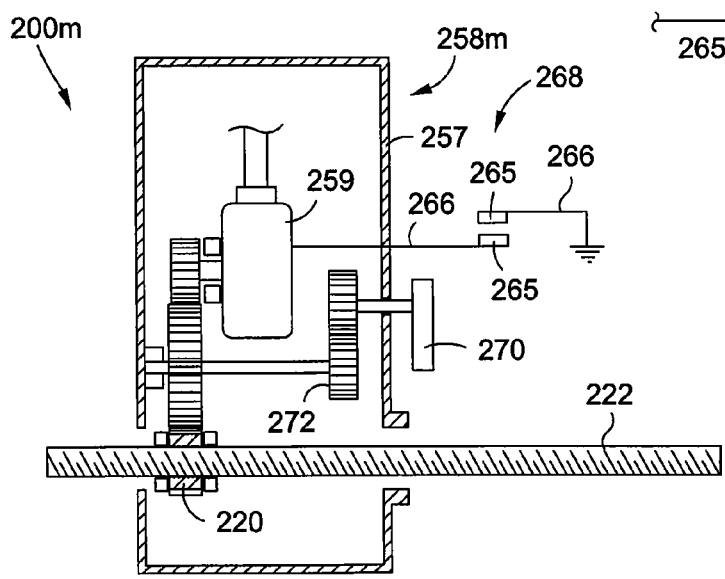

FIG. 2M illustrates a drive system 200m including a mechanical position sensor system 268 incorporated with the motor system 258m. The mechanical position sensor system 268 includes mechanically responsive electrical contacts 265, a cam device 270, and a cam gear system 272, or gear system engaged with the cam device 270. The cam gear system 272 comprises a plurality of gears that engage with the motor 259. The mechanically responsive electrical contacts 265 may be coupled to the motor 259 via the electrical lead lines 266.

In operation, the motor 259 drives the drive element, which is illustrated as a threaded screw device 222 in FIG. 2M. During operation of the motor 259, the cam gear system 272 rotates, and the cam device 270 rotates as well. The cam gear system 272 may indicate the extent to which the motor 259 has operated, which will indicate the position of the drive element. FIG. 2N illustrates the rotation of the cam device 270 that causes an extended portion of the cam device 270 to press the mechanically responsive electrical contacts 265 together. The electrical contacts 265 may transmit a signal to the motor 259 indicating the threaded screw device 222 has been driven to a designated position. The gear'ratio of the cam gear system 272 may be varied, or the size and configuration of the cam device 270 may be varied to set the position indicated by the electrical contacts 265.

It is understood that the configuration of the mechanical position sensor system 268 shown in FIG. 2M is exemplary in nature, and may be varied to provide equivalent or superior results. For example, a plurality of gear systems 272 or cam devices 270 may be used to provide multiple position signals to the motor 259. The plurality of gear systems 272 or cam devices 270 may contact a plurality of electrical contacts 265, each providing a different position signal to the motor 259. In addition, similar to the embodiment of the magnetic position sensor system 260 shown in FIG. 2L, the mechanical position sensor system 268 may provide a signal to an antenna pod, which may transmit the position in formation to an external controller, which may then provide control signals to control operation of the motor 259. In addition, the mechanical position sensor system 268 may be incorporated with the stop plug 202 and stop bumper 204 system shown, for example, in FIG. 2D. The mechanical position sensor system 268 may be configured to produce a position signal when the plug 202 contacts the bumper 204.

Figure 2O:
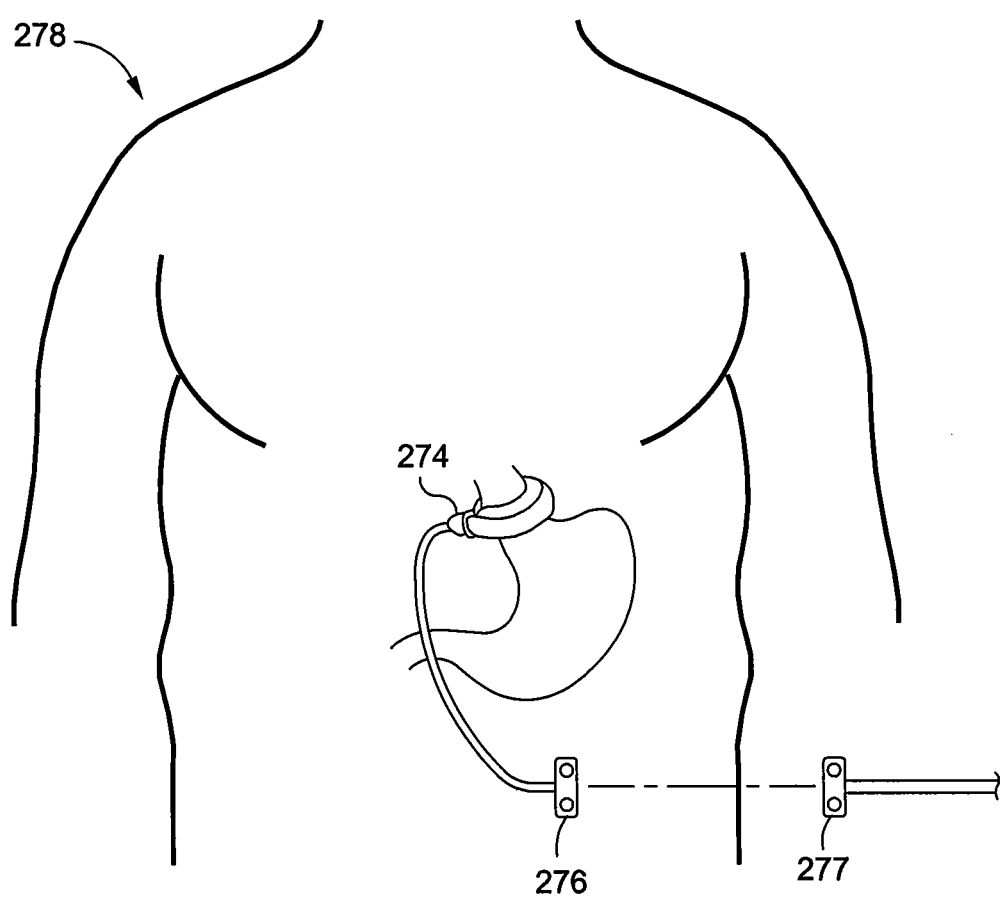
FIG. 2O illustrates a schematic view of a gastric band device according to an embodiment of the present invention.

FIG. 2O illustrates an externally positioned motor. In this embodiment, an externally controlled gastric band device 274 is shown positioned around a portion of a patient's 278 stomach to be constricted. The gastric band device 274 connects to an internal magnetic coupler device 276, which is magnetically engaged with an external magnetic coupler device 277. Rotation or motion of the external magnetic coupler device 277 causes the internal magnetic coupler device 276 to similarly rotate or move. The motion of the internal magnetic coupler device 276 causes a degree of constriction applied by the gastric band device 274 to vary. Thus, a powered motor may be positioned outside of the patient's 278 body, yet still produce motion and operate the gastric band device 274 within the patient's 278 body.

The drive systems, position systems, and external motor configurations shown in FIGS. 2A-2O are considered to be exemplary in nature, and may be varied without deviating from the scope of this invention. For example, the shape and structure of any of the motor systems and drive elements may be varied to produce an equivalent result. For example, the drive element may comprise a bicycle chain-type device, a belt, a thread, a gear system, a cable, or a bridle system. In addition, the external motor design may be incorporated into any of the drive systems, or gastric band devices shown throughout this disclosure. The drive systems may be configured to be powered with an AC current or a DC current, and may be powered externally (e.g., through an induced current) or through an internal battery system.

The drive systems, position systems, and external motor configurations shown in FIGS. 2A-2O provide many benefits that allow the gastric banding device to more efficiently operate. For example, the shown configurations of the motor systems may increase total power efficiency and decrease the total size of the motor. In addition, the position systems may be used to inform the physician about the condition of the degree of constriction, or may be used to control operation of the motor (e.g., stopping the motor from operating once the gastric band device has been fully constricted). Furthermore, the presence of an external motor may reduce the presence of a powered device, subject to failure, and producing heat within a patient's body.

Figure 3A:
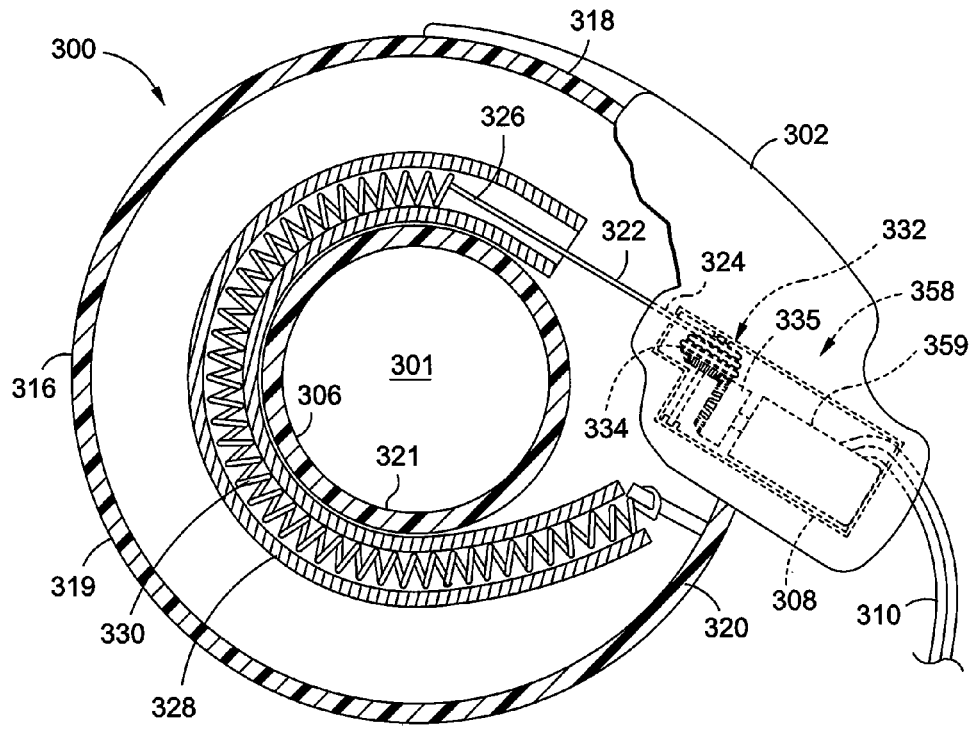
FIG. 3A illustrates a perspective view of a gastric band device according to an embodiment of the present invention.

FIG. 3A illustrates a gastric band device 300 including a cylindrical transmission device 332. The gastric band device 300 includes a band 316 having a first end 318 and a second end 320. A clip 302 couples the first end 318 to the second end 320 such that the band 316 forms a loop around a portion of the patient's stomach to be constricted. The band 316 is positioned in a loop around a portion of the patient's stomach in a manner similar to the gastric band device 100 described in relation to FIG. 1A. The gastric band device 300 serves to provide a degree of constriction to a portion of the patient's stomach, similar to the gastric band device 100 described in relation to FIG. 1A.

An elongated member 328 is positioned within a region bounded by the band 316, to apply a degree of constriction to a portion of the patient's stomach. The elongated member 328 forms a loop defining an inner region 301, which is complementary with, or configured to constrict the patient's stomach. A flexible membrane 306 may be coupled to the band 316, or extend around the band 316, similar to the membrane 106 shown in FIG. 1A, to provide a degree of biocompatibility between the gastric band device 300 and the patient's body. The band 316 may be configured to have a rigid dorsal periphery 319 and a flexible ventral periphery 321, such that a diameter of the rigid dorsal periphery 319 does not move during operation of the cylindrical transmission device 332. However, the flexible ventral periphery 321 is configured to expand and compress, to allow the size of the inner region 301 to vary during operation of the cylindrical transmission device 332.

A spring 330 may be positioned within the elongated member 328. The spring 330 may have a first end coupled to the cord 322, and a second end coupled to the band 316. The spring 330 is configured to stretch and provide a degree of constriction to the patient's stomach. The spring 330 may comprise a helical spring made stiff enough to provide a degree of constriction to the stomach, yet also flexible enough to extend around the stomach in a loop.

The cord 322 has a first end 324 coupled to the cylindrical transmission device 332, and a second end 326 coupled to the spring 330. The cord 322 is made from a strong yet flexible material, capable of withstanding the force applied to the cord 322 by the cylindrical transmission device 332, yet also being able to wrap around the inner region 301 to constrict the patient's stomach. The second end 326 of the cord 322 may extend into the elongated member 328, and may directly apply a constrictive force to the patient's stomach. The cord 322 may also wrap around the inner region 301 entirely, applying a degree of constriction to the patient's stomach.

The cylindrical transmission device 332, as shown in FIG. 3A, comprises a reel, or grooved spool 334 capable of rotating around an axis. The cylindrical transmission device 332 may also include a transmission shaft 336, more clearly illustrated, for example, in FIG. 3B. The cylindrical transmission device 332 may engage with a motor system 358, including a rotary actuator 335 coupled to a motor 359. The motor system 358 and cylindrical transmission device 332 may be contained within a motor housing 308. A cable 310 may be coupled to the motor 359 to provide power and control signals from, for example, an antenna pod 112 as illustrated and described in relation to FIGS. 1A and 1B.

In operation, to increase the degree of constriction to the stomach, the motor 359 rotates the cylindrical transmission device 332, which pulls on the cord 322. The tensioned cord 322 presses against the patient's stomach, constricting the stomach. The spring 330 provides tension to the second end 326 of the cord 322. To decrease the degree of constriction, the motor 359 operates to release the cord 322. It is understood that the embodiment shown in FIG. 3A is exemplary in nature, and the configuration or operation of the gastric band device 300 may be varied without deviating from the scope of this invention. For example, the elongated member 328 may not be incorporated in the design, leaving the spring 330 and the cord 322 to slide directly against the membrane 306 during operation. In addition, the spring 330 may not be incorporated, allowing the cord 322 to extend and fix directly to the second end 320 of the band 116. In this embodiment, a biasing element may be incorporated to provide tension to the cord 322. For example, the cord 322 may extend through the elongated member 328, which may be structured to resist deformation by the cord 322, and may tension the cord 322 to resist a pulling force exerted by the cylindrical transmission device 332.

Figure 3B:
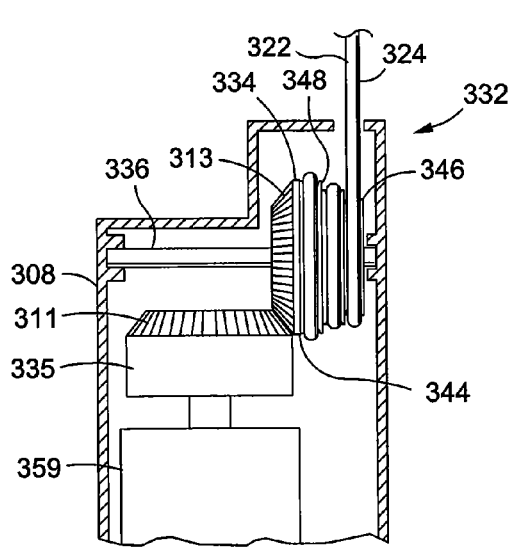

FIG. 3B illustrates a close-up schematic view of the cylindrical transmission device 332 illustrated in FIG. 3A. The cylindrical transmission device 332 comprises a spool, shown in FIG. 3B as a grooved spool 334. The spool 334 has a cylindrical shape, with a first end 344 positioned at a distance from the second end 346. The first end 344 has a diameter being greater than the second end 346. A tapered portion 348 of the spool 334 connects the ends 344, 346. The tapered portion 348 has a sloped shape to connect the different diameters of the ends 344, 346 of the spool 334. In the embodiment shown in FIG. 3B, the spool 334 has surface grooves that allow the first end 324 of the cord 322 to securely engage the spool 334.

The spool 334 rotates about a transmission shaft 336, which may be coupled to the motor housing 308. A spool grip surface 313 is positioned at the first end 344 of the spool 334. The spool grip surface 313 may comprise a friction surface or a gear surface. The spool grip surface 313 engages with an actuator grip surface 311, which similarly comprises a friction surface or gear surface, positioned on the rotary actuator 335.

In operation, the motor 359 rotates the rotary actuator 335, which rotates the cylindrical transmission device 332 via the contacting grip surfaces 311, 313. The spool 334 pulls or releases on the first end 324 of the cord 322, which correspondingly increases or decreases the degree of constriction applied to the stomach.

The spool 334 is configured to have ends 344, 346 with different sized diameters, and a tapered portion 348 connecting the ends 344, 346. The cord 322 wraps around the spool 334 such that successive wraps of the cord 322 over the tapered portion loop over a smaller diameter of the spool 334. In other words, each loop of the cord 322 around the spool 334 is positioned at a different distance from the shaft 336. The tapering of the spool 334 allows the spool 334 to serve as a variable transmission, applying a varying force to the first end 324 of the cord 322 in response to a constant force applied by the motor 359 to the spool 334.

The force applied to the first end 324 of the cord 322 is relatively low during an initial constriction of the patient's stomach, as the first end 344 of the spool 334 has a relatively large diameter. In addition, the speed the cord 322 is driven at this point is relatively large. As the spool 334 rotates to retract the cord 322, and wrap the cord 322 over the spool 334, the cord 322 loops over a successively smaller diameter of the spool 334, which increases the force applied to the cord 322, yet decreases the speed at which the cord 322 is drawn. As discussed in regard to the variable output transmission described in FIGS. 1I-1K, an increased force applied to the cord 322, offset with a decreased speed of operation, may be beneficial, as the patient's stomach will progressively increase resistance to compression. A constant force may be applied by the grip surface 311 of the motor 359 to the grip surface 313 of the spool 334, but the force exerted on the cord 322 will increase during successive wraps. As the cord 322 continues to loop around the spool 334, the force applied to the cord 322 reaches a maximum as the first end 324 of the cord 322 wraps near the second end 346 of the spool 334. Thus, similar to the embodiment shown in FIGS. 1I-1K, the present configuration provides the benefits of a constant input force, exerted by the motor 359, producing a variable output force exerted by the cord 322 to the patient's stomach.

Figure 3C:
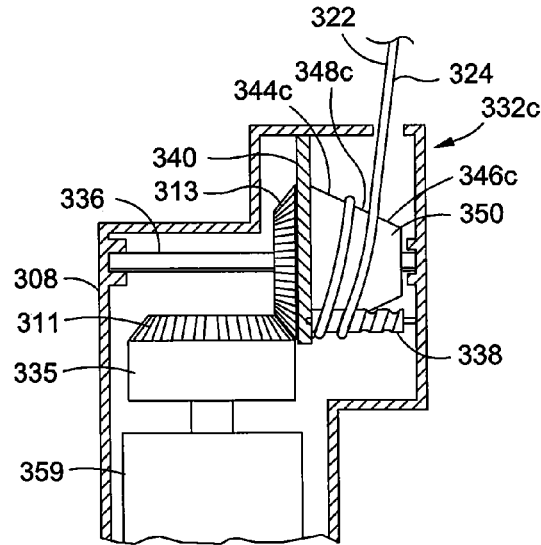

FIG. 3C illustrates a cylindrical transmission device 332c including a smooth surfaced spool 350 and a threaded cylinder 338. The spool 350 has a first end 344c and a second end 346c, and a tapered portion 348c positioned between the ends 344c, 346c. The threaded cylinder 338 may be mounted on a threaded mounting 340 and to the motor housing 308, and can freely slide along the mounting 340 and the housing 308. The threaded cylinder 338 comprises a cylinder having a helical shaped groove, capable of routing the first end 324 of the cord 322 onto the spool 350. The cord 322 is routed over the threaded cylinder 338 through the helical shaped groove. The routing places the cord 322 in position along the tapered portion 348c of the spool 350.

FIG. 3D illustrates a cylindrical transmission device 332d including a spool having a hyperbolic shape, referred to as a hyperbolic spool 354. The hyperbolic spool 354 has a first end 344d and a second end 346d and a tapered portion 348d positioned between the two ends 344d, 346d. The tapered portion 348d has a hyperbolic shape, or a shape resembling the function of "y=1/x," wherein "y" represents a diameter of the spool 354 and "x" represents a length along the axis of the spool 354. A benefit of a hyperbolic shape is to maintain a substantially constant torque applied to the cord 322 in response to an increased constriction force offered by the patient's stomach.

FIG. 3E illustrates a cylindrical transmission device 322e including a spool having a wheel shape, referred to as a wheel spool 356. The wheel spool 356 allows the first end 324 of the cord 322 to wrap over itself during operation. The wheel spool 356 provides an opposite variable force effect than shown in FIGS. 3B-3D, as the diameter of the wheel spool 356 increases during successive wraps of the cord 322. The diameter of the cord 322 may be varied along the length of the cord 322 to allow for varied sized wraps of the cord 322 around the spool 356. FIG. 3F illustrates a side view of the wheel spool 356.

FIG. 3G illustrates a cylindrical transmission device 332g including a spool having a nautilus, or logarithmic spiral shape, referred to as a nautilus spool 357. The nautilus spool 357 has a shape substantially resembling a logarithmic spiral, or a shape wherein the radius of the spool 357 from the shaft 336 is related to the base of the natural logarithm raised to the power of the angle of the spool 357 around the axis. In other words, a shape resembling the function $r=e^\theta$, as visualized in polar coordinates, wherein "r" is a radius, and "θ" is an angle of a portion of the spool 357 around the axis.

FIG. 3H illustrates a side view of the nautilus spool 357. A benefit of a nautilus shape is to maintain a substantially constant torque applied to the cord 322 in response to an increased constriction force offered by the patient's stomach.

FIG. 3I illustrates a cylindrical transmission device 332i including a spool having a double nautilus, or logarithmic spiral shape, referred to as a double nautilus spool 360. The double nautilus spool 360 has a shape substantially resembling a logarithmic spiral, and is shaped to represent a twice-spiraled embodiment of the nautilus spool 357 shown in FIGS. 3G and 3H.

The double nautilus spool 360 has a first end 344i, a second end 346i, and tapered portion 348i positioned between the two ends 344i, 346i. A surface groove 342i runs along the outer surface of the spool 360.

FIG. 3J illustrates a side view of the double nautilus spool 360. The double nautilus spool 360 is shaped to provide for a smooth increase in force to the cord 322 in response to a constant input force to the spool 360.

Figure 3K:
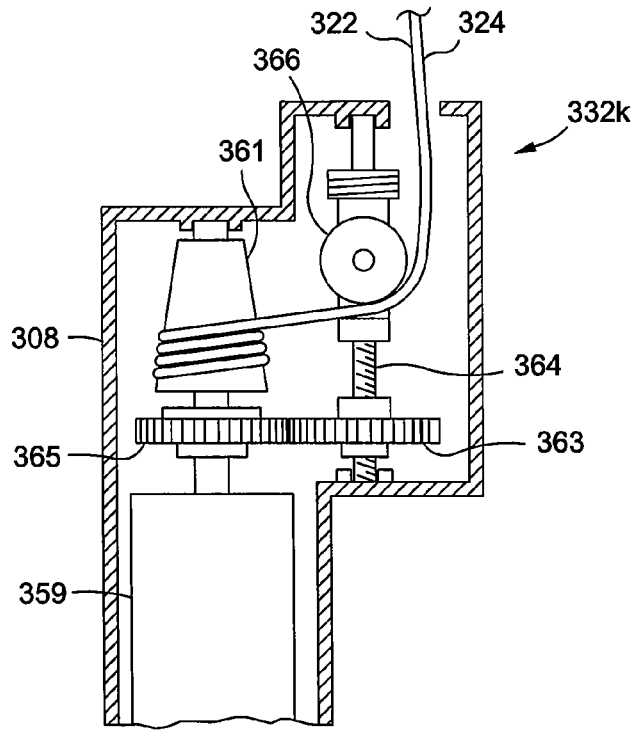
FIGS. 3K-3L illustrate perspective views of transmission systems according to an embodiment of the present invention.

FIG. 3K illustrates a cylindrical transmission device 332k including a vertically positioned spool 361 and a pulley routing system including a slidable pulley wheel 366, a screw drive 364, and gears 363, 365. In operation, the rotation produced by the motor 359 causes the gears 363, 365 to rotate, which rotates the screw drive 364. The rotating screw drive 364 causes the pulley wheel 366 to slide along the drive 364, varying the position of the first end 324 of the cord 322 along the vertically positioned spool 361. The pulley wheel 366 thus serves to position the cord 322 along the spool 361, and also serves as an additional force mechanism to retract or extend the cord 322 during operation of the motor 359.

Figure 3L:
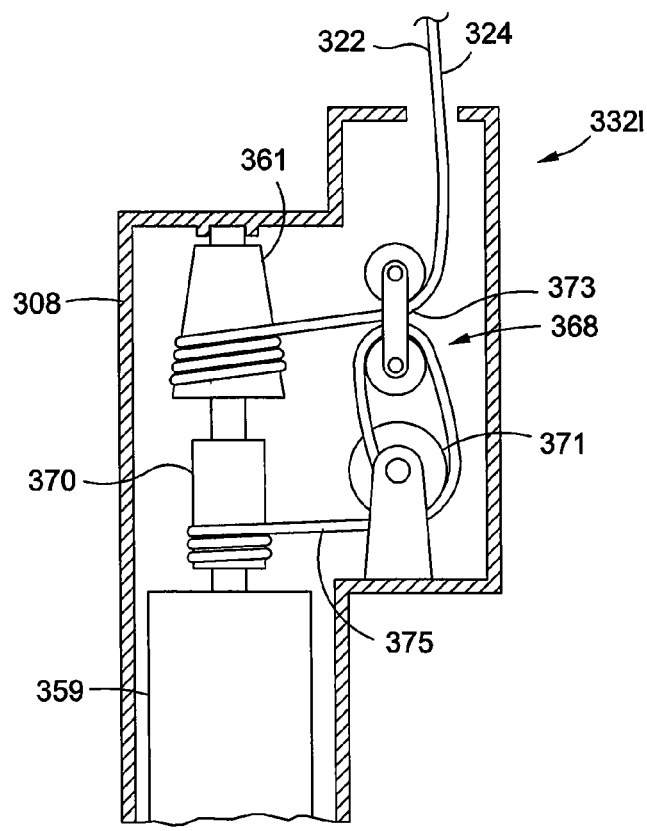

FIG. 3L illustrates a cylindrical transmission device 332l including the vertically positioned spool 361 and a pulley tackle system 368. The system 368 includes a pulley wheel 371 and a pulley block 373. A cord 375 connects the block 373 to the pulley wheel 371 and is wrapped around a cylindrical retainer 370. During operation, the motor 359 rotates both the spool 361 and the retainer 370, causing the tackle system 368 to position the cord 322 along the spool 361. In addition, the pulley tackle system 368 serves as an additional force mechanism, to retract or extend the cord 322 during operation of the motor 359, preferably serving as a leveraging mechanism during retraction of the cord 322.

The embodiments of the cylindrical transmission devices 332, 332c-332l shown in FIGS. 3B-3L are exemplary in nature, and may be varied without deviating from the scope of the invention. The cylindrical transmission device 332, 332c-332l may comprise a multitude of variations upon the design of a cord 322 wrapped around a transmission device.

The cylindrical transmission device 332, 332c-332l provides the benefit of producing a force transmission mechanism capable of varying an output force in response to a constant input. In addition, the cord 322 comprises a flexible force applicator, that may be easily cut with surgical or laparoscopic tools.

Figure 4A:
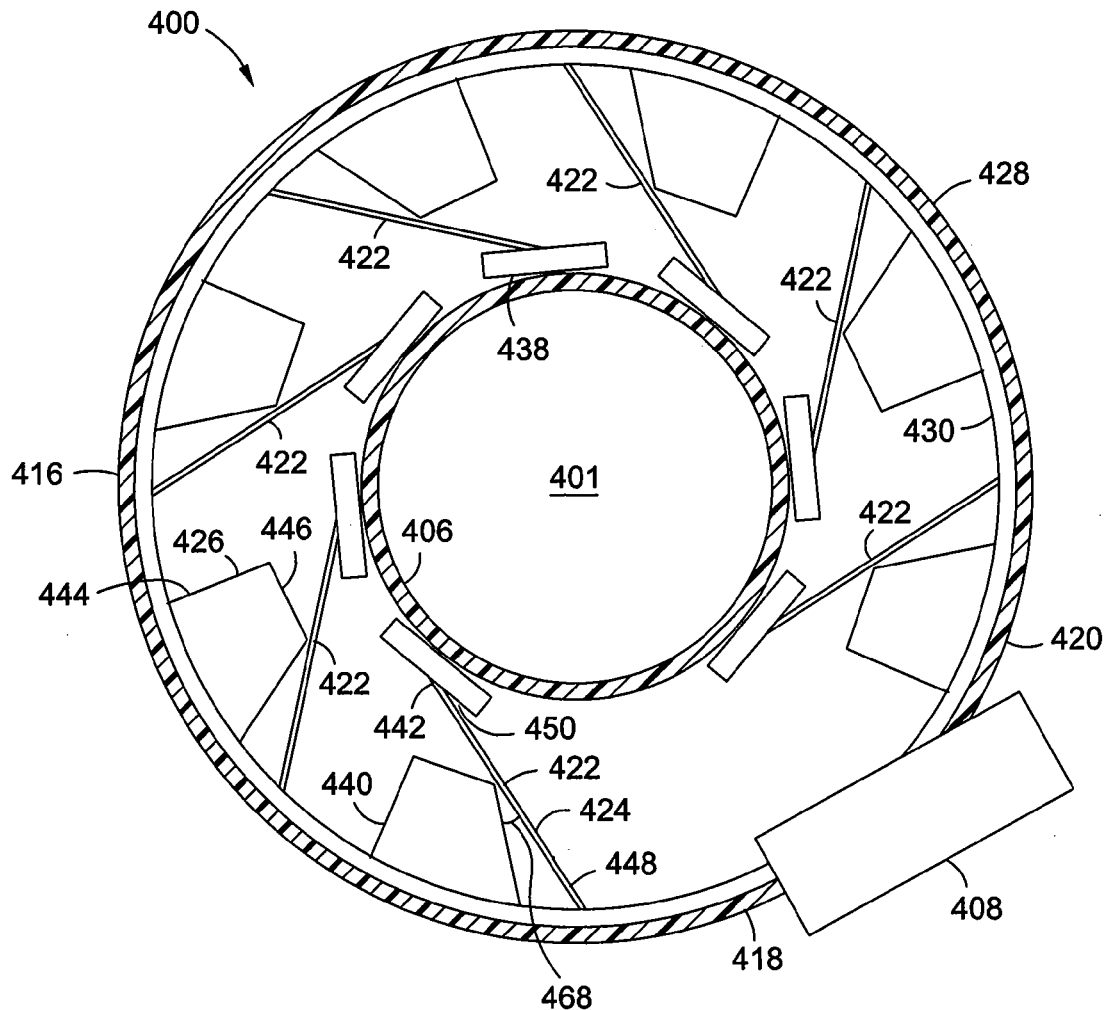
FIG. 4A illustrates a perspective view of a gastric band device according to an embodiment of the present invention.

FIG. 4A illustrates a gastric band device 400 including a plurality of force transmission devices, or slide supports 422. The gastric band device 400 includes a band 416 having a first end 418 and a second end 420 and a motor housing 408 coupled to the band 416. The band 416 is positioned in a loop around the portion of the patient's stomach, in a manner similar to the gastric band device 100 described in relation to FIG. 1A. The gastric band device 400 serves to provide a degree of constriction to a portion of the patient's stomach, similar to the gastric band device 100 described in relation to FIG. 1A.

The first end 418 of the band 416 and the second end 420 of the band 416 are coupled together to define the loop. The loop has a generally circular shape, to allow the band 416 to symmetrically fit around and encircle the portion of the patient's stomach. The motor housing 408 may be positioned between the first end 418 of the band 416 and the second end 420 of the band 416, to couple the ends 418, 420 together.

The loop shape of the band 416 defines an inner region 401 that is bounded by the band 416 and by the slide supports 422. The patient's stomach may be complementary with, or contained within, the inner region 401 formed by the loop. A flexible membrane 406 may be coupled to the band 416, or extend around the band 416, similar to the membrane 106 shown in FIG. 1A, to provide a degree of biocompatibility between the gastric band device 400 and the patient's body.

A plurality of slide supports 422 are coupled to the band 416 and extend in a direction towards the inner region 401 formed by the loop. Each slide support 422 has a first end 440 coupled to the band 416 and a second end 442 extending in a direction away from the band 416, towards the inner region 401. Each slide support 422 extends in a direction perpendicular to the portion of the band 416, towards the inner region 401, to apply a force substantially centripetal to the inner region 401. The slide supports 422 are configured to evenly apply a force radially towards the inner region 401.

Each slide support 422 is generally comprised from two force transmission supports, referred to as a first force transmission support, or a pivot lever 424, and a second force transmission support, or a lever support 426. The pivot lever 424 has a first end 448 coupled to the band 416 and a second end 450 extending in a direction away from the band 416, towards the inner region 401. The pivot lever 424 may comprise a rigid arm device, biased to deflect towards the lever support 426, or may comprise a spring with a spring force biased in the direction away from the inner region 401, and towards the lever support 426. The pivot lever 424 may be configured as a bar spring, or a non-helical spring being flexibly coupled to the band 416. The flexible coupling between the pivot lever 424 and the band 416 may produce a deflection of the pivot lever 424 in a direction away from the inner region 401 of the band 416, and towards the lever support 426.

The lever support 426 has a first end 444 coupled to the band 416 and a second end 446 extending in a direction away from the band 416, towards the inner region 401. The lever support 426 may comprise a rigid structure with a second end 446 that slidably contacts the pivot lever 424 and directs the pivot lever 424 in a direction towards the inner region 401 of the band 416. The lever support 426 may also be configured to direct the pivot lever 424 in a direction against the spring bias of the pivot lever 424, if the pivot lever 424 is configured as a spring.

The lever support 426 may have a wedge shape, including a sloped leading edge 470 (shown in FIG. 4B) directed towards the pivot lever 424. The wedge shape, or sloped shape allows the lever support 426 to define a stop position for the pivot lever 424, as more clearly shown in FIG. 4D. However, it is also understood that the shape of the lever support 426 may have any shape capable of directing the pivot lever 424 in a direction towards the inner region 401.

A pad 438 may be positioned at the second end 442 of the slide support 422. Similar to the pad 138 shown in FIG. 1B, the pad 438 may have a generally rectangular shape, and may be pivotally coupled to the second end 450 of the pivot lever 424. In addition, the pad 438 may also have any equivalent shape that offers a large surface area to transmit a force between the slide support 422 and the patient's stomach. The pad 438 has a large surface area that extends the force exerted by the slide support 422 over a larger surface area than possible without the pad. The pad 438 distributes the force exerted by the slide support 422, for example, to prevent the patient's stomach from being punctured by the force exerted by the slide support 422. The pad 438 may be made from a deformable material, such as a soft plastic, to help cushion the force of the slide support 422. In addition, the pad 438 may be made from a non-deformable material, such as a hard plastic, to rigidly transfer the force of the slide support 422 without deformation. The pad 438 may also be integrated within the membrane 406, and not directly coupled to the slide support 422.

The band 416, similar to the band 116 shown in FIG. 1A, may comprise two bands, including a first band 430, equivalently referred to as an inner band 430, and an second band 428, equivalently referred to as an outer band 428. In addition, similar to the band 116 shown in FIG. 1A, the inner band 430 may be positioned concentric with the outer band 428. Both ends of the outer band 428 may be firmly fixed to the motor housing 408, and the inner band 430 may be slidably coupled to an interior surface of the outer band 428, or the surface facing the inner region 401. An end of the inner band 430 may not be directly coupled to the motor housing 408, and an opposite end of the inner band 430 may be coupled to a motor (not shown) contained within the motor housing 408. Thus, the inner band 430 may slide with respect to the outer band 428. The motor housing 408 may contain any of the drive systems and/or motor systems shown in FIGS. 2A-2O, and the gastric band device 400 may be suitably modified to allow the drive systems and/or the motor systems to drive the slide supports 422. The motor housing 408 may also contain any other style of known motor capable of producing effective operation as contemplated by the device 400.

The first end 448 of the pivot lever 424 may be coupled to the outer band 428 and the first end 444 of the lever support 426 may be coupled to the inner band 430. Thus, when the inner band 430 is slid relative to the outer band 428, the lever support 426 may move towards or away from the pivot lever 424. The movement of the lever support 426 varies the distance between the pivot lever 424 and the lever support 426, and accordingly varies a distance of the second end 442 of the slide support 422 from the band 416.

The pivot lever 424 and the lever support 426 slidably contact each other at an angle 468. A change in the distance between the pivot lever 424 and the lever support 426 will vary a size of the angle 468. In addition, a change in the angle 468 will vary the distance of the slide support 422 from the band 416, which will correspondingly vary a degree of constriction applied towards the inner region 401, and will accordingly vary a degree of constriction applied to the patient's stomach.

Each slide support 422 may be spaced an equidistant from another slide support 422. The number of slide supports 422 may vary from one slide support 422 to as many slide supports 422 as may feasibly fit within the band 416 to produce an equivalent operation of the gastric band device 400. A single slide support 422 may be positioned within the band 416 to constrict the patient's stomach.

Figure 4B:
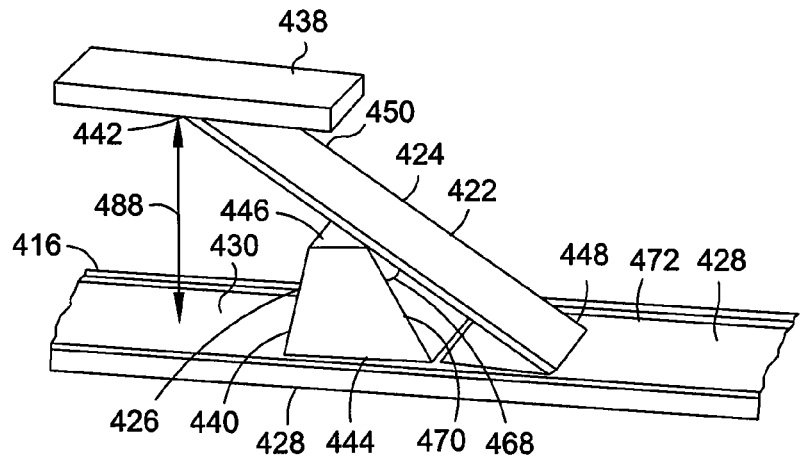
FIGS. 4B-4F illustrate perspective views of force transmission devices according to embodiments of the present invention.
Figure 4C:
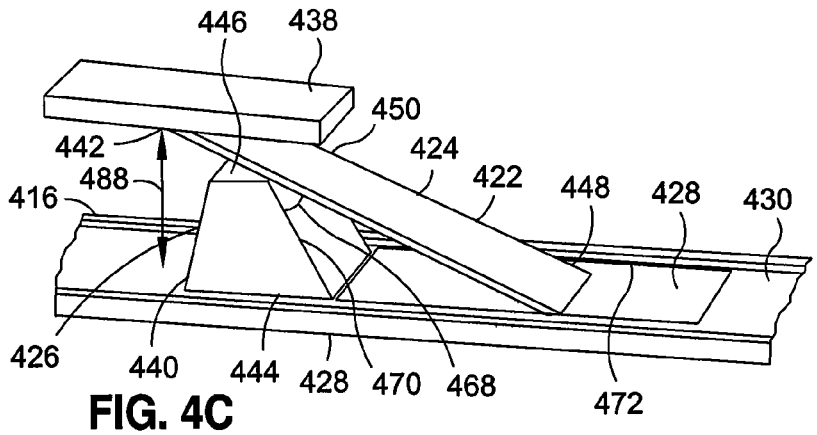
Figure 4D:
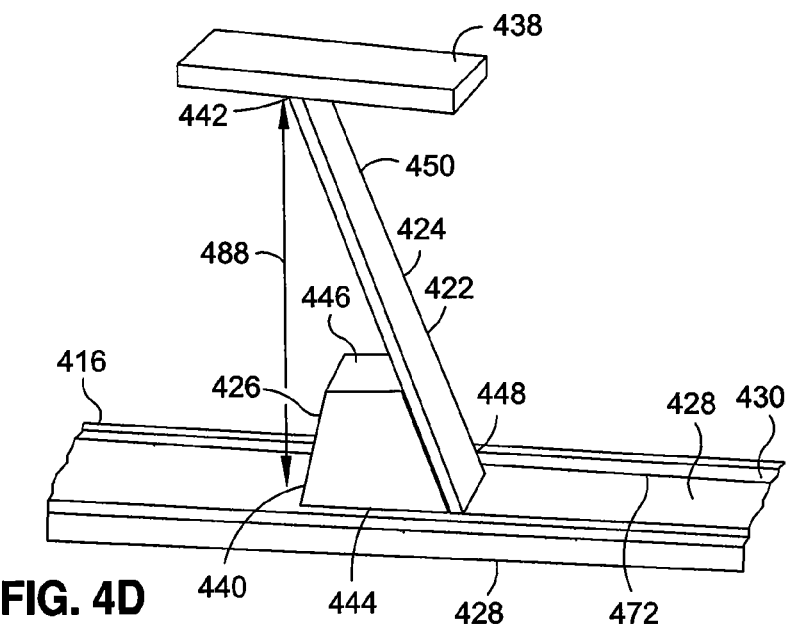

FIGS. 4B-4D illustrate the operation of the slide support 422, as shown in FIG. 4A, to vary a degree of constriction applied to the patient's stomach. FIG. 4B illustrates the slide support 422 in a partially deployed position. The lever support 426 is positioned at a distance from the pivot lever 424 and slidably contacts the pivot lever 424. Thus, in this embodiment, the lever support 426 is not directly coupled to the pivot lever 424. The bias force of the pivot lever 424 that is directed towards the lever support 426, maintains the contact between the pivot lever 424 and the lever support 426. The contact point between the lever support 426 and the pivot lever 424 forms an angle 468, which defines a distance 488 of the second end 442 of the slide support 422 from the band 416.

The pivot lever 424, as discussed in relation to FIG. 4A, may be flexibly coupled to the outer band 428. In other words, the pivot lever 424 may flex relative to the outer band 428 when the lever support 426 presses against the pivot lever 424. The pivot lever 424 may also be integral with, or a crafted portion of the outer band 428. In addition, as discussed in relation to FIG. 4A, the pivot lever 424 may comprise a spring-like device, biased to exert a force against the lever support 426. In the embodiment shown in FIG. 4B, a slot 472 in the inner band 430 may allow the inner band 430 to freely slide relative to the outer band 428, and accordingly allow the slide support 422 to slide relative to the pivot lever 424. A portion of the outer band 428 may curl over the inner band 430 to slidably secure the bands 430, 428 to each other.

FIG. 4C illustrates the slide support 422 in the retracted or undeployed state. In this configuration, the lever support 426 is positioned at a distance far from the flexible attachment point of the pivot lever 424 to the outer band 428. The angle 468 between the pivot lever 424 and the lever support 426 is large, and the corresponding distance 488 of the second end 422 of the slide support 422 from the band 416 is small. Thus, at this position, the degree of constriction applied by the slide support 422 is at a relative minimum.

FIG. 4D illustrates the slide support 422 in a fully deployed position. In this configuration, the lever support 426 has moved to a position closer to the pivot lever 424 than shown in FIG. 4B or 4C. Accordingly, the second end 442 of the slide support 422 has been raised to a distance above the band 416 greater than shown in FIGS. 4B and 4C. In this configuration, the utility of the wedge shape of the lever support 426 is demonstrated. The lever support 426 has a substantially flat surface, or a sloped leading edge 470 (shown in FIGS. 4B and 4C) positioned on the leading side of the lever support 426. The leading edge 470 is angled, or is offset from an angle perpendicular to the surface of the band 416. The offset angle allows the leading edge 470 to press against the pivot lever 424 flush. When the flat surface is flush against the pivot lever 424, the lever support's 426 mechanical advantage is greatly reduced, and prevents further movement of the pivot lever 424. Thus, FIG. 4D illustrates the locking position for the pivot lever 424, where the pivot lever 424 may be forced no further. The angle of the leading edge 470 may be varied to produce different locking positions.

Figure 4E:
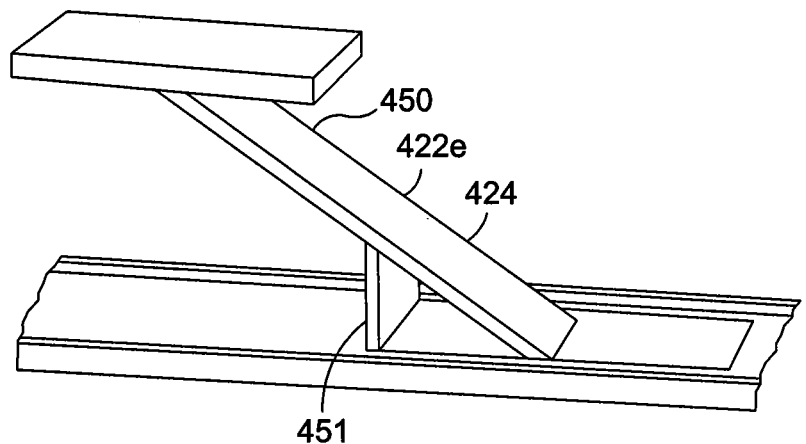

FIG. 4E illustrates a slide support 422e including a substantially vertical, or non-wedge shaped lever support 451. The substantially vertical shape of the lever support 451 still provides a force and contact point between the lever support 451 and the pivot lever 424. However, this substantially vertical shape does not offer the locking point as discussed above in relation to FIG. 4D. Accordingly, it is understood that the lever support 451 may have numerous varied shapes that serve to deflect the pivot lever 424 in a direction towards the inner region 401.

Figure 4F:
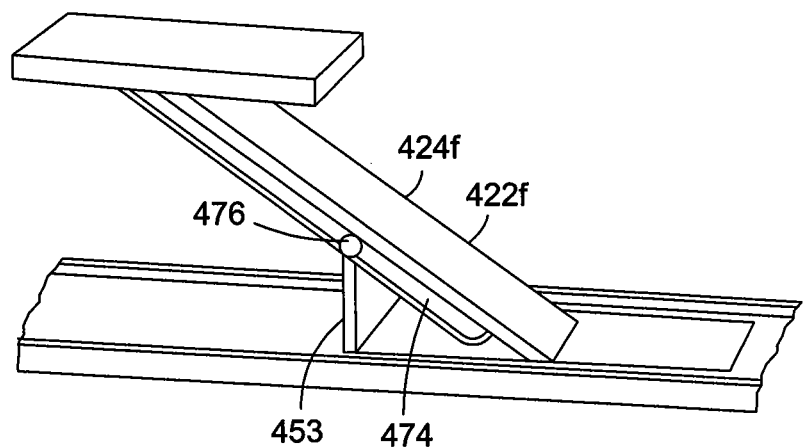

FIG. 4F illustrates a slide support 422f including a pivot lever 424f being slidably coupled with a lever support 453 via a slide linkage 474. The slide linkage 474 comprises a grooved slot formed as a portion of the pivot lever 424f. The lever support 453 contains a slide link 476 that slides along the slide linkage and may exert a force against the pivot lever 424f towards or away from the lever support 453. Thus, in this configuration, the pivot lever 424f need not be biased to exert a force against the lever support 453, because the engagement between the pivot lever 424f and the lever support 453 may drive the pivot lever 424f towards and away from the lever support 453.

The embodiments of the gastric band device 400 shown in FIGS. 4A-4F are exemplary in nature, and may be varied without deviating from the scope of the invention. The slide supports 422, 422e, 422f may comprise any mechanism wherein a degree of constriction is varied based on two sliding force transmission supports. In addition, the motor system may be configured to rotate one band, or both bands, in opposite directions.

The gastric band device 400 and the slide supports 422, 422e, 422f discussed in relation to FIGS. 4A-4F include multiple benefits, including a simplistic design and operation. Each slide support only contains two primary components. In addition, the outer diameter of the band 416 does not vary during operation of the motor, providing a firm structure for the device, similar to the gastric band device 100 discussed in relation to FIGS. 1A-1S. Furthermore, the force exerted by the slide supports is substantially centrally distributed to the patient's stomach, providing an even, centripetal, distribution of force.

Figure 5A:
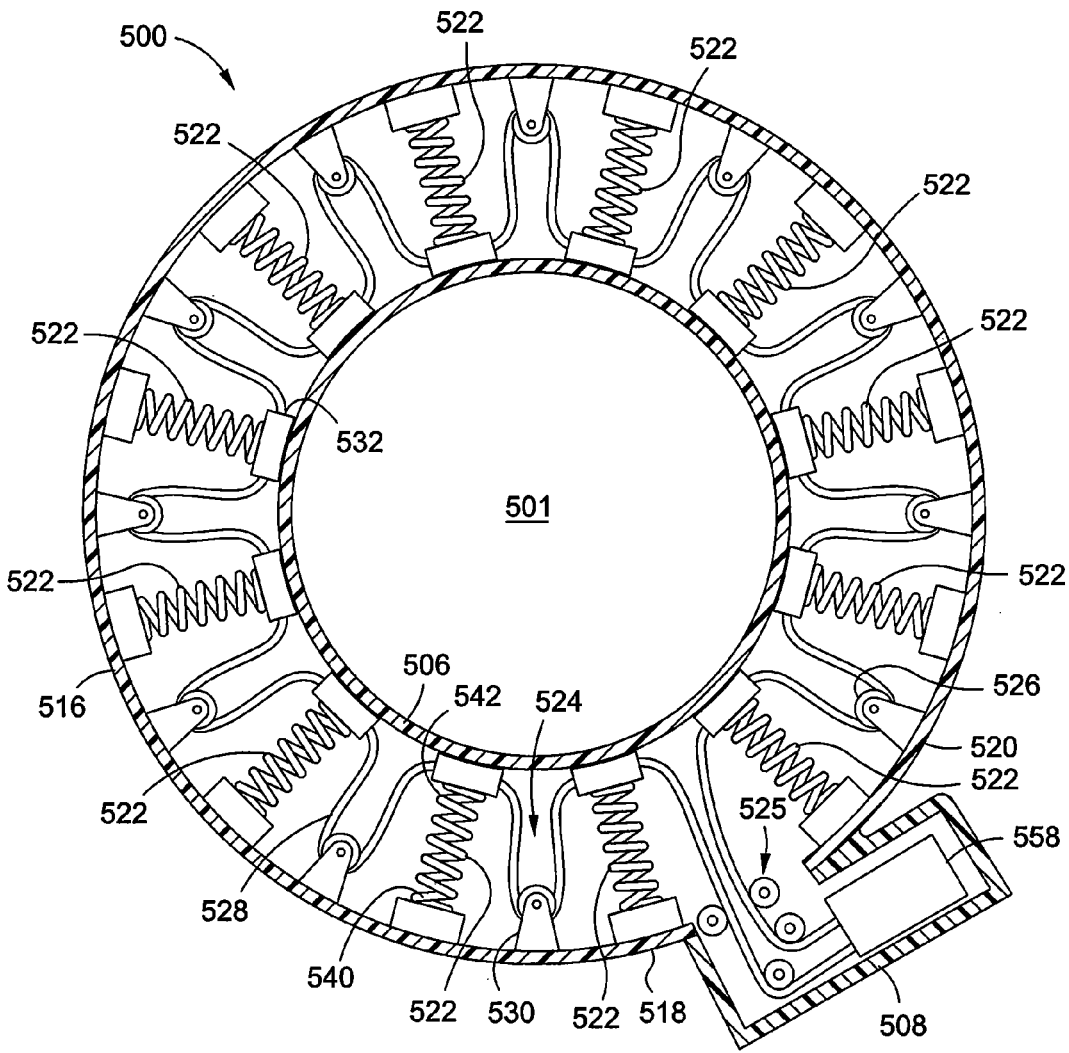
FIG. 5A illustrates a perspective view of a gastric band device according to an embodiment of the present invention.

FIG. 5A illustrates a gastric band device 500 including a plurality of force transmission devices, or springs 522, and a spring compression system 524. The gastric band device 500 also includes a band 516 having a first end 518 and a second end 520 and a motor housing 508 coupled to the band 516. The band 516 is positioned in a loop around a portion of the patient's stomach, in a manner similar to the gastric band device 100 described in relation to FIG. 1A. The gastric band device 500 serves to provide a degree of constriction to a portion of the patient's stomach, similar to the gastric band device 100 described in relation to FIG. 1A.

The first end 518 of the band 516 and the second end 520 of the band 516 are coupled together to define the loop. The loop has a generally circular shape, to allow the band 516 to symmetrically fit around and encircle a portion of the patient's stomach. The motor housing 508 may be positioned between the first end 518 of the band 516 and the second end 520 of the band 516, to couple the ends 518, 520 together.

The loop shape of the band 516 defines an inner region 501 that is bounded by the band 516 and by the springs 522. The patient's stomach may be complementary with the inner region 501 formed by the loop. A flexible membrane 506 may be coupled to the band 516, or extend around the band 516, similar to the membrane 106 shown in FIG. 1A, to provide a degree of biocompatibility between the gastric band device 500 and the patient's body.

Each spring 522 has two ends, a first end 540 and a second end 542. The first end 540 of the spring 522 couples to the band 516 and the second end 542 of the spring 522 extends from the band 516 in a direction towards the inner region 501 formed by the loop. The spring 522 extends towards the inner region 501 in a direction substantially perpendicular to the portion of the band 516 to which the spring 522 is connected. The springs 522 produce a substantially central force directed towards the inner region 501, forcing the inner region 501 in a centripetal direction.

The spring 522 may be a coil spring, or a helical spring, that is biased to direct a force towards the inner region 501 of the band, and accordingly apply a degree of constriction to the inner region 501, and the patient's stomach. The spring 522 may have any other equivalent shape that produces a force directed towards the inner region 501 of the band 516.

Figure 5B:
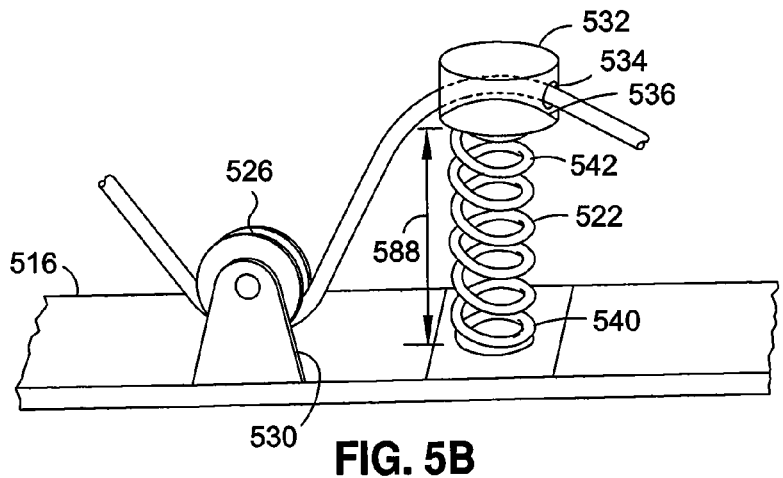
FIG. 5B illustrates a perspective view of a force transmission device according to an embodiment of the present invention.

Referring to FIG. 5B, a pad-like device, or spring cap 532 is positioned at the second end 542 of the spring 522. The spring cap 532 may have a generally circular shape, and distributes the force from the spring 522 to the patient's stomach. The spring cap 532 may additionally have an interior cavity portion formed by the connection of two apertures 534 (one aperture not shown in FIG. 5B), that allow the spring compression system 524 to engage with the spring 522. The interior cavity portion may contain a cord threader 536, indicated in FIG. 5B as a smooth, bump-like structure, that allows the spring compression system 524 to thread through the spring cap 532 substantially without friction.

Referring back to FIG. 5A, the spring compression system 524 may comprise a cord 528, a motor system 558, and a plurality of pulley wheels 526, with each pulley wheel 526 being positioned between two springs 522. The pulley wheels 526 may have a first end and a second end, a first end of the pulley wheel 526 coupled to the band through a pulley wheel mounting 530 and a second end of the pulley wheel 526 extending in a direction towards the inner region 501 of the band 516. A pulley routing system 525 may route the cord 528 to the motor system 558.

Referring to FIGS. 5A and 5B, the cord 528 may pass through the spring cap 532 and under an adjacent pulley wheel 526. The cord 528 then passes through the spring cap 532 of an adjacent spring 522, and again through an adjacent pulley wheel 526. In this manner, the cord 528 is routed through all pulley wheels 526 and all spring caps 532.

The cord 528 has a first end and a second end, the first end engages with the motor system 558 located in the motor housing 508. The second end may also be coupled to the motor system 558, or may be fixedly attached to a portion of the band 516.

In operation, the motor system 558 may retract both ends, or one end of the cord 528 to increase the size of the inner region 501 and decrease the degree of constriction applied by the springs 522 to the patient's stomach. The shortened length of the cord 528 compresses the springs 522, causing a distance 588 of the second end 542 of the springs 522 from the band 516 to be decreased, consequently increasing the size of the inner region 501. To decrease the size of the inner region 501, the motor system 558 extends the length of cord 528. The springs 522 then apply a force in a direction towards the inner region 501 of the band, causing the stomach to compress. The outer diameter of the band 516 does not vary during operation of the motor.

The motor system 558 may comprise any of the motor systems shown in FIGS. 2A-2O, and the gastric band device 500 may be suitably modified to allow a desired configuration of the motor system 558 to drive the cord 528. In addition, any of the cylindrical transmission devices shown in FIGS. 3A-3L may be incorporated into the gastric band device 500, and the gastric band device may be suitably modified to incorporate the cylindrical transmission device. Furthermore, the motor system 558 may also contain any other style of known motor capable of producing effective operation as contemplated by the device 500.

The embodiment shown in FIGS. 5A and 5B is exemplary in nature, and may be modified without deviating from the scope of this invention. For example, the pulley wheels 526 and the spring caps 532 may be suitably modified with any other equivalent routing system to allow the cord 528 to engage the springs 522. In addition, a plurality of motors or actuators may be used to drive each spring 522 individually. Furthermore, the routing of the cord 528 may be changed to produce an equivalent operation.

The number of springs 522 may vary from one spring 522 to as many springs 522 as may feasibly fit within the band 516 to produce an equivalent operation of the gastric band device 500. A single spring 522 may be positioned within the band 516 to constrict the patient's stomach.

The gastric band device 500 discussed in relation to FIGS. 5A and 5B include multiple benefits, including a simplistic design and operation. Each spring 522 is biased to apply a force toward the inner region 501. Thus, the constrictive force applied to the patient's stomach is increased by the number of springs 522 or an increased spring force offered by each spring 522. In addition, the outer diameter of the band 516 does not vary during operation of the motor system, providing a firm structure for the device, similar to the gastric band device 100 discussed in relation to FIGS. 1A-1S. Furthermore, the force exerted by the springs 522 is substantially centrally distributed to the patient's stomach, providing an even distribution of force.

Figure 6A:
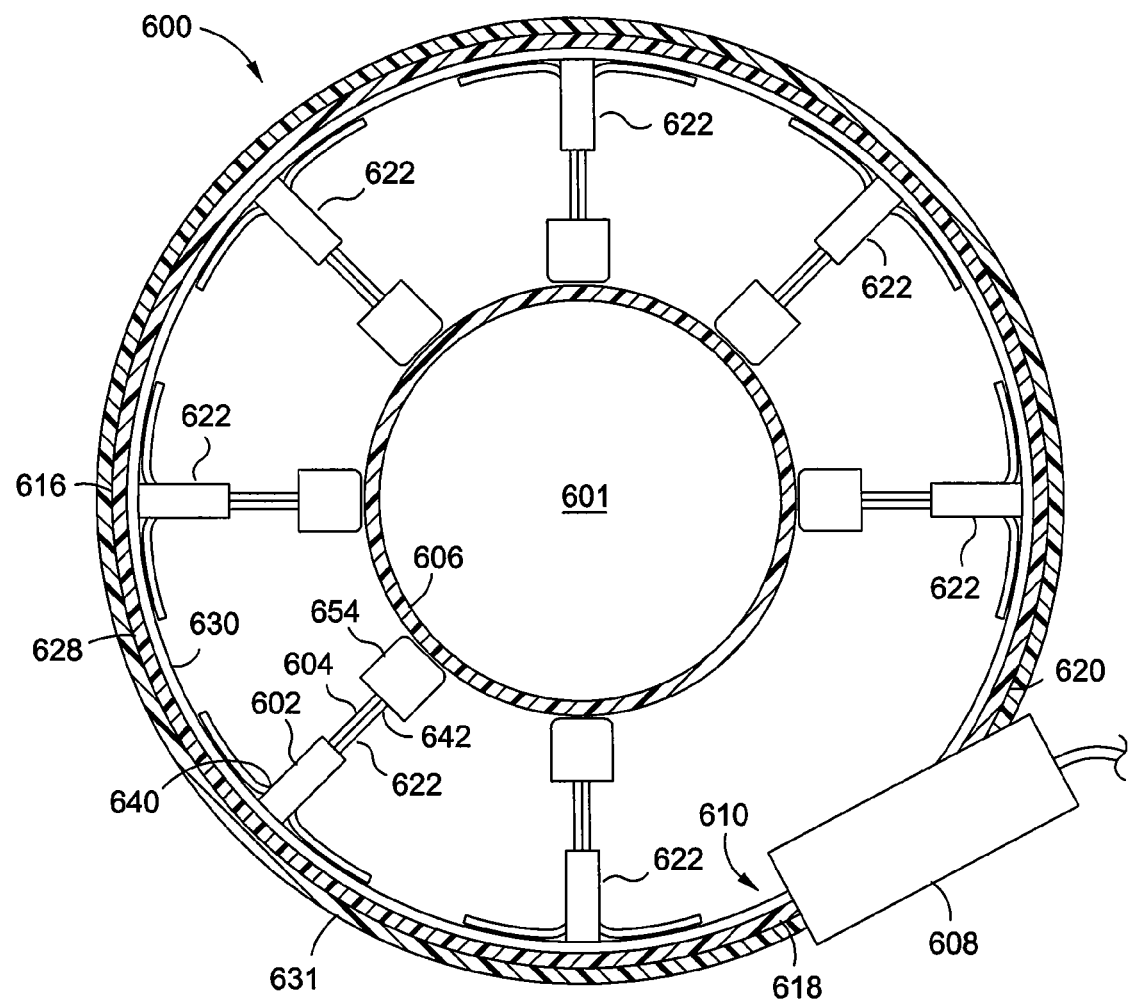
FIG. 6A illustrates a perspective view of a gastric band device according to an embodiment of the present invention.

FIG. 6A illustrates an embodiment of a gastric band device 600 including a plurality of force transmission devices, or mechanical actuators 622, and a mechanical actuator control system 610.

The gastric band device 600 includes a band 616 having a first end 618 and a second end 620 and a motor housing 608 coupled to the band 616. The band 616 is positioned in a loop around the portion of the patient's stomach, in a manner similar to the gastric band device 100 described in relation to FIG. 1A. The gastric band device 600 serves to provide a degree of constriction to a portion of the patient's stomach, similar to the gastric band device 100 described in relation to FIG. 1A.

The first end 618 of the band 616 and the second end 620 of the band 616 are coupled together to define the loop. The loop has a generally circular shape, to allow the band 616 to symmetrically fit around and encircle the portion of the patient's stomach. The motor housing 608 may be positioned between the first end 618 of the band 616 and the second end 620 of the band 616, to couple the ends 618, 620 together.

The loop shape of the band 616 defines an inner region 601 that is bounded by the band 616 and by the mechanical actuators 622. The patient's stomach may be complementary with the inner region 601 formed by the loop. A flexible membrane 606 may be coupled to the band 616, or extend around the band 616, similar to the membrane 106 shown in FIG. 1A, to provide a degree of biocompatibility between the gastric band device 600 and the patient's body.

Each mechanical actuator 622 has a first end 640 coupled to the band 616 and a second end 642 extending from the band 616 in a direction towards the inner region 601. The second end 642 applies a degree of constriction to the inner region 601, and accordingly to the patient's stomach. The mechanical actuators 622 may be spaced equidistant from each other along the band 616. The mechanical actuators 622 extend in a direction substantially perpendicular to the surface of the band 616 to which the mechanical actuator 622 is connected. This configuration allows each mechanical actuator 622 to exert a force substantially centripetal to the inner region 601.

Each mechanical actuator 622 comprises a columnar riser device 604 slidably coupled to a base 602. The base 602 couples to the band 616, and the columnar riser device 604 is directed to apply a degree of constriction to the inner region 601. The columnar riser device 604 slides relative to the base 602 to vary the degree of constriction applied by the columnar riser device 604 to the inner region 601. A columnar riser cap 654 may be positioned at the second end of the mechanical actuator 622.

The mechanical actuator control system 610 may comprise a motor system contained within the motor housing 608 and comprising any of the motor systems shown in FIGS. 2A-2O. Of particular note is the motor system 258b, shown in FIG. 2B. The motor system 258b is capable of driving two bands in opposite directions. Furthermore, the mechanical actuator control system 610 may also contain any other style of known motor capable of producing effective operation as contemplated by the device 600. The gastric band device 600 may be suitably modified to allow a desired motor system to drive the mechanical actuators 622.

The band 616 may comprise three bands, including an outer band 631, a middle band 628, and an inner band 630. The inner band 630 may be equivalently referred to as the first band 630, the middle band 628 may be equivalently referred to as the second band 628, and the outer band 631 may be equivalently referred to as the third band 631. The outer band 631 may extend around the patient's stomach. The inner band 630 may be positioned concentric with the outer band 631, and within an interior region of the outer band 631. The middle band 628 may be positioned between the outer band 631 and the inner band 630. The ends of the outer band 631 may be fixedly attached to the motor housing 608. However, the ends of the inner band 630 and the middle band 628 may not be directly coupled to the motor housing 608. Rather, one end of the inner band 630 and one end of the middle band 628 may be coupled to the motor system contained within the motor housing 608. The motor system may be configured similarly to the motor system 258b, shown in FIG. 2B, being capable of driving two bands in opposite directions. The mechanical actuator control system 610 may thus be able to drive the inner band 630 and middle band 628 in opposite directions, while retaining the outer band 631 relatively motionless.

Figure 6B:
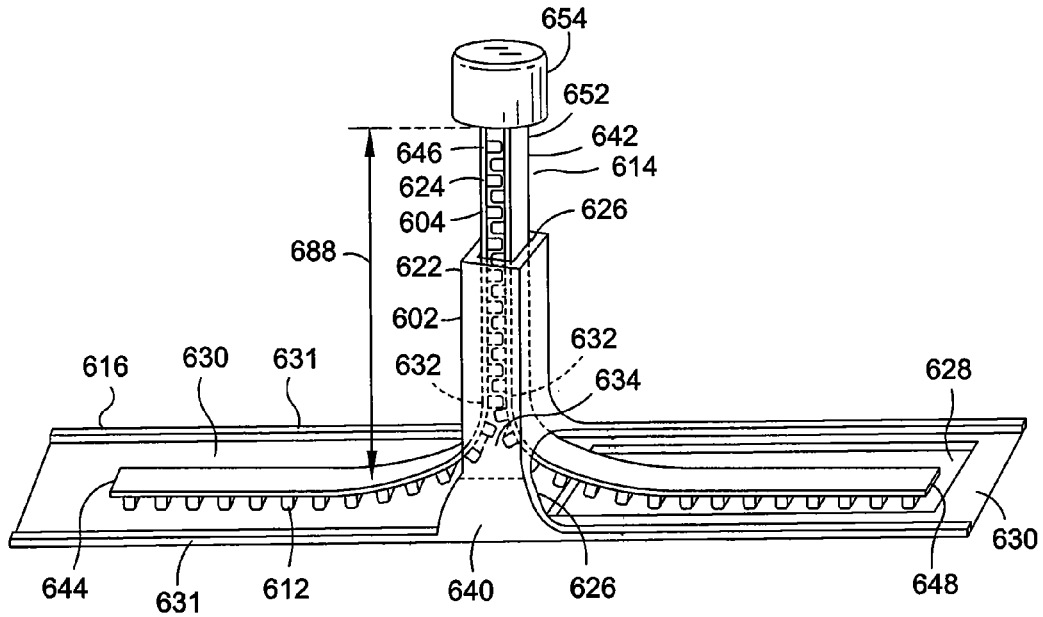
FIGS. 6B-6C illustrate perspective views of force transmission devices according to embodiments of the present invention.

Referring to FIG. 6B, the columnar riser device 604 is formed from two flexible members 614 and 624, referred to as a first flexible member 614 and a second flexible member 624. The flexible members 614, 624 combine together within the base 602 to form the columnar riser device 604. The flexible members 614, 624 each include a combining device, or teeth 612 that mate the first flexible member 614 to the second flexible member 624. The teeth 612 connect the flexible members 614, 624 together.

The first flexible member 614 comprises a flexible strap-like structure having two surfaces, one surface being smooth and a second surface including the combining device, or teeth 612. The teeth 612 may comprise ridges forming a half-zipper structure. The teeth 612 may be spaced equally apart along the length of the first flexible member 614. The teeth 612 may be structured to engage with similar teeth 612 located on one side of the second flexible member 624.

The second flexible member 624 similarly comprises a flexible strap-like structure having two surfaces, one surface being smooth and a second surface including the combining device or teeth 612. The teeth 612 are structured to interlock together when the two flexible members 614, 624 are combined.

A first end 648 of the first flexible member 614 couples to the middle band 628. A second end 652 of the first flexible member 614 extends in a direction towards the inner region 601. Similarly, a first end 644 of the second flexible member 624 couples to the inner band 630. A second end 646 of the second flexible member 624 extends in a direction towards the inner region 601. The second ends 652, 646 of the flexible members 614, 624 comprise the second end 642 of the mechanical actuator 622 and a second end of the columnar riser device 604. In addition, the first ends 648, 644 of the flexible members 614, 624 particularly the portions of the flexible members 614, 624 extending through a central cavity 634 in the base 602, define a first end of the columnar riser device 604. The first end of the columnar riser device 604 is thus slidably coupled to the base 602. The columnar riser cap 654 may be positioned at the second end of the columnar riser device 604, and may connect the flexible members 614, 624.

The base 602 has a generally columnar shape. One end of the base 602 connects to the outer band 631 and a second end of the base 602 extends in a direction towards the inner region 601 of the band 616 (shown in FIG. 6A). The base 602 includes a central cavity 634 and two sidewalls 632 positioned on opposite sides of the central cavity 634, and defines the boundaries of the central cavity 634. The two sidewalls 632 compress the first flexible member 614 and the second flexible member 624 together, causing the combining devices, or teeth 612 to engage. A base opening 626 allows the flexible members 614, 624 to enter the central cavity 634. The two flexible members 614, 624 lock together to form the columnar riser device 604. A base opening 626 near the top of the base 602 allows the columnar riser device 604 to exit the base 616.

A distance 688 of the second end 642 of the mechanical actuator 622 from the band 616 is defined by the length of the flexible members 614 that have passed through the base 602. The distance 688 of the second end 642 of the mechanical actuator 622 increases if a greater length of the flexible members 614 624 has passed through the base 602 in a direction towards the inner region 601.

Because the second end 652 of the first flexible member 614 and the second end 646 of the second flexible member 624 are connected to the respective middle band 628 and inner band 630, the mechanical actuator control system 610 may independently drive the bands 628, 630 in opposite directions to vary a distance 688 of the mechanical actuator 622 from the band 616. If the flexible members 614, 624 are drawn together, the distance 688 increases, and the degree of constriction to the patient's stomach correspondingly increases. If the flexible members 614, 624 are drawn apart, the distance 688 decreases. It is noted the distance 688 of the mechanical actuator 622 from the band 616 corresponds to the distance of the second end of the columnar riser device 604 from the band 616.

The columnar riser device 604 formed by the two flexible members 614, 624 has a rigid structure caused by the engagement of the members 614, 624. The teeth 612 form a rigid interior section of the columnar riser device 604 that prevents the columnar riser device 604 from flexing in a direction perpendicular to the portion of the band 616 to which the base 602 is fixed.

Figure 6C:
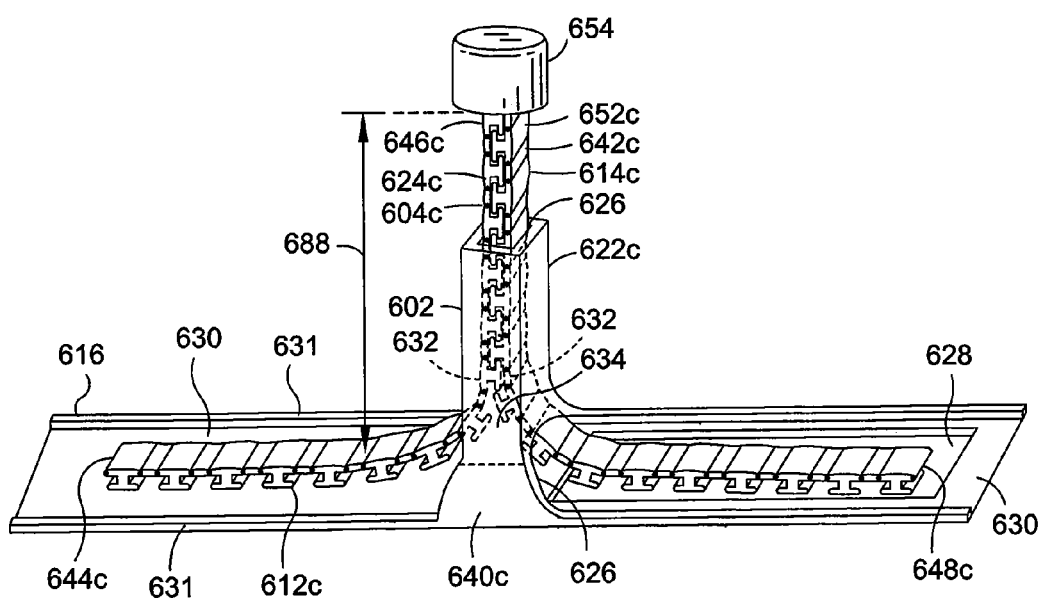

FIG. 6C illustrates a varied shape of the flexible members 614c, 624c and the teeth 612c. In this embodiment, similar to the embodiment shown in FIG. 6B, the mechanical actuator 622c has a first end 640c coupled to the band 616 and a second end 642c of the mechanical actuator 622c extending away from the band 616. The columnar riser device 604c is formed from flexible members 614c, 624c having respective first ends 648c, 644c and second ends 652c, 646c. However, the flexible members 614c, 624c in this embodiment form a chain-like structure comprising a plurality of chain links. The chain links combine in the base 602 to form the rigid columnar riser device 604c. The teeth 612c are coupled to the chain links that comprise t-shaped flanges configured to combine together.

The embodiments shown in FIGS. 6A-6C are exemplary in nature, and may be modified without deviating from the scope of this invention. For example, the flexible members 614, 624, 614c, 624c may be suitably modified with any other equivalent structures that form a columnar riser device 604, 604c. In addition, the columnar riser device 604, 604c may comprise a single piston-like device slidably coupled to a base 602, and need not be formed from two flexible members. The columnar riser device 604, 604c may be a solid rod slidably coupled to a base. In addition, the configuration of bands may be modified to provide equivalent operation. Furthermore, the mechanical actuator control system 610 may comprise a single motor or a series of motors each controlling an individual mechanical actuator, or a combination of actuators. Each mechanical actuator 622, 622c may have a dedicated control mechanism.

The number of mechanical actuators 622, 622c may vary from one mechanical actuator 622, 622c to as many mechanical actuators 622, 622c as may feasibly fit within the band 616 to produce an equivalent operation of the gastric band device 600. A single mechanical actuator 622, 622c may be positioned within the band 616 to constrict the patient's stomach.

The gastric band device 600, discussed in relation to FIGS. 6A-6C, includes multiple benefits, including a simplistic design and operation. Each mechanical actuator 622, 622c is configured to move in response to the relative motion of the bands 628, 630. However, during operation of the motor, the outer diameter of the band 616 does not vary, providing a firm structure for the device, similar to the gastric band device 100 discussed in relation to FIGS. 1A-1S. Furthermore, the force exerted by the mechanical actuators 622, 622c is substantially centrally distributed to the patient's stomach, providing an even distribution of force. In addition, the engagement of the teeth 612, 612c may provide an internal support structure that stabilizes the mechanical actuators 622, 622c, particularly during times the motor is not in operation.

Figure 7A:
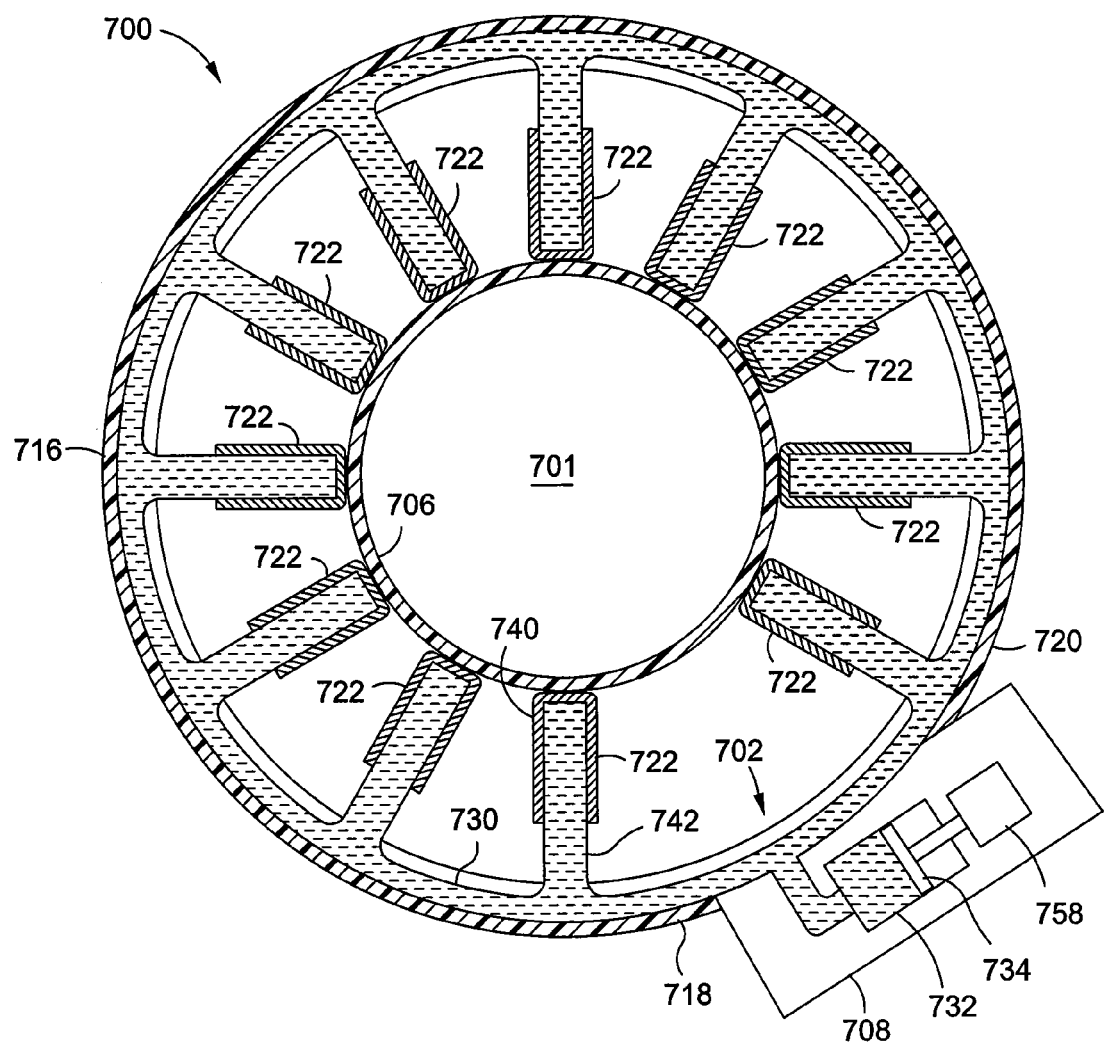
FIG. 7A illustrates a perspective view of a gastric band device according to an embodiment of the present invention.

FIG. 7A illustrates an embodiment of a gastric band device 700 including a plurality of force transmission devices, or hydraulic piston actuators 722, and a hydraulic control system 702. The gastric band device 700 includes a band 716 having a first end 718 and a second end 720 and a pump housing 708 coupled to the band 716. The band 716 is positioned in a loop around a portion of the patient's stomach, in a manner similar to the gastric band device 100 described in relation to FIG. 1A. The gastric band device 700 serves to provide a degree of constriction to a portion of the patient's stomach, similar to the gastric band device 100 described in relation to FIG. 1A.

The first end 718 of the band 716 and the second end 720 of the band 716 are coupled together to define the loop. The loop has a generally circular shape, to allow the band 716 to symmetrically fit around and encircle a portion of the patient's stomach. The pump housing 708 may be positioned between the first end 718 of the band 716 and the second end 720 of the band 716, to couple the ends 718, 720 together.

The loop shape of the band 716 defines an inner region 701 that is bounded by the band 716 and by the hydraulic piston actuators 722. The patient's stomach may be complementary with the inner region 701 formed by the loop. A flexible membrane 706 may be coupled to the band 716, or extend around the band 716, similar to the membrane 106 shown in FIG. 1A, to provide a degree of biocompatibility between the gastric band device 700 and the patient's body.

The hydraulic piston actuators 722 comprise hydraulically-controlled cylinders having a first end 742 and a second end 740. The first end 742 of the hydraulic piston actuator 722 is coupled to the band 716 and the second end 740 of the hydraulic piston actuator 722 extends in a direction towards the inner region 701. The hydraulic piston actuators 722 extend in a direction substantially perpendicular to the surface of the band 716 to which the hydraulic piston actuator 722 is connected. This configuration allows each hydraulic piston actuator 722 to exert a force substantially centripetal to the inner region 701.

The hydraulic piston actuators 722 may comprise a base cylinder 704 and a cylinder cap 712, as shown in FIG. 2. The hydraulic piston actuator 722 may have an inner cavity configured to be filled with a suitable hydraulic fluid. The hydraulic control system 702 comprises a motor system 758, a plunger 734, a fluid reservoir 732, and a fluid conduit 730. The motor system 758 is configured to drive the plunger 734 in a direction. The motor system 758 may comprise any of the motor systems shown in FIGS. 2A-2O. The gastric band device 700 may be suitably modified to allow any of the motor system shown in FIGS. 2A-2O drive the plunger 734. Furthermore, the motor system 758 may also contain any other style of known motor capable of producing effective operation as contemplated by the device 700.

The motor system 758 may be coupled to the plunger 734, which presses against fluid contained in the fluid reservoir 732. The pressure exerted by the plunger 734 is conveyed to the hydraulic piston actuators 722 via a fluid conduit 730 extending around the periphery of the band 716. In operation, the plunger 734 slides within the fluid reservoir 732 to either pressurize or depressurize the fluid contained within the hydraulic piston actuators 722. The pressure of the fluid defines the distance of the hydraulic piston actuators 722 from the band 716, and accordingly defines the degree of constriction applied to the patient's stomach.

Figure 7B:
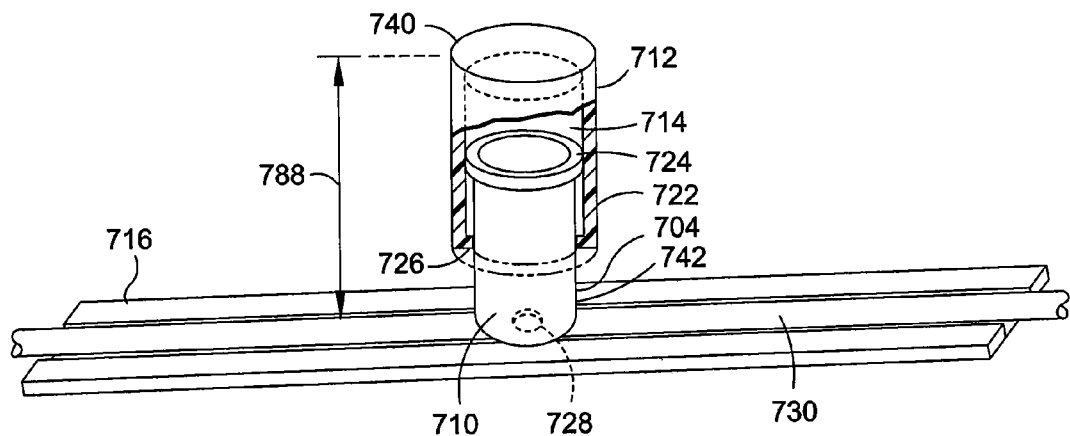
FIG. 7B illustrates a perspective view of a force transmission device according to an embodiment of the present invention.

FIG. 7B illustrates a close up perspective view of a hydraulic piston actuator 722 as shown in FIG. 7A. FIG. 7B illustrates the hydraulic piston actuator 722 comprising a cylinder cap 712 extending around a base cylinder 704. The cylinder cap 712 forms a hollow covering over the base cylinder 704. The cylinder cap 712 includes an interior fluid chamber 714 configured to be filled with a hydraulic fluid supplied by the hydraulic control system 702, shown in FIG. 7A. A seal lip 726 extends as a flange from the cylinder cap 712 and prevents the cylinder cap 712 from disengaging from the base cylinder 704 during operation.

The base cylinder 704 includes a cylindrically shaped vessel having a central fluid chamber 710 for receiving fluid from the hydraulic control system 702, shown in FIG. 7A. The fluid in the central fluid chamber 710 and the interior fluid chamber 714 intermixes, to form a central fluid filled cavity. The fluid chambers 710, 714 are in fluid communication with each other. A seal ring 724 extends from the base cylinder 704, and prevents the hydraulic fluid from leaking from the interior fluid chamber 714 and the central fluid chamber 710. The seal ring 724 may comprise an o-ring or other equivalent sealing device.

The cylinder cap 712 may be slidably engaged with the base cylinder 704, to slide along the length of the outer surface of the base cylinder 704. The cylinder cap 712 slides in accordance with the amount of fluid contained within the central fluid chamber 710 and the interior fluid chamber 714. If more fluid is contained within the chambers 710, 714, the cylinder cap 712 will slide to a greater distance from the band 716. The seal lip 726 prevents the cylinder cap 712 from sliding off the end of the base cylinder 704.

The cylinder cap 712 may define the second end 740 of the hydraulic piston actuator 722, and the relative position of the cylinder cap 712 along the base cylinder 704 may define the distance 788 of the second end 740 of the hydraulic piston actuator 722 from the band 716, and accordingly the degree of constriction applied by the hydraulic piston actuator 722 to the patient's stomach.

The respective chambers 714, 710 of the cylinder cap 712 and the base cylinder 704 are coupled to the fluid conduit 730 extending along the circumference of the band 716. The fluid conduit 730 may be housed within the band 716 and may connect to all hydraulic piston actuators 722 positioned within the interior of the band 716. An aperture 728 may couple the chambers 714, 710 to the fluid conduit 730.

In operation, the hydraulic control system 702, shown in FIG. 7A transmits fluid to or from each hydraulic piston actuator 722. The amount of fluid correspondingly slides the cylinder cap 712 along the base cylinder 704, which varies a distance 788 of the hydraulic piston actuator 722 from the band 716. The dimensions of the chambers 714, 710, and the fluid reservoir 732 may be varied to offer different degrees of force produced by the hydraulic piston actuator 722.

Figure 7C:
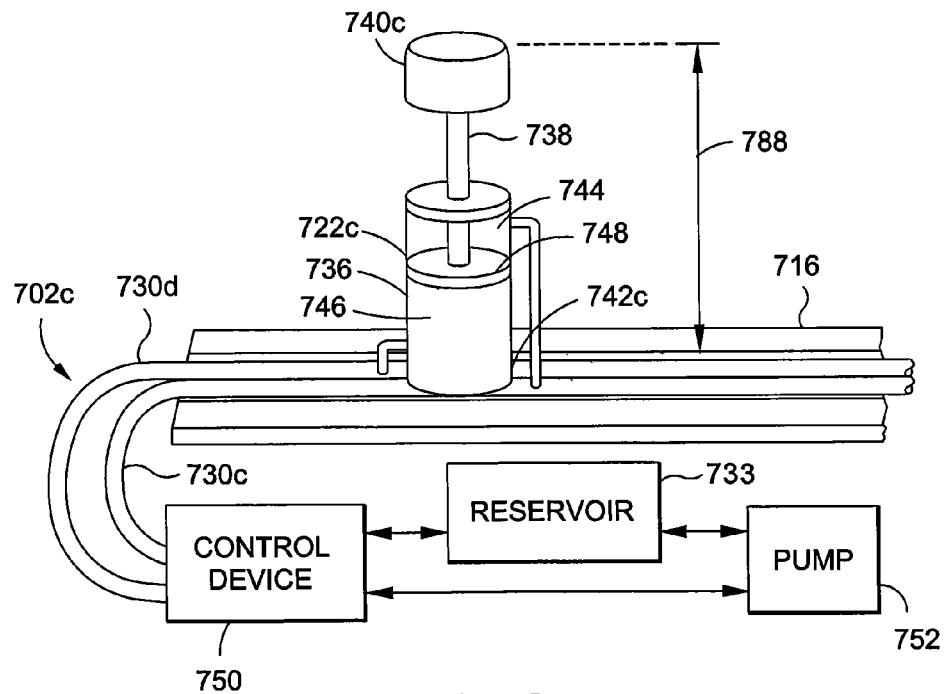
FIG. 7C illustrates a perspective view of a force transmission device and a schematic representation of a hydraulic control system according to an embodiment of the present invention.

FIG. 7C illustrates a perspective view of a hydraulic piston actuator 722c having a first end 742c and a second end 740c, and configured as a hydraulic ram, including a hydraulic piston 738, a hydraulic cylinder 736, and a piston seal 748 of the hydraulic piston 738. In this embodiment, the piston seal 748 divides the hydraulic cylinder 736 into two chambers, an upper fluid chamber 744 and a lower fluid chamber 746. The upper fluid chamber 744 of the hydraulic cylinder 736 is coupled to a hose, connecting to a fluid conduit 730c. The lower fluid chamber 746 is coupled to a hose, connecting to a fluid conduit 730d. The height of the hydraulic piston 738 and the second end 740c of the hydraulic piston actuator 722c varies based on the relative amount of fluid located in the upper fluid chamber 744 and the lower fluid chamber 746.

A hydraulic control system 702c varies the relative amount of fluid contained in the upper fluid chamber 744 and the lower fluid chamber 746. The hydraulic control system 702c comprises a pump 752, a fluid reservoir 733 and a control device 750. The pump 752 may comprise a standard pump as is known in the art. The fluid reservoir 733 is configured to retain an amount of fluid. The pump 752 couples to the fluid reservoir 733 and pressurizes the fluid contained within the fluid reservoir 733. The control device 750 is coupled to the fluid reservoir 733 and the pump 752, and may comprise a valve as is known in the art. The control device 750 couples to the fluid conduits 730c, 703d, and directs the pressurized fluid from the pump 752 to either the upper fluid chamber 744 or the lower fluid chamber 746, to vary the relative amount of fluid located in the chambers 744, 746.

The embodiments shown in FIGS. 7A-7C are exemplary in nature, and may be modified without deviating from the scope of this invention. For example, the hydraulic piston actuators 722, 722c may be configured to comprise any actuator controlled hydraulically and configured to apply a constrictive force to a patient's stomach. In addition, the hydraulic control system 702, 702c may comprise any control system capable of transmitting or receiving fluid from the actuators.

Furthermore, the hydraulic control system 702, 702c may comprise a single pump and/or a motor, or a series of pumps and/or motors, each controlling an individual hydraulic actuator, or a combination of hydraulic actuators.

The number of hydraulic piston actuators 722, 722c may vary from one hydraulic piston actuator 722, 722c to as many hydraulic piston actuators 722, 722c as may feasibly fit within the band 716 to produce an equivalent operation of the gastric band device 700. A single hydraulic piston actuator 722, 722c may be positioned within the band 716 to constrict the patient's stomach.

The gastric band device 700, discussed in relation to FIGS. 7A-7C, includes multiple benefits, including a simplistic design and operation. The force of each hydraulic piston actuator 722, 722c is transmitted hydraulically, which reduces the number of moving parts of the device 700. In addition, during operation of the hydraulic control system 702, 702c, the outer diameter of the band 716 does not vary, providing a firm structure for the device 700, similar to the gastric band device 100 discussed in relation to FIGS. 1A-1S. Furthermore, the force exerted by the hydraulic piston actuators 722, 722c is substantially centrally distributed to the patient's stomach, providing an even distribution of force.

Figure 8A:
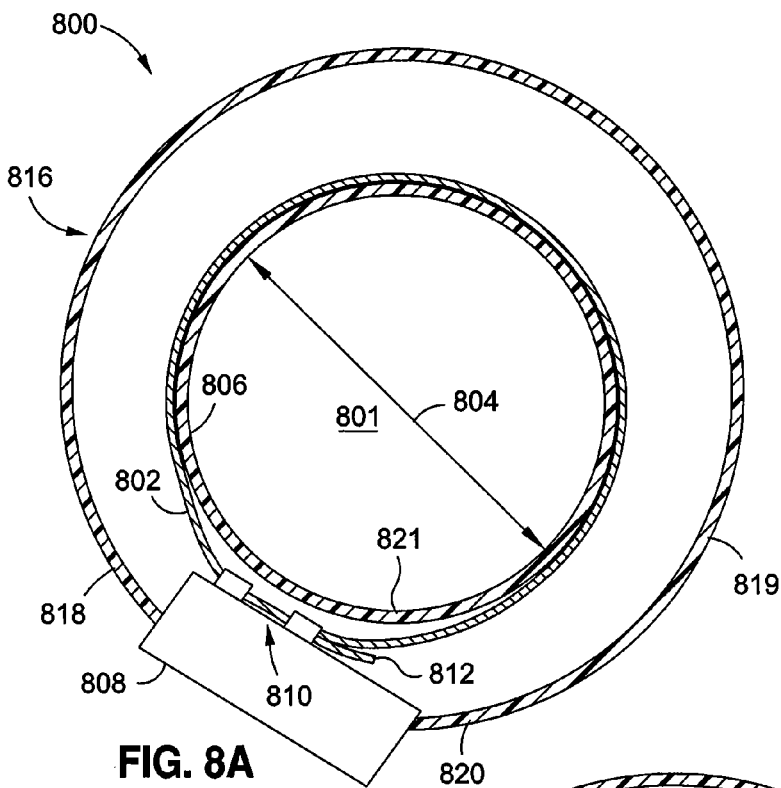
FIGS. 8A-8B illustrate perspective views of a gastric band device according to an embodiment of the present invention.

FIG. 8A illustrates a gastric band device 800 including a spring 802 formed into the shape of a loop to encircle a portion of the patient's stomach. The gastric band device 800 may also include a separate band 816 having a first end 818 and a second end 820 and a motor housing 808 coupled to the band 816. The spring 802 may be positioned within the separate band 816. The band 816 is positioned in a loop around the portion of the patient's stomach, in a manner similar to the gastric band device 100 described in relation to FIG. 1A. The gastric band device 800 serves to provide a degree of constriction to a portion of the patient's stomach, similar to the gastric band device 100 described in relation to FIG. 1A.

The first end 818 of the band 816 and the second end 820 of the band 816 are coupled together to define the loop. The loop has a generally circular shape, to allow the band 816 to symmetrically fit around and encircle the portion of the patient's stomach. The motor housing 808 may be positioned between the first end 818 of the band 816 and the second end 820 of the band 816, to couple the ends 818, 820 together.

The loop shape of the band 816 defines an inner region 801 that is bounded by the band 816 and by the spring 802. The patient's stomach may be complementary with the inner region 801 formed by the loop. A flexible membrane 806 may be coupled to the band 816, or extend around the band 816, similar to the membrane 106 shown in FIG. 1A, to provide a degree of biocompatibility between the gastric band device 800 and the patient's body.

The spring 802 may comprise the band 816, as the spring 802 is configured in a loop shape, which will encircle the stomach and provide a degree of constriction to the patient's stomach. However, the spring 802 may also be contained within a separate band 816 structure, as discussed above. If the spring 802 is contained within a separate band 816 structure, the band 816 may include a rigid dorsal periphery 819 and a flexible ventral periphery 821, to prevent movement of an outer diameter of the band 816 during operation of a motor system contained within the motor housing 808. The rigid dorsal periphery 819 and the flexible ventral periphery 821 may operate similarly as with the band 316 discussed in relation to FIG. 3A.

The spring 802 comprises a wire spring, or a bar spring, or a non-helical spring, curved in a circular shape to form a loop. The spring 802 may represent a single loop of a spring designed to ultimately form a torsion spring.

Figure 8B:
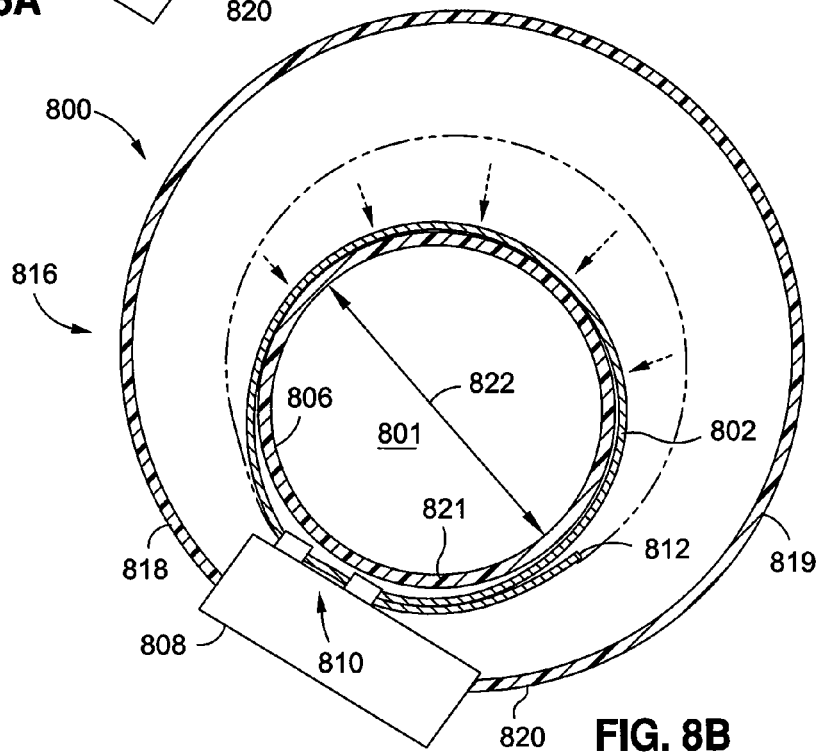
Figure 8C:
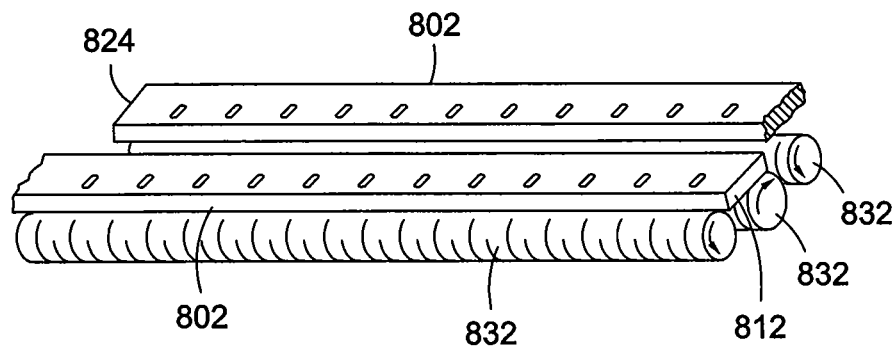
FIG. 8C illustrates a perspective view of the ends of a spring according to an embodiment of the present invention.

The spring has two ends, a first end 812 and a second end 824, shown in FIG. 8C. The ends 812, 824 of the spring 802 overlap to form the loop, or ring. The loop has a diameter 804.

The spring 802 is formed to be pre-stressed to have a rest diameter sized to apply a degree of constriction to a patient's stomach. In other words, the spring 802 is shaped and sized to constrict to a rest diameter being smaller than the natural diameter of the portion of the patient's stomach to be constricted. For example, if the patient's esophageal junction is sized at a diameter of about 25 millimeters, then the spring 802, will be biased to constrict to a size of less than about 25 millimeters. The rest diameter represents the diameter of the spring 802 without any external forces applied to the spring 802.

In addition, the spring 802 may be biased to constrict, at rest, to a size smaller than the minimum diameter, and smaller than the maximum diameter, that the gastric band device 800 will constrict the patient's stomach. The spring 802 may be configured to always be biased to exert a constrictive force to the patient's stomach. In this manner, the spring's 802 bias will aid the spring control system 810 to increase the degree of constriction applied to the patient's stomach. The rest diameter of the spring 802 may be set during manufacture, or may be set by a physician after determining the size of the patient's stomach to be constricted.

A spring control system 810 is coupled to the band 816, or, directly to the spring 802 if the spring 802 comprises the band 816. The spring control system 810 comprises a motor system contained within the motor housing 808, and a worm drive 832 (shown in FIGS. 8C and 8D) coupled to motor system and the ends 812, 824 of the spring 802. The motor system contained within the motor housing 808 may comprise any of the motor systems shown in FIGS. 2A-2O. The gastric band device 800 may be suitably modified to allow a desired motor system to drive the ends 812, 824 of the spring 802. Furthermore, the motor system contained within the motor housing 808 may also contain any other style of known motor capable of producing effective operation as contemplated by the device 800.

The spring control system 810 drives the ends 812, 824 of the spring 802 in directions opposite to each other to vary the diameter 804 of the spring 802 when configured in a loop shape.

FIG. 8A illustrates the diameter 804 formed by the spring 802 when the gastric band device 800 is positioned to exert a relatively low degree of constriction to the patient's stomach.

FIG. 8B illustrates the diameter 822 formed by the spring 802 after the ends 812, 824 of the spring have been driven away from each other. The diameter 822 shown in FIG. 8B is smaller than shown in FIG. 8A, indicating an increased degree of constriction applied by the spring 802.

FIG. 8C illustrates the overlapping ends 812, 824 of the spring 802. A worm gear 832 comprising a series of engaged cylindrically shaped gears drive the ends 812, 824 in opposite directions, to vary a diameter of the spring 802, and vary a degree of constriction applied to the patient's stomach. The worm gear 832 may engage with an appropriate engagement mechanism located on the spring 802. The engagement mechanism may comprise a series of notches or grooves in the spring 802 that engage with the worm gear 832.

Figure 8D:
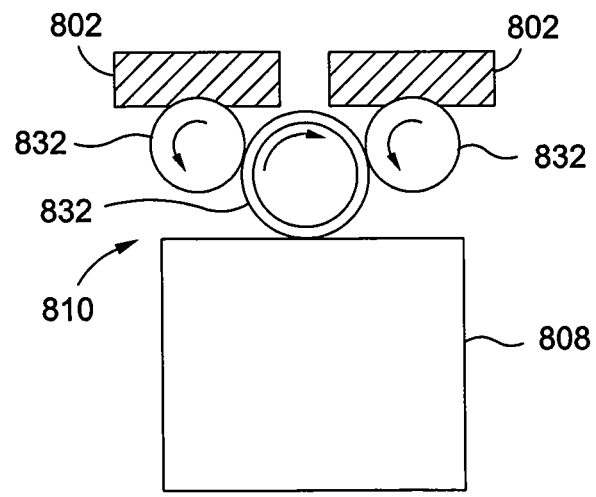
FIG. 8D illustrates a schematic view of a control system according to an embodiment of the present invention.

FIG. 8D illustrates a view of the spring control system 810 viewed in line, down the axis of the worm gear 832. The plurality of gears 832 are displayed engaging with the spring 802. The worm gear 832 engages with the motor system contained within the motor housing 808, and drives the ends 812, 824 of the spring 802 in opposite directions.

The embodiment shown in FIGS. 8A-8D is exemplary in nature, and may be modified without deviating from the scope of this invention. For example, as discussed above, the spring 802 may comprise the band 816 and may extend around the patient's stomach in a loop. In this embodiment, the banding device may be limited to a spring 802 and a spring control system 810 coupled to the spring 802. In addition, the spring 802 may be sized or shaped in an alternative manner to produce an equivalent result. For example, multiple loops of the spring 802 may extend around the patient's stomach. Furthermore, the spring 802 may be biased to a midpoint of the range of constriction, or may be biased to reduce the constriction applied to the stomach. In addition, the spring control system 810 may include alternative drive systems, or may only engage one end of the spring 802, or a different portion of the spring 802, to produce an equivalent result.

The gastric band device 800, discussed in relation to FIGS. 8A-8D, includes multiple benefits, including a simplistic design and operation. The spring 802 is biased to constrict the patient's stomach, thus aiding the spring control system 810 in operation. As discussed in relation to the gastric band device 100 shown in FIG. 1A, this property is valuable as the patient's stomach will generally require a greater constriction force as it is successively constricted.

Figure 9A:
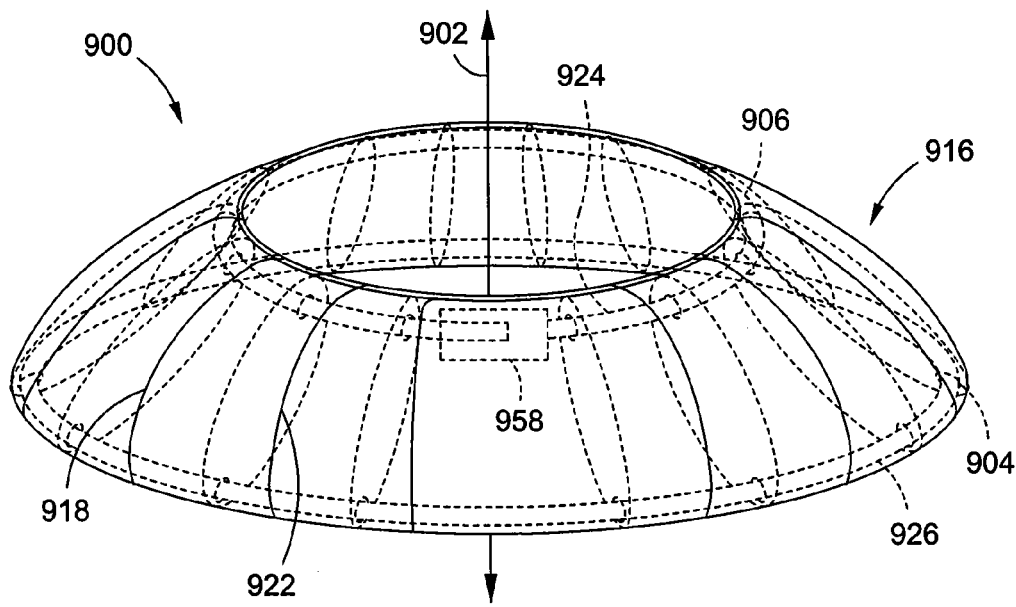
FIG. 9A illustrates a perspective view of a gastric band device according to an embodiment of the present invention.

FIG. 9A illustrates a gastric band device 900 including a band 916 having a rotatable portion 906 configured to rotate around a pivotal portion 904 of the band 916. The band 916 is positioned in a loop around the portion of the patient's stomach, in a manner similar to the gastric band device 100 described in relation to FIG. 1A. The gastric band device 900 will include a suitable mechanism (not shown) to allow the band device 900 to be looped around the portion of the patient's body. The gastric band device 900 serves to provide a degree of constriction to a portion of the patient's stomach, similar to the gastric band device 100 described in relation to FIG. 1A.

The loop has a generally circular shape, to allow the band 916 to symmetrically fit around and encircle the portion of the patient's stomach. A motor system 958 may be positioned within an interior portion of the band 916, near a suitable mechanism that binds the two ends of the band 916 into a loop.

The loop shape of the band 916 defines an inner region 901 (shown in FIG. 9E) that is bounded by the band 916. The patient's stomach may be complementary with the inner region 901 formed by the loop. The band 916 is configured to loop around an axis 902 extending centrally through the inner region 901.

The band 916 includes a rotatable portion 906, and a pivotal portion 904. The rotatable portion 906 is configured to rotate around the pivotal portion 904. A body portion 918 may connect the rotatable portion 906 to the pivotal portion 904.

In the embodiment shown in FIG. 9A, the rotatable portion 906 may comprise a rotation ring 924, or wire, that extends entirely around the axis 902 to form a circle. In addition, the pivotal portion 904 may comprise a pivot ring 926, or wire that also extends entirely around the axis 902 to form a circle. The rotation ring 924 and the pivot ring 926 may be positioned concentric about the axis 902, yet at a distance from each other along the axis 902.

In the embodiment shown in FIG. 9A, the body portion 918 may comprise a plurality of plates 922, or slats, that are shaped to have a substantially elliptical yet non-circular, cross section. The elliptical cross section is indicated by dashed lines in FIG. 9A. The plates 922 form a shell connecting the rotation ring 924 to the pivot ring 926, and provide structure for the gastric band device 900. The plates 922 are positioned adjacent to each other and may include overlapping portions, as shown in FIG. 9F.

The motor system 958 may be positioned within the body portion 918 of the band 916 and may comprise any of the motor systems shown in FIGS. 2A-2O. In the embodiment shown in FIG. 9A, the motor system 958 couples to the rotation ring 924, and drives the rotation ring 924. The gastric band device 900 may be suitably modified to allow a desired configuration of the motor system 958 to drive the rotation ring 924. Furthermore, the motor system 958 may also contain any other style of known motor capable of producing effective operation as contemplated by the device 900.

Figure 9B:
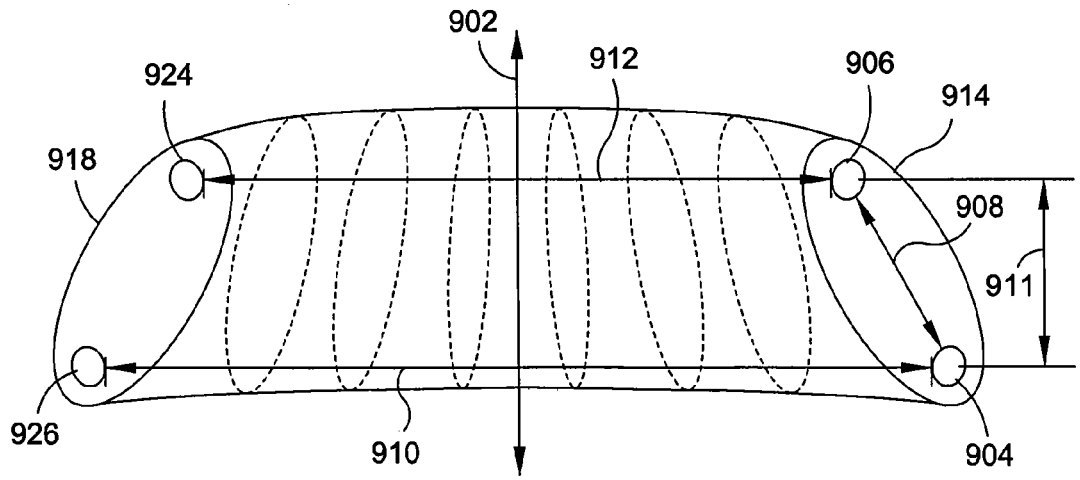
FIG. 9B illustrates a side cross-sectional view of the gastric band device shown in FIG. 9A.

FIG. 9B represents a cross sectional view of the device 900 shown in FIG. 9A. The body portion 918 has a cross section defining an ellipse 914. The rotatable portion 906 is positioned at a distance 911 from the pivotal portion 904 along the axis 902. In addition, the rotatable portion 906 and pivotal portion 904 are positioned along the major axis 908 of the ellipse 914. As the elliptical shape extends entirely around the axis 902, a toroidal structure having an elliptical cross section is formed. The elliptical torus shown in FIG. 9A has a pivot portion 904 in the sagittal direction of the ellipse 914.

The rotatable portion 906 defines a diameter 912, extending perpendicular to the axis 902. A half-value of this diameter 912 represents a radial distance of the rotatable portion 906 from the axis 902. Similarly, the pivotal portion defines a diameter 910, extending perpendicular to the axis 902. A half-value of this diameter 910 represents a radial distance of the pivotal portion 904 from the axis 902.

Referring back to FIG. 9A, the elliptical cross section of the body portion 918 forms a cam structure, producing a lever arm in the form of the rotatable portion 906. The lever arm is capable of applying a degree of constriction to the portion of the patient's stomach. The pivotal portion 904 forms a circular axis of rotation for the rotatable portion 906.

In operation, the motor system 958 rotates the rotatable portion 906 about the pivotal portion 904 to vary the degree of constriction applied to the portion of the patient's stomach. In the embodiment shown in FIG. 9A, the motor system 958 either reduces or extends the length of the pivot ring 926 comprising the rotatable portion 906, to cause a rotation. The pivot ring 926 maintains a constant length. FIG. 9A represents the device 900 in a configuration applying a relatively high degree of constriction to the patient's stomach.

Figure 9C:
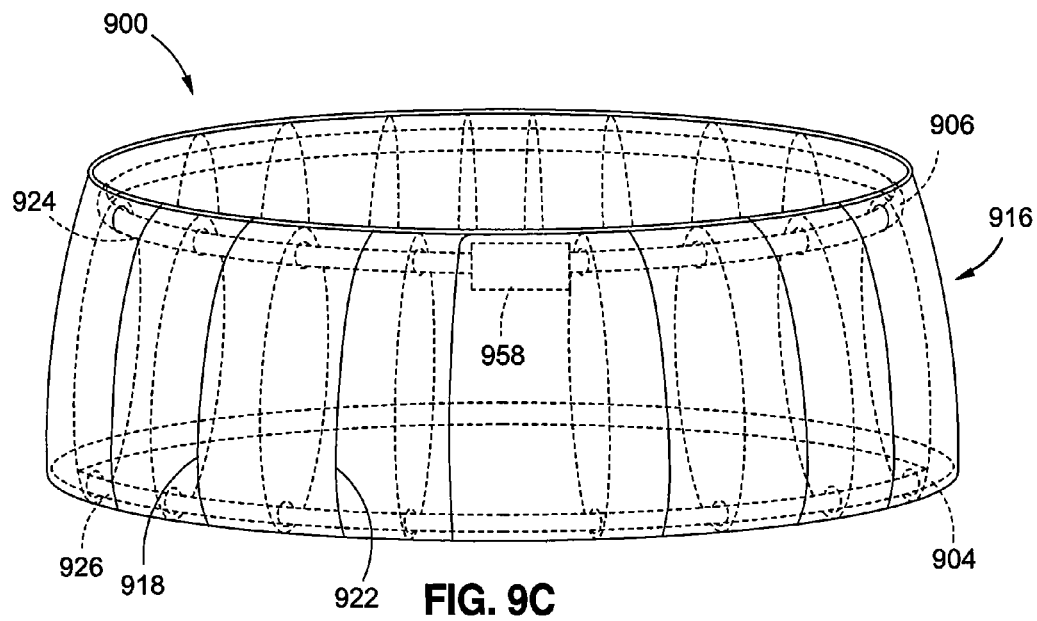
FIG. 9C illustrates a perspective view of a gastric band device according to an embodiment of the present invention.

FIG. 9C illustrates the gastric band device 900 applying a relatively low degree of constriction to the patient's stomach. In this configuration, the motor system 958 has extended the length of the rotation ring 924, increasing the size of the rotatable portion 906, and rotating the rotatable portion 906 about the pivotal portion 904. The degree of constriction applied by the rotatable portion 906 about the pivotal portion 904 has correspondingly been reduced.

Figure 9D:
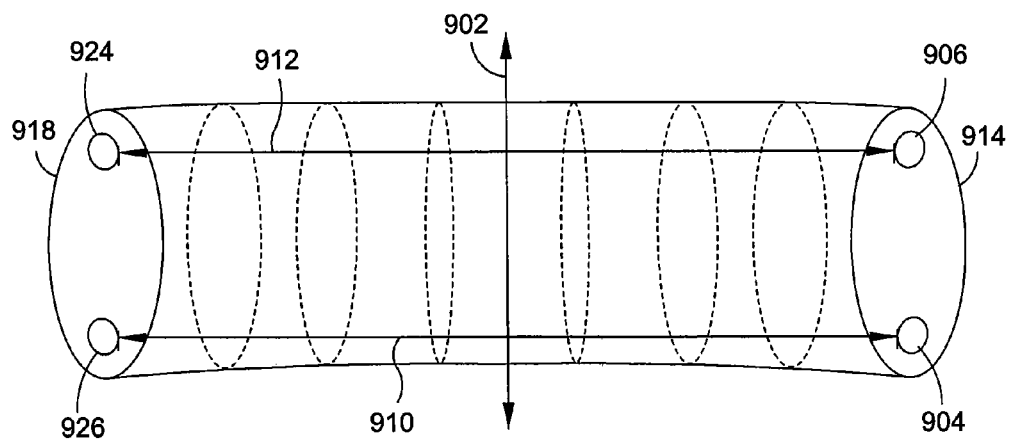
FIG. 9D illustrates a side cross-sectional view of the gastric band device shown in FIG. 9C.

FIG. 9D represents a cross sectional view of the device 900 shown in FIG. 9C. The diameter 912 of the rotatable portion 906, and the corresponding radial distance of the rotatable portion 906 from the axis 902 has been increased. The diameter 910 of the pivotal portion 904, and the corresponding radial distance of the pivotal portion 904 from the axis 902 has remained constant.

Figure 9E:
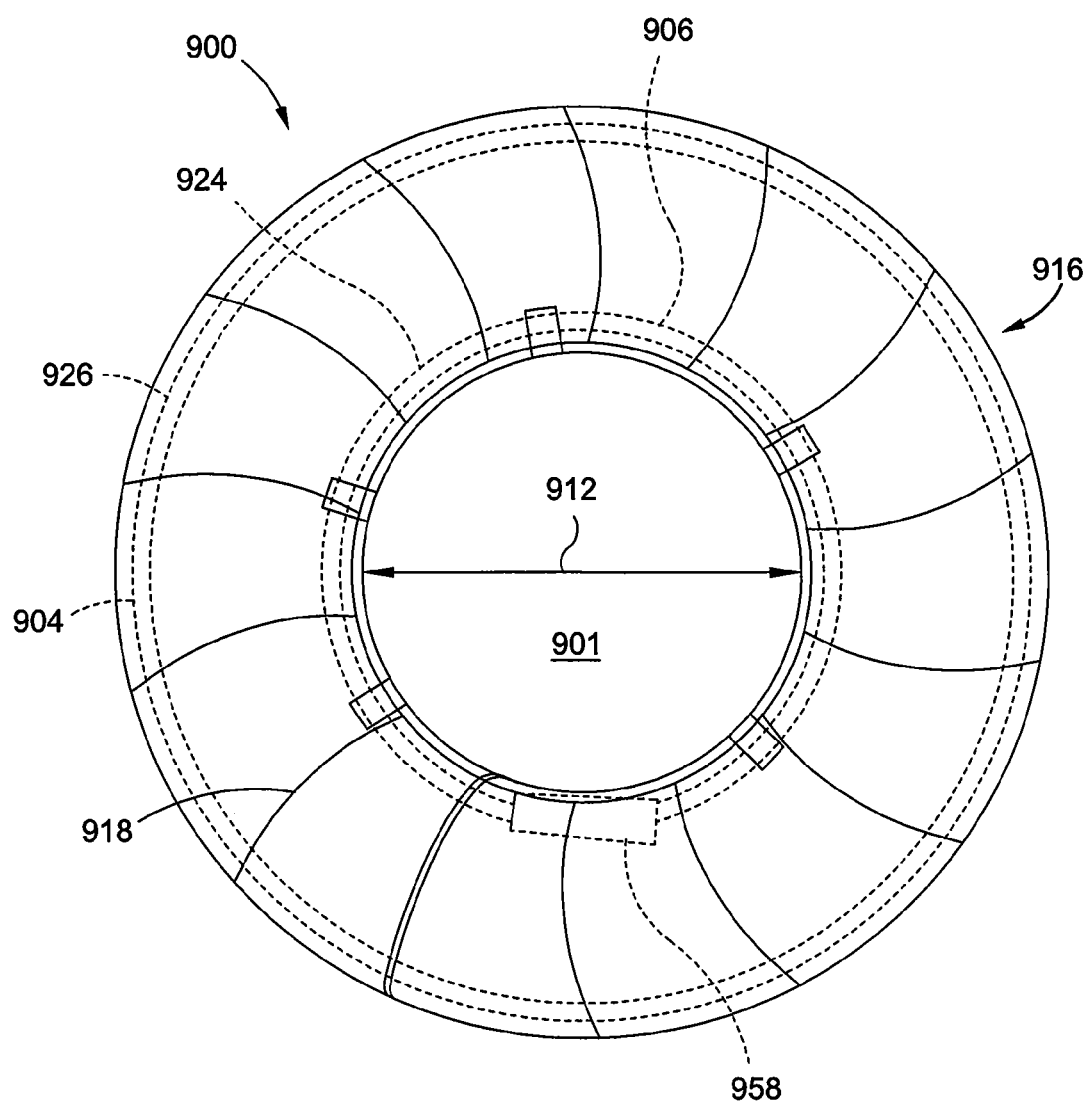
FIG. 9E illustrates a top view of the gastric band device shown in FIG. 9A.
Figure 9F:
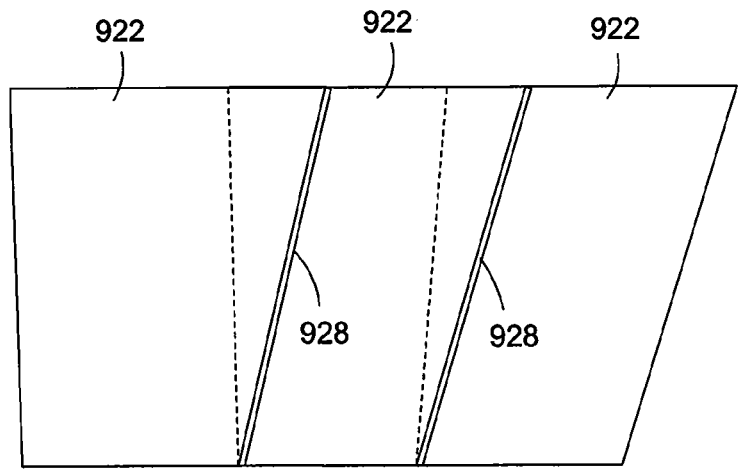
FIG. 9F illustrates a close-up view of plates according to an embodiment of the present invention.

FIG. 9E illustrates a top view of the gastric band device 900 shown in FIG. 9A. The band 916 forms a loop around a portion of the patient's stomach, contained within the inner region 901. The rotatable portion 906 applies a constriction to the stomach, defined by the size of the diameter 912.

FIG. 9F illustrates a close up view of the plates 922 discussed in relation to FIG. 9A. The plates 922 include an overlapping portion 928 that allows the plates 922 to slide relatively free of friction from each other. The overlapping portions 928 also allow the size of the rotatable portion 906 to increase or decrease during operation of the motor. As the size of the rotatable portion 906 increases, the overlap size of the overlapping portions 928 will decrease. The plates 922 are made from a sturdy material, such as a hard plastic, that allows the plates 922 to be contoured in an elliptical shape, and also provide a rigid shell structure for the body portion 918 of the band 916, shown in FIG. 9A.

Figure 9G:
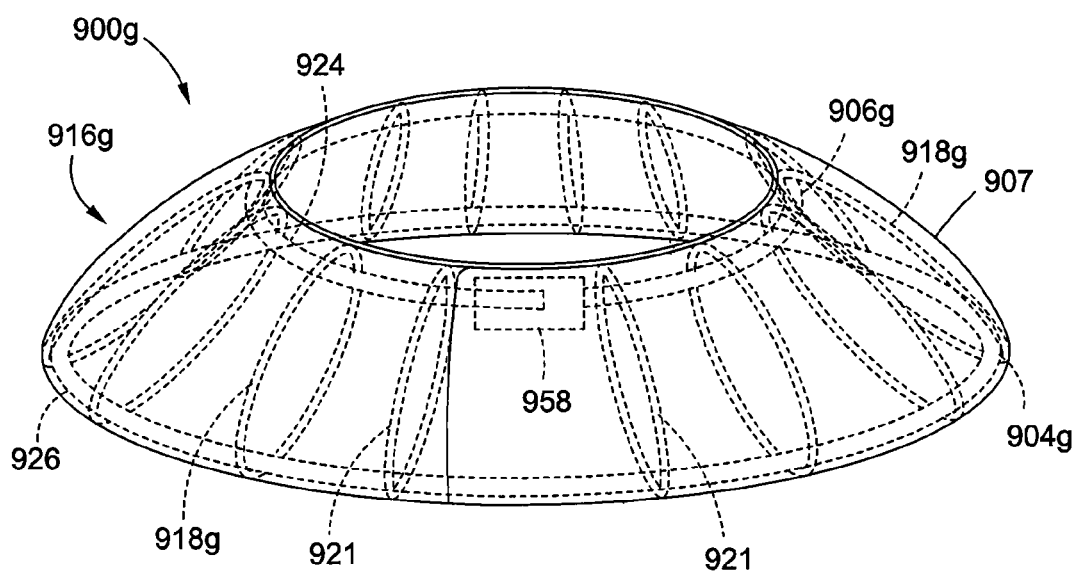
FIG. 9G illustrates a perspective view of a gastric band device according to an embodiment of the present invention.

FIG. 9G illustrates a gastric band device 900g including a plurality of skeletal structures or ribs 921, having an elliptical shape, comprising the body portion 918g of the band 916g. The ribs 921 form an interior frame connecting the rotatable portion 906g to the pivotal portion 904g. In this embodiment, the ribs 921 may be covered with a flexible membrane 907, similar to the membrane 106 shown in FIG. 1A, to provide a degree of biocompatibility between the gastric band device 900g and the patient's body. The membrane 907 may be configured to flex and stretch to accommodate a size change of the rotatable portion 906g.

Figure 9H:
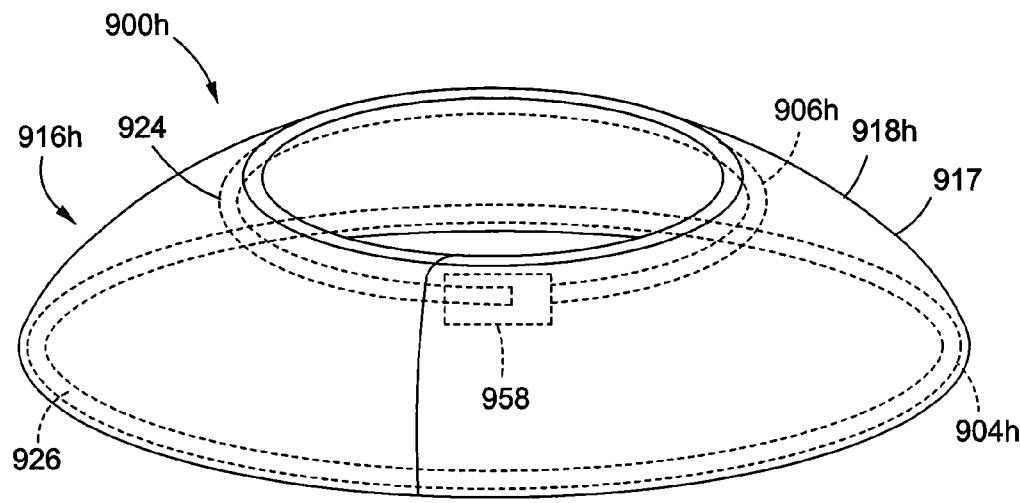
FIG. 9H illustrates a perspective view of a gastric band device according to an embodiment of the present invention.

FIG. 9H illustrates a gastric band device 900h including a substantially solid, deformable member 917 comprising the body portion 918h of the band 916h. The deformable member 917 couples the rotatable portion 906h to the pivotal portion 904h. The deformable member 917 may comprise a flexible body, made from silicone, for example, that is capable of compressing and/or stretching to accommodate a size change of the rotatable portion 906h.

Figure 9I:
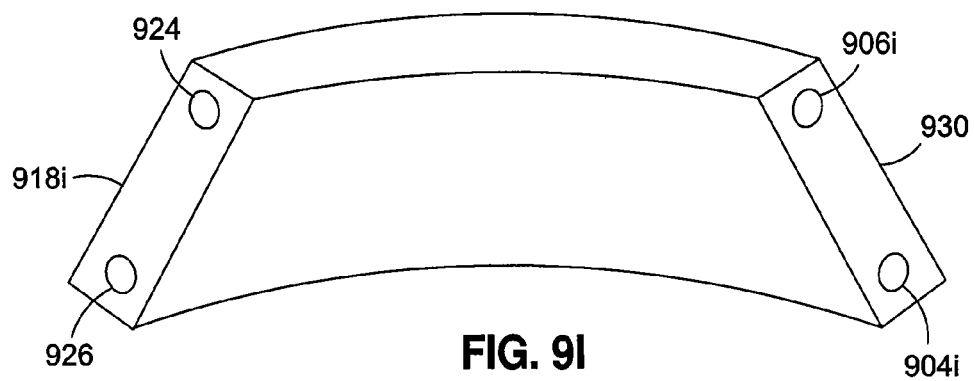
FIG. 9I illustrates a side cross-sectional view of a gastric band device according to an embodiment of the present invention.

FIG. 9I illustrates a body portion 918i connecting a pivotal portion 904i to a rotatable portion 906i, the body portion 918i having a substantially rectangular cross section. Thus, the body portion 918i is not limited to an elliptical shape, and may comprise any shape providing for equivalent operation. A rectangle 930 may form the cross-section shape, and comprise a deformable member, similar to the deformable member 917 discussed above in relation to FIG. 9H.

Figure 9J:
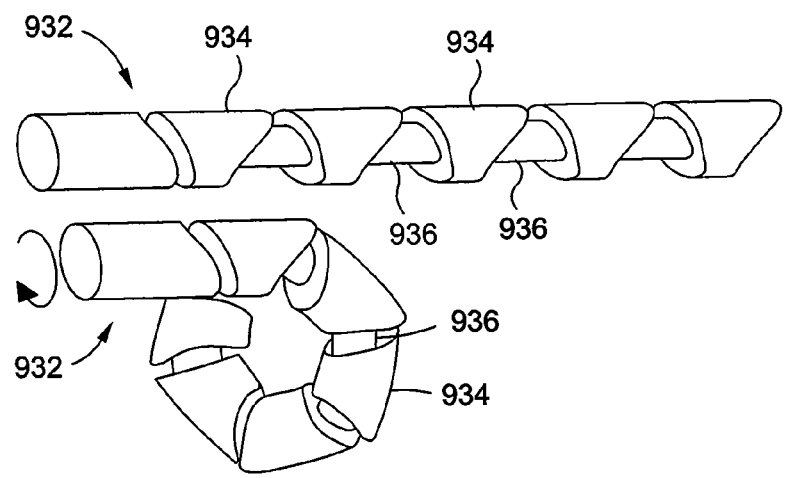
FIG. 9J illustrates a perspective view of a segmented wire according to an embodiment of the present invention.

FIG. 9J illustrates a segmented wire 932 that may be used instead of the pivot ring 926 shown in FIGS. 9A-9H. The segmented wire 932 includes hard segments 934 positioned along a flexible core wire 936. The flexible core wire 936 is configured to curl in response to a force, possibly a rotary force applied to an end of the segmented wire 932. The force may be applied by the motor system 958, causing the core wire 936 to curl and reduce the diameter 912 formed by the rotatable portion 906. The actuator of the segmented wire 932 would be induced step-by-step through a domino-type effect on the segments. A reverse force or a rotary force in an opposite direction causes the segmented wire 932 to uncurl. The segmented wire 932 may also be activated by heat, or an electrical voltage applied to the segmented wire 932. For example, the segmented wire 932 may comprise a bimorph material comprised of one material designed to swell in response to a voltage and another designed to shrink in response to a voltage. The material designed to shrink may be positioned within the inner circumference of the segmented wire 932. An applied voltage may cause the segmented wire 932 to curl, as the swelled portion increases in size and the shrunken portion decreases in size. The segmented wire 932 may uncurl in response to a reduction in voltage.

The embodiments shown in FIGS. 9A-9J are exemplary in nature, and may be modified without deviating from the scope of this invention. For example, the gastric band device 900 may comprise a series of rotatable levers configured to rotate about a pivotal region of the band. In addition, multiple shapes and configurations of the rotatable portion 906, 906g, 906h, 906i, and the pivotal portion 904, 904g, 904h, 904i may be used to produce an equivalent result. Furthermore, the pivotal portions and rotatable portions may be alternated during different modes of operation. For example, a region may serve as a rotatable portion during an increased constriction, and may also serve as a pivotal portion during a decreased constriction. In addition, the band may be structured to be biased to apply an increased constrictive force during operation of the motor. In addition, the motor system 958 may be integral with the band, or may be positioned external or exterior to the band.

The gastric band devices discussed in relation to FIGS. 9A-9J provide multiple benefits, including a simplistic design and operation. The band 916, 916g, 916h only comprises a single, self-contained element to be placed around the patient's stomach. In addition, the outer diameter of the band 916, 916g, 916h does not vary during operation, as only the rotatable portion 906, 906g, 906h, 906i moves during operation.

Figure 10A:
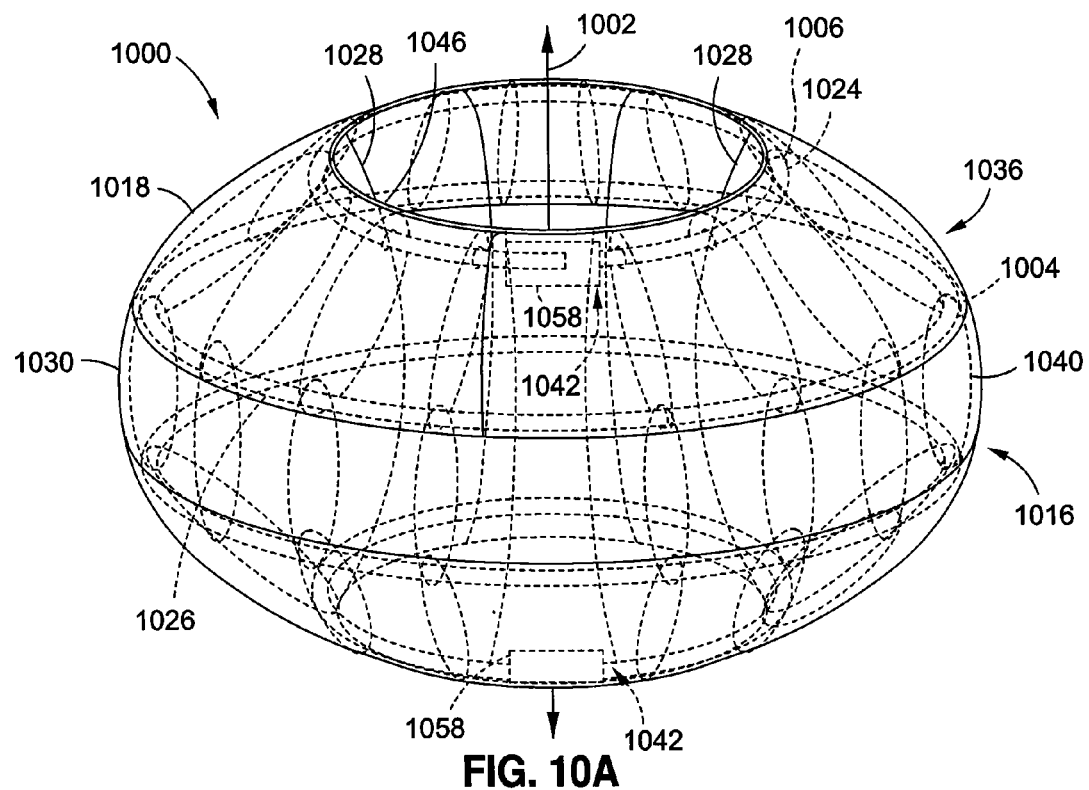
FIG. 10A illustrates a perspective view of a gastric band device according to an embodiment of the present invention.

FIG. 10A illustrates a gastric band device 1000 including a band 1016 having an incompressible body 1028. The band 1016 is positioned in a loop around the portion of the patient's stomach, in a manner similar to the gastric band device 100 described in relation to FIG. 1A. The gastric band device 1000 includes a suitable mechanism (not shown) to allow the gastric band device 1000 to be looped around the portion of the patient's body. The gastric band device 1000 serves to provide a degree of constriction to a portion of the patient's stomach, similar to the gastric band device 100 described in relation to FIG. 1A.

The loop has a generally circular shape, to allow the band 1016 to symmetrically fit around and encircle the portion of the patient's stomach. A motor system 1058 may be positioned within an interior portion of the band 1016, near a suitable mechanism that binds the two ends of the band 1016 into a loop.

The loop shape of the band 1016 defines an inner region 1001 (shown in FIG. 10D) that is bounded by the band 1016 and may be bounded by the incompressible body 1028. The patient's stomach may be complementary with the inner region 1001 formed by the loop. The band 1016 is configured to loop around an axis 1002 extending centrally through the inner region 1001.

The incompressible body 1028 may comprise the band 1016, as the incompressible body 1028 may be configured to encircle the stomach in a loop and provide a degree of constriction to the patient's stomach. However, the incompressible body may also be contained within a separate band 1016 structure, including a housing 1040, as shown in FIG. 10A.

The band 1016 is configured to include an incompressible body 1028 having a free end 1046 that deflects in response to a compressive force. The incompressible body 1028 increases a degree of constriction applied to the patient's stomach in response to the compressive force. The compressive force is applied by an incompressible body compression system 1042, which may comprise a motor system 1058, and a clamp actuator 1036.

The clamp actuator 1036 may serve as a housing 1040 that encircles and contains the incompressible body 1028. The clamp actuator 1036 may be configured similarly as two of the gastric band devices 900 shown and discussed in relation to FIG. 9A, fixed at the pivotal portions 1004 of the devices through a link 1030. Thus, similar to the device 900 discussed in relation to FIG. 9A, the clamp actuator 1036 includes a body portion 1018, a rotatable portion 1006, a pivotal portion 1004, and a motor system 1058. The rotatable portion 1006 may comprise a rotation ring 1024 and the pivotal portion 1004 may comprise a pivot ring 1026.

The motor system 1058 may be positioned within the body portion 1018 of the clamp actuator 1036 and may comprise any of the motor systems shown in FIGS. 2A-2O. The gastric band device 1000 may be suitably modified to allow a desired configuration of the motor system 1058 to drive the clamp actuator 1036. Furthermore, the motor system 1058 may also contain any other style of known motor capable of producing effective operation as contemplated by the gastric band device 1000.

Figure 10D:
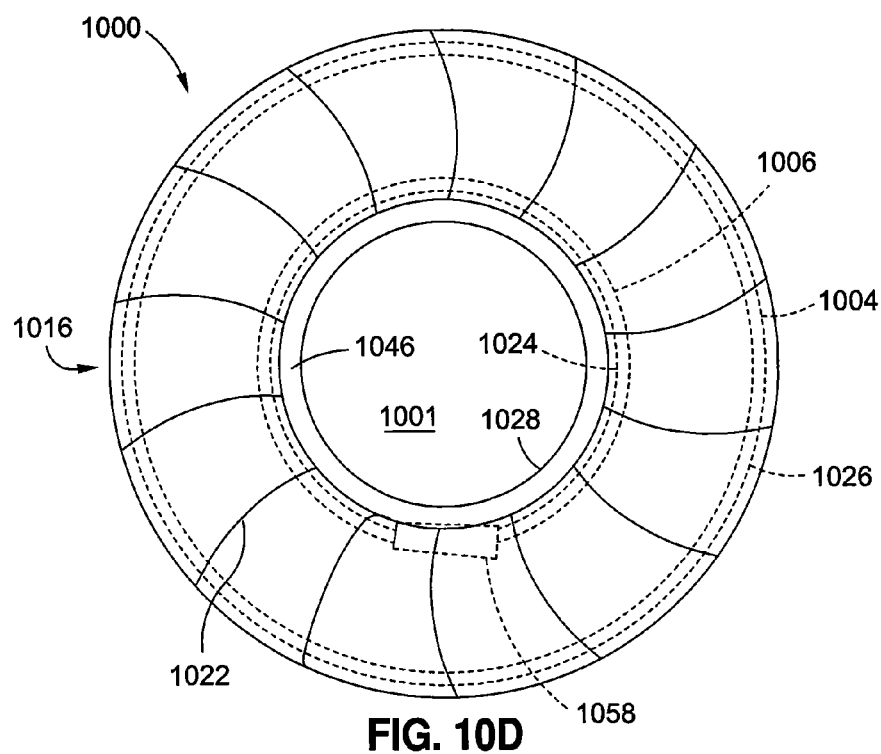
FIG. 10D illustrates a top view of the gastric band device shown in FIG. 10A.
Figure 10B:
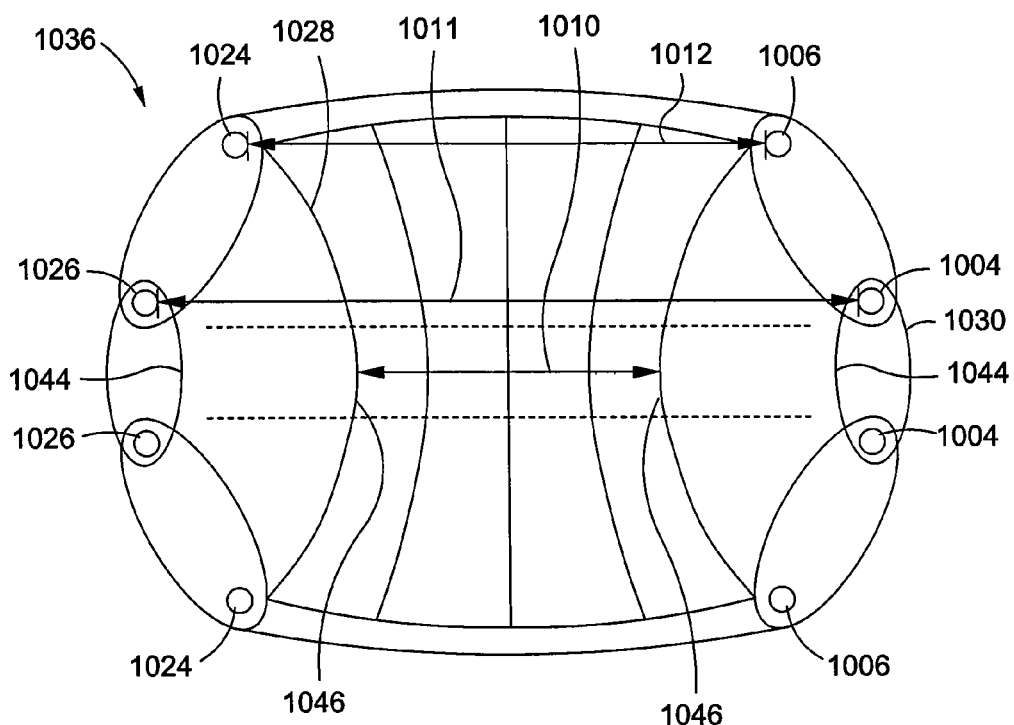
FIG. 10B illustrates a side cross-sectional view of the gastric band device shown in FIG. 10A.

Referring to FIG. 10B, the incompressible body 1028 is configured to encircle the portion of the patient's stomach to be constricted. The incompressible body 1028 has a fixed end 1044 coupled to the clamp actuator 1036 and a free end 1046 configured to deflect in a direction towards the patient's stomach. As shown in FIG. 10B, the incompressible body 1028 has a diameter 1010 when formed in a loop, and the rotatable portion 1006 and the pivotal portion 1004 of the clamp actuator 1036 similarly form respective diameters 1012, 1011.

The incompressible body 1028 may comprise a pouch of incompressible fluids or a body made from a flexible material such as silicone. The pouch of fluids may include a physiological solution, silicone oil, or the like. The incompressible body 1028 may be fixed, or adhered to the clamp actuator 1036, or may be held in position by the clamp actuator 1036. In operation, the clamp actuator 1036 applies a compressive force to the incompressible body 1028 in a direction substantially parallel with the axis 1002 shown in FIG. 10A. The free end 1046 of the incompressible body 1028 deflects in a direction towards the inner region 1001, and increases the degree of constriction applied to the patient's stomach.

Figure 10C:
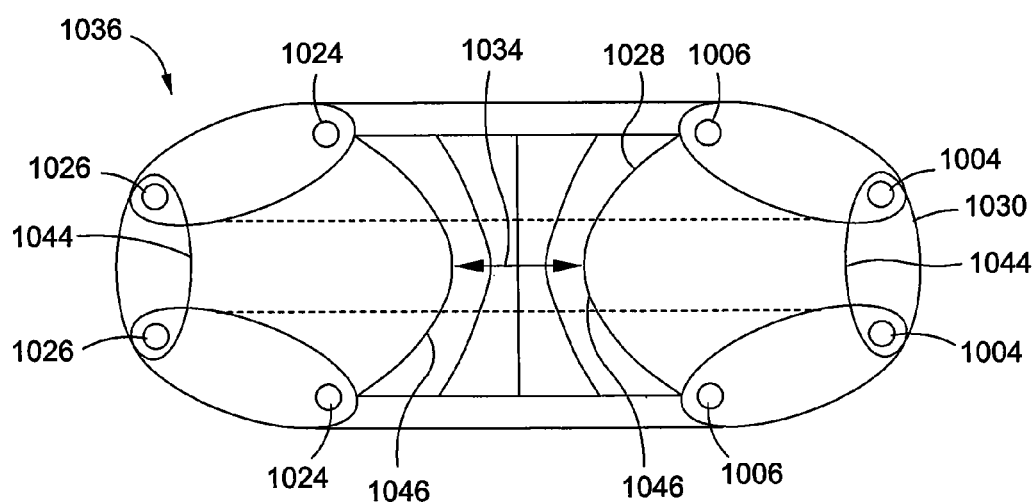
FIG. 10C illustrates a side cross-sectional view of a gastric band device shown in FIG. 10A, being configured differently than shown in FIG. 10A.

FIG. 10C illustrates the configuration of the clamp actuator 1036 and the incompressible body 1028 after the clamp actuator 1036 has exerted a force against the incompressible body 1028. The free end 1046 of the incompressible body 1028 has deflected, causing a diameter 1034 formed by the incompressible body 1028 to decrease. The free end 1046 is deflected in a direction substantially perpendicular with the axis 1002.

FIG. 10D illustrates a top view of the gastric band device 1000 shown in FIG. 10A. The incompressible body 1028 is more clearly shown to encircle the inner region 1001. In addition, the plates 1022 (not shown in FIG. 10A) are utilized with the claim actuator 1032, similar to the plates 922 discussed in relation to FIG. 9A.

Figure 10E:
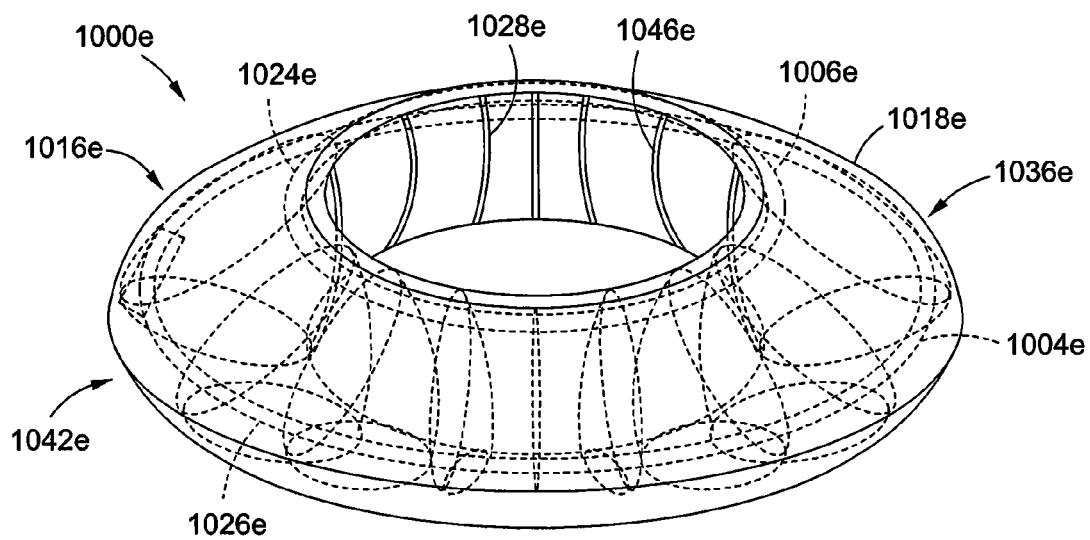
FIG. 10E illustrates a perspective view of a gastric band device according to an embodiment of the present invention.

FIG. 10E illustrates a gastric band device 1000e including an incompressible body compression system 1042e including a clamp actuator 1036e having a pivotal portion 1004e, a rotatable portion 1006e, and a body portion 1018e. The pivotal portion 1004e comprises a pivot ring 1026e, and the rotatable portion 1006e comprises a rotation ring 1024e. The incompressible body 1028e is formed in a loop contained by the clamp actuator 1036e, with the free end 1046e of the incompressible body 1028e extending towards an interior of the band 1016e. In this configuration, the clamp actuator 1036e does not include a link 1030, as shown in FIG. 10A. In addition, in this configuration, the pivot ring 1026e of the clamp actuator 1036e comprises a hinge-like structure, as two pivotal portions of the clamp actuator 1036e connect to the pivot ring 1026e (more clearly shown in FIGS. 10G and 10H). The hinge-like structure drives both rotatable portions 1006e of the clamp actuator 1036e towards each other. In addition, the rotatable rings 1024e may comprise telescoping rings, capable of expanding and contracting in length.

Figure 10F:
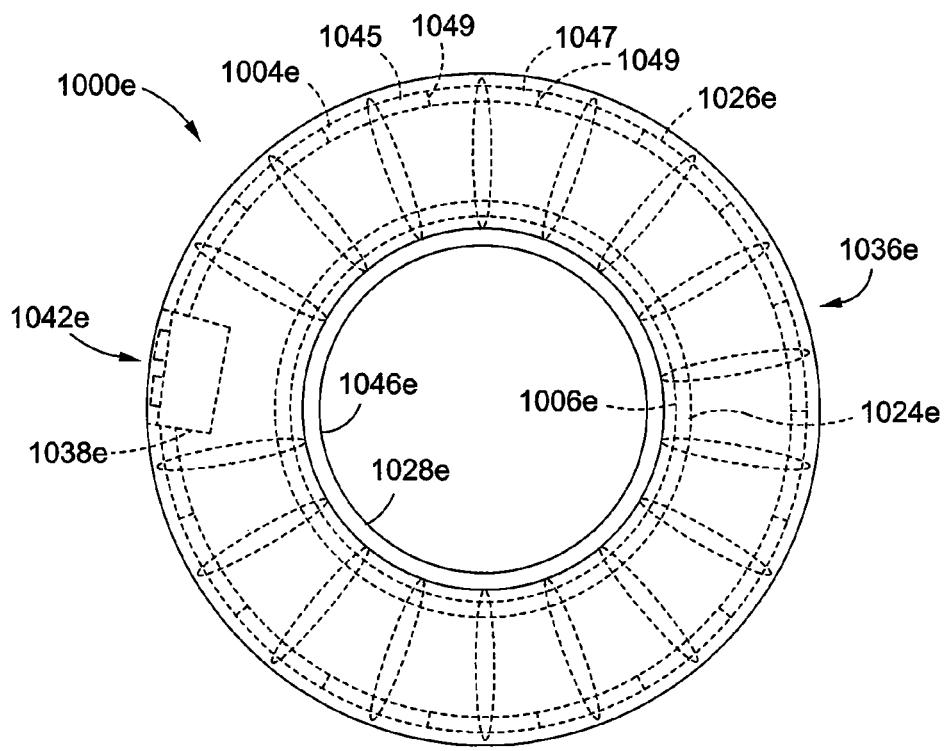
FIG. 10F illustrates a top view of the gastric band device shown in FIG. 10E.

FIG. 10F illustrates a top view of the clamp actuator 1036e, displaying the position of the hinge motor 1038e along the pivotal portion 1004e of the clamp actuator 1036e. The hinge motor 1038e is configured to apply a force to the hinge-like pivot ring 1026e that scissors the pivot ring 1026e together, similar to the operation of a conventional door hinge, although shaped in a ring. The hinge-like pivot ring 1026e may comprise a plurality of rotation points 1049 dividing the pivot ring 1026e into adjacent rotatable segments 1045, 1047. The rotatable segments 1045, 1047 may rotate relative to each other in opposite directions to form the hinge-link mechanism. The rotatable portions 1006e of the clamp actuator 1036e may be coupled to different rotatable segments 1045, 1047. The scissoring of the pivot ring 1026e causes the rotatable segments 1045, 1047 to rotate the rotatable portions 1006e of the clamp actuator 1036e, allowing the rotatable portion 1006e of the clamp actuator 1036e to be drawn towards, or apart from each other.

Figure 10G:
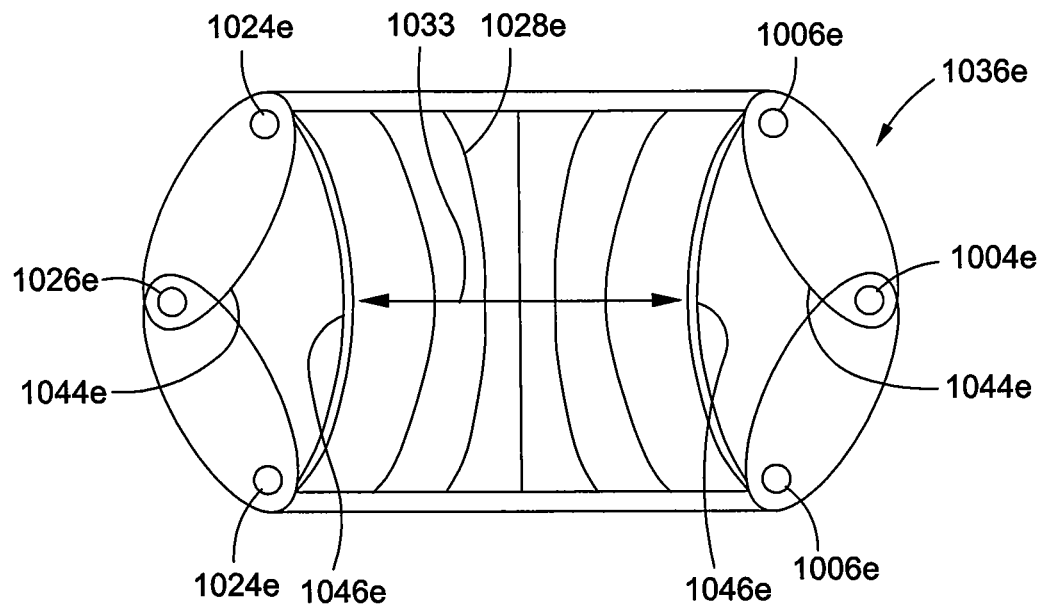
FIG. 10G illustrates a side cross-sectional view of the gastric band device shown in FIG. 10E.

FIG. 10G illustrates a cross sectional view of the gastric band device 1000e shown in FIG. 10E. The incompressible body 1028e has a fixed end 1044e coupled to the clamp actuator 1036e, and forms a diameter 1033. The clamp actuator 1036e has a single pivotal portion 1004e comprising a hinge-like pivot ring 1026e.

Figure 10H:
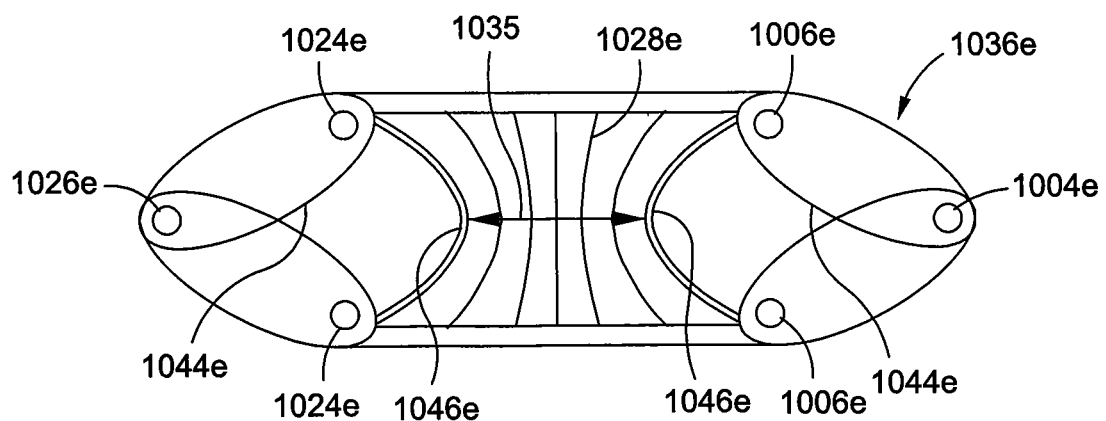
FIG. 10H illustrates a side cross-sectional view of a gastric band device shown in FIG. 10G, being configured differently than shown in FIG. 10G.

FIG. 10H illustrates the embodiment shown in FIG. 10G, after the clamp actuator 1036e has applied a compressive force to the incompressible body 1028e. The size of a diameter 1035 formed by the incompressible body 1028e is smaller than the diameter 1033 shown in FIG. 10G. The benefit of the hinge-like pivot ring 1026e is to allow for a single hinge motor 1038e that operates the clamp actuator 1036e. The clamp actuator 1036e produces a radially directed output force through only an axially directed input force.

The embodiments shown in FIGS. 10A-10H are exemplary in nature, and may be modified without deviating from the scope of this invention. For example, the incompressible body 1028, 1028e may not encircle the patient's stomach, and may exert a force in only one radial direction. In addition, the structure and configuration of the incompressible body compression system 1042, 1042e may be varied to include any mechanism capable of compressing an incompressible body, to vary a degree of constriction to a patient's stomach. Furthermore, as discussed above, the incompressible body 1028, 1028e may comprise the band 1016, 1016e itself, as the incompressible body 1028, 1028e may comprise an inner-tube-like structure extending around a portion of the patient's stomach. The motor system 1058 or hinge motor 1038e may be integral with the band 1016, 1016e, or may be positioned exterior to the band 1016, 1016e.

The gastric band devices 1000, 1000e discussed in relation to FIGS. 10A-10H provide multiple benefits, including a simplistic design and operation. The gastric band devices 1000, 1000e may exert a radial force, produced by a purely axial force, conveyed through the displacement of an incompressible body 1028, 1028e. A non-radial actuation force may this be used to produce a radial constriction. In addition, the incompressible body 1028, 1028e may exert a substantially cushioned and even force to the patient's stomach. Furthermore, the outer diameter of the band 1016, 1016e does not vary during operation, as the free end 1046, 1046e of the incompressible body 1028, 1028e only extends towards the interior of the gastric band device 1000, 1000e.

Figure 11A:
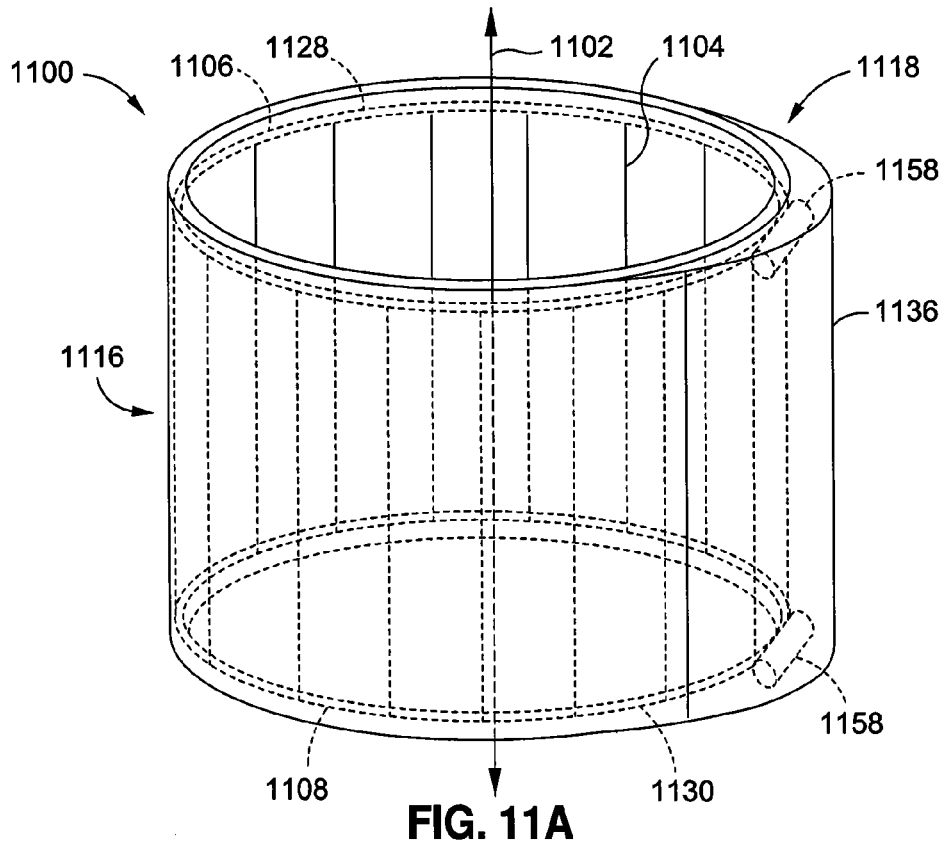
FIGS. 11A-11B illustrate perspective views of a gastric band device according to an embodiment of the present invention.

FIG. 11A illustrates a gastric band device 1100 including a band 1116 having a rotatable constriction device 1104. The band 1116 is positioned in a loop around the portion of the patient's stomach, in a manner similar to the gastric band device 100 described in relation to FIG. 1A. The gastric band device 1100 includes a suitable mechanism (not shown) to allow the gastric band device 1100 to be looped around the portion of the patient's body. The gastric band device 1100 serves to provide a degree of constriction to a portion of the patient's stomach, similar to the gastric band device 100 described in relation to FIG. 1A.

The loop has a generally circular shape, to allow the band 1116 to symmetrically fit around and encircle the portion of the patient's stomach. A motor system 1158 may be positioned within the band 1116, contained within an outer housing 1136 of the band 1116.

The loop shape of the band 1116 defines an inner region 1101 (shown in FIG. 11C) that is bounded by the band 1116 and the rotatable constriction device 1104. The patient's stomach may be complementary with the inner region 1101 formed by the loop. The band 1116 is configured to loop around an axis 1102 extending centrally through the inner region 1101.

The rotatable constriction device 1104 itself may comprise the band 1116, as the rotatable constriction device 1104 similarly encircles the patient's stomach and the axis 1102, and applies a degree of constriction to the patient's stomach. However, the rotatable constriction device 1104 may also be contained within a separate band 1116 structure, including an outer housing 1136, as shown in FIG. 11A.

The rotatable constriction device 1104 comprises a cylindrical sheath, or cylindrical membrane having a first end 1106 and a second end 1108. The rotatable constriction device 1104 may be deformable. An interior of the sheath comprises the inner region 1101. The ends 1106, 1108 are positioned along the axis 1102, at a distance 1110 from each other (as shown in FIG. 11D). The rotatable constriction device 1104 is coupled to a rotation actuator system 1118, comprising a motor system 1158, a first rotatable band 1128, and a second rotatable band 1130. The rotation actuator system 1118 may be contained within an outer housing 1136, that comprises an outer surface of the gastric band device 1100.

The motor system 1158 may comprise any of the motor systems shown in FIGS. 2A-2O. The gastric band device 1100 may be suitably modified to allow a desired configuration of the motor system 1158 to drive the rotatable bands 1128, 1130. Furthermore, the motor system 1158 may also include any other style of known motor capable of producing effective operation as contemplated by the gastric band device 1100.

The first end 1106 of the rotatable constriction device 1104 is coupled to the first rotatable band 1128 and the second end 1108 is coupled to the second rotatable band 1130. The rotation actuator system 1118 is configured to rotate rotatable bands 1128, 1130, causing the rotatable constriction device 1104 to twist. The rotatable bands 1128, 1130 are rotated in a direction opposite from each other.

Figure 11B:
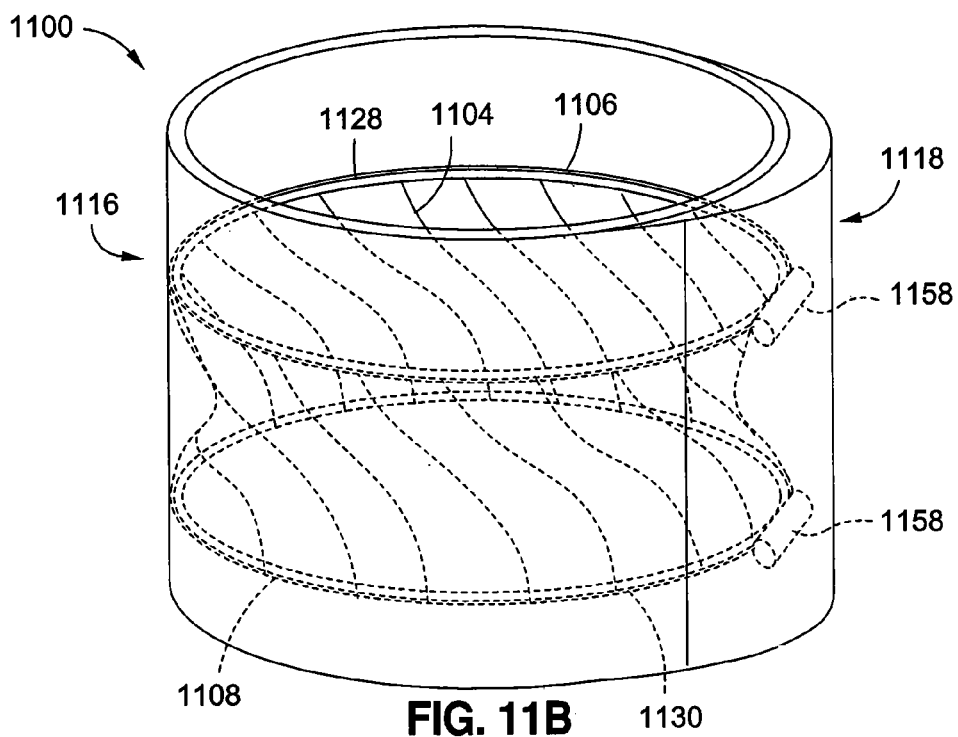

FIG. 11B illustrates the result of the twisting of the rotatable constriction device 1104. Both ends 1106, 1108 have been rotated in different directions. The twisting of the rotatable constriction device 1104 reduces an inner diameter 1126 (shown in FIG. 11F) of the rotatable constriction device 1104, causing the device to increase a degree of constriction applied to the patient's stomach. The ends 1106, 1108 of the rotatable constriction device 1104 have also been drawn to a closer distance 1110 (shown in FIG. 11F).

The rotatable constriction device 1104 is made from a material flexible enough to accommodate the twisting motion caused by the actuator system 1118, yet stiff enough to apply a force to the patient's stomach. A durable polymer material, or a fibrous material may be preferable. In addition, the rotatable constriction device 1104 may also comprise a series of rod-like structures extending along the axis 1102, and covered with a membrane, the rod-like structures being configured to produce an equivalent result.

Figure 11C:
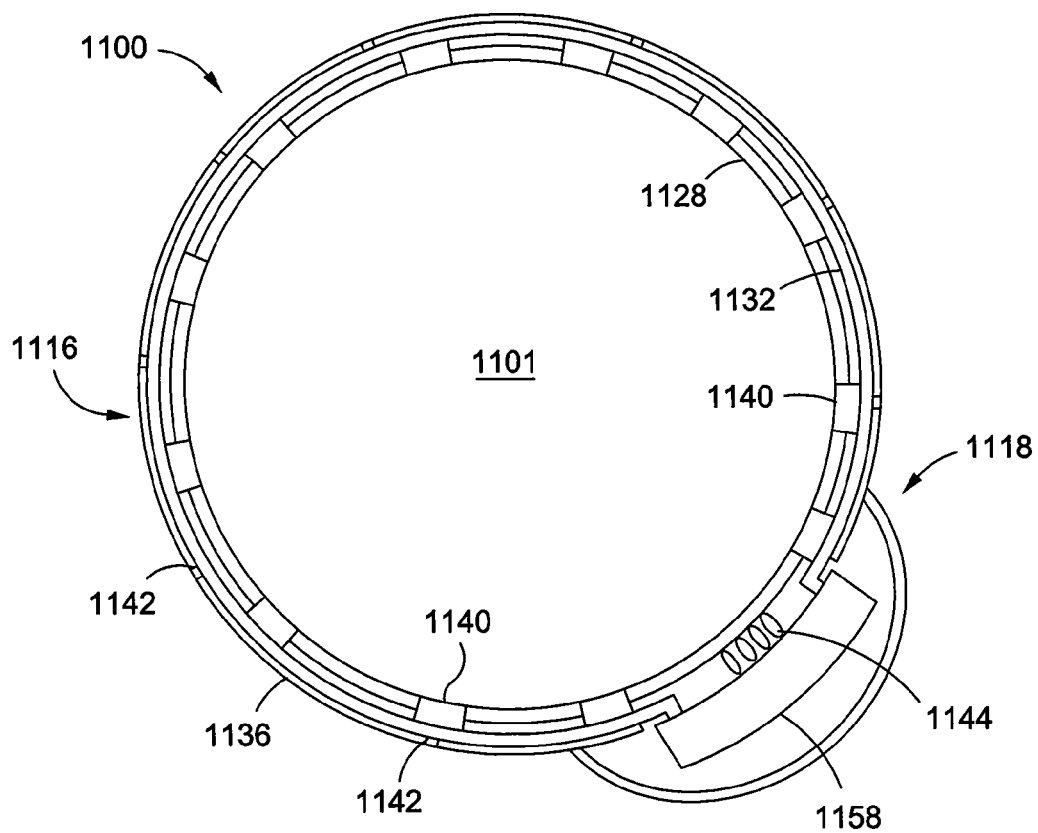
FIG. 11C illustrates a top view of the gastric band device shown in FIG. 11A.
Figure 11D:
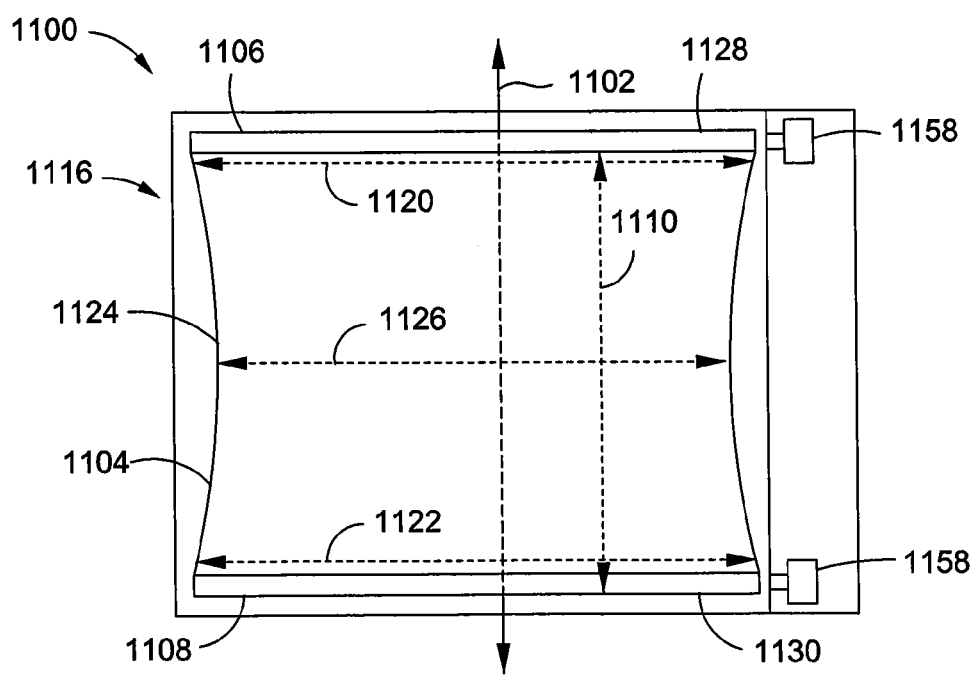
FIG. 11D illustrates a side view of the gastric band device shown in FIG. 11A.

FIG. 11C illustrates a top view of the gastric band device 1100 shown in FIG. 11A. The rotatable band 1128 may be coupled to a slide ring 1132 through a series of rotation guides 1140. The slide ring 1132 couples to the outer housing 1136 through a series of slide guides 1142, or grooves in the outer housing 1136. The motor system 1158 may couple to the slide ring 1134, to allow the motor system 1158 to slide along with the rotatable band 1128 during operation. The motor system 1158 may engage the rotatable band 1128 through a worm gear 1144, or any other equivalent mechanism. The worm gear 1144 rotates the rotatable band 1128, to correspondingly rotate the first end 1106 of the rotatable constriction device 1104, as shown in FIG. 11A.

FIG. 11D illustrates a side view of the gastric band device 1100 shown in FIG. 11A. The first end 1106 of the rotatable constriction device 1104 has a diameter 1120, and the second end 1108 of the rotatable constriction device 1104 additionally has a diameter 1122. A middle portion 1124 of the rotatable constriction device 1104 also has an inner diameter 1126. The first end 1106 is positioned at a distance 1110 from the second end 1108.

Figure 11E:
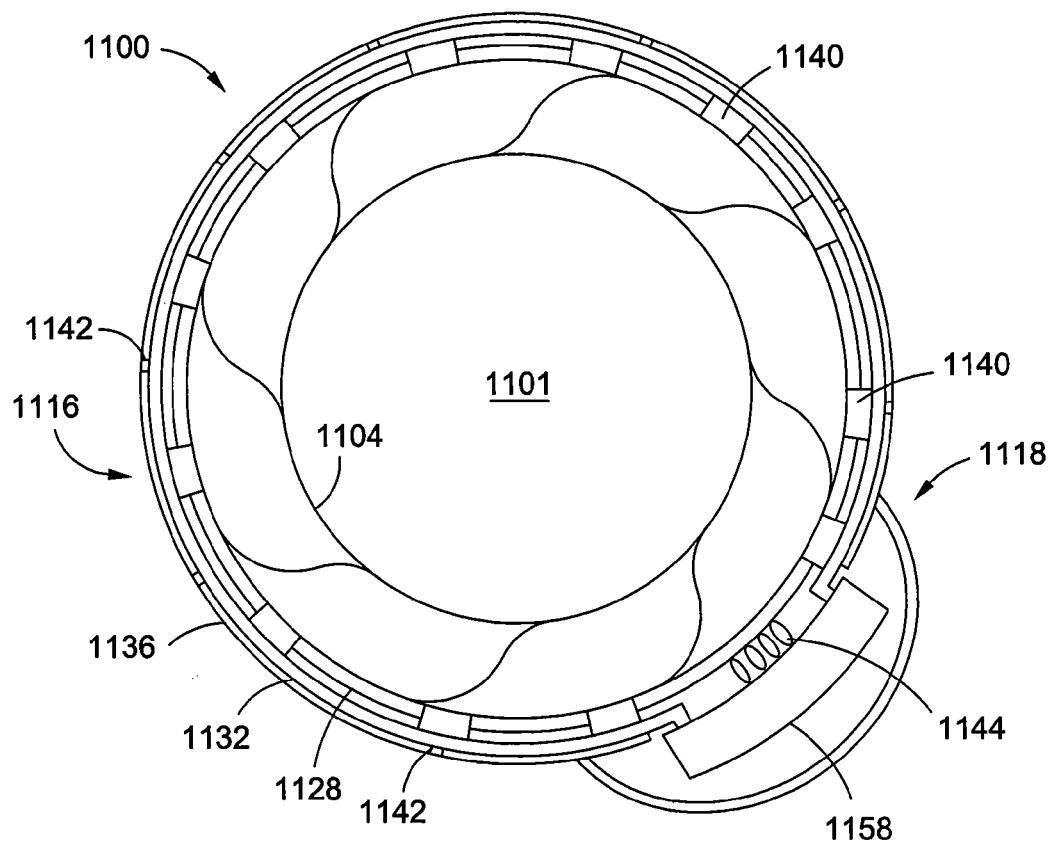
FIG. 11E illustrates a top view of the gastric band device shown in FIG. 11B.

FIG. 11E illustrates a top view of the gastric band device 1100 as shown in FIG. 11B. The rotatable constriction device 1104 is illustrated extending inwards, reducing the size of the inner region 1101, and applying an increased degree of constriction to the patient's stomach.

Figure 11F:
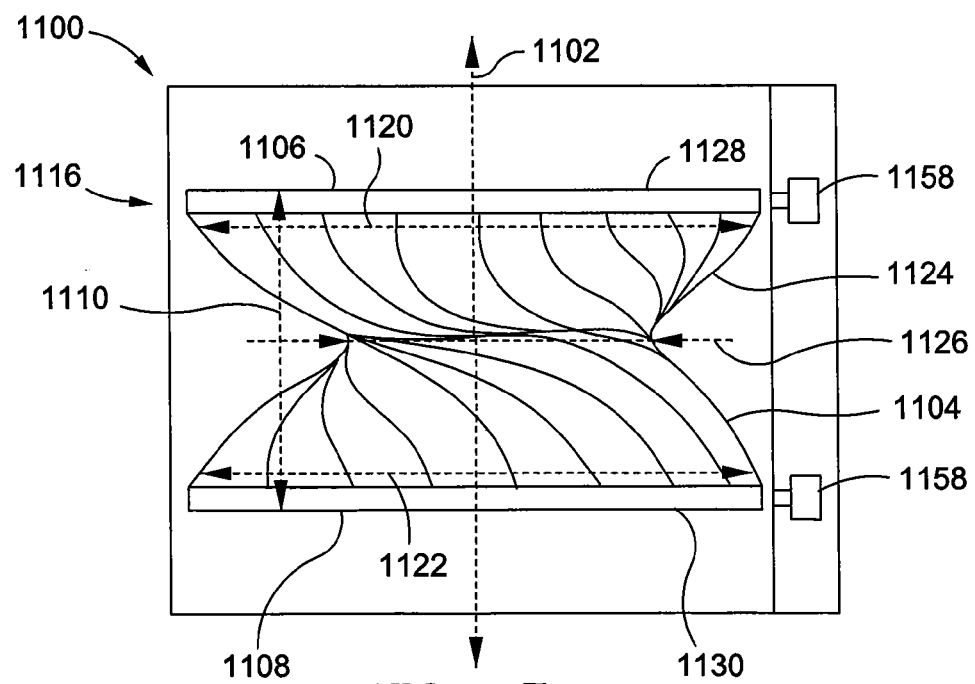
FIG. 11F illustrates a side view of the gastric band device shown in FIG. 11B.

FIG. 11F illustrates a side view of the gastric band device 1100 as shown in FIG. 11E. The rotatable constriction device 1104 has been twisted, reducing the inner diameter 1126 of the rotatable constriction device 1104. The distance 1110 between the two ends 1106, 1108 has been reduced. The diameters 1120, 1122 of the first end 1106 and the second end 1108 remain substantially constant.

The embodiment shown in FIGS. 11A-11F is exemplary in nature, and may be modified without deviating from the scope of this invention. For example, the configuration of the rotation actuator system 1118 may be varied to comprise any mechanism capable of rotating the rotatable constriction device 1104. In addition, one end of the rotatable constriction device 1104 may not be rotated, and the other end may be rotated, to produce a constricted region having a greater length than shown in FIG. 11F.

The gastric band device 1100 discussed in relation to FIGS. 11A-11F provides multiple benefits, including a simplistic design and operation. The gastric band device 1100 may exert a radial force purely through an applied rotation force. In addition, the material properties of the rotatable constriction device 1104 may be highly variable, to define various force and flexibility characteristics offered by the gastric band device 1100.

Figure 12A:
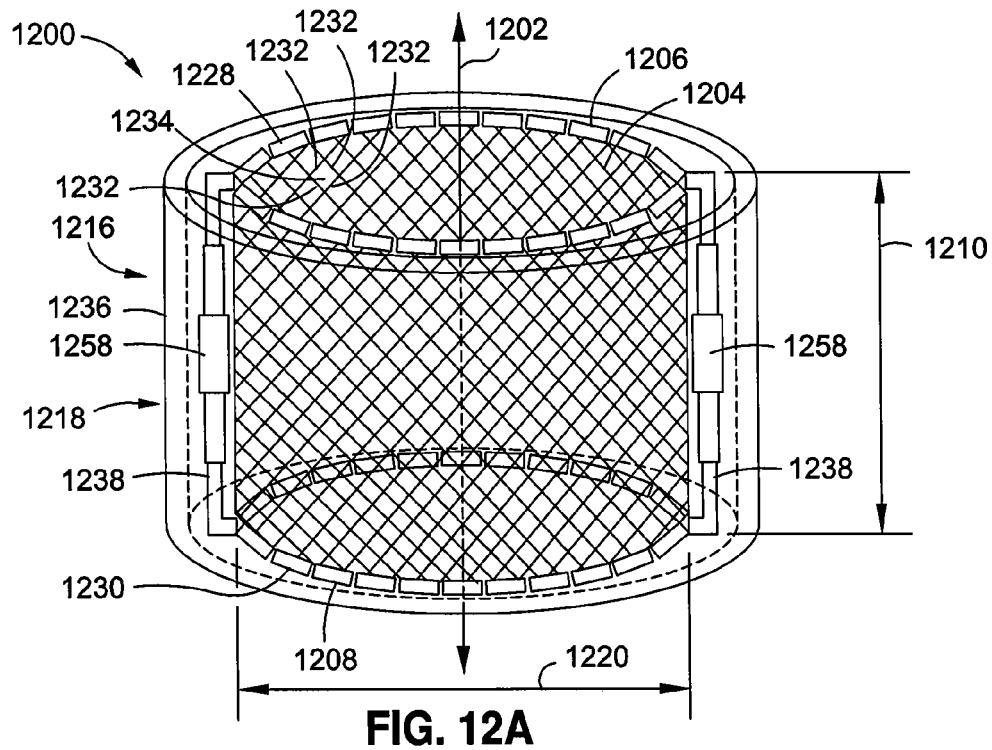
FIGS. 12A-12B illustrate perspective views of a gastric band device according to an embodiment of the present invention.

FIG. 12A illustrates an embodiment of a gastric band device 1200 including a band 1216 having a stretchable constriction device 1204. The band 1216 is positioned in a loop around the portion of the patient's stomach, in a manner similar to the gastric band device 100 described in relation to FIG. 1A. The gastric band device 1200 includes a suitable mechanism (not shown) to allow the gastric band device 1200 to be looped around the portion of the patient's body. The gastric band device 1200 serves to provide a degree of constriction to a portion of the patient's stomach, similar to the gastric band device 100 described in relation to FIG. 1A.

The loop has a generally circular shape, to allow the band 1216 to symmetrically fit around and encircle the portion of the patient's stomach. A motor system 1258 may be positioned within the band 1216, contained within an outer housing 1236 of the band 1216.

The loop shape of the band 1216 defines an inner region that is bounded by the band 1216 and the stretchable constriction device 1204. The patient's stomach may be complementary with the inner region formed by the loop. The band 1216 is configured to loop around an axis 1202 extending centrally through the inner region.

The stretchable constriction device 1204 itself may comprise the band 1216, as the rotatable constriction device 1204 similarly encircles the patient's stomach and the axis 1202, and applies a degree of constriction to the patient's stomach. However, the rotatable constriction device 1204 may also be contained within a separate band 1216 structure, including an outer housing 1236, as shown in FIG. 12A.

The stretchable constriction device 1204 comprises a cylindrical sheath, or cylindrical membrane having a first end 1206 and a second end 1208. An interior of the sheath comprises an inner region being complementary with the stomach of the patient. The ends 1206, 1208 are positioned along the axis 1202, at an axial distance 1210 from each other. The stretchable constriction device 1204 has a diameter 1220 when the constriction device 1204 is configured in the shape of a loop.

The stretchable constriction device 1204 is coupled to a constriction device actuator system 1218, comprising a motor system 1258, a first telescoping band 1228, and a second telescoping band 1230. The constriction device actuator system 1218 may be contained within an outer housing 1236, that comprises an outer surface of the gastric band device 1200.

The motor system 1258 may comprise any of the motor systems shown in FIGS. 2A-2O. The gastric band device 1200 may be suitably modified to allow a desired configuration of the motor system 1258 to drive the telescoping bands 1228, 1230. Furthermore, the motor system 1258 may also include any other style of known motor capable of producing effective operation as contemplated by the gastric band device 1200.

The first end 1206 of the stretchable constriction device 1204 is coupled to the first telescoping band 1228 and the second end 1208 is coupled to the second telescoping band 1230. The constriction device actuator system 1218 is configured to draw the telescoping bands 1228, 1230 towards each other, or away from each other. If the telescoping bands 1228, 1230 are drawn away from each other, a stretching force is applied to the stretchable constriction device 1204. If the bands 1228, 1230 are drawn towards each other, a compressive force is applied to the stretchable constriction device 1204. The telescoping bands 1228, 1230 are configured to have a variable length, to accommodate the diameter change of the constriction device 1204 (e.g., the telescoping bands 1228, 1230 have a telescoping structure). The motor system 1258 couples to the bands 1228, 1230, through control arms 1238.

The stretchable constriction device 1204 may comprise a structure capable of expanding or decreasing a diameter 1220 in response to a varied axial distance 1210 between the ends 1206, 1208 of the stretchable constriction device 1204. The stretchable constriction device 1204 may therefore be stretchable in either an axial distance 1210 or along the radial diameter 1220. The stretchable constriction device 1204 may comprise a web-like structure, including a plurality of connecting supports 1232 defining a bounded region 1234. The connecting supports 1232 are oriented to allow the size of the bounded region 1234 to vary in response to a varied orientation of the connecting supports 1232. The connecting supports 1232 may be flexibly coupled, or pivotally coupled, to each other to allow the connecting supports 1232 to pivot with respect to each other. The pivotal action varies the size of the bounded region 1234, and transforms a varied axial distance 1210 into a varied diameter 1220. The stretchable constriction device 1204 operates similarly to a stent device commonly used in cardiovascular surgery.

In operation, the constriction device actuator system 1218, either compresses or stretches the stretchable constriction device 1204. The telescoping bands 1228, 1230 transmit the corresponding force to the stretchable constriction device 1204, which causes the diameter 1220 to vary, and the degree of constriction applied by the stretchable constriction device 1204 to the patient's stomach to also vary.

Figure 12B:
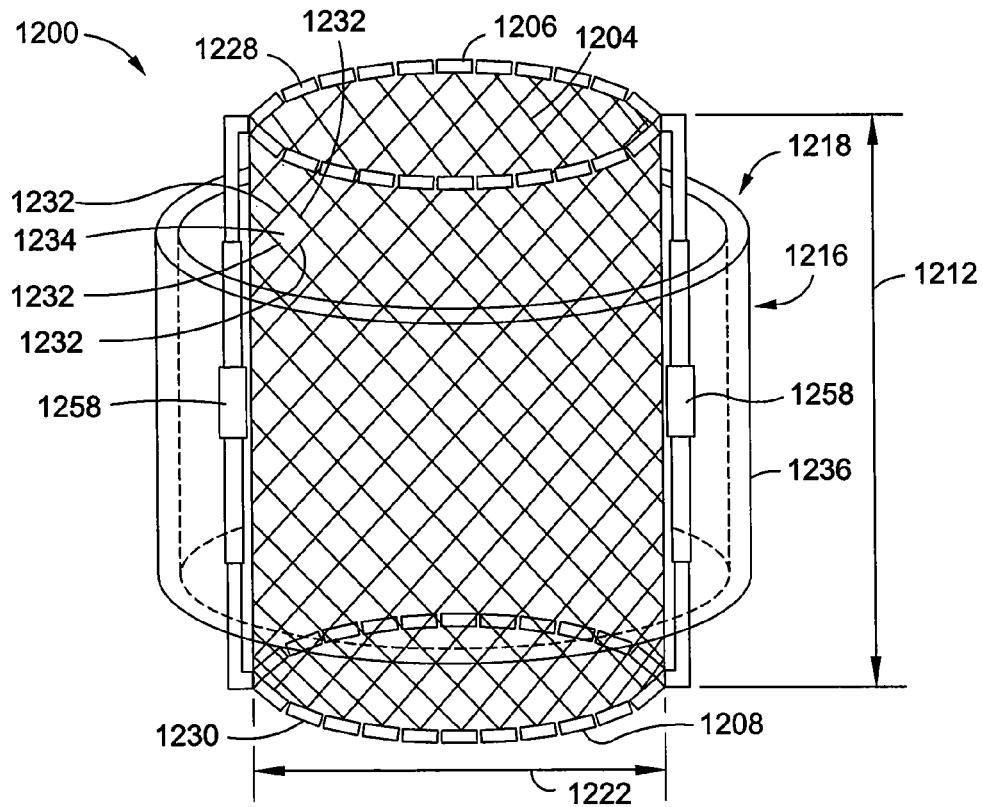

FIG. 12B illustrates the result of a stretching force applied to the stretchable constriction device 1204 by the constriction device actuator system 1218. The stretchable constriction device 1204 has a distance 1212 between two ends 1206, 1208 being greater than the axial distance 1210 shown in FIG. 12A. The stretchable constriction device 1204 additionally has a diameter 1222 being greater than the diameter 1222 shown in FIG. 12A. A size of the bounded region 1234 has varied and increased from shown in FIG. 12A, although the size may decrease as the stretchable constriction device 1204 continues to stretch (e.g., the connecting supports 1232 are drawn nearer to increase the length of the bounded region 1234 in an axial direction). A compressive force applied to the stretchable constriction device 1204 shown in FIG. 12B returns the stretchable constriction device 1204 back to the configuration shown in FIG. 12A. The size of the bounded region 1234 will vary, and will eventually decrease as the stretchable constriction device 1204 continues to compress (e.g., the connecting supports 1232 are drawn nearer to increase the width of the bounded region 1234 in a direction perpendicular to the axial direction).

The embodiment shown in FIGS. 12A-12B is exemplary in nature, and may be modified without deviating from the scope of this invention. For example, the configuration of the constriction device actuator system 1218 may be varied to comprise any mechanism capable of stretching or compressing the stretchable constriction device 1204. In addition, the structure of the stretchable constriction device 1204 may be varied to comprise any structure designed to narrow in diameter in response to a stretching force. The stretchable constriction device 1204 may comprise a mesh-like structure, or a scissoring structure that telescopes in length. The stretchable constriction device 1204 may comprise a woven metallic mesh having the property of varying the stretchable constriction device's 1204 diameter in response to a change in length. In addition, the stretchable constriction device 1204 may comprise a spring-like structure, biased to either increase or decrease the constrictive force exerted by the gastric band device 1200.

The gastric band device discussed in relation to FIGS. 12A-12B provides multiple benefits, including a simplistic design and operation. The gastric band device 1200 may exert a radial force purely through an applied axial force. In addition, the material properties of the stretchable constriction device 1204 may be highly variable, to define various force and flexibility characteristics offered by the gastric band device 1200.

Figure 13A:
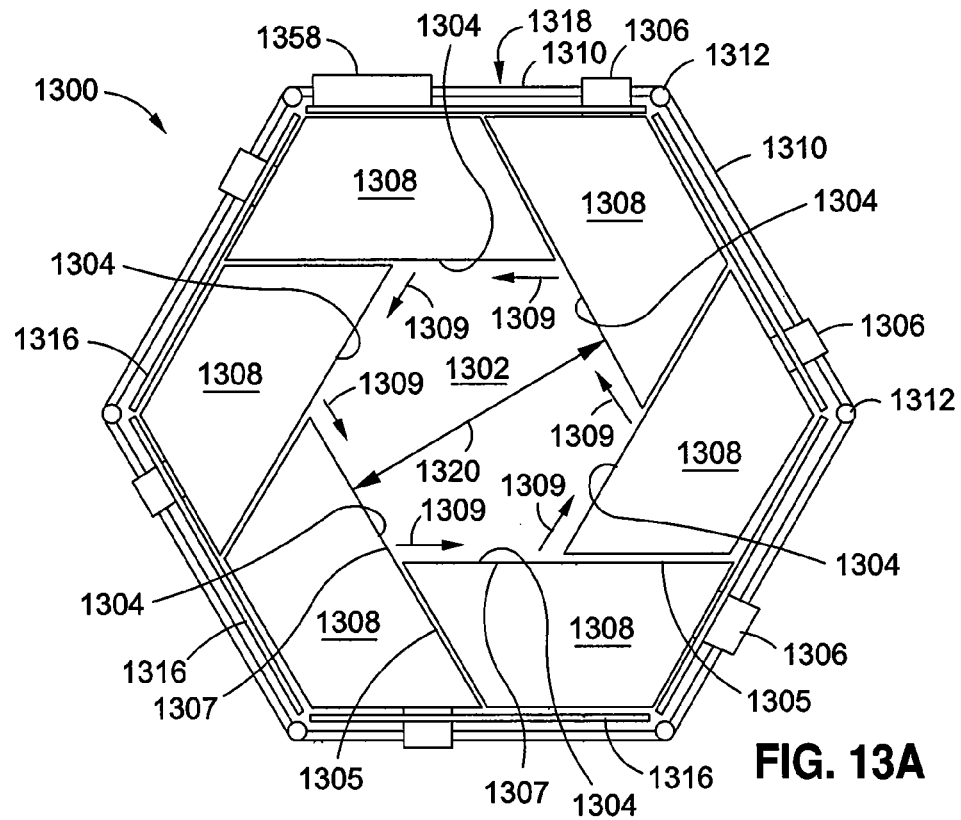
FIGS. 13A-13B illustrate top views of a gastric band device according to an embodiment of the present invention.

FIG. 13A illustrates a gastric band device 1300 including a band 1316 having a plurality of force transmission surfaces 1304. The band 1316 is positioned in a loop around the portion of the patient's stomach, in a manner similar to the gastric band device 100 described in relation to FIG. 1A. The gastric band device 1300 includes a suitable mechanism (not shown) to allow the gastric band device 1300 to be looped around the portion of the patient's body. The gastric band device 1300 serves to provide a degree of constriction to a portion of the patient's stomach, similar to the gastric band device 100 described in relation to FIG. 1A.

The loop has a generally circular shape, or encircling shape, to allow the band 1316 to symmetrically fit around and encircle the portion of the patient's stomach. A motor system 1358 may be coupled to an outer surface of band 1316.

The loop shape of the band 1316 defines an inner region 1302 that is bounded by the band 1316 and the force transmission surfaces 1304. The patient's stomach may be complementary with the inner region 1302 formed by the loop.

Each force transmission surface 1304 comprises a flattened contact surface that applies a degree of constriction to the portion of the patient's stomach to be constricted. The force transmission surface 1304 is oriented to define the inner region 1302, which in FIG. 13A has a substantially polygonal, or hexagonal shape. The force transmission surface 1304 may comprise a surface 1304 of a force transmission structure 1308, the surface 1304 being directed towards the inner region 1302.

The force transmission structure 1308 is a structure coupling the force transmission surface 1304 to the band 1316. In the embodiment shown in FIG. 13A, each force transmission structure 1308 has a substantially polygonal, or trapezoidal shape. One surface of the force transmission structure 1308 comprises the force transmission surface 1304 and another surface of the force transmission structure 1308 couples the force transmission surface 1304 to the band 1316.

The band 1316 is shaped to have a substantially polygonal, or hexagonal shape. The force transmission structures 1308 are shaped to fit within the shape defined by the band 1316. A force transmission surface control system 1318 is coupled to the band 1316 and comprises a motor system 1358 and a plurality of linking members 1310. The motor system 1358 may comprise any of the motor systems shown in FIGS. 2A-2O. The gastric band device 1300 may be suitably modified to allow a desired configuration of the motor system 1358 to drive the linking members 1310. Furthermore, the motor system 1358 may also include any other style of known motor capable of producing effective operation as contemplated by the gastric band device 1300.

The linking members 1310 may comprise cords extending around routing mechanisms, or pulley wheels 1312 positioned along the exterior of the band 1316. Each linking member 1310 may couple to a force transmission structure 1308 through a slide coupler device 1306. The slide coupler devices 1306 additionally couple the force transmission structures 1308 to the band 1316, and allow the force transmission structures 1308 to slide relative to the band 1316. The force transmission structures 1308 slide, or translate in a circular manner around the inner region 1302. The slide coupler device 1306 guides the force transmission structure 1308, and correspondingly the force transmission surface 1304 in a direction 1309 substantially towards the inner region 1302.

The configuration of the gastric band device 1300 shown in FIG. 13A, represents a relatively minimal degree of constriction applied by the force transmission surfaces 1304 to the patient's stomach. In this configuration, the inner region 1302 has a diameter 1320 defined by the distance of opposing force transmission surfaces 1304 from each other. In addition, the structure and placement of the force transmission structures 1308 has divided each force transmission surface 1304 into a non-contacting surface 1305 and a contacting surface 1307. The non-contacting surface 1305 represents the portion of the transmission surface 1304 that is not abutting the patient's stomach. The contacting surface 1307 represents the portion of the transmission surface 1304 abutting the patient's stomach. During operation of the force transmission surface control system 1318, the system 1318 slides each force transmission surface 1304 in a direction 1309 substantially towards the inner region 1302.

Figure 13B:
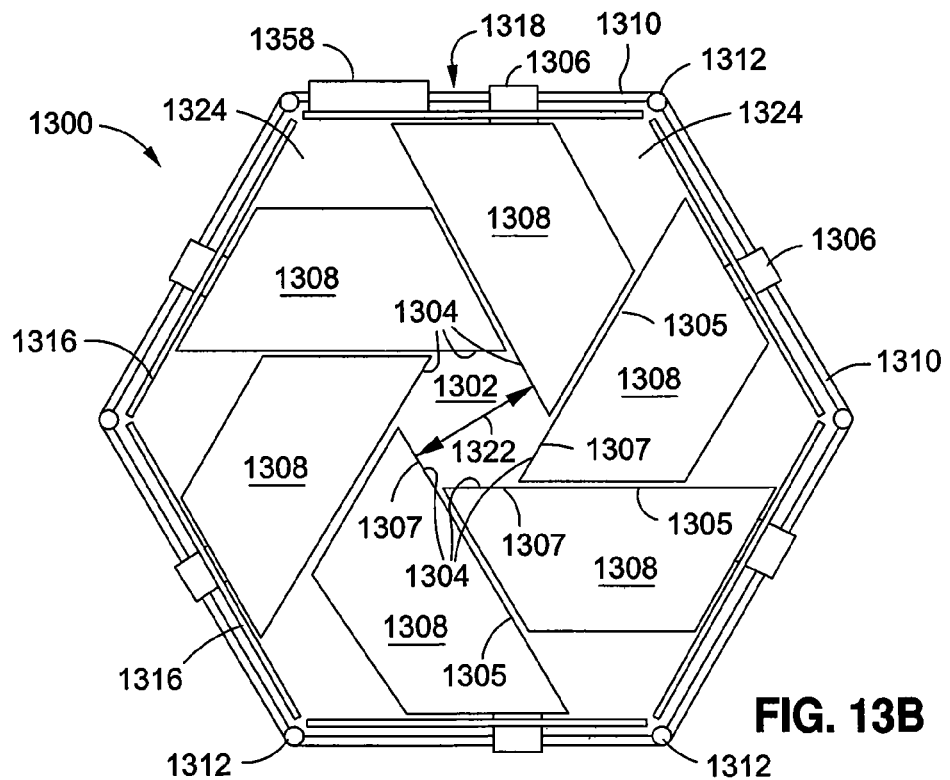

FIG. 13B illustrates the configuration of the gastric band device 1300 shown in FIG. 13A after the force transmission surface control system 1318 has slid each force transmission surface 1304 in a direction substantially towards the inner region 1302. In this configuration, the size of the inner region 1302, and the diameter 1322 of the inner region 1302 formed by the force transmission surfaces 1304 has decreased from the configuration shown in FIG. 13A. In addition, the ratio of the contacting surface 1307 and the non-contacting surface 1305 has been varied, with a smaller portion of the force transmission surface 1304 abutting the patient's stomach. The decreased size of the inner region 1302 is compensated for by the presence of voids 1324 positioned within the band 1316, produced by the motion of the force transmission structures 1308. In one embodiment, the polygonal shape of the inner region 1302 has remained substantially similar, yet the size of the region 1302 has decreased. In addition, it is understood the inner region 1302 remains substantially bounded by the force transmission surfaces 1304.

The configuration shown in FIG. 13B represents an increased degree of constriction applied by the force transmission surfaces 1304 to the patient's stomach. To reduce the degree of constriction, the force transmission surface control system 1318 operates to slide the force transmission surfaces 1304 in a direction opposite to the direction 1309 shown in FIG. 13A.

Figure 13C:
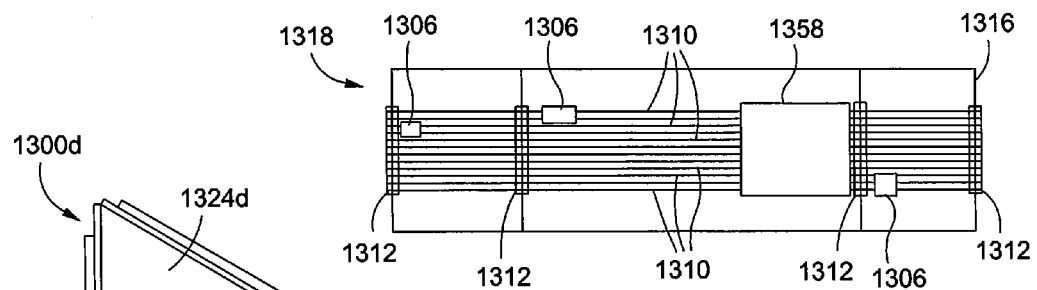
FIG. 13C illustrates a side view of the gastric band device shown in FIG. 13A.

FIG. 13C illustrates a side view of the gastric band system 1300 shown in FIG. 13A, specifically illustrating the force transmission surface control system 1318. The motor system 1358 is visibly being coupled to the band 1316. In addition, the plurality of linking members 1310 or cords are visible extending around the band 1316 and over the pulley wheels 1312. The linking members 1310 are visibly positioned along the exterior of the band 1316.

Figure 13D:
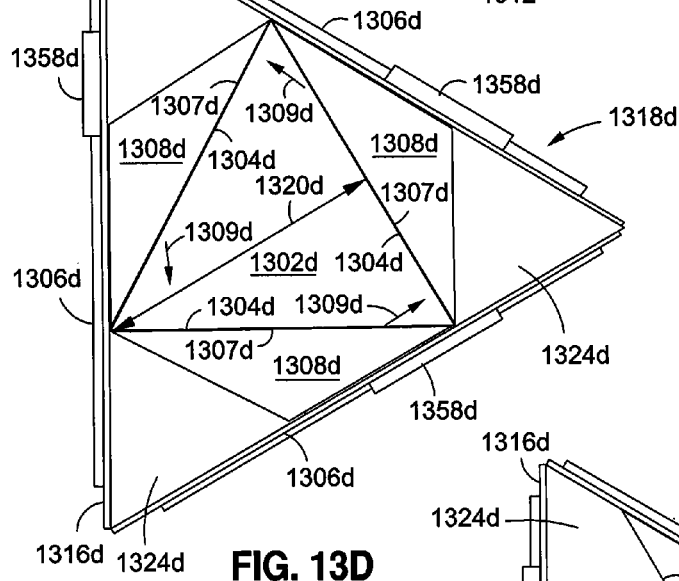
FIGS. 13D-13E illustrate top views of a gastric band device according to an embodiment of the present invention.

FIG. 13D illustrates a gastric band device 1300*d* including force transmission structures 1308*d* having a substantially triangular shape. In this embodiment, the force transmission surfaces 1304*d* bound an inner region 1302*d* having a diameter 1320*d*. In addition, the force transmission surfaces 1304*d* only include a contacting surface 1307*d*, and do not include a non-contacting surface, as discussed in relation to FIG. 13A. The force transmission surface control system 1318*d* comprises a series of motor systems 1358*d* engaged with a slide coupler device 1306*d*. In this embodiment, the slide coupler device 1306*d* may comprise a track system, or series of runners that the force transmission structure 1308*d* runs along. The band 1316*d* has a triangular shape in this embodiment, and a plurality of voids 1324*d* are positioned within the band 1316*d*.

Figure 13E:
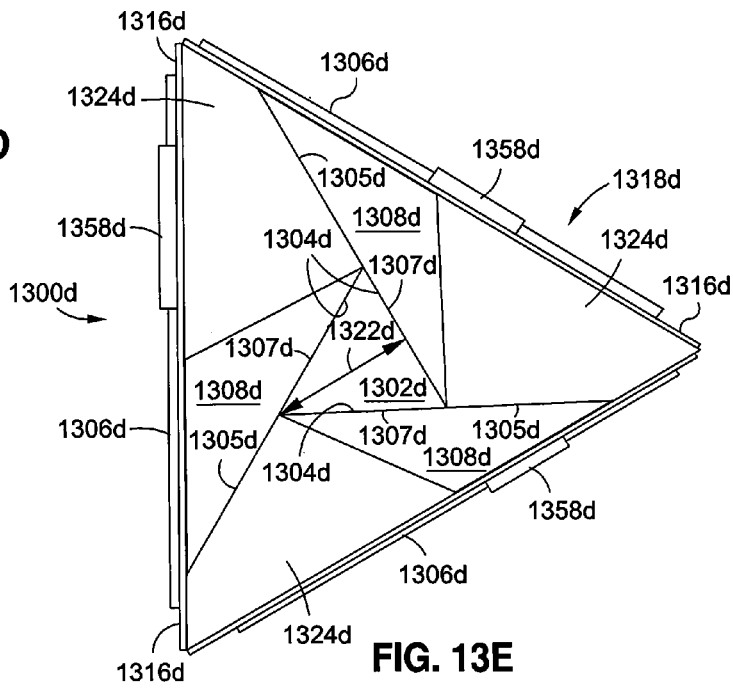

FIG. 13E illustrates the embodiment shown in FIG. 13D after the force transmission surface control system 1318*d* has driven each force transmission surface 1304*d* in a direction 1309*d* (shown in FIG. 13D) substantially towards the inner region 1302. The motion of the surfaces 1304*d* has decreased a size of the inner region 1302*d* and accordingly increased a degree of constriction applied to the patient's stomach. The inner region 1302*d* has a diameter 1322*d* being smaller than shown in FIG. 13D. Each force transmission surface 1304*d* has a non-contacting surface 1305*d* that is proportionally larger than the contacting surface 1307*d*. The size of the voids 1324*d* has also increased.

The embodiments shown in FIGS. 13A-13E are exemplary in nature, and may be modified without deviating from the scope of this invention. For example, the configuration of the force transmission surface control system 1318, 1318*d* may be varied to comprise any mechanism capable of sliding the force transmission surfaces 1304, 1304*d* along the band 1316. In addition, the shape or structure of the force transmission surfaces 1304, 1304*d* may be varied to produce an equivalent result, and need not be substantially flat. In addition, the force transmission surfaces 1304, 1304*d* need not be integral with a polygonal shaped force transmission structure 1308, 1308*d*, and need not be positioned within a polygonal shaped band. The shapes of and sizes of the bands and the force transmission surfaces and structures may be varied to produce an equivalent result.

The gastric band devices 1300, 1300*d* discussed in relation to FIGS. 13A-13E provide multiple benefits, including a simplistic design and operation. The gastric band device 1300, 1300*d* may slide each surface 1304, 1304*d* in a relatively frictionless manner along the band, with the band providing structure for the gastric band device 1300, 1300*d*. In addition, the interlocking nature of the force transmission structures 1308, 1308*d* provides strength and support for the force transmission surfaces 1304, 1304*d*.

Figure 14A:
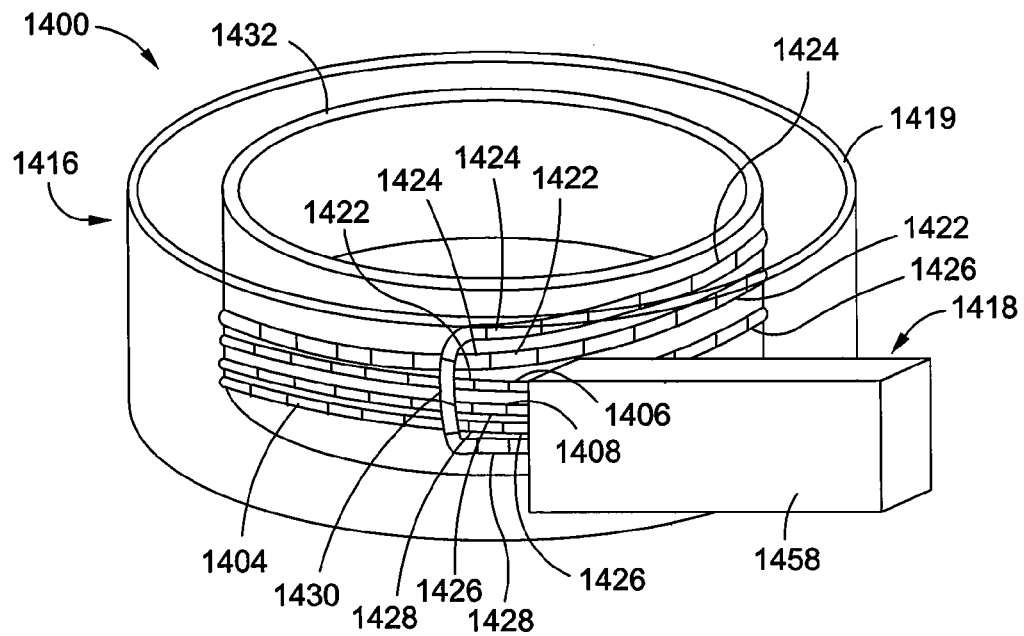
FIG. 14A illustrates a perspective view of a gastric band device according to an embodiment of the present invention.

FIG. 14A illustrates a gastric band device 1400 including a band 1416 having a cord 1404. The band 1416 is positioned in a loop around the portion of the patient's stomach, in a manner similar to the gastric band device 100 described in relation to FIG. 1A. The gastric band device 1400 includes a suitable mechanism (not shown) to allow the band device 1400 to be looped around a portion of the patient's body. The gastric band device 1400 serves to provide a degree of constriction to a portion of the patient's stomach, similar to the gastric band device 100 described in relation to FIG. 1A.

The loop has a generally circular shape, to allow the band 1416 to symmetrically fit around and encircle the portion of the patient's stomach. A motor system 1458 may be coupled to a portion of the band 1416.

The loop shape of the band 1416 defines an inner region 1401 (shown in FIG. 14B) that is bounded by the band 1416 and the cord 1404. The patient's stomach may be complementary with the inner region 1401 formed by the loop.

The cord 1404 itself may comprise the band 1416, as the cord 1404 similarly encircles the patient's stomach and applies a degree of constriction to the patient's stomach. However, the cord 1404 may also be contained within a separate band 1416 structure, as shown in FIG. 14A. If the cord 1404 is contained within a separate band 1416 structure, the band 1416 may include a rigid dorsal periphery 1419 to prevent movement of the outer diameter of the band 1416 during operation of the motor system 1458. The rigid dorsal periphery 1419 may operate similarly as with the band 316 discussed in relation to FIG. 3A.

The cord 1404 has a first end 1406 and a second end 1408, and has a portion that loops multiple times around the inner region 1401. The first end 1406 and the second end 1408 of the cord 1404 are coupled to a cord control system 1418, which is coupled to the band 1416 and comprises a motor system 1458. The motor system 1458 may comprise any of the motor systems shown in FIGS. 2A-2O, and the gastric band device 1400 may be suitably modified to allow a desired configuration of the motor system 1458 to drive the cord 1404. In addition, any of the cylindrical transmission devices shown in FIGS. 3A-3L may be incorporated into the gastric band device 1400, and the gastric band device 1400 may be suitably modified to incorporate the desired cylindrical transmission device. Furthermore, the motor system 1458 may also contain any other style of known motor capable of producing effective operation as contemplated by the device 1400.

The first end 1406 of the cord 1404 extends out from the motor system 1458, and loops around the inner region 1401. The initial loop is referred to as the first portion 1422 of the cord 1404. The first portion 1422 of the cord 1404 continues to loop around the inner region 1401, and becomes the second portion 1424 of the cord 1404 forming a second loop around the inner region 1401. The second portion 1424 of the cord 1404 then loops around the inner region 1401 until it becomes the fifth portion 1430 of the cord 1404.

The second end 1408 of the cord 1404 extends out from the motor system 1458, and loops around the inner region 1401. The initial loop is referred to as the third portion 1426 of the cord 1404. The third portion 1426 of the cord 1404 continues to loop around the inner region 1401, and becomes the fourth portion 1428 of the cord 1404 forming a second loop around the inner region 1401. The fourth portion 1428 of the cord 1404 then loops around the inner region 1401 until it becomes the fifth portion 1430 of the cord 1404.

The fifth portion 1430 of the cord 1404 extends over a part of the second portion 1424, the first portion 1422, the third portion 1426, and a part of the fourth portion 1428 of the cord 1404. The fifth portion 1430 presses against the overlapped portions 1424, 1422, 1426, 1428 of the cord 1404 to securely tension the cord 1404 when the cord control system 1418 retracts the cord 1404. The routing of the cord 1404 substantially resembles a prusik knot shape, as is known in the art of mountain climbing.

Figure 14B:
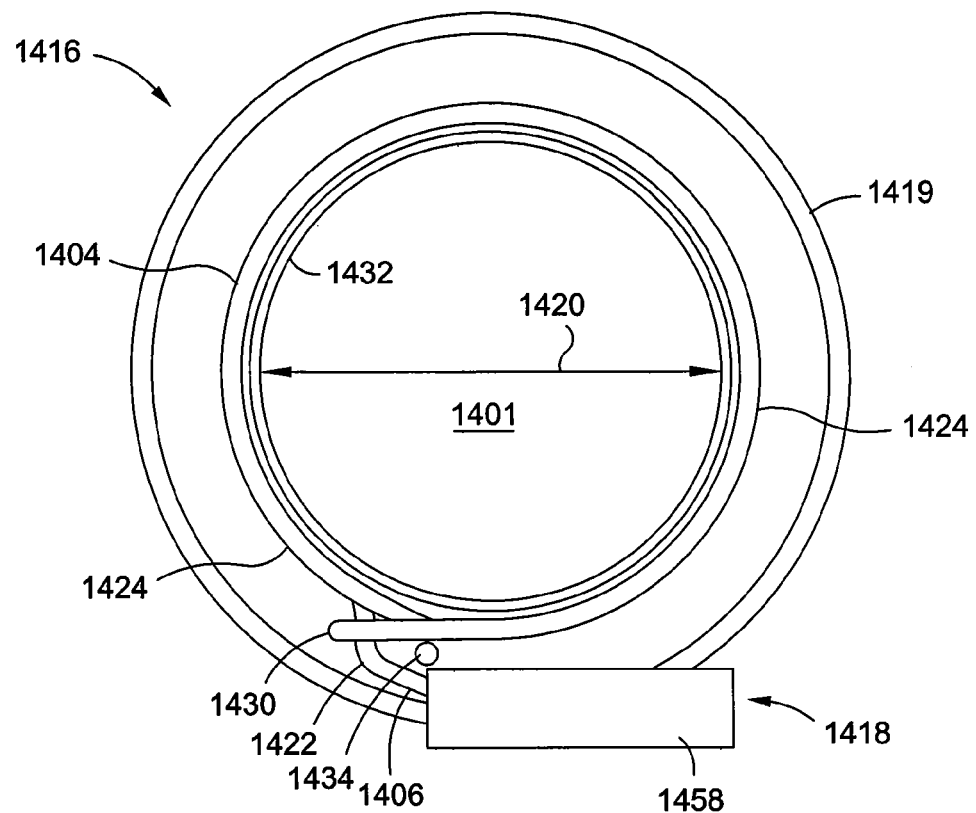
FIG. 14B illustrates a top view of the gastric band device shown in FIG. 14A.

In operation, the cord control system 1418 tensions the ends 1406, 1408 of the cord 1404 to increase the degree of constriction applied to the patient's stomach. A resilient membrane 1432 may be positioned to have the cord 1404 encircle the resilient membrane 1432, the resilient membrane 1432 resisting the tensioning force. The tensioning of the cord 1404 decreases a diameter 1420 formed by the loops of the cord 1404, as shown in FIG. 14B. To reduce the degree of constriction, the cord control system 1418 releases the cord 1404, and the resilient membrane 1432 expands the diameter 1420 formed by the cord 1404.

FIG. 14B illustrates a top view of the gastric band device 1400 shown in FIG. 14A. The inner region 1401 and the diameter 1420 formed by the loops of the cord 1404 are illustrated. A support mast 1434 may aid to route the loops of the cord 1404.

Figure 14C:
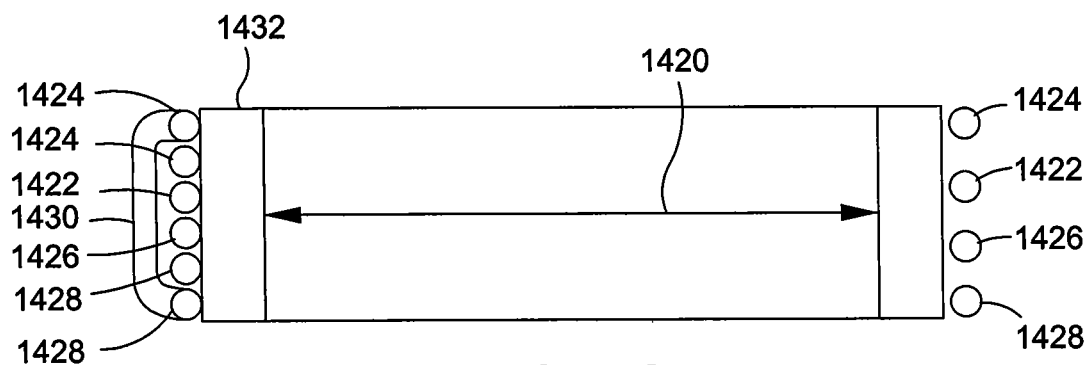
FIG. 14C illustrates a side cross-sectional view of the gastric band device shown in FIG. 14A.

FIG. 14C illustrates a cross sectional view of the gastric band device 1400 shown in FIG. 14A. The portions of the cord positioned relative to the resilient membrane 1432 are illustrated.

Figure 14D:
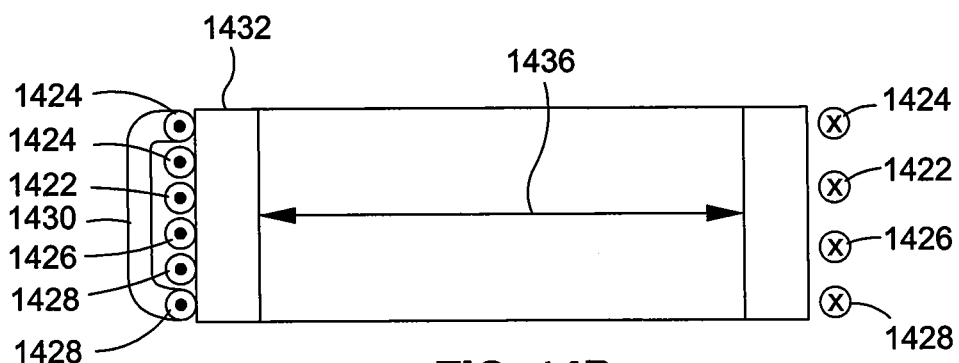
FIG. 14D illustrates a side cross-sectional view of the gastric band device shown in FIG. 14C, being configured differently than shown in FIG. 14C.

FIG. 14D illustrates the cross sectional view shown in FIG. 14D during an increased degree of constriction being applied to the patient's stomach. The "circles" or "dots" illustrated on the portions of the cord 1404 represent a force direction between directed out of the page. The "x"'s illustrated on the portions of the cord 1404 represent a force direction being directed towards the page. The cord 1404 produces a decreased diameter 1436 size, being smaller than the diameter 1420 shown in FIGS. 14B and 14C.

The embodiment shown in FIGS. 14A-14D is exemplary in nature, and may be modified without deviating from the scope of this invention. For example, the configuration of the cord control system 1418 may be varied to comprise any mechanism capable of tensioning or releasing the cord 1404. In addition, the cord control system 1418 may comprise a mounting to which the one end or both ends of the cord 1404 are fixed, to secure the cord 1404 in place while another mechanism tensions the cord 1404. In addition, the cord 1404 loops may be routed or formed in a multitude of shapes, yet equivalently comprising a cord 1404 being looped around an inner region.

The gastric band device discussed in relation to FIGS. 14A-14D provide multiple benefits, including a simplistic design and operation. The cord 1404 forms a loop that easily constricts the patient's stomach. The multiple loops of the cord 1404 and the knot-like shape of the cord 1404 strengthen and secure the cord 1404 around the patient's stomach.

Figure 15A:
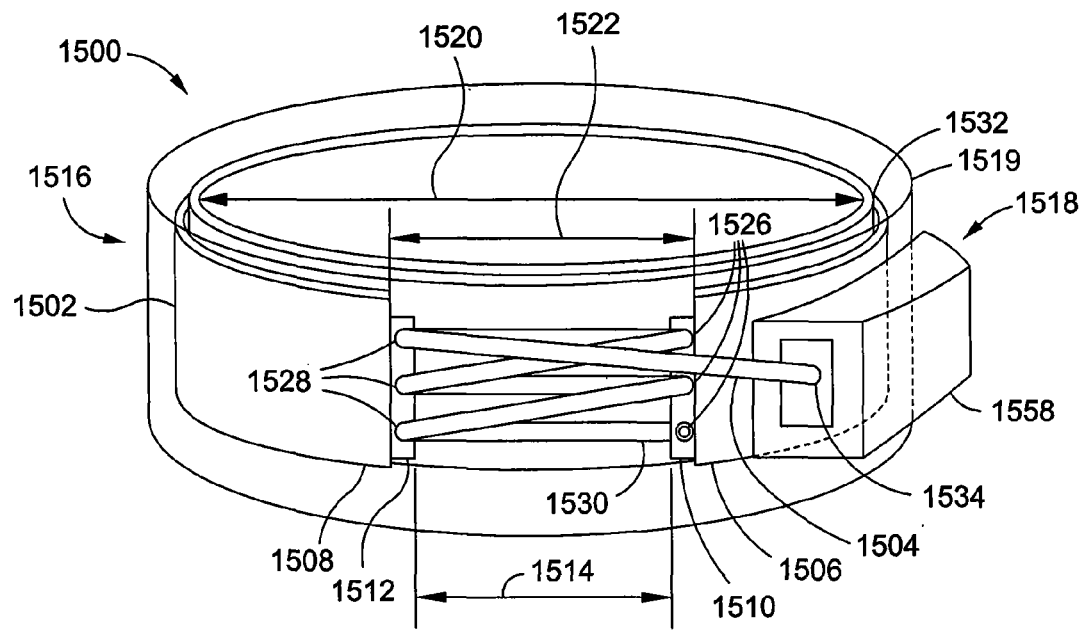
FIGS. 15A-15B illustrate perspective views of a gastric band device according to an embodiment of the present invention.

FIG. 15A illustrates a gastric band device 1500 including a band 1516 having a collar 1502 including cord routing devices 1510, 1512. The band 1516 is positioned in a loop around the portion of the patient's stomach, in a manner similar to the gastric band device 100 described in relation to FIG. 1A. The gastric band device 1500 includes a suitable mechanism (not shown) to allow the gastric band device 1500 to be looped around the portion of the patient's body. The gastric band device 1500 serves to provide a degree of constriction to a portion of the patient's stomach, similar to the gastric band device 100 described in relation to FIG. 1A.

The loop has a generally circular shape, to allow the band 1516 to symmetrically fit around and encircle the portion of the patient's stomach. A motor system 1558 may be coupled to a portion of the band 1516.

The loop shape of the band 1516 defines an inner region 1501 (shown in FIG. 15C) that is bounded by the band 1516 and the collar 1502. The patient's stomach may be complementary with the inner region 1501 formed by the loop.

The collar 1502 itself may comprise the band 1516, as the collar 1502 similarly encircles the patient's stomach and applies a degree of constriction to the patient's stomach. However, the collar 1502 may also be contained within a separate band 1516 structure, as shown in FIG. 15A. If the collar 1502 is contained within a separate band 1516 structure, the band 1516 may include a rigid dorsal periphery 1519 to prevent movement of the outer diameter of the band 1516 during operation of the motor system 1558. The rigid dorsal periphery 1519 may operate similarly as with the band 316 discussed in relation to FIG. 3A.

Figure 15B:
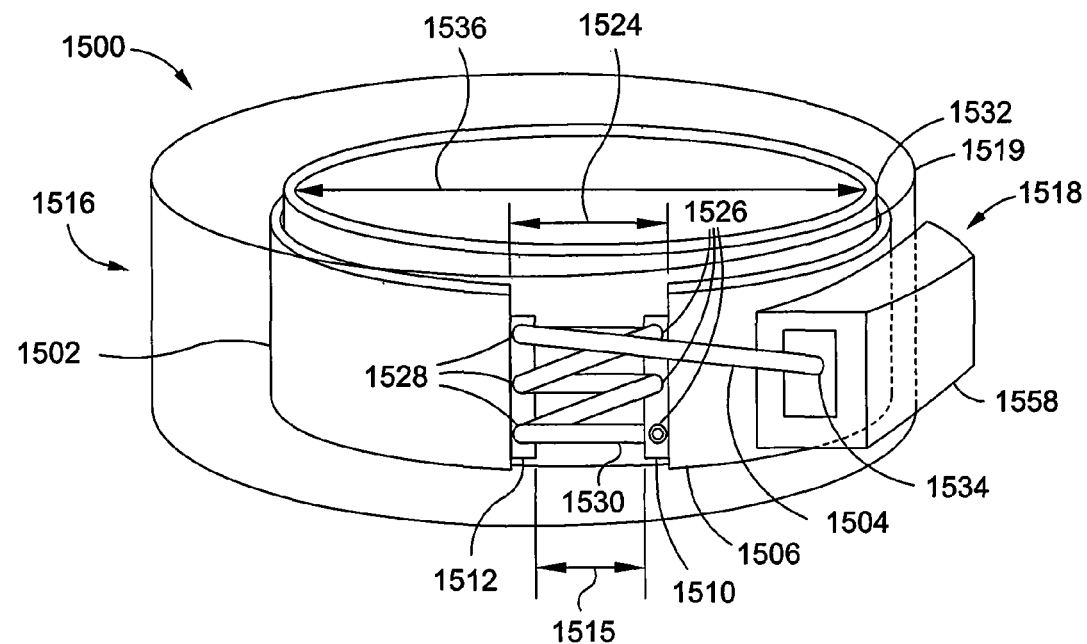
Figure 15C:
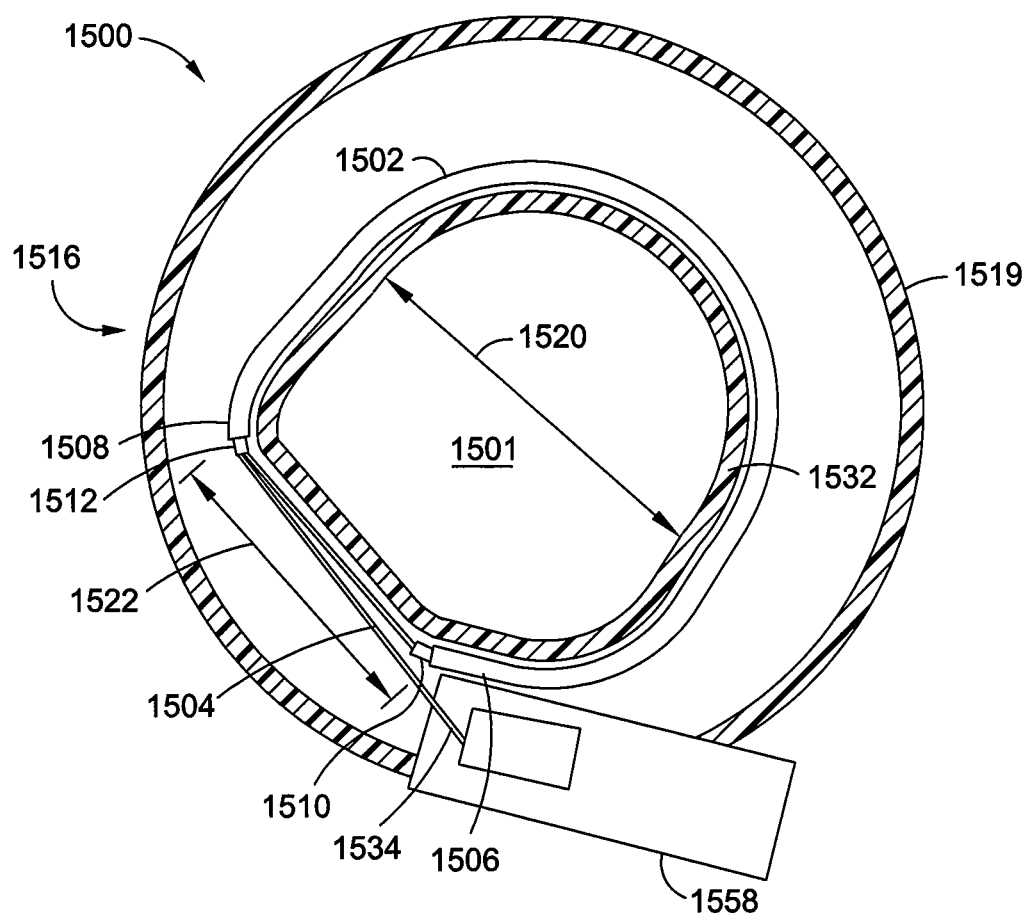
FIG. 15C illustrates a top view of the gastric band device shown in FIG. 15A.

The collar 1502 has a first end 1506 and a second end 1508, and loops around the inner region 1501, as shown in FIG. 15C. The collar 1502 forms a diameter 1520, defining the degree of constriction applied by the collar 1502 to the patient's stomach. The first end 1506 and the second end 1508 of the collar 1502 are positioned at a distance 1522 from each other. The distance 1522 of the first end 1506 from the second end 1508 defines the degree of constriction applied by the collar 1502 to the patient's stomach. The collar 1502 may comprise a strap-like device, or any other structure capable of equivalently extending around the patient's stomach and applying degree of constriction.

A first cord routing device 1510 is coupled to the first end 1506 of the collar 1502. The first cord routing device 1510 includes a plurality of apertures 1526 sized to have a cord 1504 threaded therethrough. A second cord routing device 1512 is coupled to the second end 1508 of the collar 1502, and includes a plurality of apertures 1528 sized to have a cord 1504 threaded therethrough. The cord routing devices 1510, 1512 may comprise equivalent structures capable of routing a cord 1504, including a series of hooks, threaders, pulleys, latches, or the like.

The cord 1504 has a first end 1530 and a second end 1534, the first end 1530 connecting to the first cord routing device 1510 and the second end 1534 connecting to the motor system 1558. The cord 1504 is routed through the plurality of apertures 1528, 1526 in an alternating manner, to link the first end 1506 of the collar 1502 to the second end 1508 of the collar 1502. The passes of the cord 1504 may resemble a lace structure. The number of passes of the cord 1504 through the routing devices 1510, 1512 is shown to be five in FIG. 15B, but this number may be varied to produce equivalent results. The multiple passes of the cord 1504 through the routing devices 1510, 1512 may be considered a form of force multiplier, as each successive pass of the cord 1504 increases a leveraging effect. This leveraging effect may assist the cord length control system 1518 during operation.

A length 1514 of the cord 1504 extending between the first end 1506 and second end 1508 of the collar 1502 defines the distance between the ends 1506, 1508 of the collar 1502, and the degree of constriction applied by the collar 1502 to the patient's stomach. A smaller length 1514 indicates a greater degree of constriction applied to the stomach.

A cord length control system 1518 is coupled to the band 1516 and to the second end 1534 of the cord 1504. The cord length control system 1518 comprises a motor system 1558 that may comprise any of the motor systems shown in FIGS. 2A-2O. The gastric band device 1500 may be suitably modified to allow a desired configuration of the motor system 1558 to drive the cord 1504. In addition, any of the cylindrical transmission devices shown in FIGS. 3A-3L may be incorporated into the gastric band device 1500, and the gastric band device 1500 may be suitably modified to incorporate the desired cylindrical transmission device. Furthermore, the motor system 1558 may also contain any other style of known motor capable of producing effective operation as contemplated by the device 1500.

In operation, the cord length control system 1518 tensions the cord 1504 to decrease the length 1514 of cord 1504 extending between the ends 1506, 1508 of the collar 1502, and correspondingly increase the degree of constriction applied to the patient's stomach. A resilient membrane 1532 may be positioned to have the collar 1502 encircle the resilient membrane 1532, the resilient membrane 1532 resisting the constrictive force applied by the collar 1502. To reduce the degree of constriction, the cord length control system 1518 releases the cord 1504, and the resilient membrane 1532 expands the diameter 1520 formed by the collar 1502. The size of the inner region 1501, shown in FIG. 15C, correspondingly increases.

FIG. 15B illustrates the gastric band device 1500 shown in FIG. 15A in a configuration including a relatively high degree of constriction. In this configuration, the cord length control system 1518 has applied a tension force to the second end 1534 of the cord 1504. The tension force has caused the cord 1504 to be drawn through the routing devices 1510, 1512, reducing the length 1515 of the cord 1504 extending between the devices 1510, 1512. The collar ends 1506, 1508 have been drawn closer together to define a distance 1524 being smaller than the distance 1522 shown in FIG. 15A. The diameter 1536 formed by the collar 1502 is smaller than the diameter 1520 shown in FIG. 15A.

FIG. 15C illustrates a top view of the gastric band device as shown in FIG. 15A. The inner region 1501 is illustrated encircled by the collar 1502. The embodiment shown in FIGS. 15A-15C is exemplary in nature, and may be modified without deviating from the scope of this invention. For example, the configuration of the cord length control system 1518 may be varied to comprise any mechanism capable of tensioning or releasing the cord 1504. In addition, the cord length control system 1518 may comprise a mounting to which the one end or both ends of the cord 1504 are fixed, to secure the cord 1504 in place while another mechanism tensions the cord 1504. In addition, the cord routing devices 1512, 1510 may be varied to include any mechanism capable of routing the cord 1504. The number of connections of the cord 1504 between the cord routing devices 1512, 1510 may be varied to produce variable leveraging, and force multiplication effects.

The gastric band device 1500 discussed in relation to FIGS. 15A-15C provides multiple benefits, including a simplistic design and operation. The multiple passes of the cord 1504 through the cord routing devices 1512, 1510 produces a force multiplier effect, assisting the cord length control system 1518 during operation. In addition, the cord connection between the ends of the collar 1502 provides a sturdy and durable mechanism to constrict the patient's stomach.

Figure 16A:
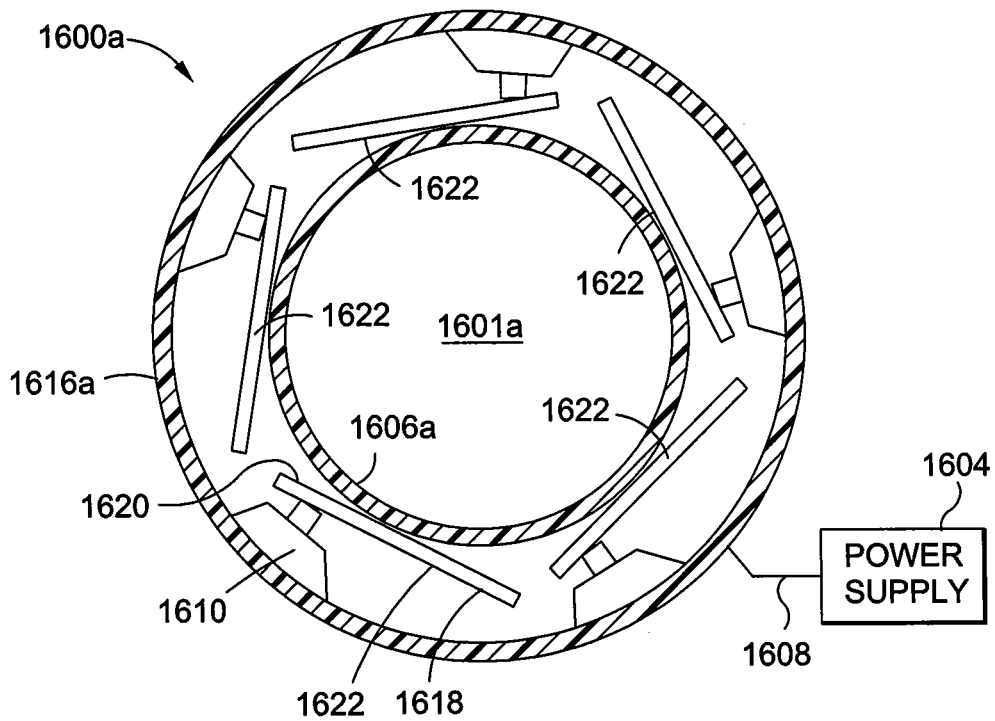
FIGS. 16A-16F illustrate perspective views of gastric band devices according to embodiments of the present invention.

FIG. 16A illustrates a gastric band device 1600a including a plurality of electroactive polymer devices, or deflectable electroactive polymer devices 1622. The gastric band device 1600a also includes a band 1616a configured to be positioned in a loop around a portion of the patient's stomach to be constricted, in a manner similar to the gastric band device 100 described in relation to FIG. 1A. The gastric band device 1600a serves to provide a degree of constriction to a portion of the patient's stomach, similar to the gastric band device 100 described in relation to FIG. 1A. The gastric band device 1600 includes a suitable mechanism (not shown) to allow the gastric band device 1600 to be looped around the portion of the patient's body.

The loop shape of the band 1616a defines an inner region 1601a that is bounded by the band 1616a and by deflectable electroactive polymer devices 1622. The patient's stomach may be complementary with the inner region 1601a formed by the loop. A flexible membrane 1606a may be coupled to the band 1616a, or extend around the band 1616a, similar to the membrane 106 shown in FIG. 1A, to provide a degree of biocompatibility between the gastric band device 1600a and the patient's body.

Each deflectable electroactive polymer device 1622 is positioned within an interior region of the band 1616a, and connects to the band 1616a through a mounting 1610. The deflectable electroactive polymer devices 1622 are positioned substantially equidistant from each other along the interior of the band 1616a.

The deflectable electroactive polymer device 1622 shown in FIG. 16A may comprise an ion polymer-metal composite, wherein an applied voltage redistributes ions contained within the deflectable electroactive polymer device 1622. The redistributed ions cause one portion of the deflectable electroactive polymer device 1622 to inflate, or swell, causing the deflectable electroactive polymer device 1622 to deflect. The deflectable electroactive polymer device 1622 may also comprise a conductive polymer, wherein an applied voltage causes a portion of the polymer to inflate, causing the deflectable electroactive polymer device 1622 to deflect. The deflectable electroactive polymer device 1622 may also equivalently comprise a piezoelectric polymer, a gel polymer, a conductive polymer, an electrostrictive polymer, or combinations thereof.

Each deflectable electroactive polymer device 1622 may have a deflection portion 1618 and a stationary portion 1620. The deflection portion 1618 may be configured to deflect relative to the stationary portion 1620 in response to a voltage applied to the deflectable electroactive polymer device 1622. The deflection portion 1618 may also be positioned to deflect in a direction to apply an increased degree of constriction to the inner region 1601a.

A voltage source, or a power supply 1604 couples to the band 1616a through a electrical line 1608. The band 1616a may be suitably configured to transfer a voltage supplied by the power supply 1604 to the electroactive polymer device 1622.

Figure 16B:
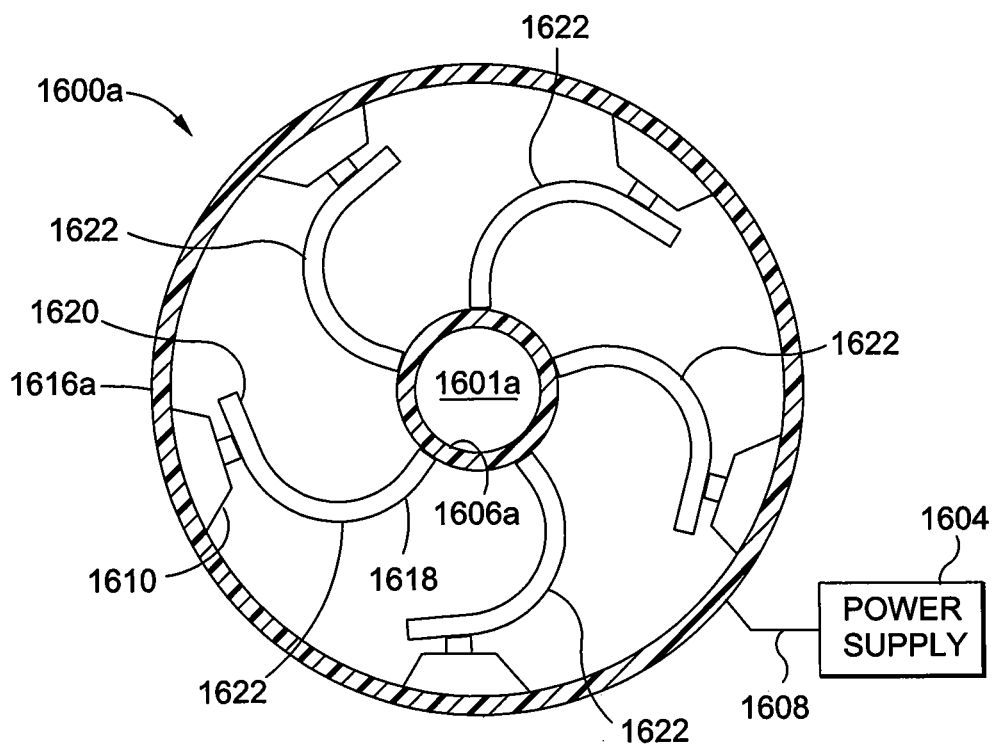

FIG. 16B illustrates the gastric band device 1600a shown in FIG. 16A, after a voltage has been applied to the deflectable electroactive polymer devices 1622. The deflection portion 1618a of the deflectable electroactive polymer devices 1622 have been directed in a direction towards the inner region 1601a, and have increased the degree of constriction applied by the deflectable electroactive polymer devices 1622 to the patient's stomach. The power supply 1604 reduces the voltage applied to the deflectable electroactive polymer devices 1622 to return the gastric band device 1600a back to the configuration shown in FIG. 16A, and accordingly reduce the degree of constriction applied by the deflectable electroactive polymer devices 1622 to the inner region 1601a.

Figure 16C:
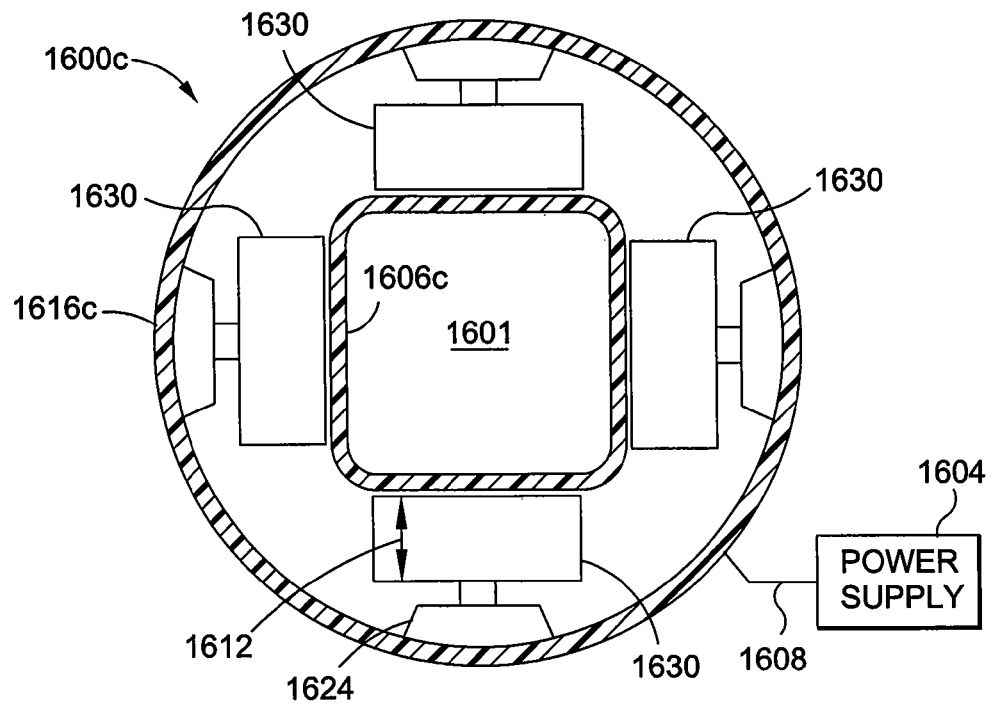

FIG. 16C illustrates a gastric band device 1600c including a plurality of electroactive polymer devices, or expandable electroactive polymer devices 1630. The gastric band device 1600a includes a band 1616c similarly configured as the band 1616a shown in FIG. 16A. The band 1616c may include a membrane 1606c, and may loop around an interior portion 1601c.

Each expandable electroactive polymer device 1630 is positioned within an interior region of the band 1616c, and connects to the band 1616c through a mounting 1624. The expandable electroactive polymer devices 1630 are positioned substantially equidistant from each other along the interior of the band 1616c. Each expandable electroactive polymer device 1630 is configured to have dimensions that vary in response to a voltage applied to the expandable electroactive polymer device 1630. For example, a length 1612 of the expandable electroactive polymer device 1630 may vary in response to a voltage applied to the expandable electroactive polymer device 1630. The expandable electroactive polymer device 1630 may be configured to have an expanded length extend towards the inner region 1601c. The expandable electroactive polymer device 1630 shown in FIG. 16A may comprise a dielectric polymer, wherein an incompressible elastomer is sandwiched between two electrodes. An applied voltage causes compression of the elastomer through electrostatic forces. The compression generates the expansion of the elastomer in a free direction (e.g., towards the patient's stomach. The expandable electroactive polymer device 1630 may equivalently be replaced with a piezoelectric polymer, a gel polymer, an ionic polymer-metal composite, a conductive polymer, an electrostrictive polymer, or combinations thereof.

Figure 16D:
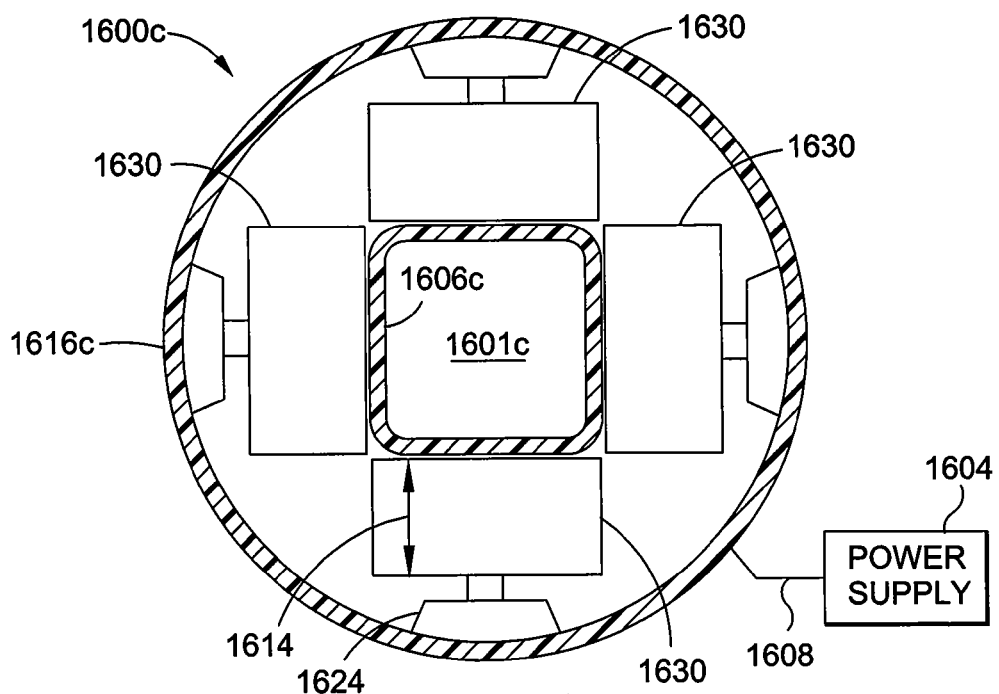

FIG. 16D illustrates the gastric band device 1600c shown in FIG. 16C, after a voltage has been applied to the expandable electroactive polymer devices 1630 by the power supply 1604. A length 1614 of the expandable electroactive polymer device 1630 has extended in a direction towards the inner region 1601c, and has increased the degree of constriction applied by the expandable electroactive polymer device 1630 to the patient's stomach. The power supply 1604 reduces the voltage applied to the expandable electroactive polymer device 1630 to return the gastric band device 1600c back to the system shown in FIG. 16C, and accordingly reduce the degree of constriction applied by the expandable electroactive polymer device 1630 to the inner region 1601c.

Figure 16E:
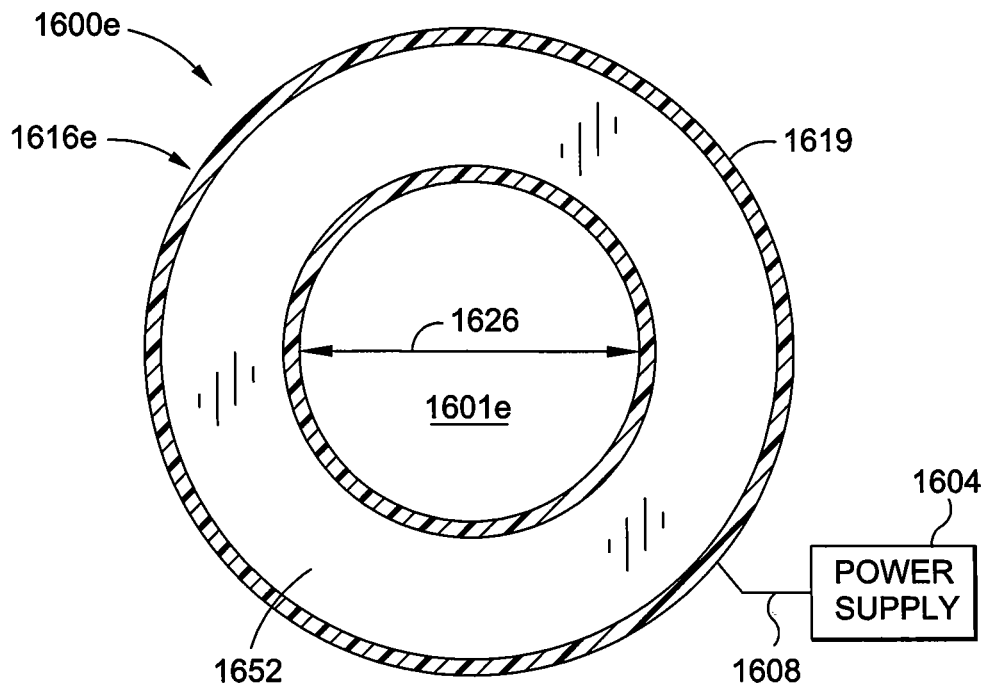

FIG. 16E illustrates a gastric band device 1600e including an encircling electroactive polymer device 1652 that comprises a band 1616e. The encircling electroactive polymer device 1652 is configured in a loop around a portion of the patient's stomach, and has an inner diameter 1626. In addition, the loop defines an inner region 1601e, bounded by the encircling electroactive polymer device 1652. The encircling electroactive polymer device 1652 may also have a rigid dorsal periphery 1619, to prevent an increase in the outer diameter of the encircling electroactive polymer device 1652 during expansion of the encircling electroactive polymer device 1652.

The encircling electroactive polymer device 1652 is configured to expand in a direction towards the inner region 1601e, or extend in a direction towards the inner region 1601e in response to a voltage applied to the encircling electroactive polymer device 1652 by the power supply 1604. The expansion or extension reduces the inner diameter 1626 of the encircling electroactive polymer device 1652 and increases a degree of constriction applied by the encircling electroactive polymer device 1652 to the patient's stomach.

The encircling electroactive polymer device 1652 may comprise a piezoelectric polymer, a gel polymer, an ionic polymer-metal composite, a conductive polymer, a dielectric polymer, an electrostrictive polymer, or combinations thereof.

Figure 16F:
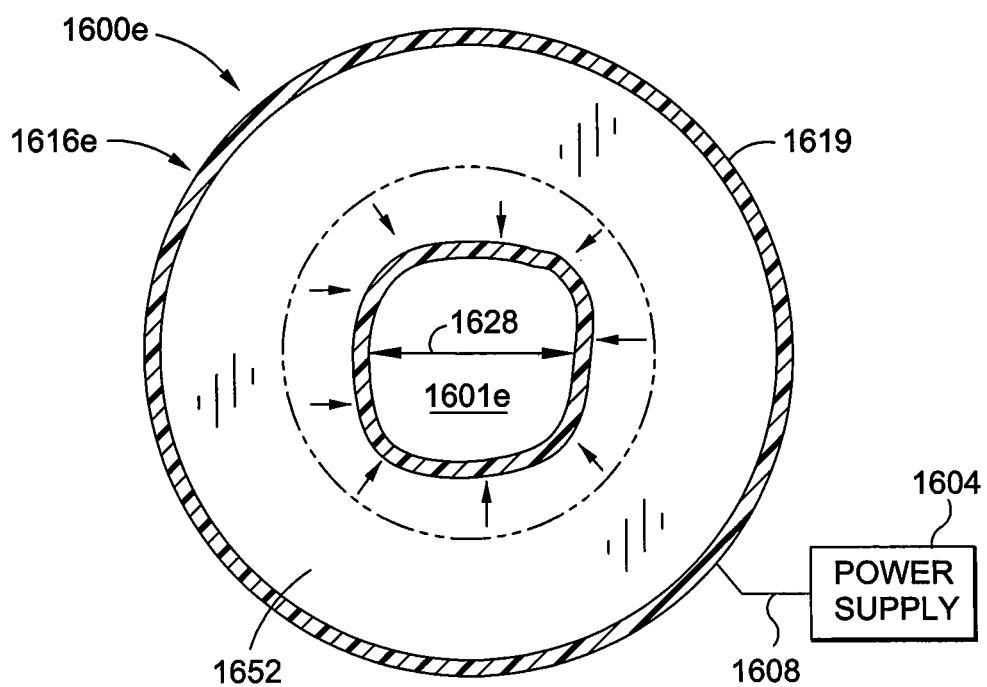

FIG. 16F illustrates the gastric band device 1600e shown in FIG. 16E, after a voltage has been applied to the encircling electroactive polymer device 1652. The encircling electroactive polymer device 1652 forms a diameter 1628 being smaller than shown in FIG. 16E, and reduces the size of the inner region 1601e. The power supply 1604 reduces the voltage applied to the encircling electroactive polymer device to return the gastric band device 1600e back to the configuration shown in FIG. 16E, and accordingly reduce the degree of constriction applied by the encircling electroactive polymer device 1652 to the inner region 1601e.

The embodiments shown in FIGS. 16A-16F are exemplary in nature, and may be modified without deviating from the scope of this invention. For example, the number, configuration, and position of any of the electroactive polymer devices 1622, 1630, 1652 may be varied to produce an equivalent result of varying the degree of constriction applied to the patient's stomach. In addition, any of the devices 1622, 1630, 1652 may be equivalently replaced with a piezoelectric polymer, a gel polymer, an ionic polymer-metal composite, a conductive polymer, a dielectric polymer, an electrostrictive polymer, or combinations thereof. In addition, the position or configuration of the power supply 1604 may be varied to produce an equivalent result.

The gastric band devices 1600a, 1600c, 1600e discussed in relation to FIGS. 16A-16C provide multiple benefits, including a simplistic design and operation. The gastric band devices 1600a, 1600c, 1600e do not include any moving mechanical parts subject to wear or failure. Rather, the molecular properties of the polymer devices 1622, 1630, 1652 provide the actuation required to restrict the patient's stomach. A power supply 1604, or voltage source, which may be internally or externally controlled, replaces a motor system used in other gastric banding systems.

An additional approach to constricting a patient's stomach includes a chicane mechanism, wherein the stomach is bent to increase the food flow resistance. A series of strong bends of the stomach can reduce food flow.

Another approach to constricting a patient's stomach includes a twisted stomach mechanism, wherein the stomach is twisted to increase the food flow resistance.

Another approach to constricting a patient's stomach includes placing a gastric band device inside the patient's stomach. In addition, a control mechanism that could be placed in the patient's stomach, to control actuation of a banding device positioned internal or external to the stomach.

Another approach to constricting a patient's stomach includes storing unused constriction energy in a mechanical device. The mechanical device may store the energy for future use.

The banding devices, referred to as gastric band devices throughout this application, may be equivalently applied to constrict other bodily organs, human or otherwise. In addition, the transmission systems, and drive systems discussed throughout this application may be applied and used to constrict body organs different than the stomach. For example, any of the devices or systems discussed in this application may be applied to control urinary tracts, cardiovascular tracts, and other portions of the digestive system, including intestines, rectums, and various parts of the stomach, without deviating from the scope of this invention. The devices or systems may be applied to control various ailments other than obesity, including urinary or anal incontinence.

In addition, any element discussed with regard to one gastric band device, transmission device, or drive system may be equivalently introduced and/or interchanged with an element in another gastric band device, transmission device, or drive system. For example, the cylindrical transmission systems may be equivalently applied to other gastric band devices or drive systems where appropriate. In addition, the corrugated membrane discussed in relation to FIG. 1B may be equivalently applied to other gastric band devices. Furthermore, any element viewed in the art as critical to proper operation of any of the banding devices, transmission devices, or drive systems, may be incorporated in any of the above-described devices and systems to ensure proper operation.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A gastric band device for the treatment of obesity, suitable for placement around the stomach of a patient and constriction of the stomach of the patient, comprising:
   a band configured to form a loop around a portion of the stomach of the patient; and
   a plurality of lever devices, each lever device is configured to apply a degree of constriction to the stomach of the patient, each lever device having a first end and a second end, the first end of each lever device being coupled to the band, and the second end of each lever device being positioned at a distance from the band, the distance being variable and defining the degree of constriction applied by each lever device to the stomach of the patient;
   wherein each lever device comprises a first lever arm and a second lever arm, and a first pivot device couples the first lever arm to the second lever arm, the first lever arm being coupled to the band and the second lever arm being coupled to the band, the first lever arm being coupled to the second lever arm to form an angle, a size of the angle being variable and defining the distance of the second end of each lever device from the band.

2. The gastric band device of claim 1, wherein a second pivot device couples the first lever arm to the band and a third pivot device couples the second lever arm to the band.

3. The gastric band device of claim 1, wherein an interior region on the band is bounded by the first lever arm and the second lever arm and the band, the interior region having a substantially triangular shape.

4. The gastric band device of claim 3, wherein a size of the interior region is variable and is defined by the size of the angle formed between the first lever arm and the second lever arm.

5. The gastric band device of claim 4, wherein each lever device has a substantially triangular shape.

6. The gastric band device of claim 1, wherein the first lever arm has a substantially columnar shape and the second lever arm has a substantially columnar shape.

7. The gastric band device of claim 1, wherein the first lever arm has a first end and a second end, the first end of the first lever arm being coupled to the band and the second end of the first lever arm comprising the second end of the lever device.

8. The gastric band device of claim 7, wherein the second lever arm has a first end and a second end, the first end of the second lever arm being coupled to the band and the second end of the second lever arm being coupled to the second end of the first lever arm to form the angle.

9. The gastric band device of claim 8, wherein the band comprises a first band and a second band, the first band being positioned concentric with the second band and being slidably clamped to an interior surface of the second band.

10. The gastric band device of claim 9, wherein the first end of the first lever arm is coupled to the first band and the first end of the second lever arm is coupled to the second band.

11. The gastric band device of claim 10, further comprising a motor coupled to the first band, the motor configured to apply a force to the first band during operation of the motor, the force varying the angle formed between the first lever arm and the second lever arm.

12. The gastric band device of claim 11, wherein the second band has an outer diameter that remains substantially constant during the operation of the motor.

13. The gastric band device of claim 11, wherein a constant force applied by the motor to the first band during the operation of the motor varies the distance of the second end of each lever device from the band at a variable speed.

14. The gastric band device of claim 10, further comprising a motor coupled to the first band and the second band, the motor configured to apply a force to the first band and the second band during operation of the motor, the force varying the angle formed between the first lever arm and the second lever arm.

15. The gastric band device of claim 7, wherein the second lever arm has a first end and a second end, the first end of the second lever arm being coupled to the band and the second end of the second lever arm being coupled to a midpoint of the first lever arm to form the angle.

16. The gastric band device of claim 7, wherein the first end of the first lever arm has a substantially forked shape and the first end of the second lever arm has a substantially forked shape.

17. The gastric band device of claim 1, further comprising a plurality of pads, each pad coupled to the second end of a corresponding lever device.

18. The gastric band device of claim 1, further comprising a membrane substantially covering the gastric band device.

19. The gastric band device of claim 1, wherein the band has a first end and a second end, the first end of the band configured to couple to the second end of the band to form the loop around the portion of the patient's stomach.

20. A gastric band device for the treatment of obesity, suitable for placement around the stomach of a patient and constriction of the stomach of the patient, comprising:
   a band configured to form a loop around a portion of the stomach of the patient; and
   a plurality of lever devices, each lever device is configured to apply a degree of constriction to the stomach of the patient, each lever device having a first end and a second end, the first end of each lever device being coupled to the band, and the second end of each lever device being positioned at a distance from the band, the distance being variable and defining the degree of constriction applied by each lever device to the stomach of the patient;

wherein each lever device comprises a first lever arm and a second lever arm, the first lever arm being coupled to the band and the second lever arm being coupled to the band, and an interior region on the band is bounded by the first lever arm and the second lever arm and the band, the interior region having a substantially triangular shape, the first lever arm being coupled to the second lever arm to form an angle, a size of the angle being variable and defining the distance of the second end of each lever device from the band.

21. The gastric band device of claim 20, wherein a size of the interior region is variable and is defined by the size of the angle formed between the first force lever arm and the second lever arm.

22. The gastric band device of claim 21, wherein each lever device has a substantially triangular shape.

23. The gastric band device of claim 20, further comprising a membrane substantially covering the gastric band device.

24. The gastric band device of claim 20, wherein the band has a first end and a second end, the first end of the band configured to couple to the second end of the band to form the loop around the portion of the patient's stomach.

25. A gastric band device for the treatment of obesity, suitable for placement around the stomach of a patient and constriction of the stomach of the patient, comprising:

a band configured to form a loop around a portion of the stomach of the patient; and a plurality of lever devices, each lever device is configured to apply a degree of constriction to the stomach of the patient, each lever device having a first end and a second end, the first end of each lever device being coupled to the band, and the second end of each lever device being positioned at a distance from the band, the distance being variable and defining the degree of constriction applied by each lever device to the stomach of the patient;

wherein each lever device comprises a first lever arm and a second lever arm, the first lever arm has a first end and a second end, the first end of the first lever arm being coupled to the band and the second end of the first lever arm comprising the second end of each lever device, and the second lever arm being coupled to the band, the first lever arm being coupled to the second lever arm to form an angle, a size of the angle being variable and defining the distance of the second end of each lever device from the band.

26. The gastric band device of claim 25, wherein the second lever arm has a first end and a second end, the first end of the second lever arm being coupled to the band and the second end of the second lever arm being coupled to the second end of the first lever arm to form the angle.

27. The gastric band device of claim 26, wherein the band comprises a first band and a second band, the first band being positioned concentric with the second band and being slidably clamped to an interior surface of the second band.

28. The gastric band device of claim 27, wherein the first end of the first lever arm is coupled to the first band and the first end of the second lever arm is coupled to the second band.

29. The gastric band device of claim 28, further comprising a motor coupled to the first band, the motor configured to apply a force to the first band during operation of the motor, the force varying the angle formed between the first lever arm and the second lever arm.

30. The gastric band device of claim 29, wherein the second band has an outer diameter that remains substantially constant during the operation of the motor.

31. The gastric band device of claim 29, wherein a constant force applied by the motor to the first band during the operation of the motor varies the distance of the second end of the lever device from the band at a variable speed.

32. The gastric band device of claim 28, further comprising a motor coupled to the first band and the second band, the motor configured to apply a force to the first band and the second band during operation of the motor, the force varying the angle formed between the first lever arm and the second lever arm.

33. The gastric band device of claim 25, wherein the second lever arm has a first end and a second end, the first end of the second lever arm being coupled to the band and the second end of the second lever arm being coupled to a midpoint of the first lever arm to form the angle.

34. The gastric band device of claim 25, wherein the first end of the first lever arm has a substantially forked shape and a first end of the second lever arm has a substantially forked shape.

35. The gastric band device of claim 25, further comprising a membrane substantially covering the gastric band device.

36. The gastric band device of claim 25, wherein the band has a first end and a second end, the first end of the band configured to couple to the second end of the band to form the loop around the portion of the patient's stomach.

37. A gastric band device for the treatment of obesity, suitable for placement around the stomach of a patient and constriction of the stomach of the patient, comprising:

a band configured to form a loop around a portion of the stomach of the patient;

a plurality of lever devices, each lever device is configured to apply a degree of constriction to the stomach of the patient, each lever device having a first end and a second end, the first end of each lever device being coupled to the band, and the second end of each lever device being positioned at a distance from the band, the distance being variable and defining the degree of constriction applied by each lever device to the stomach of the patient; and a plurality of pads, each pad coupled to the second end of a corresponding lever device, wherein each lever device comprises a first lever arm and a second lever arm, the first lever arm being coupled to the band and the second lever arm being coupled to the band, the first lever arm being coupled to the second lever arm to form an angle, a size of the angle being variable and defining the distance of the second end of each lever device from the band.

38. The gastric band device of claim 37, further comprising a membrane substantially covering the gastric band device.

39. The gastric band device of claim 37, wherein the band has a first end and a second end, the first end of the band configured to couple to the second end of the band to form the loop around the portion of the patient's stomach.

* * * * *